(12) United States Patent
Ambavaram et al.

(10) Patent No.: US 11,072,798 B2
(45) Date of Patent: Jul. 27, 2021

(54) TRANSCRIPTIONAL REGULATION FOR IMPROVED PLANT PRODUCTIVITY

(71) Applicant: YIELD10 BIOSCIENCE, INC., Woburn, MA (US)

(72) Inventors: Madana M. R. Ambavaram, Norwood, MA (US); Mariya Somleva, Cambridge, MA (US)

(73) Assignee: YIELD 10 BIOSCIENCE, INC., Woburn, MA (US)

( * ) Notice: Subject to any disclaimer, the term of this patent is extended or adjusted under 35 U.S.C. 154(b) by 0 days.

(21) Appl. No.: 16/570,489

(22) Filed: Sep. 13, 2019

(65) Prior Publication Data

US 2020/0048651 A1  Feb. 13, 2020

Related U.S. Application Data

(63) Continuation of application No. 15/897,958, filed on Feb. 15, 2018, now Pat. No. 10,450,580, which is a continuation of application No. 14/653,431, filed as application No. PCT/US2013/076308 on Dec. 18, 2013, now abandoned.

(60) Provisional application No. 61/738,675, filed on Dec. 18, 2012.

(51) Int. Cl.
*C12N 15/82* (2006.01)
*C07K 14/415* (2006.01)

(52) U.S. Cl.
CPC ........ *C12N 15/8261* (2013.01); *C07K 14/415* (2013.01); *C12N 15/8241* (2013.01); *C12N 15/8245* (2013.01); *C12N 15/8251* (2013.01); *C12N 15/8271* (2013.01); *C12N 15/8273* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 6,706,866 B1 | 3/2004 | Thomashow et al. | |
| 7,663,025 B2 | 2/2010 | Heard et al. | |
| 8,110,723 B2 | 2/2012 | Bloksberg et al. | |
| 2005/0086718 A1 | 4/2005 | Heard et al. | |
| 2006/0272060 A1* | 11/2006 | Heard ................ | C12N 15/8273 800/289 |
| 2007/0022495 A1 | 1/2007 | Reuber et al. | |

(Continued)

FOREIGN PATENT DOCUMENTS

WO  2005/112608 A2  12/2005
WO  2014/093614 A1  6/2014

OTHER PUBLICATIONS

Abate et al., "Separation and structural characterization of cyclic and open chain oligomers produced in the partial pyrolysis of microbial poly(hydroxybutyrates)," Macromolecules, 28(23): 7911-7916 (1995).

(Continued)

*Primary Examiner* — Ashley K Buran
(74) *Attorney, Agent, or Firm* — Pearne & Gordon LLP

(57) ABSTRACT

Methods comprising DNA constructs and polynucleotides of functional transcription factors for improving photosynthetic capacity, biomass and/or grain yield and stress tolerance in various crop and model plants, dicots and monocots with the $C_3$ or $C_4$ photosynthetic pathways are described herein.

15 Claims, 21 Drawing Sheets

Specification includes a Sequence Listing.

(56) References Cited

U.S. PATENT DOCUMENTS

| | | | |
|---|---|---|---|
| 2008/0072340 A1 | 3/2008 | Troukhan et al. | |
| 2009/0094717 A1* | 4/2009 | Troukhan | C12Q 1/6895 800/290 |
| 2011/0167514 A1* | 7/2011 | Brover | C12N 15/8242 800/278 |
| 2012/0005773 A1 | 1/2012 | Aasen et al. | |
| 2012/0060413 A1* | 3/2012 | Somleva | C10G 3/00 44/605 |

OTHER PUBLICATIONS

Dietz et al., "AP2/EREBP transcription factors are part of gene regulatory networks and integrate metabolic, hormonal and environmental signs in stress acclimation and retrograde signalling," Protoplasma, 245(1-4): 3-14 (2010).

International Search Report and Written Opinion for International Application No. PCT/US2013/076308 dated Jun. 4, 2014 (our reference MBQ-01125).

Invitation to Pay Additional Fees for PCT/US2013/076308, "Transcriptional Regulation for Improved Plant Productivity;" dated Mar. 27, 2014. (4614.1011-001).

Jaglo et al., "Components of the Arabidopsis C-Repeat/Dehydration-Responsive Element Binding Factor Cold-Response Pathway are Conserved in Brassica napus and Other Plant Species," Plant Physiology, 127: 910-917 (Nov. 2001).

Mizoi et al., "AP2/ERF family transcription factors in plant abiotic stress responses," Biochim Biophys Acta., 1819(2): 86-96 (2012).

Nakano et al., "Genome-Wide Analysis of the ERF Gene Family in *Arabidopsis* and Rice," Plant Physiology, 140: 411-432 (Feb. 2006).

Notification of Transmittal of the International Search Report and the Written Opinion of the International Search Authority for PCT/US2013/076308, "Transcriptional Regulation for Improved Plant Productivity;" dated Jun. 4, 2014.(4614.1011-001).

Ohto et al., "Control of seed mass by APETALA2," PNAS, 102(8): 3123-3128 (2005).

Saibo et al., "Transcription factors and regulation of photosynthetic and related metabolism under environmental stresses," Annals of Botany, 103(4): 609-623 (2009).

Zhang et al., "Overexpression of the Soybean GmERF3 Gene, a AP2/ERF Type Transcription Factor for Increased Tolerances to Salt, Drought, and Diseases in Transgenic Tobacco," J Exp Botany, 60(13): 3781-3796 (2009).

Zhang et al., "Progresses on Plant AP2/ERF Transcription Factors," Hereditas, 34(7): 835-847 (2012).

* cited by examiner

```
SEQ ID NO:
Panicum      29  VTS--------RKRKTQYRGIRRRPWGKWAAEIRDPQKGVRVWLGTFSTAEEAARAYDVEALRIRGKKAKMNFETTITAAGKHHRQRVARP--------------------AKRT
Setaria      30  VAR--------RKRKJQYRGIRRRPWGKWAAEIRDPCKGVRVWLGTFSTAEEAARAYDVAARRIRGKKAKRLPGRVPRP--------------------AKKV
Sorghum      31  VAS--------RKRRTQYRGIRRRPWGKWAAEIRDPRKGVRVWLGTYNTAEEAARAYDTAAWRIRGKKRARVNFESAITNPEKRRRGRVARP-----------------RKKI
Oryza        32  GGS--------RKRKTRYRGIRQRPWGKWAAEIRDPRKGVRVWLGTYSTAEEAARAYDVGTAEEAARAYDVNFEDAAAAAPKRPRRSSAKHSPQQQKA-----------RSSS
Jatropha     33  FNG--QAEKSAKRKRKNQYRGIRQRPWGKWAAEIRDPRKGVRVWLGTFNTAEEAARAYDAEARRIRGKKAKVNFPEEEAPHASFKRPSKANSQKSLGKTN-------LAENLNYLDNPEQ
Populus      34  FSG--PAEKSAKRKRKRNQFRGIRQRPWGKWAAEIRDPRKGVRVWLGTFNTAEEAARAYDSEARRIRGKKAKVNFPDEAPCASARHPIKENSQKRLTKAN-------LSQDFSYLSNPET
Gossypium    35  FNG--QAEKCAKRKRKRNQYRGIRQRPWGKWAAEIRDPRKGVRVWLGTFNTAEEAARAYDAEARRIEGKKAKVNFPNETPRTSPKHAVKTNSQKPLSKSNSSPV-QPNLMQNYNYLNQPEQ
Theobroma    36  FNG--QAEKSAKRKRKNQYRGIRQRPWGKWAAEIRDPRKGVRVWLGTFNTAEEAARAYDAEARRIRGKKAKVNFPDEAPRTSPKRAVKANSQKSLSRNLSPV-QPMLDQNFNYLSKPEQ
Malus        37  FDG--QAEKSAKRKRKNQYRGIRQRPWGKWAAEIRDPRKGVRVWLGTFNTAEEAARAYDAEARRIRGKKAKVNFPEETPCASAKRSIKENPQKLIAKTNLNGTQSNPN-QNFNFVNDSSE
Morus        38  SDG--QAEKSAKRKRKNQYRGIRQRPWGKWAAEIRDPRKGVRVWLGTFNTAEEAARAYDAEARRIRGKKAKVNFEDETPRALPKHPVKESPKRSLPKENSNSTESNLNNQSFNSVNNSDL
Cucumis      39  FNE--QAEKSANTKRKRNQYRGIRQRPWGKWAAEIRDPRKGARVWLGTFNTAEEAARAYDAEARRIEGNKARVNFPDEFLPNTQKR---KNSQKSKQHIK---------ENVKAMQHPNQ
Solanum      40  SNC--EADRSSKRKRKNQYRGIRQRPWGKWAAEIRDPRKGIRVWLGTFNSAEEAARAYDAEARRIEGKKAKVNFPDEAPVSVSRRAIKQNFQKALREETLN------TVQFNMTYISNLDG
Capsicum     41  SSC--DTEKSSKRKRKNQYRGIRQRPWGKWAAEIRDPRKGIRVWLGTFNSABEAARAYDVEARRIRGKKAKVNFPDGSPASASRKAVRKPNPQEALREEILN------TVQPNTYINNLDG
Nicotiana    42  SDK--DADRSSKRKRKNQYRGIRQRPWGKWAAEIRDPRKGVRVWLGTFNTAEEAARAYDVEARRIRGKKAKVNFPEAPGTSSVKR-SKVNPQENLKTVQEN-------SVQPDSTIINNMED
Glycine      43  FQG--RABISANRKRKNQYRGIRQRPWGKWAAEIRDPRKGVRVWLGTFNTAEEAARAYDAEARRIRGKKAKVNFPEAPGTSSVKR-SKVNPQENLKTVQEN--------LGHKFSAGNN-
Arachis      44  VKA--QSEKSAKRKRKNQYRGIRQRPWGKWAAEIRDPRKGVRVWLGTFNTAEEAARAYDAEARRIRGKKAKVNFPEEAPRTPPKR-ARPN----LNAVQPN----------LSHKFSVGNRM
Medicago     45  SKSNEQGEKELKRKRKNQYRGIRQRPWGKWAAEIRDPRKGVRVWLGTFNTAEEAARAYDAEARRIRGKKAKVNFPEEAPNASSKE-LKTN--SETQLLDKN--------LN-SFKCENIE
Zea          46  YDA--PAARLAKRKRKNQFRGIRRRPWGKWAAEIRDPRKGVRVWLGTFSPEEAARAYDAEARRIRGKKAKVNFPDAPAVGQKCRSSSASAKALKSCVEQKPI----VKTDMNILANTNA
Brachypodium 47  FDG--PAERSAKRKRKNQFRGIRQRPWGKWAAEIRDPNKGVRVWLGTPNSAEEAARAYDAEARRIRGNKAKVNFEEPRAAQKERAGFAAAKVFKSRVEQKPN-----VKPAVNNLANTNA
Triticum     48  DDD--CASGSAXRKRKNQFRGIRRRPWGKWAAEIRDPRKGVRVWLGTFNSAEEAARAYDVEARRIRGKKAEVNFPEEAPMAPQQR-CATAVKVPEENTEQKP--------VLNTMGNADV
Hordeum      49  YDGGRAAHAASRKKRTQHLHGIRQRPWGKWAAEIRDPRKGTRVWLGFRTQADDAARANDVAARRLEGSKAKVNFRDAARTGARPRRASRRTAQKPQCPP-----------------ART
                  **  :  :****:*********** ** ******:.:.:.:** *** * *;**.**.**.;.:***
```

FIG. 4A

```
             SEQ ID NO:
Zea          50  TLTTTMRHYRGVRRRPWGKWAAEIRDPAKAARVWLGTFDTAEAAAAYDRAALQFKGAKAKLNFPERVRGRTGQGA---------FLVSPGIP--------QPPP--VSAP---
Sorghum      51  TSTTTMHHYRGVRRRPWGKWAAEIRDPAKAARVWLGTFDTAEAAAAAYDDAALRFKGAKAKLNFPERVRGRTGQGA---------FLVSPGIP--------QPPPPVSAPPL-
Panicum      52  ---YGTRMHYRGVRRRPWGKWAAEIRDPAKAARVWLGTFDTAEAAAAAYDDAALRFKGAKAKLNFPERVRGRTGQGA---------FLVSPGVP--------QQPPP--SSLP--
Hordeum      53  ---GRKRHYRGVRQRPWGKWAAEIRDPKKAARVWLGTFDTETAEDAAIAYDEAALRFKGTKAKLNFPERVQGRTDLG---------FVVTRGIPDR--LQQQQHYPAAVGAPAMRP-
Brachypodium 54  ---GRKRHYRGVRQRPWGKWAAEIRDPKKAARVWLGTFDTETAEDAAIAYDEAALRFKGTKAKLNFPERVQGRTDLG---------FVVTRGIPDRSLLHHQQHYP---GSTAMRP-
Oryza        55  ---GRRRHYRGVRQRPWGKWAAEIRDPKKAARVWLGTFDTAEDAAIAYDEAALRFKGTKAKLNFPERVQGRTDLG----------FLVTRGIPPAA-THGGGYYPSSSPAAGACP-
Jatropha     56  --NTRRRHYRGVRQRPWGKWAAEIRDPKKAARVWLGTFDTAEDAALKFKGTKAKLNFPERVQGKPEFS-----------YPMTSSGDSSSALAPEQNPMAAAASAPSRHYL
Populus      57  --NTRRRHYRGVRQRPWGKWAAEIRDPKKAARVWLGTFDTAEDAAVAYDKAALKFKGTKAKLNFPERVQGRTEFG---------YYMG-SGTSTNVLT-EQSPRPVAPPPPPP--
Theobroma    58  EENTRRRHYRGVRQRPWGKWAAEIRDPKKAARVWLGTFDTAEDAALAYDEAALKFKGTKAKLNFPERVQGNTEVS---------YFTG-HGDSSTVRP-DQNPTPAAT--
Medicago     59  --TKKKEHYRGVRQRPWGKWAAEIRDPKKAARVWLGTFDTAEDAALAYDKAALKFKGTKAKLNFPERVVQ---------------CNSYSSTANNAIQQSDYVS-----
Glycine      60  --VTKKEHYRGVRQRPWGKWAAEIRDPKKAARVWLGTFETAEDAALAYDKAALKFKGTKAKLNFPERLHQNVPYMQQHQQGSSNRNVPFFHATSSTSSSATGSVSSLDAVAP--
Malus        61  --TVRRRHYRGVRQRPWGKWAAEIRDPKKAARVWLGTFETAEDAAIAYDNAALRFKGTKAKLNFPERVQGRTDFG---------ILMGSSGTTTNSSSGAASTQRTQNLMRPAGQTAPA
Capsicum     62  ---GSGRRHYRGVRQRPWGKWAAEIRNPKKAARVWLGTFDRAEDAALAYDEAAVRFKGSKAKLNFPERLVQGQPQL---------LSQDTSPQHNSHHPEFFNT-----
Brassica     63  SGDGPQRRYRGVRQRPWGKWAAEIRDPFKKAARVWLGTFENAESAARAYDEAALRFKGNIKAKLNFPENVKLVRPAST------TPTLSVPQTAVQRPTQLRNSGSTSTILPVRH
Solanum      64  NNEKRRRQYRGVRQRPWGKWAAEIRDPKKAARVWLGTFPHTAEDAALKFKGNKAKLNFPERVQSTTDQFG--------ISYLITNTNHQQHQFQPTNFLPNSD
Cucumis      65  RVKRLKNYRGVRQRPWGKWAAEIRDPIRAARVWLGTFPNTAEDAARAYDEAAIKFPRGPRAKLNFPFFPDYSLSSTFHS------SPPPASTTTSASASFSPAAFPPPLLPTST
                 *. *  **********.*:.***************:* .** ** **** **::*;.* :*******.
```

FIG. 4B

| | SEQ ID NO: | |
|---|---|---|
| Populus | 66 | MADSDNESGEQNNSNTNVSTETSPREQDRLLPIANVSRIMKKALPANAKISKDAKETVQECVSEFISFITGEASDKCQREKRKTINGDDLLWAMTTLGFEDYVEPLKIYLQKFREMEGEK |
| Solanum | 67 | MADSDNESGGHNNANS----BGSTREQDRFLPIANVSRIMKKALPANAKISKDAKETVQECVSEFISFITGEASDKCQREKRKTINGDDLLWAMTTLGFEEYVEPLKIYLAKYREMEGEK |
| Theobroma | 68 | MADSDNDSGGHNNSNAN--NELSPREQDRFLPIANVSRIMKKALPANAKISKDAKETVQECVSEFISFITGEASDKCQREKRKTINGDDLLWAMTTLGFEDYVEPLKVVLHKFREMEGER |
| Panicum | 69 | MPDSDNESGGPSN------AEFSSPREQDRFLPIANVSRIMKKALPANAKISKDAKETVQECVSEFISFISFITGEASDKCQREKRKTINGDDLLWAMTTLGFEDYIEPLKLYLHKFRELEGEK |
| Setaria | 70 | MPDSDNESGGPSN------AEFSSPREQDRFLPIANVSRIMKKALPANAKISKDAKETVQECVSEFISFISFITGEASDKCQREKRKTINGDDLLWAMTTLGFEDYIEPLKLYLHKFRELEGEK |
| Sorghum | 71 | MPDSDNESGGPSN------ADFSSPREQDRFLPIANVSRIMKKALPANAKISKDAKETVQECVSEFISFISFITGEASDKCQREKRKTINGDDLLWAMTTLGFEDYIEPLKLYLHKFRELEGEK |
| Zea | 72 | MPDSDNESGGPSN------AEFSSPREQDRFLPIANVSRIMKKALPANAKISKDAKETVQECVSEFISFISFITGEASDKCQREKRKTINGDDLLWAMTTLGFEDYVEPLKLYLHKFRELEGEK |
| Hordeum | 73 | MPDSDNDSGGPSN------ADFSSPKEQDRFLPIANVSRIMKKALPANAKISKDAKETVQECVSEFISFISFITGEASDKCQREKRKTINGDDLLWAMTTLGFEDYMEPLKLYLHKFRELEGEK |
| Oryza | 74 | MPDSDNDSGGPSNYAG---GELSSPREQDRFLPIANVSRIMKKALPANAKISKDAKETVQECVSEFISFISFITGEASDKCQREKRKTINGDDLLWAMTTLGFEDYVDPLKHYLHKFREIEGER |
| Brachypodium | 75 | MPDSDNDSGGPSN-TG---GELSSPREQDRFLPIANVSRIMKKALPANAKISKDAKETVQECVSEFISFISFITGEASDKCQREKRKTINGDDLLWAMTTLGFEDYVDPLKHYLHKFREIEGER |
| Triticum | 76 | MPDSDNED---SGNAG---GELSSPREQDRFLPIANVSRIMKKALPANAKISKDAKETVQECVSEFISFISFITGEASDKCQREKRKTINGDDLLWAMTTLGFEDYVDPLKHYLHKFREIEGER |
| Glycine | 77 | MADSDNDSGGAHNAGK---GSEMSPREQDRFLPIANVSRIMKKALPANAKISKDAKETVQECVSEFISFITGEASDKCQREKRKTINGDDLLWAMTTLGFEDYVEPLKGYLQRFREMEGEK |
| | | *.****:. . *.:***;********************************** ::;**: *:*****:*.:;;:**:  ;;;**; |

FIG. 4C

TRANSCRIPTIONAL REGULATION FOR IMPROVED PLANT PRODUCTIVITY

CROSS-REFERENCE TO RELATED APPLICATIONS

This application is a continuation of U.S. application Ser. No. 15/897,958, filed Feb. 15, 2018, which is a continuation of U.S. application Ser. No. 14/653,431, filed Jun. 18, 2015, which is the U.S. National Stage of International Application No. PCT/US2013/076308, filed on Dec. 18, 2013, published in English, which claims the benefit of U.S. Provisional Application No. 61/738,675, filed on Dec. 18, 2012, all of which are hereby incorporated by reference.

GOVERNMENT SUPPORT

This invention was made with government support under Award Number DE-EE0004943 awarded by Department of Energy. The government has certain rights in the invention.

REFERENCE TO A "SEQUENCE LISTING," A TABLE, OR A COMPUTER PROGRAM LISTING APPENDIX SUBMITTED AS AN ASCII TEXT FILE

The material in the ASCII text file, named "YTEN-60124US3-Sequence-Listing_ST25.txt", created Sep. 9, 2019, file size of 180,224 bytes, is hereby incorporated by reference.

BACKGROUND OF THE INVENTION

The increasing size of the global population, the increasing standard of living in emerging nations such as China and the use of renewable resources such as plants to produce biofuels and bio-based chemicals has placed additional pressure on agriculture. These factors together with the limited availability of additional arable land and water resources means that crop productivity or yield is the key to feeding these demands. Agriculture needs to deliver greater output with reduced inputs. In addition to traditional and marker assisted breeding programs there is an increased need for the identification and application of novel genes which can broadly impact crop yield as well as reduce the impact of environmental stress conditions such as drought, frost, heat and salinity and require fewer chemical inputs such as fertilizer, herbicides, pesticides and fungicides. For example, the 2010 worldwide biofuel production (mainly supplied by bioethanol derived from plant carbohydrate sources, such as starch, sugar from maize, sugarcane and biodiesel from plant oil (from palm and soybean)) reached 28 billion gallons of output providing roughly 2.7% of the world's fuels for road transport. One of the keys to achieving higher yield is to enhance the photosynthetic capacity of plants such that more carbon dioxide is fixed per plant together with up-regulating key metabolic pathways leading to increased levels of storage carbohydrates such as starch and sucrose or lipids such as fatty acids and triglycerides (oils) in plant tissues. In the case of biomass crops used for forage or energy production, increasing the total biomass per plant is also a highly desirable outcome. In many cases efforts to increase storage carbohydrates or oil in plants have been focused on genetic modification using genes encoding individual enzymes in specific metabolic pathways i.e. "single enzyme" or metabolic pathway approaches.

Transcription factors (TFs) are considered potential alternatives to "single enzyme" approaches for the manipulation of plant metabolism (Grotewold, 2008, Curr. Opin. Biotechnol. 19: 138-144). They are critical regulators of differential gene expression during plant growth, development and environmental stress responses. Transcription factors either directly interact with genes involved in key biological processes or interact with the regulation of other TFs that then bind to target genes thus achieving high levels of specificity and control. The resulting outcome is a multilayered regulatory network that affects multiple genes and leads to, for example, fine-tuned changes in the flux of key metabolites through interconnected or competing metabolic pathways (Ambavaram et al., 2011, Plant Physiol. 155: 916-931). There is limited information on transcription factors directly involved in the regulation of photosynthesis-related genes in plants, improvement of photosynthetic parameters has been reported in transgenic crop and model plants overexpressing members of the AP2/EREB, bZIP, NF-X1, NF-Y(HAP), and MYB families of TFs (Saibo et al., 2009, Ann. Bot.-London 103: 609-623). Most of these TFs are stress-induced and confer tolerance to an array of abiotic stress factors, such as drought, salinity, high or low temperatures, and photoinhibition (Hussain et al., 2011, Biotechnology Prog. 27: 297-306, see also WO 2005/112608 A2 and U.S. Pat. No. 6,835,540 B2 to Broun). Only a few TFs, such as Dof1 and MNF from maize are associated with expression of genes involved in $C_4$ photosynthesis (Weissmann & Brutnell, 2012, Curr. Opin. Biotechnol. 23: 298-304; Yanagisawa, 2000, Plant J. 21: 281-288). Increased growth of different vegetative and/or floral organs resulting in improved biomass production have been reported in plants overexpressing TFs, such as ARGOS, AINTEGUMENTA, NAC1, ATAF2, MEGAINTEGUMENTA, and ANGUSTIFOLIA (Rojas et al., 2010, GM Crops 1: 137-142 and references therein; see also WO 2011/109661 A1, WO 2010/129501, WO 2009/040665 A2, WO 02/079403 A2 and U.S. Pat. Nos. 7,598,429 B2 to Heard et al. and 7,592,507 B2 to Beekman et al.). Modifications of plant metabolic pathways by altering the expression of transcription factors regulating genes in the biosynthesis of lignin (US 2012/0117691 A1 to Wang et al.) and secondary metabolites (U.S. Pat. No. 6,835,540 B2 to Broun) have also been reported.

Thus, a need exists for identification of transcription factors whose increased or modified expression not only results in increased levels of the light harvesting pigments used in photosynthesis and improved photosynthetic capacity of the plants but which also up-regulate key metabolic pathways resulting in one or more additional desirable effects selected from the group comprising: increased levels of starch, glucose or sucrose (non-structural carbohydrates) in plant tissues; increased levels of fatty acids; increased production of biomass and/or grain yield; and enhanced stress tolerance. It is also desirable to be able to identify suitable variants of such transcription factors in a wide range of crop species and to be able to engineer these genes in a wide range of crops including dicots and monocots with $C_3$ or $C_4$ photosynthetic pathways.

Specific crops of interest for practicing this invention include: switchgrass, Miscathus, Medicago, sweet sorghum, grain sorghum, sugarcane, energy cane, elephant grass, maize, wheat, barley, oats, rice, soybean, oil palm, safflower, sesame, flax, cotton, sunflower, Camelina, Brassica napus, Brassica carinata, Brassica juncea, pearl millet, foxtail millet, other grain, oilseed, vegetable, forage, woody and biomass crops.

SUMMARY OF THE INVENTION

This invention is generally in the area of novel genes and methods for increasing plant crop yield using those novel genes. Described herein is the use of novel transcription factors that when overexpressed in a plants of interest affect the regulation of multiple biological pathways in the crop resulting in, for example, higher levels of photosynthetic pigments in green tissue, increased photosynthetic efficiency, increased content of non-structural carbohydrates (starch, sucrose, glucose) and fatty acids in leaf tissues, increased biomass yield and improved stress tolerance.

Screening of a number of transcription factor candidates has resulted in the identification of novel transcription factors that when expressed from a heterologous promoter in transgenic plants results in plants having increased expression of these transcription factors. The increased expression levels can be up to 1.2 fold 1.3 fold, 1.5 fold, 2 fold, 3 fold, 4 fold, 5 fold, 6 fold, 7 fold, 8 fold, a 9 fold or greater than 10 fold the level of background expression found in a wild-type plant (e.g., non-transgenic plant, test plant or control plant). As a result of the increased expression of these transcription factors a number of beneficial traits are achieved including but not limited to: increased levels of photosynthetic pigments; increased photosynthetic capacity; increased levels of non-structural carbohydrates, including starch, sucrose and glucose in plant tissues; increased levels of fatty acids in plant tissues; increased biomass growth rate and yield; and improved stress tolerance in comparison to wild-type plants. Methods for identifying transcription factors and producing the transgenic plants are also described herein. The transcription factor genes, their homologs and/or orthologs and the methods described herein for increasing their expression or for expressing them in heterologous hosts can achieve yield improvements in a wide range of crop plants.

A higher photosynthesis rate in plants transformed with the transcription factors of the invention and their homologs and/or orthologs combined with elevated levels of photosynthetic pigments achieved by the methods described lead to increased accumulation of products of the central carbon metabolism, such as starch, soluble sugars and fatty acids as well as improved biomass and grain production. It is also likely that plants with elevated levels of expression of these transcription factors will also be useful for increasing the production of other products produced in plants by genetic engineering including for example, storage starches. The overall potential impact of increasing the expression of these transcription factors in plants is illustrated in FIG. 1. Improved stress tolerance mediated by the transcription factors of the invention, produce transgenic plants with better agronomic performance under abiotic and biotic stress conditions than non-transformed controls or test plants (also referred to as wild type). In another related aspect, a quick and reliable method for testing the stress response of large populations of transgenic and wild type plants (e.g., crops) is also described. Also described herein are novel gene sequences, polypeptides encoded by them, gene constructs and methods for their use to produce transgenic plants, plant products, crops and seeds.

These transgenic plants, portions of transgenic plants, transgenic crops and transgenic seeds generated by the introduction of or increased expression of the functional transcription factors and their homologs, orthologs and function fragments identified herein have improved photosynthetic capacity, improved biomass production, and/or improved grain yield and stress tolerances compared to wild-type plants.

This invention relates to the identification of transcription factor genes which when expressed to higher levels than is found in wild type plants or expressed in heterologous plants results in one or more desirable traits selected from: higher levels of photosynthetic pigments; higher photosynthetic activity; higher levels of starch and/or sucrose and/or glucose; higher yield of biomass; and improved stress tolerances.

In one aspect of the invention, genes encoding transcription factors belonging to the APETALA2 (AP2)/ETHYLENE RESPONSE FACTOR (ERF) family (e.g., SEQ ID NOs: 1 and 2) and transcription factors from the Nuclear-Factor Y (NF-YB) family (e.g., SEQ ID NO: 3) and their homologues and orthologs from other plant species are described as well as methods of producing transgenic plants overexpressing these transcription factors genes in a wide range of plants to achieve one or more traits selected from: higher levels of photosynthetic pigments; higher photosynthetic activity; higher levels of starch and/or sucrose and/or glucose; higher yield, and improved stress tolerance.

Host plants include but are not limited to food crops, forage crops, bioenergy and biomass crops, perennial and annual plant species. Examples of specific crops of interest for practicing this invention include: switchgrass, *Miscathus, Medicago,* sweet sorghum, grain sorghum, sugarcane, energy cane, elephant grass, maize, wheat, barley, oats, rice, soybean, oil palm, safflower, sesame, flax, cotton, sunflower, *Camelina, Brassica napus, Brassica carinata, Brassica juncea,* pearl millet, foxtail millet, other grain, oilseed, vegetable, forage, woody and biomass crops.

In a first aspect, a transgenic plant, or a portion of a plant, or a plant material, or a plant seed, or a plant cell comprising one or more nucleotide sequences encoding one or more AP2/ERF and/or NF-YB transcription factors, wherein the AP2/ERF transcription factor is encoded by the nucleotide sequence of SEQ ID NOs: 1 or 2 and the NF-YB transcription factor is encoded by the nucleotide sequence of SEQ ID NO: 3 and the increased expression of one or more transcription factors is increased resulting in one or more traits selected from: higher levels of photosynthetic pigments; higher photosynthetic activity; higher levels of starch and/or sucrose and/or glucose; higher yield; and improved stress tolerance in the transgenic plant, portion of a plant, plant material, plant seed, or plant cell is described. The increased expression of the transcription factors can be measured in a number of ways including a fold increase over the wild type plant such as 1.5 fold, 2 fold, 3 fold, 4 fold, 5 fold 6 fold 7 fold 8 fold greater than 9 fold higher than the expression of the same gene in a wild type plant. In some cases the increased expression results from the expression of the transcription factor gene through genetic manipulation to express the transcription factor in a heterologous plant host. An example of this particular embodiment would be expressing one of the genes, including homolog or orthologs, isolated from switchgrass in a plant selected from *Miscathus, Medicago,* sweet sorghum, grain sorghum, sugarcane, energy cane, elephant grass, maize, wheat, barley, oats, rice, soybean, oil palm, safflower, sesame, flax, cotton, sunflower, *Camelina, Brassica napus, Brassica carinata, Brassica juncea,* pearl millet, foxtail millet, other grain, oilseed, vegetable, forage, woody and biomass crops.

In a first embodiment of the first aspect, the expression of the one or more transcription factors increases the level of photosynthetic pigments including chlorophyll and/or carotenoids. The improvement is compared to a non-transgenic plant and such improvement can be measured in a variety of ways, including a fold increase or percent increase, such as 10%, 20%, 50% or 75%.

In a second embodiment of the first aspect, as compared to the wild type plant, the increased expression of the one or more transcription factors improves the rate of photosynthesis in the plant. The improvement is compared to a non-transgenic plant and such improvement can be measured in a variety of ways, including a fold increase or percent increase, such as 10%, 20%, 30%, 40%, 50% or higher.

In a third embodiment of the first aspect, as compared to the wild type plant, the increased expression of one or more transcription results in increased levels of starch and/or sucrose and/or glucose in the plant tissue. The increase in levels of starch and/or sucrose and/or glucose in the plant tissue alone or in combination can be measured as a % of dry weight of the plant tissue analyzed for example 2%, 3%, 4%, 5%, 10%, 15%, 20% of the dry weight of the plant tissue.

In a fourth embodiment as compared to the wild type plant, the expression of the one or more transcription factors results in plants with higher biomass yields. The improvement is compared to a non-transgenic plant and such improvement can be measured in a variety of ways, percent increase such as 10%, 20%, 50% or greater than 50% increase in the dry weight of the plant as compared to a wild type plant.

In a fifth embodiment as compared to the wild type plant, the expression of one or more transcription factors improves tolerance to one or more abiotic stress factors selected from excess or deficiency of water and/or light, high or low temperature, and high salinity. The improvement is compared to a non-transgenic plant and such improvement can be measured in a variety of ways, including a fold increase or percent increase, such as 10%, 20%, 50% or 75%.

In a second embodiment of the first aspect or of the first embodiment, the transcription factor is encoded by an ortholog, homolog, or functional fragment of SEQ ID NOs: 1, 2, or 3. In a third embodiment of the first aspect or other embodiment, a promoter is operably linked to one or more nucleotide sequence of SEQ ID NOs: 1, 2, or 3 in a plant transformation vector.

In a third embodiment of the first aspect or other embodiment, the plant has increased starch content, soluble sugar content, grain yield, plant size, organ size, leaf size, and/or stem size when compared to a non-transgenic plant.

In a fourth embodiment of the first aspect or other embodiment, the expression of one or more transcription factors increases the production of food crops, feed crops, or crops used in the production of fuels or industrial products, when compared to a non-transgenic plant.

In a second aspect, an isolated nucleotide sequence comprising a nucleic acid sequence encoding an AP2/ERF or an NF-YB transcription factor; wherein the transcription factor is functional in a plant, selected from the group consisting of SEQ ID NOs: 1, 2, and 3; and expression of the transcription factor result in higher levels of starch and/or sucrose and/or glucose in the plant.

In a first embodiment of the second aspect, the expression resulting in higher levels of one or more of starch, sucrose and glucose and higher biomass, or higher levels of one or more of starch, sucrose and glucose with no significant increase in biomass.

In a second embodiment of the second aspect or of the first embodiment of the second aspect, the nucleic acid sequence further comprises at least 60%, 65%, 70%, 75%, 80%, 85%, 90%, 95%, or 99% sequence identity to SEQ ID NOs: 1, 2, or 3.

In a third embodiment of the second aspect or the embodiments, the plant further comprises a temporal promoter for expression of all transcription factors such that the gene is overexpressed one the plant is fully grown and the accumulation of storage materials in the seed is initiated. Methods of screening for plants with this outcome are also contemplated. Alternatively, other select promoters for desirable expression of the transcription factors are contemplated.

In a fourth embodiment of the second aspect or of the embodiments, the expression of the transcription factor increases photosynthetic activity, carbon flow and/or total content of photosynthetic pigments when compared to a non-transgenic plant.

In a fifth embodiment of the second aspect or of any of the other embodiments, the nucleic acid sequence encoding a polypeptide of SEQ ID NOs: 4, 5, or 6.

In a third aspect, a transcription factor, comprising an AP2/ERF or a NF-YB transcription factor polypeptide selected from SEQ ID NOs: 4, 5, and 6; wherein the transcription factor is functional in a plant and the expression of the transcription factor increases a carbon flow in the transgenic plant is described.

In a first embodiment of the third aspect, the transcriptional factor is functional in a $C_3$ or $C_4$ dicotyledonous plant, a $C_3$ or $C_4$ monocotyledonous plant, In a second embodiment of the third aspect or of any of the other embodiments, the polypeptide sequence further comprises at least 60%, 65%, 70%, 75%, 80%, 85%, 90%, 95%, or 99% sequence identity to SEQ ID NOs: 4, 5, or 6.

In a third embodiment of the third aspect or of any of the other embodiments, the increased carbon flow is due to increased biomass yield, or increased starch, glucose or sucrose in plant tissues when compared to a non-transgenic plant.

In a fourth embodiment of the third aspect or of any of the other embodiments, expression the transcription factor increases photosynthetic activity, carbon flow and/or total content of photosynthetic pigments when compared to a non-transgenic plant.

In a fourth aspect, a biobased transgenic plant product obtained from the transgenic plant of the first aspect and any of the embodiment described having a 100% biobased carbon flow is described. In certain embodiments of this fourth aspect, the product is an article having a biobased content of at least 50%, at least 60%, at least 70%, at least 75%, at least 80%, at least 85%, 90% or 95%.

In a fifth aspect, a method of producing a transgenic plant, comprising coexpressing one or more AP2/ERF and a NF-YB transcription factor, wherein the AP2/ERF transcription factor is encoded by the nucleotide sequence of SEQ ID NOs: 1 or 2 and the NF-YB transcription factor is encoded by the nucleotide sequence of SEQ ID NO: 3 is described.

In a sixth aspect, a method for testing the response of plants to different abiotic stress factors in tissue culture for identification of plants with increased tolerance to the stress factors, comprising comparing a test plant with the transgenic plant of claim 1 under one or more conditions that cause stress including adverse changes in water, light, temperature, and salinity is described.

In a seventh aspect methods for transformation comprising incorporating into the genome of a plant with one or more vectors comprising the nucleotide sequences described herein are described.

In an eighth aspect or of any of the embodiments of the first aspect, the transgenic plant of the first aspect has an increased photochemical quantum yield than the yield of a non-transgenic plant.

In a ninth aspect or of any of the embodiments of the first aspect, the transgenic plant of the first aspect has a starch content (e.g., yield) increased by at least 2 fold greater than the corresponding starch content of a non-transgenic plant.

In a tenth aspect or of any of the embodiments of the first aspect, the transgenic plant of the first aspect has a starch content of at least 2 fold greater to about 4.3 greater than the content of a non-transgenic plant.

In an eleventh aspect or of any of the embodiments of the first aspect, the transgenic plant of the first aspect has a chlorophyll content that is greater than the content of a non-transgenic plant or has a chlorophyll content that is at least 1.1 greater to about 2.5-fold greater than the content of a non-transgenic plant.

In a twelfth aspect or of any of the embodiments of the first aspect, the transgenic plant of the first aspect has a sucrose content that is higher than the content of a non-transgenic plant or a sucrose content that is at least two fold greater to about 4.3 fold greater than the content of a non-transgenic plant.

In a thirteenth aspect or of any of the embodiments of the first aspect, the transgenic plant of the first aspect has an electron transport rate above the rate of a non-transgenic plant.

In a further embodiment of any of the aspects, the plant is selected from switchgrass, *Miscathus, Medicago,* sweet sorghum, grain sorghum, sugarcane, energy cane, elephant grass, maize, wheat, barley, oats, rice, soybean, oil palm, safflower, sesame, flax, cotton, sunflower, *Camelina, Brassica napus, Brassica carinata, Brassica juncea,* pearl millet, foxtail millet, other grain, oilseed, vegetable, forage, industrial, woody and biomass crops.

In a further embodiment, transgenic plants of the previous embodiments can be screened to identify plants where the overall biomass yield is similar to the wild type plant but the levels of one or more traits selected from: increased concentration of photosynthetic pigments; increased photosynthesis efficiency; increased levels of starch and/or sucrose and/or glucose; increased levels of fatty acids and increased stress tolerance higher than the levels in the wild-type plants. For example a transgenic plant with a biomass yield similar to a wild type plant but with a cumulative level of starch plus glucose plus sucrose 1.5 fold, 2 fold, 5 fold, 10 fold or more higher can be identified.

In a further embodiment, a screening method for identifying specific genes or combinations of genes which can be used to achieve some of the individual trait improvements is described herein.

In certain embodiments, methods related to upregulation of the central carbon metabolism by PvSTR1, PvSTIF1 and PvBMY1 leading to increased photosynthetic pigments and activity and elevated levels of starch, soluble sugars and fatty acids as well as improved stress tolerance and productivity of plants and plant products are described. These methods include the incorporation of one or more of the transcription factors described by SEQ ID NOs: 1, 2 and 3 and homologs, orthologs and functional fragments thereof. For example, the transgenic plant can comprise SEQ ID NO: 1, SEQ ID NO: 2 or SEQ ID NO: 3, or a homolog, ortholog or functional fragment thereof or any combination of two or more of SEQ ID NO: 1, SEQ ID NO: 2 and SEQ ID NO: 3, including their homologs, orthologs or functional fragments thereof (e.g., SEQ ID NO: 1 and SEQ ID NO: 2; SEQ ID NO: 1 and SEQ ID NO: 3; homolog of SEQ ID NO: 1 and SEQ ID NO: 2; homolog of SEQ ID NO: 1 and a homolog of SEQ ID NO: 2; etc.).

In a fourteenth aspect of the invention, a transgenic plant, or a portion of a plant, or a plant material, or a plant seed, or a plant cell comprising one or more nucleotide sequences encoding a family of AP2/ERF or NF-YB transcription factor, wherein the AP2/ERF transcription factor is encoded by the nucleotide sequence of SEQ ID NOs: 1 or 2 and the NF-YB transcription factor is encoded by the nucleotide sequence of SEQ ID NO: 3; wherein the expression of the one or more transcription factors increases carbon flow in the transgenic plant, portion of a plant, plant material, plant seed, or plant cell is described. In a first embodiment of the fourteenth aspect, the expression of the one or more transcription factors improves tolerance to one or more abiotic stress factors selected from excess or deficiency of water and/or light, from high or low temperature, and high salinity. In a second embodiment of the fourteenth aspect or of the first embodiment of the aspect, the transcription factor is encoded by an ortholog, homolog, or functional fragment encoded by SEQ ID NOs: 1, 2, or 3. In a third embodiment of the fourteenth aspect or of any of the embodiments of the aspect, the transgenic plant, portion of a plant or plant material, plant seed or plant cell, further comprises a vector containing a promoter operably linked to one or more nucleotide sequence of SEQ ID NOs: 1, 2, or 3. In a fourth embodiment of the fourteenth aspect or of any of the embodiments of the aspect the plant is selected from a crop plant, a model plant, a monocotyledonous plant, a dicotyledonous plant, a plant with C3 photosynthesis, a plant with C4 photosynthesis, an annual plant, a perennial plant, a switchgrass plant, a maize plant, or a sugarcane plant. In a fifth embodiment of the fourteenth aspect or of any of the embodiments of the aspect the annual or perennial plant is a bioenergy or biomass plant. In a sixth embodiment of the fourteenth aspect or of any of the embodiments of the aspect expression of one or more transcription factors increases photosynthetic activity, carbon flow and/or total content of photosynthetic pigments. In a seventh embodiment of the fourteenth aspect or of any of the embodiments of the aspect the increased carbon flow results in increased biomass yield when compared to a non-transgenic plant. In an eighth embodiment of the fourteenth aspect or of any of the embodiments of the aspect, wherein the plant has an increase of one or more of the following: starch content, soluble sugars content, grain yield, plant size, organ size, leaf size, and/or stem size when compared to a non-transgenic plant. In a ninth embodiment of the fourteenth aspect or of any of the embodiments of the aspect the expression of one or more transcription factors leads to increases in the production of food crops, feed crops, or crops for the production of fuels or industrial products, when compared to a non-transgenic plant.

In a fifteenth aspect of the invention, an isolated nucleotide sequence comprising a nucleic acid sequence encoding an AP2/ERF or an NF-YB transcription factor; wherein the transcription factor selected from the group consisting of SEQ ID NOs: 1, 2, and 3 is functional in a plant; and expression of the transcription factor increases carbon flow in the transgenic plant is described. In a first embodiment of the fifteenth aspect, the plant is selected from the group consisting of a C3 or C4 dicotyledonous plant, a C3 or C4 monocotyledonous plant, grass, a switchgrass plant, a maize plant, or a sugarcane plant. In a second embodiment of the fifteenth aspect or of any of the embodiments of the aspect, the nucleic acid sequence further comprises at least 60%, 65%, 70%, 75%, 80%, 85%, 90%, 95%, or 99% sequence identity to SEQ ID NOs: 1, 2, or 3. In a third embodiment of the fifteenth aspect or of any of the embodiments of the aspect, the increased biomass yield is due to increased carbon flow when compared to a non-transgenic plant. In a fourth embodiment of the fifteenth aspect or of any of the embodiments of the aspect, expression of the transcription factor increases photosynthetic activity, carbon flow and/or total content of photosynthetic pigments when compared to a non-transgenic plant. In a fifth embodiment of the fifteenth aspect or of any of the embodiments of the aspect, the nucleic acid sequence encodes a polypeptide of SEQ ID NOs: 4, 5, or 6. In a sixth embodiment of the fifteenth aspect or of any of the embodiments of the aspect, the increased carbon flow increases the starch, sucrose and glucose levels in a transgenic plant without the same corresponding increase in biomass yield.

In a sixteenth aspect, a transcription factor, comprising an AP2/ERF or a NF-YB transcription factor polypeptide selected from SEQ ID NOs: 4, 5, and 6; wherein the transcription factor is functional in a plant and the expression of the transcription factor increases a carbon flow in the transgenic plant is described. In a first embodiment of the sixteenth aspect, the plant is selected from the group consisting of a C3 or C4 dicotyledonous plant, a C3 or C4 monocotyledonous plant, grass, or a switchgrass plant, a maize plant, or a sugarcane plant. In a second embodiment of the sixteenth aspect or of the first embodiment of the aspect, the polypeptide sequence further comprises at least 60%, 65%, 70%, 75%, 80%, 85%, 90%, 95%, or 99% sequence identity to SEQ ID NOs: 4, 5, or 6. In a third embodiment of the sixteenth aspect or of the first or second embodiment of the aspect, the increased biomass yield is due to increased carbon flow when compared to a non-transgenic plant. In a fourth embodiment of the sixteenth aspect or of the first, second or third embodiment of the aspect, expression of the transcription factor increases photosynthetic activity, carbon flow and/or total content of photosynthetic pigments when compared to a non-transgenic plant.

In a seventeenth aspect, a method for manufacturing a transgenic seed for producing a crop of transgenic plants with an enhanced trait resulting from the expression of one or more transcription factors or homologs, orthologs or functional fragments thereof, encoded by the nucleotide sequence of SEQ ID NOs: 1, 2 or 3, comprising: a) screening a population of plants transformed with transcription factor (s) for the enhanced trait; b) selecting from the population one or more plants that exhibit the trait; and c) collecting seed from the selected plant is described. In a first embodiment of the seventeenth aspect, the seed is maize seed or sorghum seed and the enhanced trait is seed carbon content.

In an eighteen aspect, a method of producing a transgenic plant, comprising coexpressing one or more AP2/ERF and NF-YB transcription factors in a plant, wherein the AP2/ERF transcription factor is encoded by the nucleotide sequence of SEQ ID NOs: 1 or 2 and the NF-YB transcription factor is encoded by the nucleotide sequence of SEQ ID NO: 3 is described.

In a nineteenth aspect, a method for testing the response of a plant to different stress factors in tissue culture for identification of plants with increased tolerance to the stress factors, comprising comparing a test plant with the transgenic plant of the fourteenth aspect under one or more conditions that cause stress including changes in water, light, temperature, and salinity is described. In an embodiment of the seventeenth, eighteen or nineteen aspect, further comprising introducing into a plant one or more vectors comprising the nucleotide sequences of the invention.

In any of the aspects or embodiments described above, the photochemical quantum yield of the plant is at least 2-fold greater than the yield of a corresponding non-transgenic plant. In any of the aspects or embodiments described above, the plant has a starch yield increased by at least 2-fold the content of a corresponding non-transgenic plant. In any of the aspects or embodiments described above, the plant has a starch yield increased by at least 2-fold to about a 4.5-fold content of a corresponding non-transgenic plant. In any of the aspects or embodiments described above, the plant has a chlorophyll content that is 1.5 times greater than the content of a corresponding non-transgenic plant. In any of the aspects or embodiments described above, the plant has a chlorophyll content that is at least 1.5 fold greater to about 2.5 fold greater than the content of a corresponding non-transgenic plant. In any of the aspects or embodiments described above, the plant has a sucrose content that is at least 1.5 fold greater than the content of a corresponding non-transgenic plant. In any of the aspects or embodiments described above, the plant has a sucrose content that is at least two fold greater to about 4.3 fold greater than the content of a corresponding non-transgenic plant. In any of the aspects or embodiments described above, the plant has a plant grown rate increased by at least 10% above the rate of a corresponding non-transgenic plant. In any of the aspects or embodiments described above, the plant is switchgrass, maize, or sugar cane.

In a twentieth aspect, a method for enhancing a trait in a transgenic plant relative to a control non-transgenic plant, comprising: (a) increasing expression of at least one nucleic acid sequence encoding a transcription factor from AP2/ERF and NF-YB families, selected from the nucleic acid sequence of SEQ ID NO: 1, SEQ ID NO: 2, and SEQ ID NO: 3, or an ortholog, homolog or functional fragment thereof; and (b) selecting for a transgenic plant having an enhanced trait relative to a control plant is described. In a first embodiment of the twentieth aspect, the trait is selected from one or more of the following: carbon flow, primary metabolites, tolerance to one or more abiotic stress factors, and one or more photosynthetic pigments.

In a twenty-first aspect, a transgenic plant having a trait modification relative to a corresponding non-transgenic plant, comprising one or more nucleotide sequences encoding a AP2/ERF or NF-YB transcription factors, wherein the AP2/ERF transcription factor is encoded by the nucleotide sequence of SEQ ID NOs: 1 or 2 and the NF-YB transcription factor is encoded by the nucleotide sequence of SEQ ID NO: 3 or a ortholog, homolog, or functional fragment thereof, wherein the trait modification is selected from one or more of the following: carbon flow, levels of photosynthetic pigments; photosynthetic capacity; levels of starch, sucrose and glucose in plant tissues, levels of fatty acids in plant tissues; biomass growth rate and yield; and stress tolerance is described. In a first embodiment of the twenty-first aspect, the trait modification is a greater than 3 fold yield of starch or soluble sugars and the increase in biomass production is less than 1.5 fold.

In a twenty-second aspect, a transgenic maize plant having an increased non-structural carbohydrate content comprising, a) introducing into a plant cell one or more nucleotides encoding AP2/ERF and/or NF-YB transcription factor, wherein the AP2/ERF transcription factor is encoded by the nucleotide sequence of SEQ ID NOs: 1 or 2 and the NF-YB transcription factor is encoded by the nucleotide sequence of SEQ ID NO: 3 or a ortholog, homolog, or functional fragment thereof, and b) producing a transgenic plant from the plant cell having an increased non-structural carbohydrate content compared to a corresponding non-transgenic plant is described. In a first embodiment of the aspect a seed or plant tissue is obtained by the transgenic maize or sorghum plant.

In a twenty-third aspect, a method of identifying a drought and salinity resistant transgenic plant having one or more nucleotides encoding an AP2/ERF and/or NF-YB transcription factor, wherein the AP2/ERF transcription factor is encoded by the nucleotide sequence of SEQ ID NOs: 1 or 2 and the NF-YB transcription factor is encoded by the nucleotide sequence of SEQ ID NO: 3 or a ortholog, homolog, or functional fragment thereof comprising, (a) growing a population of transgenic and wild-type plants under conditions of drought and salinity stress; (b) selecting a transgenic plant that exhibits tolerance to drought and salinity, thereby identifying a transgenic plant that comprises a genotype associated with tolerance to drought and salinity is described.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 4A-C shows the multiple sequence alignment for the conserved domains of PvSTR1 (FIG. 4A), PvSTIF1 (FIG. 4B) and PvBMY1 (FIG. 4C) in switchgrass (*Panicum virgatum* L.) and other plant species. The alignments of the DNA-binding domain sequences (AP2/ERF for STIF1 and STR1 and NFYB-HAP3 for BMY1) obtained using Clustal W program (Thompson et al., 1994, *Nucleic Acids Res.* 11: 4673-4680) are shown in the boxes.

DETAILED DESCRIPTION OF THE INVENTION

Figure 1:
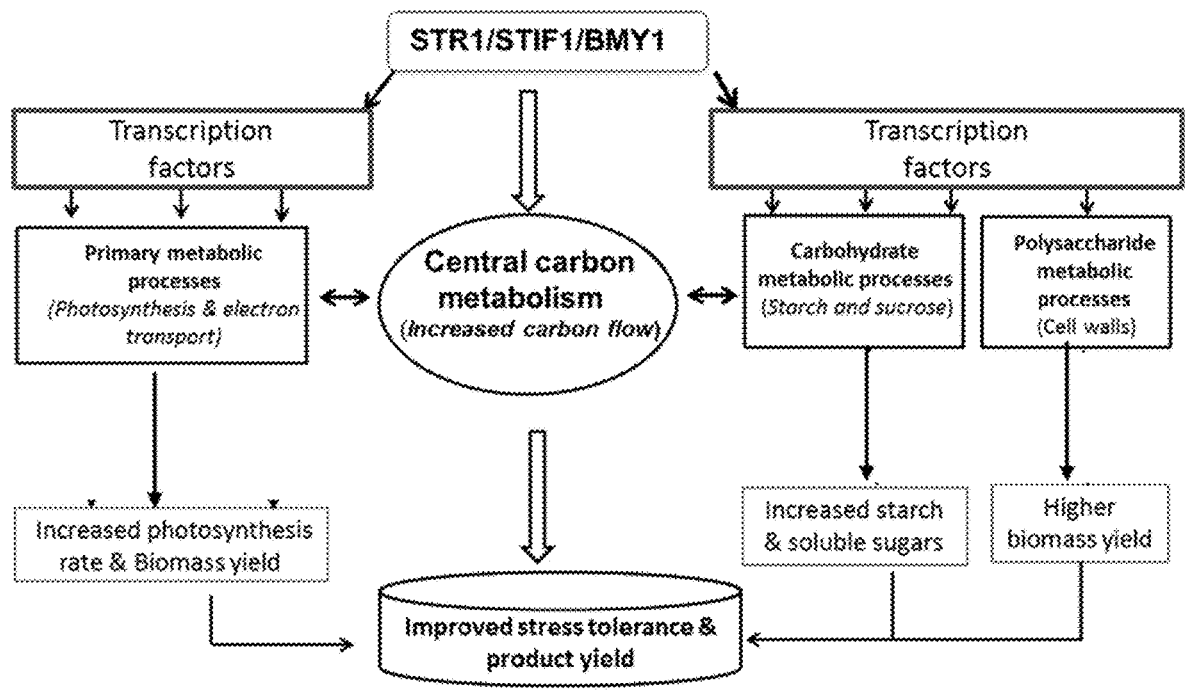
FIG. 1 graphically illustrates the transcriptional regulatory network model of the switchgrass transcription factors PvSTR1, PvSTIF1 and PvBMY1 and their association to improved plant productivity and stress tolerance. The thick arrows illustrate the observed increased carbon flow directly regulated by the transcription factors, whereas the small arrows indicate the interactions with downstream TFs for regulation of key genes in major metabolic pathways.

A description of example embodiments of the invention follows.

I. Definitions

Unless otherwise indicated, the disclosure encompasses all conventional techniques of plant transformation, plant breeding, microbiology, cell biology and recombinant DNA, which are within the skill of the art. See, e.g., Sambrook and Russell, *Molecular Cloning: A Laboratory Manual*, 3rd edition, 2001; *Current Protocols in Molecular Biology*, F. M. Ausubel et al. eds., 1987; *Plant Breeding: Principles and Prospects*, M. D. Hayward et al., 1993; *Current Protocols in Protein Science*, Coligan et al., eds., 1995, (John Wiley & Sons, Inc.); the series *Methods in Enzymology* (Academic Press, Inc.): *PCR 2: A Practical Approach*, M. J. MacPherson, B. D. Hames and G. R. Taylor eds., 1995.

Unless otherwise noted, technical terms are used according to conventional usage. Definitions of common terms in molecular biology may be found in Lewin, *Genes VII*, 2001 (Oxford University Press), *The Encyclopedia of Molecular Biology*, Kendrew et al., eds., 1999 (Wiley-Interscience) and *Molecular Biology and Biotechnology, a Comprehensive Desk Reference*, Robert A. Meyers, ed., 1995 (VCH Publishers, Inc), *Current Protocols In Molecular Biology*, F. M. Ausubel et al., eds., 1987 (Green Publishing), Sambrook and Russell, *Molecular Cloning: A Laboratory Manual*, 3rd edition, 2001.

A number of terms used herein are defined and clarified in the following section.

As used herein, a "vector" is a replicon, such as a plasmid, phage, or cosmid, into which another DNA segment may be inserted so as to bring about the replication of the inserted segment. The vectors described herein can be expression vectors.

As used herein, an "expression vector" is a vector that includes one or more expression control sequences.

As used herein, an "expression control sequence" is a DNA sequence that controls and regulates the transcription and/or translation of another DNA sequence.

As used herein, "operably linked" means incorporated into a genetic construct so that expression control sequences effectively control expression of a coding sequence of interest.

As used herein, "transformed" and "transfected" encompass the introduction of a nucleic acid (e.g., a vector) into a cell by a number of techniques known in the art.

"Plasmids" are designated by a lower case "p" preceded and/or followed by capital letters and/or numbers.

The term "plant" is used in its broadest sense. It includes, but is not limited to, any species of woody, ornamental or decorative, crop or cereal, fruit or vegetable plant, and photosynthetic green algae (e.g., *Chlamydomonas reinhardtii*). It also refers to a plurality of plant cells that is largely differentiated into a structure that is present at any stage of a plant's development. Such structures include, but are not limited to, a fruit, shoot, stem, leaf, flower petal, etc.

The term "plant tissue" includes differentiated and undifferentiated tissues of plants including those present in roots, shoots, leaves, inflorescences, anthers, pollen, ovaries, seeds and tumors, as well as cells in culture (e.g., single cells, protoplasts, embryos, callus, etc.). Plant tissue may be in planta, in organ culture, tissue culture, or cell culture.

The term "plant part" as used herein refers to a plant structure, a plant organ, or a plant tissue.

A "non-naturally occurring plant" refers to a plant that does not occur in nature without human intervention. Non-naturally occurring plants include transgenic plants, plants created through genetic engineering and plants produced by non-transgenic means such as traditional or market assisted plant breeding.

The term "plant cell" refers to a structural and physiological unit of a plant, comprising a protoplast and a cell wall. The plant cell may be in the form of an isolated single cell or a cultured cell, or as a part of a higher organized unit such as, for example, a plant tissue, a plant organ, or a whole plant.

The term "plant cell culture" refers to cultures of plant units such as, for example, protoplasts, cells and cell clusters in a liquid medium or on a solid medium, cells in plant tissues and organs, microspores and pollen, pollen tubes, anthers, ovules, embryo sacs, zygotes and embryos at various stages of development.

The term "plant material" refers to leaves, stems, roots, inflorescences and flowers or flower parts, fruits, pollen, anthers, egg cells, zygotes, seeds, cuttings, cell or tissue cultures, or any other part or product of a plant.

A "plant organ" refers to a distinct and visibly structured and differentiated part of a plant, such as a root, stem, leaf, flower bud, inflorescence, spikelet, floret, seed or embryo.

The term "non-transgenic plant" refers to a plant that has not been genetically engineered with heterologous nucleic acids. These non-transgenic plants can be the test or control plant when comparisons are made, including wild-type plants.

A "corresponding non-transgenic plant" refers to the plant prior to the introduction of heterologous nucleic acids. This plant can be the test plant or control plant, including wild type plants.

A "trait' refers to morphological, physiological, biochemical and physical characteristics or other distinguishing feature of a plant or a plant part or a cell or plant material.

The term "trait modification" refers to a detectable change in a characteristic of a plant or a plant part or a plant cell induced by the expression of a polynucleotide or a polypeptide of the invention compared to a plant not expressing them, such as a wild type plant. Some trait modifications can be evaluated quantitatively, such as content of different metabolites, proteins, pigments, lignin, vitamins, starch, sucrose, glucose, fatty acids and other storage compounds, seed size and number, organ size and weight, total plant biomass and yield of genetically engineered products.

Trait modifications of further interest include those to seed (such as embryo or endosperm), fruit, root, flower, leaf, stem, shoot, seedling or the like, including: enhanced tolerance to environmental conditions including freezing, chilling, heat, drought, water saturation, radiation and ozone; improved growth under poor photoconditions (e.g., low light and/or short day length), or changes in expression levels of genes of interest. Other phenotype that can be modified relate to the production of plant metabolites, such as variations in the production of photosynthetic pigments, enhanced or compositionally altered protein or oil production (especially in seeds), or modified sugar (insoluble or soluble) and/or starch composition. Physical plant characteristics that can be modified include cell development (such as the number of trichomes), fruit and seed size and number, yields and size of plant parts such as stems, leaves and roots, the stability of the seeds during storage, characteristics of the seed pod (e.g., susceptibility to shattering), root hair length and quantity, internode distances, or the quality of seed coat. Plant growth characteristics that can be modified include growth rate, germination rate of seeds, vigor of plants and seedlings, leaf and flower senescence, male sterility, apomixis, flowering time, flower abscission, rate of nitrogen uptake, biomass or transpiration characteristics, as well as plant architecture characteristics such as apical dominance, branching patterns, number of organs, organ identity, organ shape or size.

As used herein "abiotic stress" includes but is not limited to stress caused by any one of the following: drought, salinity, extremes or atypical temperature, chemical toxicity and oxidative variation. The ability to improve plant tolerance to abiotic stress would be of great economic advantage to farmers worldwide and would allow for the cultivation of crops during adverse conditions and in territories where cultivation of crops may not otherwise be possible.

Methods and Transgenic Plants, Plant Tissue, Seed and Plant Cell of the Invention Described herein are methods of producing a transgenic plant, plant tissue, seed, or plant cell, wherein said plant, plant tissue, seed or plant cell comprises incorporated in the genome of said plant, plant tissue, seed, or plant cell: a polynucleotide encoding a plant transcription factor together with sequences to enable its increased expression or regulatory sequences inserted to increase the expression of a heterologous plant transcription factor.

It was found that incorporation of transcription factors encoded by the nucleotides SEQ ID NOs: 1, 2, and 3 modified expression of certain genes in a transgenic plant and increased the carbon flow of the transgenic plant without the corresponding increase in biomass. For example, increases in the levels of non-structural carbohydrates such as starch, sucrose and glucose levels in a transgenic plant are found to be greater than 2 fold increase but without an increase in the biomass or an insignificant increase in the biomass compared to the increases in the non-structural carbohydrates.

II. Transcriptional Regulation of Gene Expression in Plants

Transcription factors (TFs) are known to be involved in various biological processes, acting as activators or repressors of other genes or gene families, suggesting the function of various transcriptional regulatory mechanisms in regulating downstream signal transduction pathways. The regulatory logic that drives any plant response is governed by the combination of signaling regulators, TFs, their binding site in the regulatory regions of target genes (cis-regulatory elements; CREs) and other regulatory molecules (e.g., chromatin modifiers and small RNAs), as well as protein and RNA degradation machinery (Krishnan & Pereira, 2008, *Brief Funct. Genomic. Proteomic.* 7: 264-74). TFs control the expression of many target genes through specific binding of the TF to the corresponding CRE in the promoters of respective target genes. For example, recent reports suggest that the maize Dof1 and MNF factors bind to the promoter of PEPC, an enzyme in the $C_4$ cycle of photosynthesis (reviewed in Weissmann & Brutnell, 2012, *Current Opinion Biotech.* 23: 298-304). Several TFs are known to be induced by stress, acting as activators or repressors, suggesting the function of various transcriptional regulatory mechanisms in regulating specific biological processes and or pathways.

Identification and Mapping Regulatory Domains of TFs:

Targeted gene regulation via designed transcription factors has great potential for precise phenotypic modification and acceleration of novel crop trait development. Over the past few years many transcription factors have been shown to contain regulatory domains, which can increase or decrease their transcriptional and/or DNA-binding activity. The mechanisms by which this regulation takes place frequently involve phosphorylation, dimer formation or interaction with negative or positive cofactors (Facchinetti et al., 1997, *Biochem. J.* 324: 729-736). Nevertheless, different organisms have evolved with diverse temporal and spatial regulation of transcription. In general, the temporal and spatial regulations are mediated by different classes of DNA binding transcriptional activator proteins. Unlike DNA binding domains, the transcription activation domains (TAD) have less primary amino acid sequence similarity. The TADs have been classified into acidic, glutamine-rich, proline-rich and serine/threonine-rich. We have identified putative transcription activation domains of the transcription factors of the invention based on the bioinformatics analysis.

Spatio-Temporal Gene Expression Through Novel cis-Regulatory Elements:

Spatio-temporal gene expression is the activation of genes within specific tissues of an organism at specific times during development. Plant promoters have attracted increasing attention because of their irreplaceable role in modulating the spatio-temporal expression of genes interacting with transcription factors (TFs). The control of gene expression is largely determined by cis-regulatory modules localized in the promoter sequence of regulated genes and their cognate transcription factors. While there has been a substantial progress in dissecting and predicting cis-regulatory activity, our understanding of how information from multiple enhancer elements converge to regulate a gene's expression remains elusive. Constitutive promoters are widely used to functionally characterize plant genes in transgenic plants but their lack of specificity and poor control over protein expression can be a major disadvantage. On the other hand, promoters that provide precise regulation of temporal or spatial transgene expression facilitate such studies by targeting overexpression or knockdown of target genes to specific tissues and/or at particular developmental stages. Promoter-based transgenic technologies have already been applied to a great effect in wheat, where a heat-inducible promoter in transgenic plants effectively controlled the spatio-temporal expression of a transgene (Freeman et al., 2011, *Plant Biotech. J.* 9: 788-796). A modular synthetic promoter for the spatio-temporal control of transgene expression in stomata has been reported by fusing a guard cell-specific element from the promoter of the potato phosphoenolpyruvate carboxylase (PEPC) gene with the ethanol-inducible gene switch AlcR/alcA (Xiong et al., 2009, *J. Exp. Bot.* 60: 4129-4136). Recently, a chimeric inducible system was developed, which combined the cellular specificity of the AtMYB60 minimal promoter with the positive responsiveness to dehydration and ABA of the rd29A promoter (Rusconi et al., 2013, *J. Exp. Bot.* 64: 3361-3371). Remarkably, the synthetic module specifically up-regulated gene expression in guard cells of *Arabidopsis*, tobacco, and tomato in response to dehydration or ABA. Likewise, promoter cloning and subsequent manipulation of spatio-temporal gene expression together with transcription activation domains from the switchgrass transcription factors described in the presented invention offers a significant promise in genetically engineering novel adaptive traits in biomass and bioenergy crops.

III. Plant Transformation Technologies

The transcription factor genes of this invention can be introduced into the genome of any plant by any of the methods for nuclear transformation known in the art. Methods for transformation of a range of plants useful for practicing the current invention are described in the examples herein. Any other genes of interest can be introduced into the genome and/or plastome of any plant by any of the methods for nuclear and plastid transformation known in the art. Other genes of interest can include herbicide resistance genes, pest resistance genes, fungal resistance genes, genes for enhancing oil yield or genes for novel metabolic pathways enabling the production of non-plant products to be made by the plant. The product of any transgene can be targeted to one or more of the plant cell organelles using any of the targeting sequences and methods known in the art.

A. Genetic Constructs for Transformation

DNA constructs useful in the methods described herein include transformation vectors capable of introducing transgenes into plants. As used herein, "transgenic" refers to an organism in which a nucleic acid fragment containing a heterologous nucleotide sequence has been introduced. The transgenes in the transgenic organism are preferably stable and inheritable. The heterologous nucleic acid fragment may or may not be integrated into the host genome.

Several plant transformation vector options are available, including those described in *Gene Transfer to Plants,* 1995, Potrykus et al., eds., Springer-Verlag Berlin Heidelberg New York, *Transgenic Plants: A Production System for Industrial and Pharmaceutical Proteins,* 1996, Owen et al., eds., John Wiley & Sons Ltd. England, and *Methods in Plant Molecular Biology: A Laboratory Course Manual,* 1995, Maliga et al., eds., Cold Spring Laboratory Press, New York. Plant transformation vectors generally include one or more coding sequences of interest under the transcriptional control of 5' and 3' regulatory sequences, including a promoter, a transcription termination and/or polyadenylation signal, and a selectable or screenable marker gene. For the expression of two or more polypeptides from a single transcript, additional RNA processing signals and ribozyme sequences can be engineered into the construct (U.S. Pat. No. 5,519,164). This approach has the advantage of locating multiple transgenes in a single locus, which is advantageous in subsequent plant breeding efforts.

Engineered minichromosomes can also be used to express one or more genes in plant cells. Cloned telomeric repeats introduced into cells may truncate the distal portion of a chromosome by the formation of a new telomere at the integration site. Using this method, a vector for gene transfer can be prepared by trimming off the arms of a natural plant chromosome and adding an insertion site for large inserts (Yu et al., 2006, *Proc. Natl. Acad. Sci. USA* 103: 17331-17336; Yu et al., 2007, *Proc. Natl. Acad. Sci. USA* 104: 8924-8929).

An alternative approach to chromosome engineering in plants involves in vivo assembly of autonomous plant minichromosomes (Carlson et al., 2007, *PLoS Genet.* 3: 1965-74). Plant cells can be transformed with centromeric sequences and screened for plants that have assembled autonomous chromosomes de novo. Useful constructs combine a selectable marker gene with genomic DNA fragments containing centromeric satellite and retroelement sequences and/or other repeats.

Another approach useful to the described invention is Engineered Trait Loci ("ETL") technology (U.S. Pat. No. 6,077,697; US 2006/0143732). This system targets DNA to a heterochromatic region of plant chromosomes, such as the pericentric heterochromatin, in the short arm of acrocentric chromosomes. Targeting sequences may include ribosomal DNA (rDNA) or lambda phage DNA. The pericentric rDNA region supports stable insertion, low recombination, and high levels of gene expression. This technology is also useful for stacking of multiple traits in a plant (US 2006/0246586).

Zinc-finger nucleases (ZFNs) are also useful for practicing the invention in that they allow double strand DNA cleavage at specific sites in plant chromosomes such that targeted gene insertion or deletion can be performed (Shukla et al., 2009, *Nature* 459: 437-441; Townsend et al., 2009, *Nature* 459: 442-445). This approach may be particularly useful for the present invention which can involve transcription factor genes which are naturally present in the genome of the plant of interest. In this case the ZFNs can be used to change the sequences regulating the expression of the TF of interest to increase the expression or alter the timing of expression beyond that found in a non-engineered or wild type plant.

A transgene may be constructed to encode a multifunctional transcription factor combining different domains of the transcription factors identified herein as useful for practicing the claimed invention through gene fusion techniques in which the coding sequences of different domains of the different genes are fused with or without linker sequences to obtain a single gene encoding a single protein with the activities of the individual genes. Such synthetic fusion gene/TF combinations can be further optimized using molecular evolution technologies.

B. Tissue Culture-Based Methods for Nuclear Transformation

Transformation protocols as well as protocols for introducing nucleotide sequences into plants may vary depending on the type of plant or plant cell, i.e., monocot or dicot, targeted for transformation.

Suitable methods of introducing nucleotide sequences into plant cells and subsequent insertion into the plant genome are described in US 2010/0229256 A1 to Somleva & Ali and US 2012/0060413 to Somleva et al.

The transformed cells are grown into plants in accordance with conventional techniques. See, for example, McCormick et al., 1986, *Plant Cell Rep.* 5: 81-84. These plants may then be grown, and either pollinated with the same transformed variety or different varieties, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

C. In Planta Transformation Methods

Procedures for in planta transformation can be simple. Tissue culture manipulations and possible somaclonal variations are avoided and only a short time is required to obtain transgenic plants. However, the frequency of transformants in the progeny of such inoculated plants is relatively low and variable. At present, there are very few species that can be routinely transformed in the absence of a tissue culture-based regeneration system. Stable Arabidopsis transformants can be obtained by several in planta methods including vacuum infiltration (Clough & Bent, 1998, *The Plant J.* 16: 735-743), transformation of germinating seeds (Feldmann & Marks, 1987, *Mol. Gen. Genet.* 208: 1-9), floral dip (Clough and Bent, 1998, *Plant J.* 16: 735-743), and floral spray (Chung et al., 2000, *Transgenic Res.* 9: 471-476). Other plants that have successfully been transformed by in planta methods include rapeseed and radish (vacuum infiltration, Ian and Hong, 2001, *Transgenic Res.,* 10: 363-371; Desfeux et al., 2000, *Plant Physiol.* 123: 895-904), *Medicago truncatula* (vacuum infiltration, Trieu et al., 2000, *Plant J.* 22: 531-541), camelina (floral dip, WO/2009/117555 to Nguyen et al.), and wheat (floral dip, Zale et al., 2009, *Plant Cell Rep.* 28: 903-913). In planta methods have also been used for transformation of germ cells in maize (pollen, Wang et al. 2001, *Acta Botanica Sin.,* 43, 275-279; Zhang et al., 2005, *Euphytica,* 144, 11-22; pistils, Chumakov et al. 2006, *Russian J. Genetics,* 42, 893-897; Mamontova et al. 2010, *Russian J. Genetics,* 46, 501-504) and *Sorghum* (pollen, Wang et al. 2007, *Biotechnol. Appl. Biochem.,* 48, 79-83)

D. Transformation of Plants with Genes of Interest

Transgenic plants can be produced using conventional techniques to express any genes of interest in plants or plant cells (*Methods in Molecular Biology*, 2005, vol. 286, Transgenic Plants: Methods and Protocols, Pena L., ed., Humana Press, Inc. Totowa, N.J.). Typically, gene transfer, or transformation, is carried out using explants capable of regeneration to produce complete, fertile plants. Generally, a DNA or an RNA molecule to be introduced into the organism is part of a transformation vector. A large number of such vector systems known in the art may be used, such as plasmids. The components of the expression system can be modified, e.g., to increase expression of the introduced nucleic acids. For example, truncated sequences, nucleotide substitutions or other modifications may be employed. Expression systems known in the art may be used to transform virtually any plant cell under suitable conditions. A transgene comprising a DNA molecule encoding a gene of interest is preferably stably transformed and integrated into the genome of the host cells. Transformed cells are preferably regenerated into whole plants. Detailed description of transformation techniques are within the knowledge of those skilled in the art.

1. Genes for Transcription Factors

Crop improvement using transcription factors (TFs) is a promising approach as they are likely to regulate a wide range of target genes whose products contribute to plant agronomic performance under normal and stress conditions. TF-mediated improvement of stress tolerance has been reported in diverse crop species, both dicots and monocots (Hussain et al., 2011, *Biotechnology Prog.* 27: 297-306). The first efforts included overexpression of the AP2/ERF factors CBF1, DREB1A and CBF4 that resulted in drought/salt/cold tolerance in *Arabidopsis* (Jaglo-Ottosen et al., 1998, *Science* 280: 104-106). Since then, the orthologous genes of CBF/DREB have been identified in many crop plants and functional tests revealed conservation of function (reviewed in Xu et al., 2011. *J. Int. Plant Biol.* 53: 570-585). It has also been shown that ectopic overexpression of these TF genes caused, in addition to increased stress tolerance, some specific phenotypic changes—dark-green, dwarfed plants with higher levels of soluble sugars and proline have been obtained. More recent evidence suggested the role of an AP2 family protein SHINE/WAX INDUCER 1 (SHN) as a global level regulator of cell wall biosynthesis which could be economically valuable for biofuel production from lignocellulosic crops (Ambavaram et al., 2011, *Plant Physiol.* 155: 916-931).

In studies with model plants, it has been shown that transcription factors belonging to the AP2/ERF, NF-Y, bZIP, MYB, Zinc-finger and NAC families confer tolerance to both biotic and abiotic stresses. Comparative genomics has also been used to find genes with conserved functions between model plants (mainly *Arabidopsis*) and crop plants, such as rice and maize demonstrating the utility of using the dicot-monocot models together. For example, expression of an *Arabidopsis* AP2/ERF-like transcription factor in rice resulted in an increase in leaf biomass and bundle sheath cells that probably contributed to the enhanced photosynthetic assimilation and efficiency (Karaba et al., 2009, *Proc. Natl. Acad. Sci.* USA 104: 15270-15275).

2. Reporter Genes and Selectable Marker Genes

Reporter genes or selectable marker genes may be included in an expression cassette as described in US Patent Applications 20100229256 and 20120060413 incorporated by reference herein. An expression cassette including a promoter sequence operably linked to a heterologous nucleotide sequence of interest can be used to transform any plant by any of the methods described above. Useful selectable marker genes and methods of selection transgenic lines for a range of different crop species are described in the examples herein.

E. Transgene Expression in Plants

Plant promoters can be selected to control the expression of the transgene in different plant tissues or organelles for all of which methods are known to those skilled in the art (Gasser & Fraley, 1989, *Science* 244: 1293-1299). In one embodiment, promoters are selected from those of eukaryotic or synthetic origin that are known to yield high levels of expression in plant and algae. In a preferred embodiment, promoters are selected from those that are known to provide high levels of expression in monocots.

1. Inducible Promoters

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1 promoter which is activated by salicylic acid. Other chemical-regulated promoters include steroid-responsive promoters [see, for example, the glucocorticoid-inducible promoter (Schena et al., 1991, *Proc. Natl. Acad. Sci. USA* 88: 10421-10425; McNellis et al., 1998, *Plant J.* 14: 247-257) and tetracycline-inducible and tetracycline-repressible promoters (see, for example, Gatz et al., 1991, *Mol. Gen. Genet.* 227: 229-237; U.S. Pat. Nos. 5,814,618 and 5,789,156, herein incorporated by reference in their entirety).

A three-component osmotically inducible expression system suitable for plant metabolic engineering has recently been reported (Feng et al., 2011, *PLoS ONE* 6: 1-9).

2. Constitutive Promoters

Constitutive promoters include, for example, the core promoter of the Rsyn7 promoter and other constitutive promoters disclosed in WO 99/43838 and U.S. Pat. No. 6,072,050, the core CaMV 35S promoter (Odell et al., 1985, *Nature* 313: 810-812), rice actin (McElroy et al., 1990, *Plant Cell* 2: 163-171), ubiquitin (Christensen et al., 1989, *Plant Mol. Biol.* 12: 619-632; Christensen et al., 1992, *Plant Mol. Biol.* 18: 675-689), pEMU (Last et al., 1991, *Theor. Appl. Genet.* 81: 581-588), MAS (Velten et al., 1984, *EMBO J.* 3: 2723-2730), and ALS promoter (U.S. Pat. No. 5,659,026). Other constitutive promoters are described in U.S. Pat. Nos. 5,608,149; 5,608,144; 5,604,121; 5,569,597; 5,466,785; 5,399,680; 5,268,463; and 5,608,142.

3. Weak Promoters

Where low level expression is desired, weak promoters may be used. Generally, the term "weak promoter" is intended to describe a promoter that drives expression of a coding sequence at a low level. Where a promoter is expressed at unacceptably high levels, portions of the promoter sequence can be deleted or modified to decrease expression levels. Such weak constitutive promoters include, for example, the core promoter of the Rsyn7 promoter (WO 99/43838 and U.S. Pat. No. 6,072,050).

4. Tissue Specific Promoters

"Tissue-preferred" promoters can be used to target gene expression within a particular tissue. Compared to chemically inducible systems, developmentally and spatially regulated stimuli are less dependent on penetration of external factors into plant sells. Tissue-preferred promoters include those described by Van Ex et al., 2009, *Plant Cell Rep.* 28: 1509-1520; Yamamoto et al., 1997, *Plant J.* 12: 255-265; Kawamata et al., 1997, *Plant Cell Physiol.* 38: 792-803; Hansen et al., 1997, *Mol. Gen. Genet.* 254: 337-343; Russell et al., 199), *Transgenic Res.* 6: 157-168; Rinehart et al., 1996, *Plant Physiol.* 112: 1331-1341; Van Camp et al., 1996, *Plant Physiol.* 112: 525-535; Canevascini et al., 1996, *Plant Physiol.* 112: 513-524; Yamamoto et al., 1994, *Plant Cell Physiol.* 35: 773-778; Lam, 1994, *Results Probl. Cell Differ.* 20: 181-196, Orozco et al., 1993, *Plant Mol. Biol.* 23: 1129-1138; Matsuoka et al., 1993, *Proc. Natl. Acad. Sci. USA* 90: 9586-9590, and Guevara-Garcia et al., 1993, *Plant J.* 4: 495-505. Such promoters can be modified, if necessary, for weak expression.

4.i. Seed/Embryo Specific Promoters

"Seed-preferred" promoters include both "seed-specific" promoters (those promoters active during seed development such as promoters of seed storage proteins) as well as "seed-germinating" promoters (those promoters active during seed germination). See Thompson et al., 1989, *BioEssays* 10: 108-113, herein incorporated by reference. Such seed-preferred promoters include, but are not limited to, Cim1 (cytokinin-induced message), cZ19B1 (maize 19 kDa zein), milps (myo-inositol-1-phosphate synthase), and celA (cellulose synthase). Gamma-zein is a preferred endosperm-specific promoter. Glob-1 is a preferred embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, and globulin 1. The stage specific developmental promoter of the late embryogenesis abundant protein gene LEA has successfully been used to drive a recombination system for excision-mediated expression of a lethal gene at late embryogenesis stages in the seed terminator technology (U.S. Pat. No. 5,723,765 to Oliver et al.).

4.ii. Leaf Specific Promoters

Leaf-specific promoters are known in the art. See, for example, WO/2011/041499 and U. S. Patent No 2011/0179511 A1 to Thilmony et al.; Yamamoto et al., 1997, *Plant J.* 12: 255-265; Kwon et al., 1994, *Plant Physiol.* 105: 357-367; Yamamoto et al., 1994, *Plant Cell Physiol.* 35: 773-778; Gotor et al., 1993, *Plant J.* 3: 509-518; Orozco et al., 1993, *Plant Mol. Biol.* 23: 1129-1138, and Matsuoka et al., 1993, *Proc. Natl. Acad. Sci. USA* 90: 9586-9590.

4.iii. Temporal Specific Promoters

Also contemplated are temporal promoters that can be utilized during the developmental time frame, for example, switched on after plant reaches maturity in leaf to enhance carbon flow.

4iv. Anther/Pollen Specific Promoters

Numerous genes specifically expressed in anthers and/or pollen have been identified and their functions in pollen development and fertility have been characterized. The specificity of these genes has been found to be regulated mainly by their promoters at the transcription level (Ariizumi et al., 2002, *Plant Cell Rep.* 21: 90-96 and references therein). A large number of anther- and/or pollen-specific promoters and their key cis-elements from different plant species have been isolated and functionally analyzed.

4.v. Floral Specific Promoters

Floral-preferred promoters include, but are not limited to, CHS (Liu et al., 2011, *Plant Cell Rep.* 30: 2187-2194), OsMADS45 (Bai et al., 2008, *Transgenic Res.* 17: 1035-1043), PSC (Liu et al., 2008, *Plant Cell Rep.* 27: 995-1004), LEAFY, AGAMOUS, and AP1 (Van Ex et al., 2009, *Plant Cell Rep.* 28: 1509-1520), AP1 (Verweire et al., 2007, *Plant Physiol.* 145: 1220-1231), PtAGIP (Yang et al., 2011, *Plant Mol. Biol. Rep.* 29: 162-170), Lem1 (Somleva & Blechl, 2005, *Cereal Res. Comm.* 33: 665-671; Skadsen et al., 2002, *Plant Mol. Biol.* 45: 545-555), Lem2 (Abebe et al., 2005, *Plant Biotechnol. J.* 4: 35-44), AGL6 and AGL13 (Schauer et al., 2009, *Plant J.* 59: 987-1000).

4.vi. Combinations of Promoters

Certain embodiments use transgenic plants or plant cells having multi-gene expression constructs harboring more than one promoter. The promoters can be the same or different.

Any of the described promoters can be used to control the expression of one or more of the transcription factor genes of the invention, their homologs and/or orthologs as well as any other genes of interest in a defined spatiotemporal manner.

F. Requirements for Construction of Plant Expression Cassettes

Nucleic acid sequences intended for expression in transgenic plants are first assembled in expression cassettes behind a suitable promoter active in plants. The expression cassettes may also include any further sequences required or selected for the expression of the transgene. Such sequences include, but are not restricted to, transcription terminators, extraneous sequences to enhance expression such as introns, vital sequences, and sequences intended for the targeting of the gene product to specific organelles and cell compartments. These expression cassettes can then be transferred to the plant transformation vectors described infra. The following is a description of various components of typical expression cassettes.

1. Transcriptional Terminators

A variety of transcriptional terminators are available for use in expression cassettes. These are responsible for the termination of transcription beyond the transgene and the correct polyadenylation of the transcripts. Appropriate transcriptional terminators are those that are known to function in plants and include the CaMV 35S terminator, the tm1 terminator, the nopaline synthase terminator and the pea rbcS E9 terminator. These are used in both monocotyledonous and dicotyledonous plants.

2. Sequences for the Enhancement or Regulation of Expression

Numerous sequences have been found to enhance gene expression from within the transcriptional unit and these sequences can be used in conjunction with the genes to increase their expression in transgenic plants. For example, various intron sequences such as introns of the maize Adh1 gene have been shown to enhance expression, particularly in monocotyledonous cells. In addition, a number of non-translated leader sequences derived from viruses are also known to enhance expression, and these are particularly effective in dicotyledonous cells.

G. Coding Sequence Optimization

The coding sequence of the selected gene may be genetically engineered by altering the coding sequence for optimal expression in the crop species of interest. Methods for modifying coding sequences to achieve optimal expression in a particular crop species are well known (Perlak et al., 1991, *Proc. Natl. Acad. Sci. USA* 88: 3324 and Koziel et al., 1993, *Biotechnology* 11: 194-200).

H. Construction of Plant Transformation Vectors

Numerous vectors available for plant transformation are known to those of ordinary skill in the plant transformation arts. The genes pertinent to this disclosure can be used in conjunction with any such vectors. The choice of vector depends upon the selected transformation technique and the target species.

Many vectors are available for transformation using *Agrobacterium tumefaciens*. These typically carry at least one T-DNA sequence and include vectors such as pBIN19. Typical vectors suitable for *Agrobacterium* transformation include the binary vectors pCIB200 and pCIB2001, as well as the binary vector pCIB 10 and hygromycin selection derivatives thereof. (See, for example, U.S. Pat. No. 5,639,949).

Transformation without the use of *Agrobacterium tumefaciens* circumvents the requirement for T-DNA sequences in the chosen transformation vector and consequently vectors lacking these sequences are utilized in addition to vectors such as the ones described above which contain T-DNA sequences. The choice of vector for transformation techniques that do not rely on *Agrobacterium* depends largely on the preferred selection for the species being transformed. Typical vectors suitable for non-*Agrobacterium* transformation include pCIB3064, pSOG 19, and pSOG35. (See, for example, U.S. Pat. No. 5,639,949).

I. Transformation and Selection of Cultures and Plants

Plant cultures can be transformed and selected using one or more of the methods described above which are well known to those skilled in the art. In switchgrass, selection occurs by incubating the cultures on a callus growth medium containing bialaphos. In an alternative embodiment, selection can occur in the presence of hygromycin. Resistant calluses are then cultured on a regeneration medium (Somleva, 2006, *Agrobacterium Protocols*, Wang K., ed., Vol. 2, pp 65-74, Humana Press; Somleva et al., 2002, *Crop Sci.* 42: 2080-2087) containing the preferred selection agent. Examples of specific selectable markers and transgenic plant selection methods for a number of crop species are described in the examples herein.

EXAMPLES

Example 1

Identification and Functional Characterization of Candidate Transcription Factor Genes Potentially Involved in Photosynthesis and Biomass Related Traits The following approaches were used to identify and annotate potential switchgrass transcription factors (TFs):

A. Gene Prediction Based on Systems Biology Approach

A rice regulatory association network that has been developed based on genome wide expression profiles (Ambavaram et al., 2011, *Plant Physiol.* 155: 916-931) was used to identify switchgrass orthologs of TFs with predicted function in the regulation of genes involved in photosynthesis and biomass related traits. Publicly available databases were used to perform BlastN and BlastP reciprocal searches between the genomes of rice (a $C_3$ monocot; website: rice.plantbiology.msu.edu), maize (a monocot possessing the NADP-ME subtype of $C_4$ photosynthesis; found at world wide web maizesequence.org and switchgrass an NAD-ME $C_4$ monocot at phytozome.net/search.php?show=blast&org=Org_Pvirgatum to identify candidate genes for functional validation and experimental analysis. Comparisons of gene ontology (GO) terms from the molecular function category revealed the most obvious functions of DNA binding and transcriptional regulatory activity of the identified TFs.

Based on genome-wide orthologous prediction, candidate genes were retrieved from the corresponding websites and their percentage of identity was evaluated (TABLE 1).

TABLE 1

| Candidate transcription factor genes. | | | | |
|---|---|---|---|---|
| Rice gene | Maize gene | Switchgrass ortholog | % identity | E-value |
| LOC_Os02g10480 | GRMZM2G138349 | Pavirv00027905m | 87.75 | 1e-86 |
| LOC_Os07g41580 | GRMZM2G384528 | Pavirv00029298m | 94.83 | 4e-58 |
| LOC_Os02g52670 | GRMZM2G103085 | Pavirv00031839m | 78.00 | 3e-11 |
| LOC_Os09g11480 | EU942421 | Pavirv00046166m | 75.44 | 2e-13 |
| LOC_Os03g09170 | GRMZM2G113060 | Pavirv00021049m | 61.11 | 3e-37 |
| LOC_Os02g32140 | GRMZM2G016434 | Pavirv00013751m | 97.26 | 8e-27 |
| LOC_Os09g29960 | GRMZM2G089850 | Pavirv00059600m | 94.59 | 3e-17 |
| LOC_Os11g06770 | GRMZM2G544539 | Pavirv00009307m | 91.94 | 1e-19 |
| LOC_Os04g52090 | GRMZM2G068967 | Pavirv00015875m | 98.31 | 2e-21 |
| LOC_Os04g55520 | GRMZM2G119865 | Pavirv00033364m | 66.67 | 4e-18 |

B. Functional Annotation of Select Switchgrass TFs

According to the plant transcription factor database (see world wide web at planttfdb.cbi.edu.cn) and switchgrass genome (world wide web at phytozome.net), SEQ ID NO: 1 (Pavirv00046166m) and SEQ ID NO: 2 (Pavirv00013751m) are switchgrass transcription factors belonging to the APETALA2 (AP2)/ETHYLENE RESPONSE FACTOR (ERF) family and SEQ ID NO: 3 (Pavirv00029298m) is a switchgrass transcription factor from the Nuclear-Factor Y (NF-YB) family. The analysis of their protein sequences using a database of protein domains, families and functional sites (world wide web at expacy.org) revealed the characteristic AP2 domain (SEQ ID NO: 4 and SEQ ID NO: 5, underlined) and NFYA-HAP2 motif (SEQ ID NO: 6, underlined), respectively. Comparisons of gene ontology terms for the switchgrass genes SEQ ID NO: 1 and SEQ ID NO: 2 revealed the 'transcription factor' activity (GO: 0003700), whereas SEQ ID NO: 3 belongs to the MNFs based on its sequence-specific transcription regulator activity (GO: 00030528). According to the TF-function association network, these switchgrass orthologous TF genes may be associated with functions in "primary" carbon metabolism and several "cellular metabolic" processes.

C. Expression Analysis of Novel Transcription Factors in Switchgrass.

For validation of the bioinformatics findings, the tissue specific expression of the candidate TF genes (TABLE 1) in switchgrass was analyzed by RT-PCR. Total RNA was isolated from root (R), culm (C), leaf sheath (LS), young leaf (YL), mature leaf (ML), and panicle (P) tissues of wild type plants. After DNase treatment and column purification, total RNA (200 ng per reaction) was subjected to reverse transcription and PCR in a one-step RT-PCR assay (Qiagen) with gene-specific primers.

Figure 2:
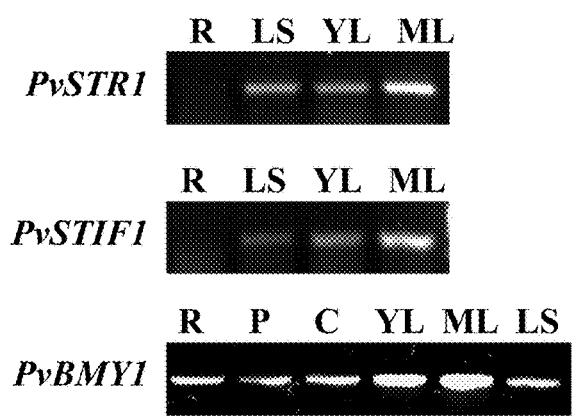
FIG. 2 illustrates the tissue specific expression pattern of the transcription factor genes PvSTR1, PvSTIF1 and PvBMY1 in wild type switchgrass analyzed by RT-PCR. Total RNA was isolated from roots (R), young leaves (YL), culms (C), mature leaves (ML), leaf sheaths (LS), and/or panicles (P) of wild-type plants and subjected to reverse transcription and PCR using One Step RT-PCR Kit (Qiagen) and primers specific for the coding regions of the TF genes.

The results revealed the differences in the expression levels of the candidate TF genes (listed in TABLE 1) in young and mature leaves, roots, and stem tissues (culm, leaf sheath and panicle). Based on their expression patterns we identified three genes which were highly expressed in mature leaf and these, three genes (SEQ ID NO: 1, SEQ ID NO: 2, and SEQ ID NO: 3) were selected for overexpression and functional analysis in switchgrass. The highest transcript accumulation for these three genes was observed in mature leaves (FIG. 2). No expression of the selected AP2/ERF transcription factors (SEQ ID NO: 1 and SEQ ID NO: 2) was detected in roots under the experimental conditions, while transcripts of the switchgrass NF-Y gene (SEQ ID NO: 3) were present at different levels in all tissues analyzed (FIG. 2).

Based on the effects of these TFs on plant metabolism and phenotype (see Example 5), the genes and the encoded polypeptides were designated as PvSTR1 (STarch Regulator 1; SEQ ID NO: 1 and SEQ ID NO: 4), PvSTIF1 (STress Inducible Factor 1; SEQ ID NO: 2 and SEQ ID NO: 5), and PvBMY1 (BioMass Yield 1, SEQ ID NO: 3 and SEQ ID NO: 6).

D. Identification of Homologous Genes of PvSTR1, PvSTIF1 and PvBMY1 Transcription Factors:

The sequence homology search was performed by comparing the deduced amino acid sequences of PvSTR1, PvSTIF1 and PvBMY1 to a translated non-redundant nucleotide database found on the world wide web at blast.ncbi.nlm.nih.gov and phytozome.net using tBLASTN and to a protein database using BLASTP. Transcription factor genes that are homologous to the transcription factors of the invention will typically have a polypeptide sequence of their conserved domain or the entire coding region 80% or more identical to the SEQ ID NOs: 4-6. As used herein, a "homolog" means a protein that performs the same biological function as another protein including these identified by sequence identity search. In silico analysis resulted in the identification of several homologs of each of the three transcription factors of the invention indicated as PvSTR2-5 (SEQ ID NOs: 7-10), PvSTIF2-4 (SEQ ID NOs: 11-13), and PvBMY2-6 (SEQ ID NOs: 14-18) for the homologs of PvSTR1, PvSTIF1 and PvBMY1, respectively.

Figure 3:
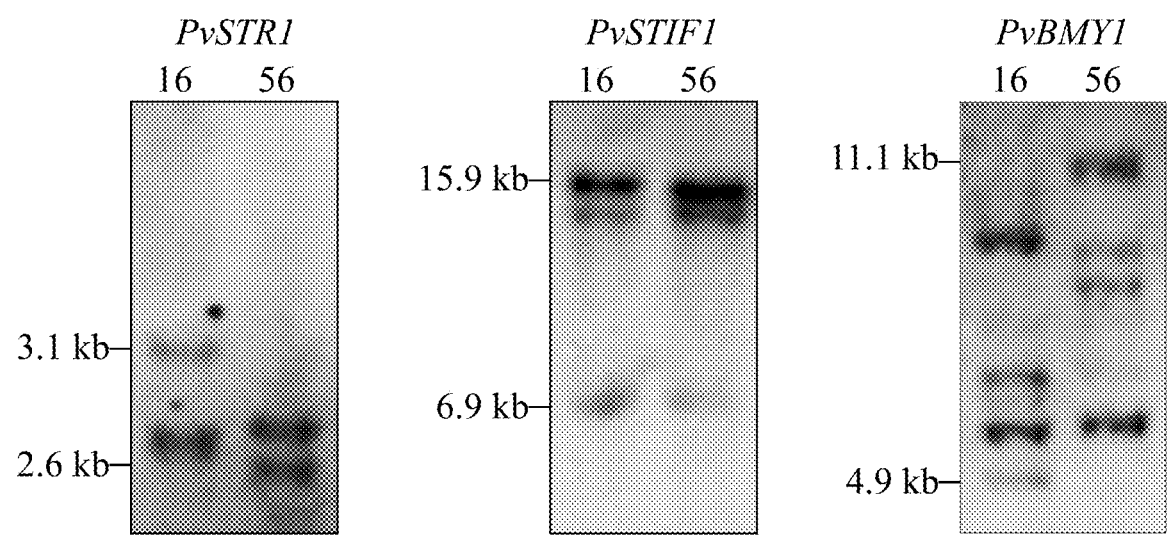
FIG. 3 demonstrates the presence of genes homologous to the transcription factor genes PvSTR1, PvSTIF1 and PvBMY1 in the switchgrass genome as detected by Southern blot hybridization. Genomic DNA isolation, digestion with EcoRI and hybridization with probes specific for the coding regions of the transcription factor genes was performed as described previously (Somleva et al., 2008, *Plant Biotechnol J*, 6: 663-678). 16 and 56, Alamo genotypes (our designation).

The copy number of each of the TF genes in the switchgrass genome was also determined by Southern blot hybridizations. Two genotypes from the switchgrass cultivar Alamo—56 and 16 (our designation) were studied. Callus cultures from these genotypes were used in all the experiments on switchgrass transformation (as described in Example 3). The results revealed the presence of the same number of homologs of PvSTR1, PvSTIF1 and PvBMY1 in the two genotypes analyzed (FIG. 3).

Based on the existing sequential similarity, including the presence of identical DNA-binding domains, overexpression of the identified homologous genes PvSTR2-5, PvSTIF2-4, and PvBMY2-6 can readily be tested for trait modifications similar to the ones induced by PvSTR1, PvSTIF1 and PvBMY1.

E. Identification of Orthologous Genes of PvSTR1, PvSTIF1 and PvBMY1 Transcription Factors:

"Orthologs" and "paralogs" refer to polynucleotide and polypeptide sequences which are homologous to the claimed sequences. These genes are related because they originate from a common ancestral gene and potentially retain a similar function in the course of evolution. Orthologs are structurally related genes in different species that are derived by speciation, while paralogs are structurally related genes in the same species that are derived by genetic duplication. Orthologous genes are identified based upon percentage similarity or identity of the complete sequence or of a conserved domain. Closely related transcription factors can share about 70%, 75%, or about 80% or more amino acid sequence identity. Sequences with sufficient similarity may also bind to the same DNA binding sites of transcriptional regulatory elements.

Figure 5A:
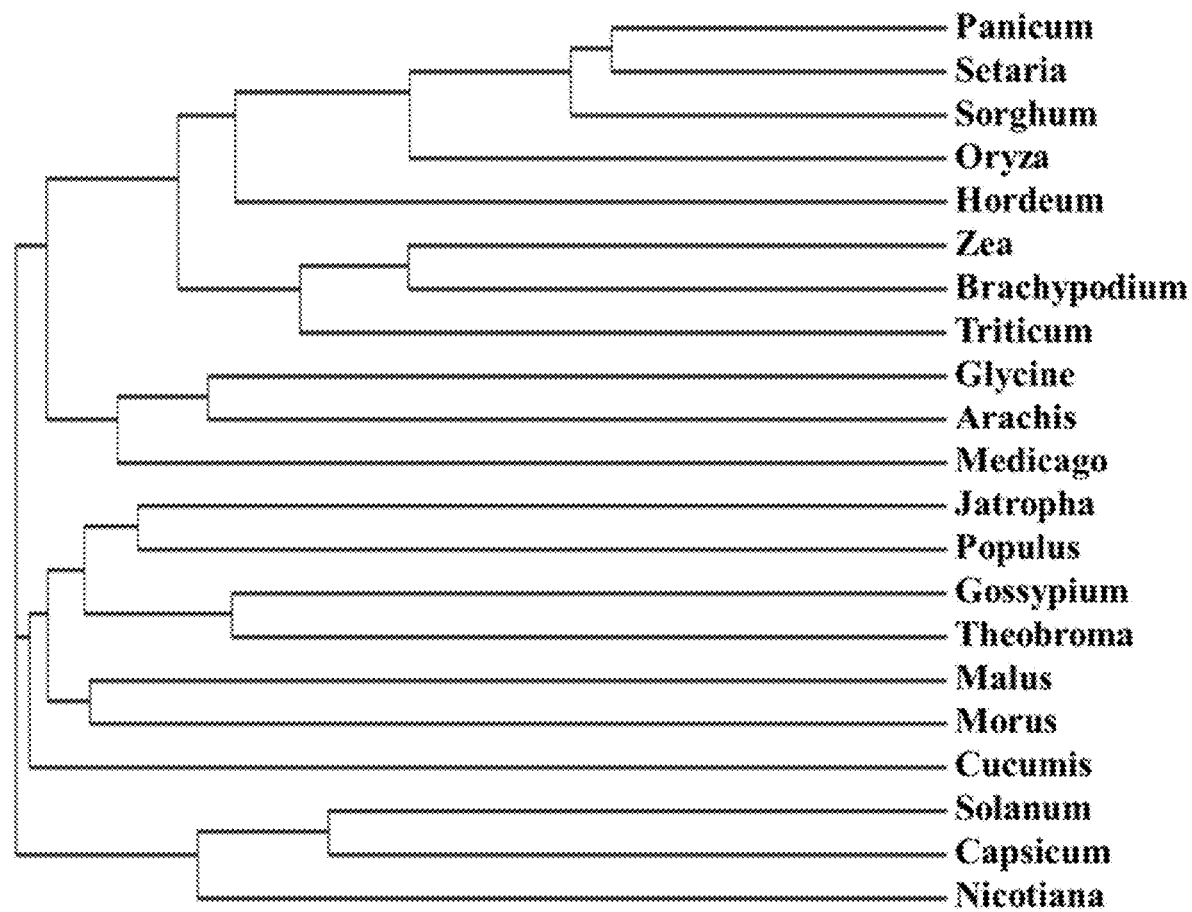
FIG. 5A-C illustrates the possible phylogenetic relationships among the higher plant taxa, including monocotyledonous and dicotyledonous species, based on the conservative domains of PvSTR1 (A), PvSTIF1 (B) and PvBMY1 (C).
Figure 5B:
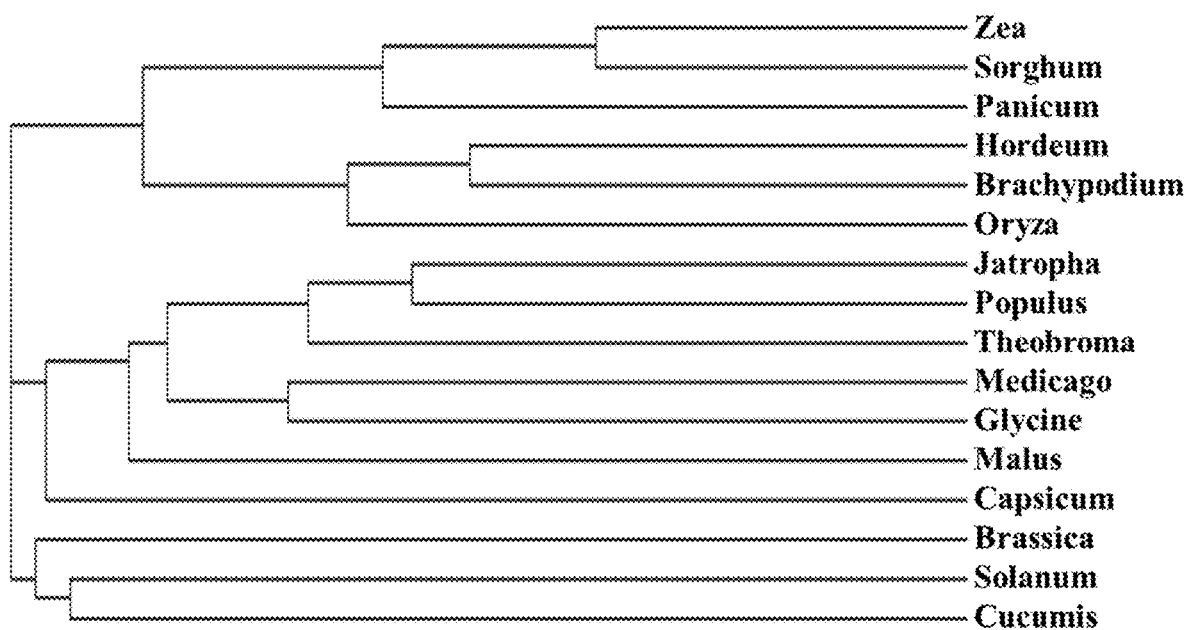
Figure 5C:
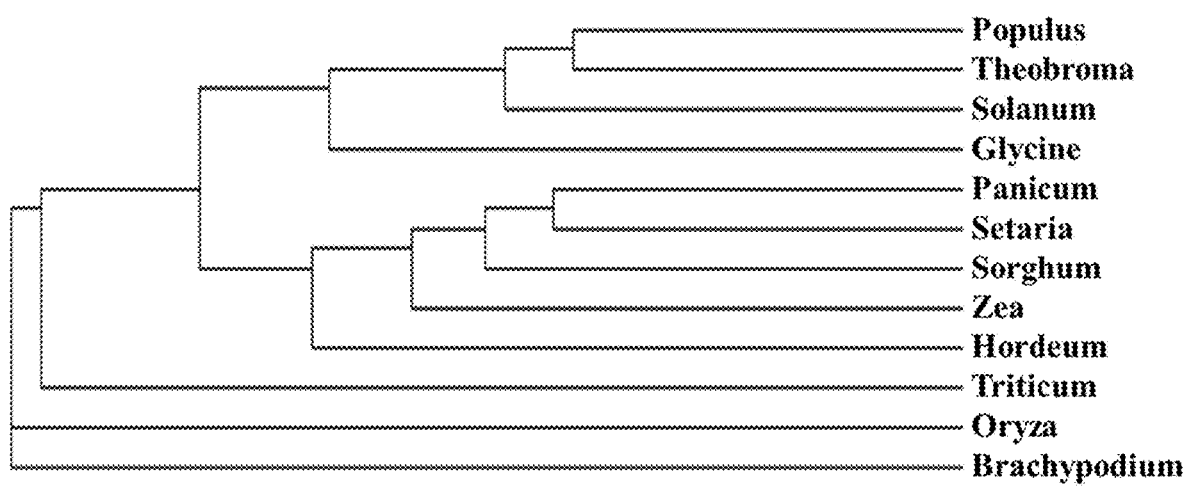

Orthologs of the switchgrass transcription factor genes PvSTR1, PvSTIF1 and PvBMY1 were identified using methods well known in the art. Orthologous polypeptide sequences from different plant species with more than 75%, 80%, 85%, greater than 90% identity of the conserved binding domains are shown in FIG. 4. The phylogenetic relationships were also estimated based on the conserved domain sequences of PvSTR1, PvSTIF1 and PvBMY1 (FIG. 5).

Example 2

Design and Construction of Transformation Vectors for Overexpression of Transcription Factor Genes in Switchgrass.

All gene constructs were made using widely available genetic components and standard molecular biology techniques. Each of the genes was cloned in an individual expression cassette and 2-5 cassettes were assembled in one vector for plant transformation.

Figure 6A:
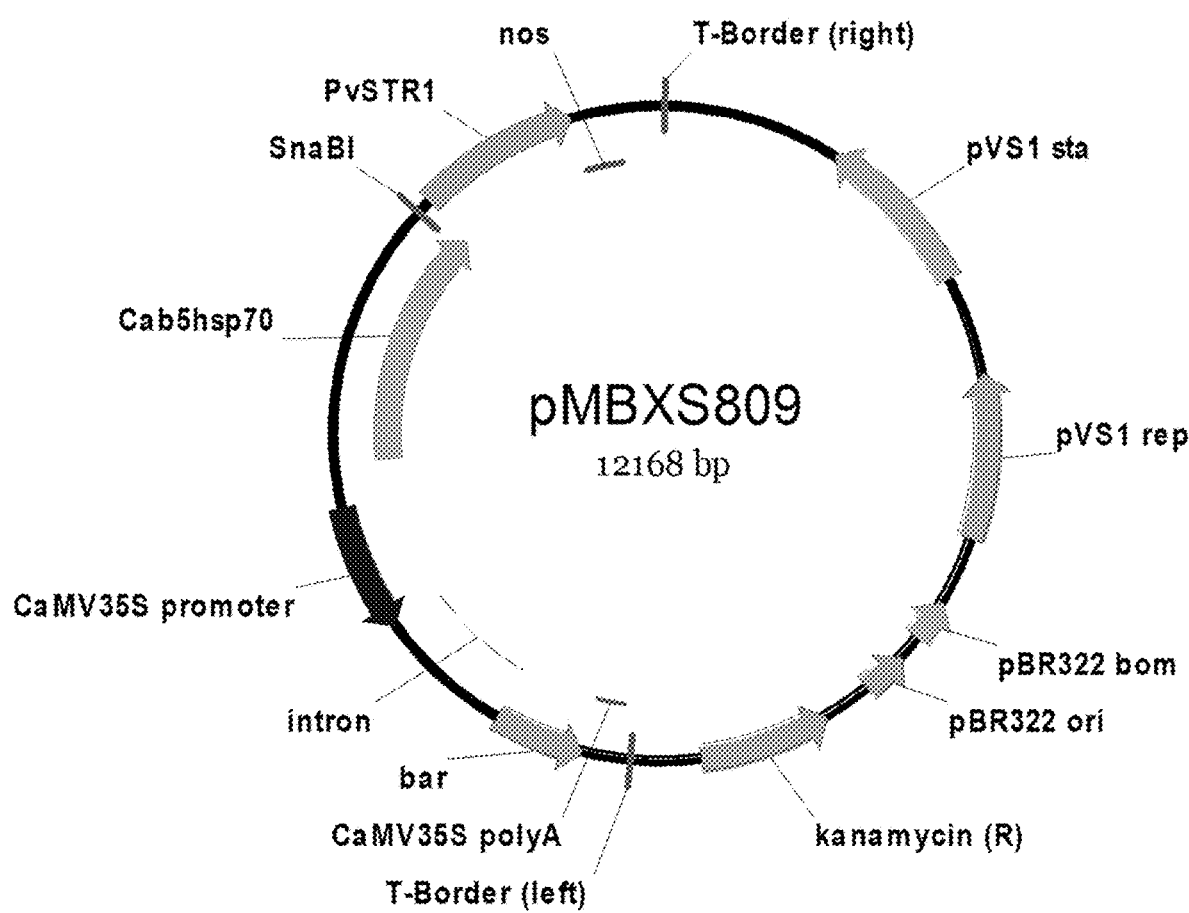
FIG. 6A-C shows the vectors pMBXS809 (A), pMBXS810 (B) and pMBXS855 (C) harboring the TF genes and the marker gene bar.
Figure 6B:
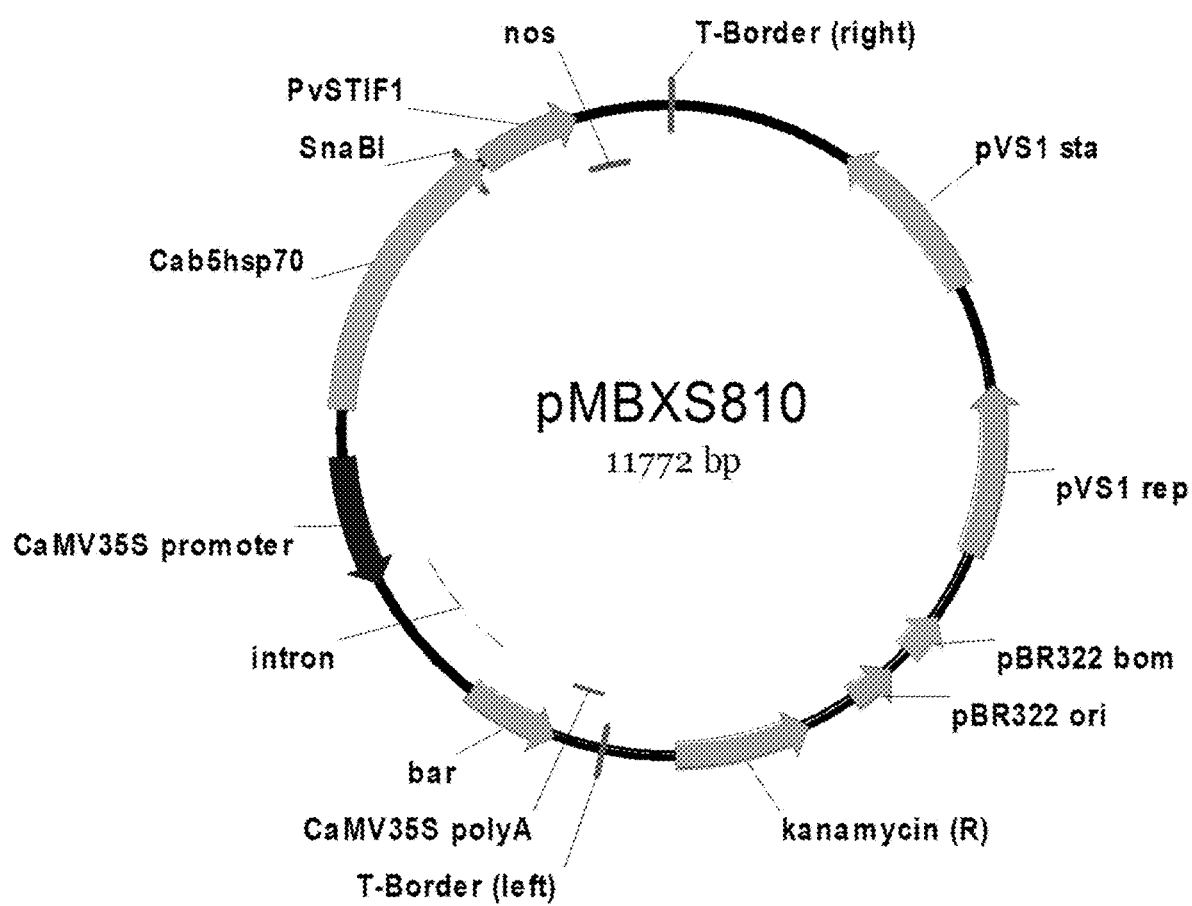
Figure 6C:
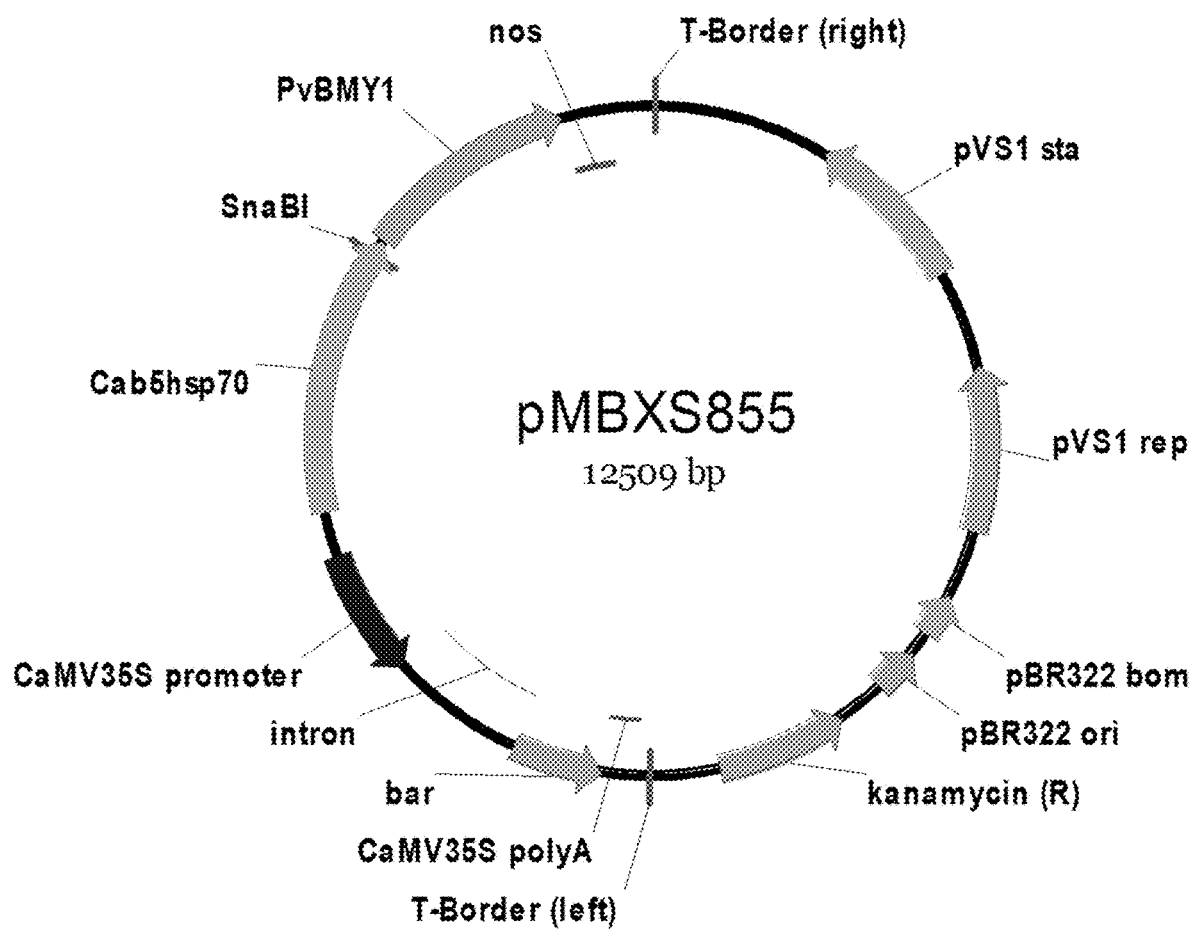
Figure 7A:
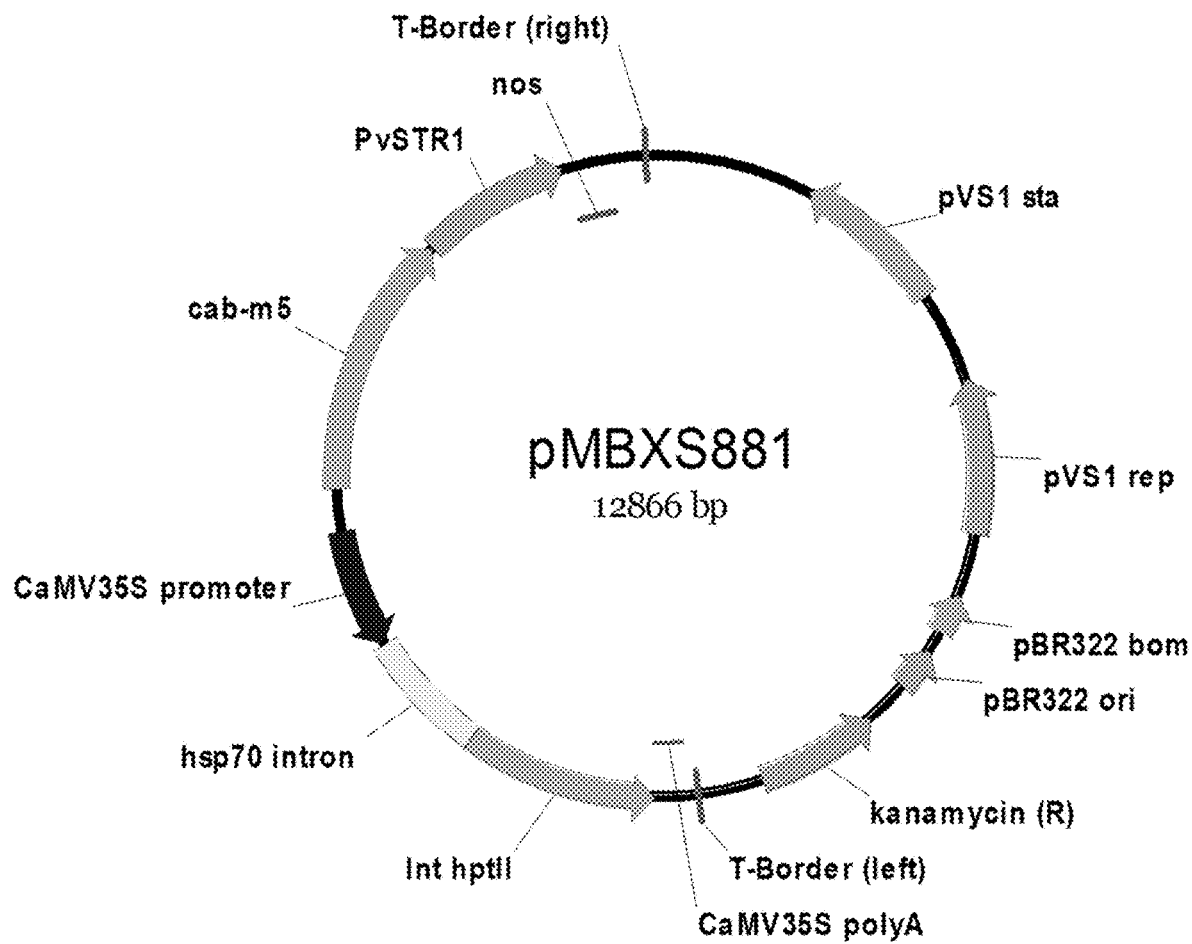
FIG. 7A-C depicts the vectors pMBXS881 (A), pMBXS882 (B) and pMBXS883 (C) harboring the TF genes and the marker gene hptII.
Figure 7B:
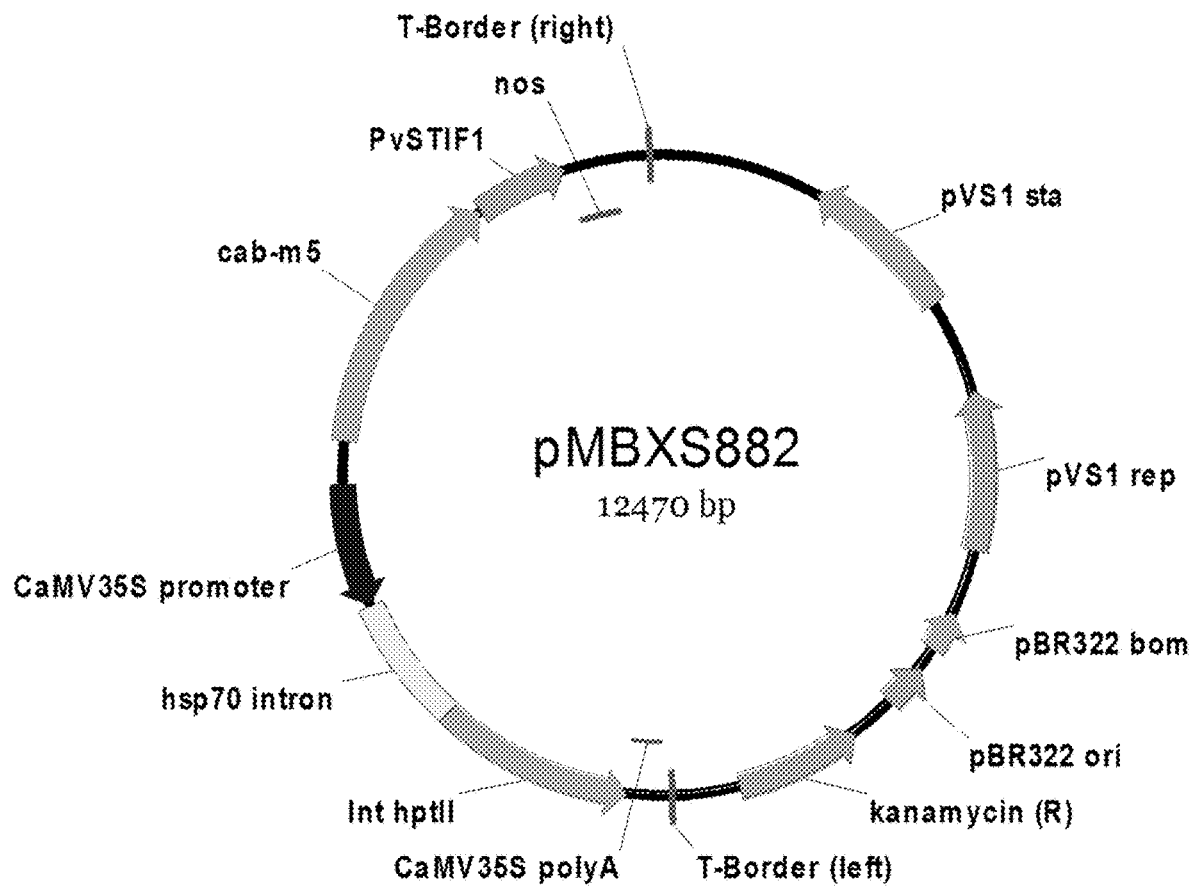
Figure 7C:
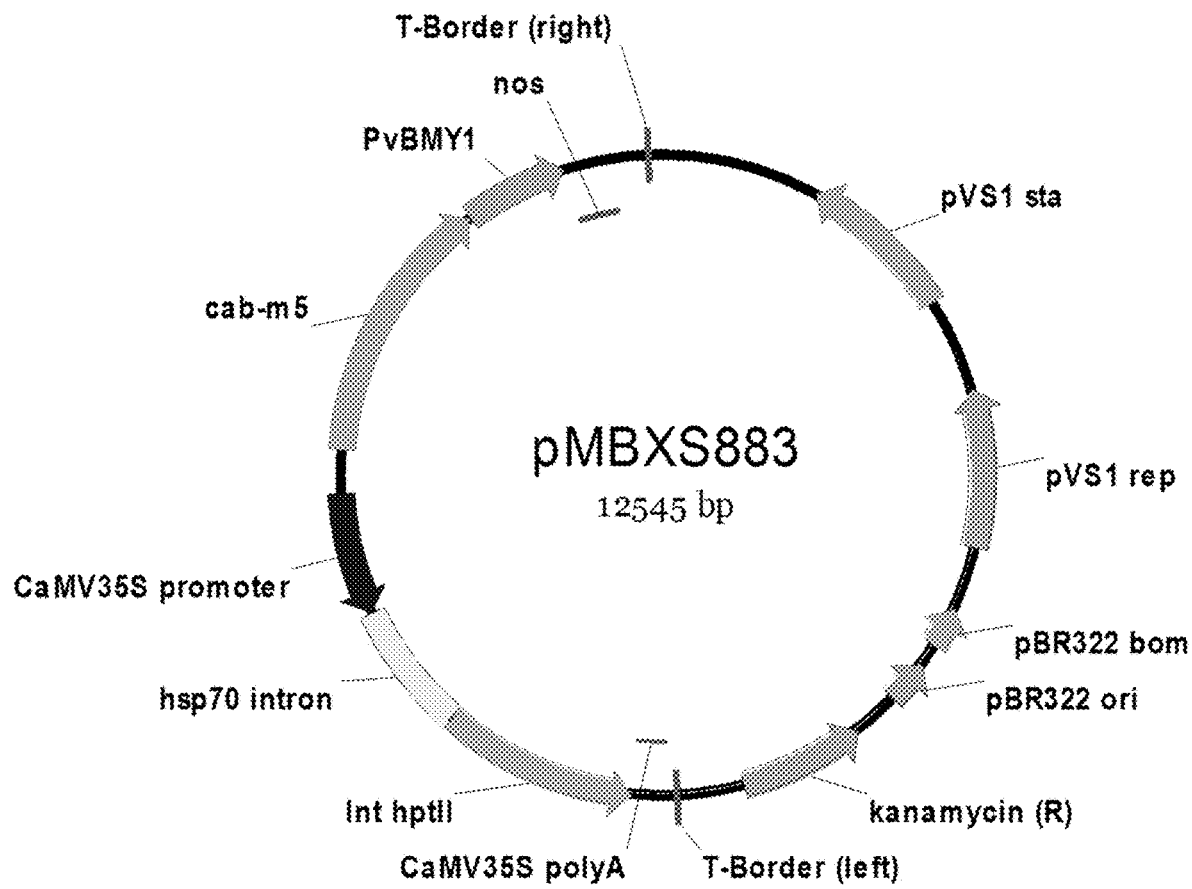

Two sets of gene constructs, one set containing the bar gene (conferring resistance to bialaphos) as a selectable marker and another one with the hptII gene (conferring resistance to hygromycin), were created for overexpression of the transcription factor genes of the invention in switchgrass (TABLE 2, FIG. 6, FIG. 7).

TABLE 2

Summary of plant transformation vectors for expression of transcription factors and PHB biosynthesis genes.

| Vector | Locus Name | Gene of interest[1] | Marker gene[2] |
|---|---|---|---|
| pMBXS809 | Pavirv00046166m | PvSTR1 | bar |
| pMBXS810 | Pavirv00013751m | PvSTIF1 | bar |
| pMBXS855 | Pavirv00029298m | PvBMY1 | bar |
| pMBXS881 | Pavirv00046166m | PvSTR1 | hptII |
| pMBXS882 | Pavirv00013751m | PvSTIF1 | hptII |
| pMBXS883 | Pavirv00029298m | PvBMY1 | hptII |

[1]Driven by the maize cab-m5 promoter fused to the maize hsp70 intron;
[2]Driven by the 35S promoter.

The vectors pMBXS809, pMBXS810, and pMBXS855 (FIG. 6) were used for *Agrobacterium*-mediated transformation of switchgrass for generation of transgenic lines for functional analyses of the novel transcription factors (see Example 3). In each vector, the transcription factor gene is under the control of the cab-m5 light-inducible promoter of the chlorophyll a/b-binding protein in maize (Sullivan et al., 1989, *Mol. Gen. Genet.* 215: 431-440; Becker et al., 1992, *Plant Mol. Biol.* 20: 49-60) fused to the heat shock protein 70 (hsp70) intron (U.S. Pat. No. 5,593,874), while the marker genes are driven by the 35S promoter (TABLE 2).

The annotation of the genes and genetic elements assembled in the vectors pMBXS809, pMBXS810, and pMBXS855 are presented in TABLE 3 (see also FIG. 6 and FIG. 7).

Example 3

Transformation of Switchgrass

Highly embryogenic callus cultures initiated from different explants were used for introduction of the gene constructs described in Example 2.

Culture Initiation and Plant Regeneration:

Callus cultures were initiated from mature caryopses of cv. Alamo following a previously published procedure (Denchev & Conger, 1994, *Crop Sci.*, 34: 1623-1627). Their embryogenic potential and plant regeneration ability were evaluated as described previously (U.S. Pat. No. 8,487,159 to Somleva et al.).

Switchgrass plants from Alamo genotype 56 (Somleva et al., 2008, *Plant Biotechnol. J.* 6: 663-678; U.S. Pat. No. 8,487,159 to Somleva et al.) grown under greenhouse conditions were used for initiation of immature inflorescence-derived callus cultures. The top culm nodes of elongating tillers with 3-4 visible nodes were used for development of inflorescences in tissue culture following a previously published procedure (Alexandrova et al., 1996, *Crop Sci.* 36: 175-178). Callus cultures were initiated from individual spikelets from in vitro developed panicles and propagated by transferring on to a fresh medium for callus growth (Denchev and Conger, 1994, *Crop Sci.* 34: 1623-1627) every four weeks.

Callus cultures were grown at 27° C., in the dark and maintained by monthly subcultures on a fresh medium for callus growth (Somleva et al., 2002, *Crop Sci.* 42: 2080-2087). For plant regeneration, calluses were plated on MS basal medium supplemented with 1.4 µM gibberellic acid

TABLE 3

Plant transformation vectors for overexpression of the transcription factor genes PvSTR1, PvSTIF1 and PvBMY1 in switchgrass.

| Vector ID* | TF gene/marker | Annotation | SEQ ID | Coordinates (bp) |
|---|---|---|---|---|
| pMBXS809 | PvSTR1/bar | *Agrobacterium* T-DNA right border | 19 | 1 to 26 |
| | | Cab-m5 promoter with hsp70 intron to drive PvSTR1 gene | | 8951 to 10645 |
| | | PvSTR1 coding region | | 10646 to 11636 |
| | | nos terminator | | 11637 to 11891 |
| | | CaMV35S promoter to drive bar gene | | 7911 to 8680 |
| | | bar coding region | | 6543 to 7094 |
| | | CaMV35S polyA terminator | | 6335 to 6537 |
| | | *Agrobacterium* T-DNA left border | | 6260 to 6285 |
| pMBXS810 | PvSTIF1/bar | *Agrobacterium* T-DNA right border | 20 | 1 to 26 |
| | | Cab-m5 promoter with hsp70 intron to drive PvSTIF1 gene | | 8951 to 10645 |
| | | PvSTIF1 coding region | | 10646 to 11240 |
| | | nos terminator | | 11241 to 11495 |
| | | CaMV35S promoter to drive bar gene | | 7911 to 8680 |
| | | bar coding region | | 6543 to 7094 |
| | | CaMV35S polyA terminator | | 6335 to 6537 |
| | | *Agrobacterium* T-DNA left border | | 6260 to 6285 |
| pMBXS855 | PvBMY1/bar | *Agrobacterium* T-DNA right border | 21 | 1 to 26 |
| | | Cab-m5 promoter with hsp70 intron to drive PvBMY1 gene | | 8951 to 10645 |
| | | PvBMY1 coding region | | 10646 to 11961 |
| | | nos terminator | | 11978 to 12232 |
| | | CaMV35S promoter to drive bar gene | | 7911 to 8680 |
| | | bar coding region | | 6543 to 7094 |
| | | CaMV35S polyA terminator | | 6335 to 6537 |
| | | *Agrobacterium* T-DNA left border | | 6260 to 6285 |

*All vectors are based on the transformation vector pCambia3300 found at world wide web at cambia.org; the bar gene (conferring resistance to bialaphos) is used as a marker for selection of transformed callus cultures and plants.

and incubated at 27° C. with a 16-h photoperiod (cool white fluorescent bulbs, 80 μmol/m²/s).

Transformation of Mature Caryopsis- and Immature Inflorescence-Derived Cultures:

Highly embryogenic callus cultures were transformed with *Agrobacterium tumefaciens* following previously published protocols (Somleva et al., 2002, *Crop Sci.* 42: 2080-2087; Somleva, 2006, *Agrobacterium Protocols,* Wang K., ed., pp 65-74: Humana Press). Transformed cultures and plants regenerated from them were selected with 200 mg/L hygromycin (WO 2010/102220 A1 and US 2010/0229256 A1 to Somleva & Ali) or 10 mg/L bialaphos (Somleva et al., 2002, *Crop Sci.* 42: 2080-2087; Somleva, 2006, *Agrobacterium Protocols,* Wang K., ed., pp 65-74: Humana Press). Transgenic plants overexpressing the transcription factor genes PvSTR1, PvSTIF1, and PvBMY1 were obtained from cultures transformed with the vectors pMBXS809, pMBXS810, and pMBXS855 (TABLE 2). The presence of the transcription factor and marker genes in putative transformants was confirmed by PCR using primers specific for the coding regions of the transgenes and the amplification conditions described previously (Somleva et al., *Plant Biotechnol. J.* 6: 663-678). More than 200 $T_0$ plants representing 58 independent transformation events were identified (TABLE 4). Plants regenerated from untransformed callus cultures and grown under the same conditions were used as controls (non-transgenic plants; wild-type plants) in expression and functional analyses of transgenic lines.

TABLE 4

Transformations for overexpression of transcription factors in switchgrass.

| Vector | Gene of interest | Alamo genotype 56[1] | | Alamo genotype 16[2] | |
|---|---|---|---|---|---|
| | | # events[3] | # plants[4] | # events[3] | # plants[4] |
| pMBXS809 | PvSTR1 | 8 | 60 | 6 | 31 |
| pMBXS810 | PvSTIF1 | 14 | 44 | 12 | 60 |
| pMBXS855 | PvBMY1 | 9 | 27 | 9 | 14 |
| | Total: | 31 | 111 | 27 | 105 |

[1]immature inflorescence-derived callus cultures from this genotype were transformed;
[2]mature caryopsis-derived callus cultures from this genotype were transformed;
[3]number of bialaphos-resistant callus lines producing at least one transgenic plant;
[4]number of primary transformants (as confirmed by PCR).

After transfer to soil, transgenic and wild-type plants obtained from different transformation experiments were grown in a greenhouse at 27° C./24° C. (day/night) with supplemental lighting (16-h photoperiod, sodium halide lamps).

Example 4

Expression Analyses of Transgenic Switchgrass Plants Transformed with the Genes Encoding the Transcription Factors PvSTR1, PvSTIF1, and PvBMY1

Figure 8:
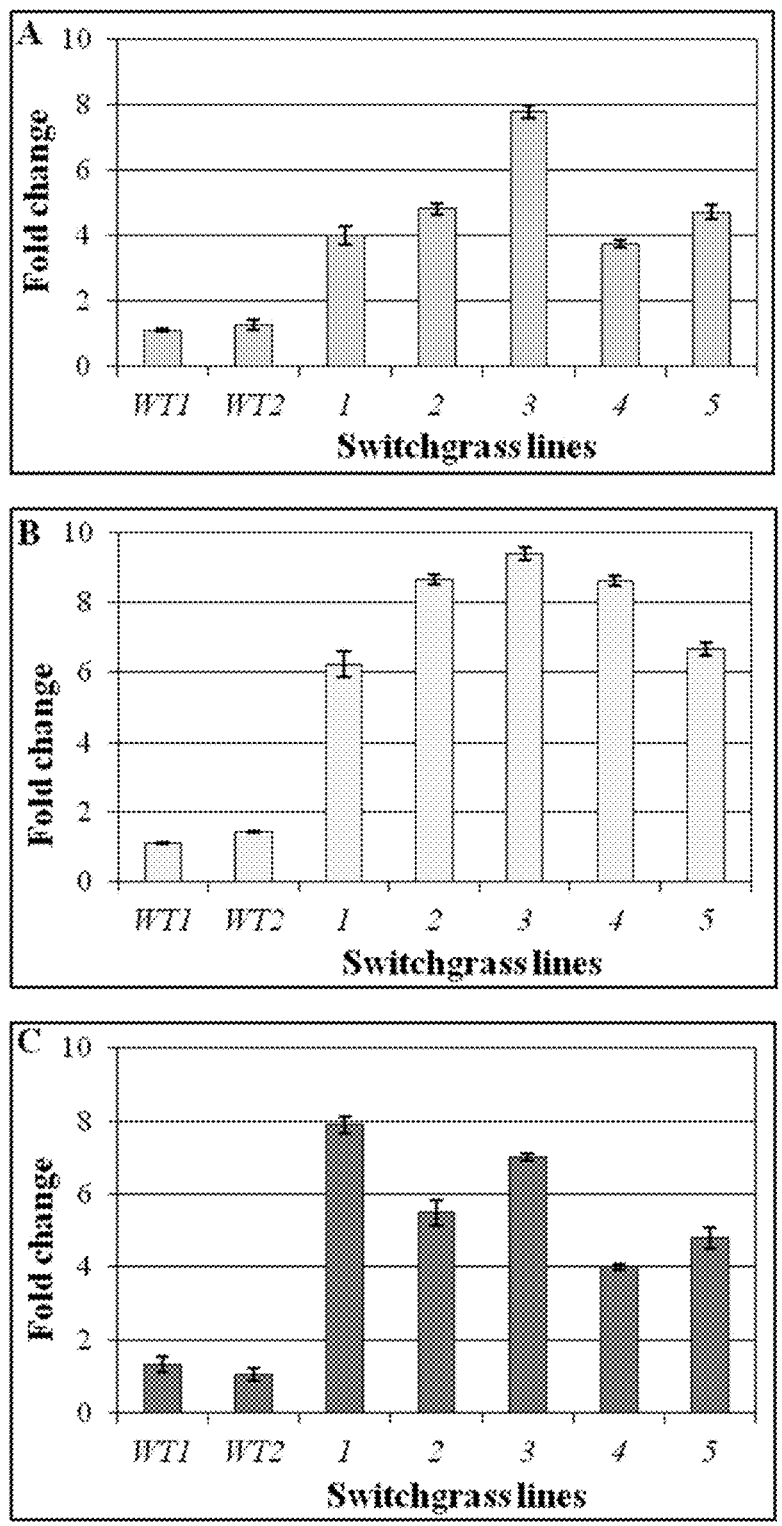
FIG. 8 shows results from qRT-PCR (quantitative reverse transcription polymerase chain reaction or real-time RT-PCR) analysis of the overexpression of the transcription factor genes PvSTR1 (A), PvSTIF1 (B) and PvBMY1 (C) in transgenic switchgrass plants prior to transfer to soil. β-actin amplification was used for transcript normalization. WT1, plants regenerated from non-transformed mature caryopsis-derived callus cultures from genotype 16; WT2, plants regenerated from non-transformed immature inflorescence-derived cultures from genotype 56; 1-5, transgenic lines representing independent transformation events. Data presented as mean values±SE (n=3).

In all experiments, total RNA was isolated from the second youngest leaf of primary transformants and control wild-type plants (3 plants per line) prior to transfer to soil using RNeasy Plant Mini Kit (Qiagen). After DNase treatment and column purification, different amounts of RNA were used for RT-PCR and qRT-PCR (quantitative reverse transcription polymerase chain reaction or real-time RT-PCR). Quantitative analysis of the differences in the expression levels of the TF genes in transgenic and control lines was performed by qRT-PCR using β-actin as a reference. For each sample, 500 ng of total RNA was converted into cDNA using iScript cDNA synthesis kit (Bio-Rad). The cDNA was diluted and subjected to real-time PCR using Fast SYBR® Green Master Mix (Life Technologies) in an Applied Biosystems 7500 Fast Real-Time PCR system. The amplification curves for each line were generated and used to calculate the relative expression ratio (fold change) compared to the wild type control. All of the transgenic lines analyzed showed significantly higher levels of expression of the transcription factor genes in the transgenic lines as compared to the control plants transcript accumulation (from 3 to 9.5 times higher as shown in FIG. 8).

Example 5

Effects of the Overexpression of the Transcription Factors PvSTR1, PvSTIF1 and PvBMY1 on Biomass Production and Photosynthetic Activity in Transgenic Switchgrass Plants For functional characterization of PvSTR1, PvSTIF1 and PvBMY1 transcription factors, biochemical and physiological analyses were performed with transgenic and control wild-type switchgrass plants grown in soil for two months. Both groups of plants were from two Alamo genotypes—56 and 16 (our designation) differing in their morphology.

Measurements of Photosynthetic Activity:

For analyses of the photosynthesis rate in plants overexpressing the TF genes of the invention, various parameters were measured in light adapted leaves using a Dual-PAM-100 Measuring System (Heinz Walz GmbH). All measurements were performed with the leaf attached to the second node from the base of vegetative tillers with the forth emerging leaf.

The functioning of photosystem I (PSI) and photosystem II (PSII) was studied in terms of photochemical quantum yield (Y) and electron transport rate (ETR). Transgenic lines with improved photosynthetic capacity compared to wild type controls from the corresponding genotypes were identified (results are summarized in TABLE 5 for PvSTR1, PvSTIF1 and PvBMY1 lines, respectively). In some of the transgenic plants analyzed, the quantum yield of PSI and PSII were significantly increased at photosynthetically active radiation (PAR) of 30-37 μmol m$^{-2}$ s$^{-1}$ (TABLE 5). The electron transport rates of PSI and PSII in some of the transgenic plants were significantly elevated compared to the wild type control plants at PAR≥119 μmol m$^{-2}$ s$^{-1}$ (TABLE 5).

TABLE 5

Effect of the overexpression of transcription factors on photosynthesis.

| TF gene | Y(I) | | Y(II) | | ETR(I) | | ETR(II) | |
|---|---|---|---|---|---|---|---|---|
| | Max value[1] | % to control[2] | Max value[1] | % to control[2] | Max value[1] | % to control[2] | Max value[1] | % to control[2] |
| PvSTR1 | 0.802 | 137 | 0.735 | 112 | 46.8 | 131 | 12.2 | 130 |
| PvSTIF1 | 0.746 | 125 | 0.714 | 108 | 49.7 | 139 | 12.8 | 136 |
| PvBMY1 | 0.887 | 148 | 0.722 | 110 | 48.5 | 136 | 13.2 | 140 |

[1]The maximum value measured in individual transgenic switchgrass plants;
[2]Compared to the average values (5-6 plants, 2-3 measurements per plant) measured in the corresponding wild-type controls in terms of genotype, growth period and sampling date;
Abbreviations: Y(I), photochemical quantum yield of photosystem I (PSI) - reflects the efficiency of quantum energy absorption by PSI reaction centers; Y(II), effective quantum yield of photosystem II (PSII) - represents the portion (from 0 to 1) of absorbed quanta that is converted into chemically fixed energy by the PSII reaction centers (the other portion of the quanta is dissipated into heat and fluorescence); ETR(I), electron transport rate of PSI - represents the rate of the cyclic or non-cyclic transfer of electrons from the excited reaction-center chlorophyll a molecule to the electron acceptor(s); ETR(II), electron transport rate of PSII - reflects the efficiency of the non-cyclic electron transfer.

Because of the linear correlation between the quantum yield of PSII and $CO_2$ fixation in $C_4$ plants (Leipner et al., 1999, Environ. Exp. Bot. 42: 129-139; Krall & Edwards, 1992, Physiol. Plant. 86: 180-187), the data suggested that the overexpression of the transcription factors resulted in improvement of the overall rate of photosynthesis (TABLE 5). This suggestion was supported by the significant increase in the electron transport rate (TABLE 5) based on the linear correlation between photosynthesis rate and ETR due to the lack of photorespiration in $C_4$ species (Kakani et al., 2008, Photosynthetica 46: 420-430). In addition, the enhanced ETR of PSI in some of the transgenic lines (TABLE 5) could indicate increased cyclic electron transport around PSI which provides the additional ATP needed for the $CO_2$ fixation cycle of the $C_4$ photosynthesis (Kiirats et al. 2010, Photosynth. Res. 105: 89-99).

After measurements of the photosynthetic activity, the leaf blades were sampled and used for determination of the contents of primary metabolites and photosynthetic pigments as well as for RNA and protein isolation.

Primary Metabolites:

Leaf tissue was ground in liquid nitrogen and freeze-dried for 3 days. Resultant leaf powder was used for measurements of the levels of primary metabolites using different analytical methods: a quantitative, enzymatic assay for starch (Starch Assay Kit, Sigma) and HPLC for soluble sugars and fatty acids.

The levels of products of the central carbon metabolism (starch, sucrose, glucose, and fatty acids) were measured in more than 80 transgenic plants representing 30 independent lines (10 lines/TF gene). The results are summarized in TABLE 6.

Photosynthetic Pigments:

Chlorophyll a, chlorophyll b, and carotenoids were determined in freshly harvested leaf tissue following a previously described procedure (Lichtenhaler, 1987, Methods Enzymol., 148: 350-382). The experiments were performed with 97 transgenic plants representing 30 independent lines (10 lines/TF gene). The results are summarized in TABLE 6.

This initial screening resulted in the identification of transgenic lines (2-5 plants per line) accumulating primary metabolites and pigments at levels significantly higher than the control untransformed plants grown under the same conditions. The data confirmed the predicted function of the tested TF genes as global regulators of the central carbon metabolism (see Example 1) and correlated with the results from the gene expression microarray analysis (see Example 7).

TABLE 6

Summary of the results from screening of transgenic switchgrass lines overexpressing the TF genes PvSTR1, PvSTIF1, and PvBMY1.

| TF gene | Line ID | Metabolites | | | | | Biomass | |
|---|---|---|---|---|---|---|---|---|
| | | Starch | Soluble sugars | Fatty acids | Pigments | | Dry weight | No. of tillers |
| | | | | | Chlorophyll | Carotenoids | | |
| PvSTR1 | 56-1 | 128 | 101 | 123 | 144 | 133 | 132 | 118 |
| | 56-2 | 125 | 97 | 111 | 137 | 125 | 112 | 111 |
| | 56-3 | 123 | 156 | 107 | 88 | 79 | 102 | 95 |
| | 56-7 | 160 | 138 | 117 | 144 | 141 | 139 | 131 |
| | 56-9 | 159 | 120 | 115 | 116 | 111 | 140 | 128 |
| | 56-13 | 152 | 125 | 107 | 201 | 181 | 143 | 152 |
| | 56-14 | 339 | 244 | 80 | 109 | 100 | 113 | 112 |
| | 16-4 | n.a. | n.a. | 85 | 93 | 80 | 91 | 114 |
| | 16-5 | 113 | 129 | 89 | 104 | 78 | n.a. | n.a. |
| | 16-6 | 168 | 115 | 90 | 119 | 124 | 103 | 111 |
| PvSTIF1 | 56-2 | 180 | 93 | 130 | 142 | 129 | 94 | 68 |
| | 56-3 | 104 | 123 | 128 | 136 | 121 | 105 | 108 |
| | 56-4 | n.a. | 86 | 128 | 158 | 134 | 98 | 107 |
| | 56-8 | 223 | 73 | 122 | 163 | 141 | 107 | 102 |
| | 16-1 | 184 | 119 | 91 | 136 | 142 | 131 | 120 |
| | 16-2 | 222 | 101 | 84 | 135 | 134 | 116 | 112 |

TABLE 6-continued

Summary of the results from screening of transgenic switchgrass
lines overexpressing the TF genes PvSTR1, PvSTIF1, and PvBMY1.

| | | | Metabolites | | | | Biomass | |
| | | | | Soluble | Fatty | Pigments | | Dry | No. of |
| TF gene | Line ID | Starch | sugars | acids | Chlorophyll | Carotenoids | weight | tillers |
|---|---|---|---|---|---|---|---|---|
| | 16-3 | 134 | 105 | 89 | 115 | 126 | n.a. | n.a. |
| | 16-4 | 153 | 114 | 88 | 131 | 132 | 137 | 129 |
| | 16-6 | 201 | 88 | 90 | 125 | 139 | 142 | 138 |
| | 16-9 | 186 | 117 | 101 | 125 | 139 | 111 | 126 |
| PvBMY1 | 56-1 | 97 | 96 | 106 | 113 | 113 | 120 | 149 |
| | 56-4 | 174 | 100 | n.a. | 106 | 84 | 115 | 142 |
| | 56-6 | 136 | 137 | 94 | 112 | 98 | 123 | 135 |
| | 56-7 | 123 | 127 | 110 | 117 | 117 | 123 | 156 |
| | 56-8 | 141 | 152 | 99 | 103 | 101 | 133 | 148 |
| | 56-9 | 223 | 192 | 104 | 80 | 73 | 124 | 158 |
| | 16-1 | n.a. | 104 | 71 | 79 | n.a. | n.a. | n.a. |
| | 16-2 | 126 | 99 | 106 | 111 | 111 | 124 | 194 |
| | 16-3 | 270 | 158 | 75 | 92 | 91 | n.a. | 79 |
| | 16-5 | 109 | 71 | 81 | 103 | 122 | 99 | 88 |

Values are average from measurements of 2-5 plants per transgenic line or wild type and are presented as % to the corresponding wild-type control in terms of genotype, growth period and sampling date; n.a.—not analyzed.

Individual plants with significantly higher levels of starch (4.2-fold increase), sucrose (4.4-fold increase), glucose (2.7-fold increase), fatty acids (1.5-fold increase), and total chlorophyll (2.5-fold increase) were identified (TABLE 7).

TABLE 7

Effect of the overexpression of transcription factors
on the levels of primary metabolites and photosynthetic
pigments in switchgrass leaves.

| TF gene | Metabolite/ Pigment | No. of plants analyzed | Max value measured[1] | % to control[2] |
|---|---|---|---|---|
| | Starch | 26 | 11.659 | 405 |
| PvSTR1 | Sucrose | 27 | 5.150 | 331 |
| | Glucose | 27 | 0.575 | 192 |
| (10 lines; | Total fatty acids | 19 | 4.065 | 148 |
| 30 plants | Chlorophyll a + b | 28 | 2.337 | 203 |
| in total) | Carotenoids | 28 | 0.335 | 187 |
| | Starch | 38 | 5.558 | 415 |
| PvSTIF1 | Sucrose | 38 | 2.681 | 165 |
| | Glucose | 38 | 0.735 | 269 |
| (10 lines; | Total fatty acids | 32 | 4.159 | 150 |
| 41 plants | Chlorophyll a + b | 39 | 2.960 | 252 |
| in total) | Carotenoids | 39 | 0.359 | 199 |
| | Starch | 29 | 12.272 | 426 |
| PvBMY1 | Sucrose | 27 | 6.768 | 435 |
| | Glucose | 27 | 0.432 | 132 |
| (10 lines; | Total fatty acids | 23 | 3.916 | 143 |
| 31 plants | Chlorophyll a + b | 30 | 1.589 | 135 |
| in total) | Carotenoids | 30 | 0.259 | 144 |

[1] Data for starch, sucrose, glucose and fatty acids presented as % DW; data for chlorophyll a + b and carotenoids presented as mg/g FW;
[2] Values compared to the corresponding wild-type control in terms of genotype, growth period and sampling date.

A similar increase in the levels of primary metabolites was also detected in other plant parts. For example, the starch content in the second leaf of a plant from line 56-14 was 405% to the control (TABLE 6 and TABLE 7). The third and flag leaves from this plant also contained 4 times more starch than the corresponding leaves from wild-type control plants.

Unexpectedly, some of the transgenic switchgrass plants with significantly increased levels of starch and soluble sugars produced the same or slightly higher amounts of biomass compared to the control plants. For example, a plant from the PvBMY1 line 56-8 (TABLE 6) contained 3.2× more starch and 2.2× more sucrose and glucose than the corresponding control plants but its biomass was only 1% higher than the average biomass of the wild type plants. The total biomass yield of the plant with the highest starch content (415% to control) among the PvSTIF1 plants was similar to the biomass of the control wild-type plants. A 20% increase in biomass production was measured in a plant from the PvSTR1 line 56-14 (TABLE 6) despite the fact that the content of starch and soluble sugars in the leaves of this plant was 333% to the control.

Figure 9:
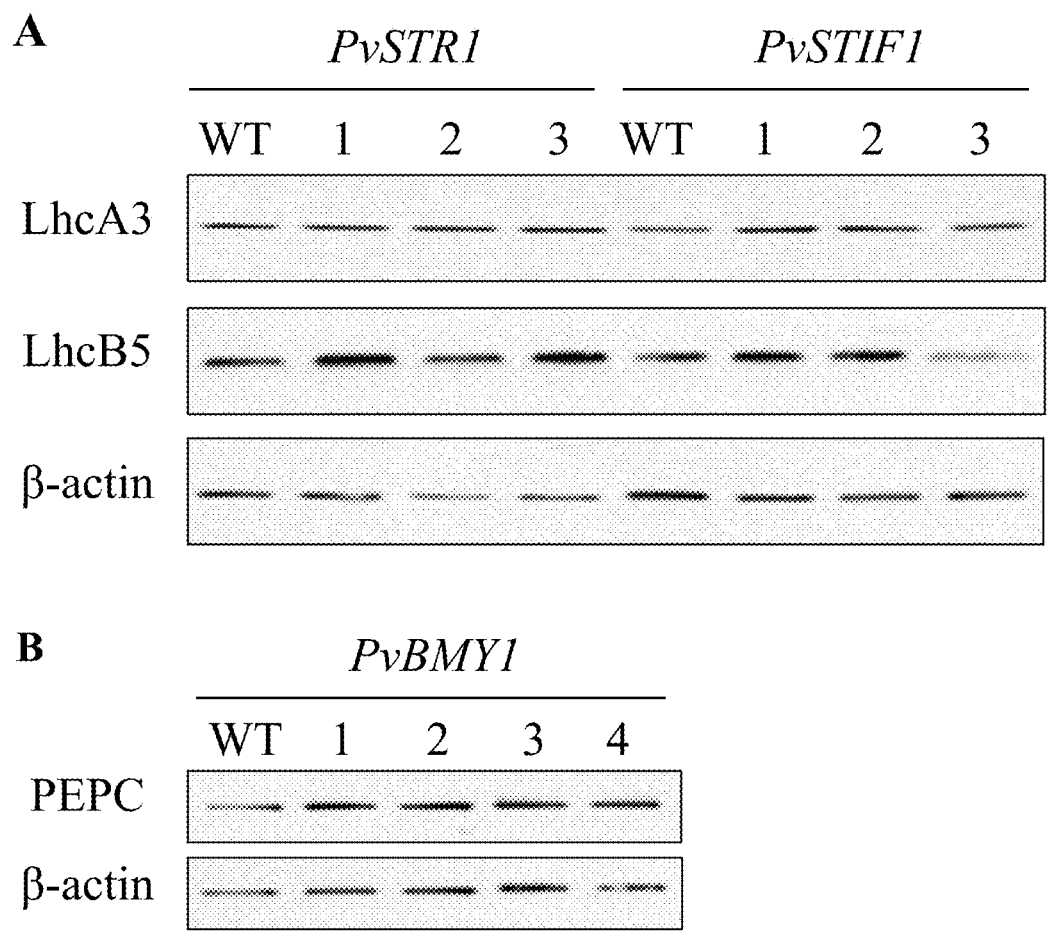
FIG. 9 shows Western blots of total proteins from transgenic and wild-type switchgrass plants. A Protein extracts (6 μg per lane) from PvSTR1 and PvSTIF1 lines incubated with antibodies against the proteins of the light harvesting centers of photosystem I (LhcA3) and photosystem II (LhcB5). β-actin was used as a loading control. B Total protein extracts (6 μg per lane) from PvBMY1 lines incubated with an antibody against phosphoenolpyruvate carboxylase (PEPC). β-actin was used as a loading control. Protein isolation and membrane blotting were performed as described previously (Somleva et al., 2008, *Plant Biotechnol J*, 6: 663-678). Commercially available antibodies (Agrisera) were used for protein detection. An ultra-sensitive chemiluminescent substrate system (Thermo Scientific) was used for signal development. Lanes: WT—a control, wild-type plant; 1 to 4—transgenic switchgrass plants representing different TF lines.

Protein Analyses:

Western blot analysis of total proteins was performed as described previously (Somleva et al., 2008, *Plant Biotechnol. J.* 6: 663-678). An increase in the abundance of the proteins of the light harvesting centers of PSI (LhcA proteins) and PSII (LhcB proteins) was detected in most of the PvSTR1 and PvSTIF1 lines analyzed compared to the corresponding wild-type control (examples for LhcA3 and LhcB5 are shown in FIG. 9A). These findings are in agreement with the enhanced chlorophyll content in these lines (TABLE 6 and TABLE 7). The accumulation of phosphoenolpyruvate (PEPC) protein in most of the PvBMY1 lines was higher than in the wild-type plants (an example is shown in FIG. 9B).

This is the first report on the effect of any transcription factor on the abundance of Lhc and PEPC proteins.

Biomass Accumulation and Plant Development:

The growth and development of transgenic switchgrass plants overexpressing the transcription factors of the invention were monitored in terms of plant height and number of tillers after transfer to soil. All of the transgenic plants had larger leaf blades and longer internodes compared to the wild type plants from the corresponding genotype.

Total biomass yield was evaluated in plants grown under greenhouse conditions for five months as described in publications, WO 2012/037324 A2 and US 2012/0060413 to Metabolix. All vegetative and reproductive tillers at different developmental stages from each plant were counted and cut below the basal node. Leaves and stem tissues were separated, cut into smaller pieces, air-dried at 27° C. for 12-14 days and dry weight measurements were obtained. The number and ratio of vegetative to reproductive tillers were evaluated to compare the developmental patterns of transgenic and control plants.

The total biomass of 82 transgenic plants representing 29 TF lines and 12 wild type plants was measured. Transgenic lines with increased biomass yield (up to 142% to the control) and number of tillers (up to 194% to the control) were obtained (TABLE 6).

Most of the transgenic plants—81.5% of the analyzed PvSTR1 plants, 66.7% of the PvSTIF1 plants, and 82.1% of the PvBMY1 plants had higher biomass yield (up to 162%) compared to the control plants (TABLE 8). TF-overexpressing plants with significantly increased number of tillers (up to 216% to the control) were also identified.

TABLE 8

Effect of the overexpression of transcription factors on switchgrass biomass production.

| TF gene | Biomass | Max value measured [g DW] | % to control[1] |
|---|---|---|---|
| PvSTR1 | Total | 90.6 | 162 |
| (10 lines; | Leaves | 25.9 | 149 |
| 27 plants | Stem | 71.4 | 184 |
| analyzed) | No. of tillers[2] | 45 | 190 |
| PvSTIF1 | Total | 70.9 | 153 |
| (10 lines; | Leaves | 17.5 | 162 |
| 27 plants | Stem | 53.4 | 150 |
| analyzed) | No. of tillers[2] | 25 | 166 |
| PvBMY1 | Total | 79.6 | 142 |
| (9 lines; | Leaves | 25.2 | 145 |
| 28 plants | Stem | 56.8 | 146 |
| analyzed) | No. of tillers[2] | 51 | 216 |

[1]Values compared to the corresponding wild-type control in terms of genotype, growth period and sampling date;
[2]Total number of vegetative and reproductive tillers at different developmental stages (emerging tillers not included).

Similar patterns in the biomass productivity were observed in plants grown in soil for six months after repotting. For example, a plant from line 16-6 whose biomass was 148.8% to the control 4 months after transfer to soil yielded about 300 g DW total biomass after repotting which was 182.3% to the corresponding control.

Example 6

Evaluation of the Stress Response of Switchgrass Lines Overexpressing Transcription Factors To validate the role of the transcription factors of the invention in improvement of plant stress tolerance, a novel method for screening of large populations of transgenic and control plants for their response to drought and salinity has been developed. It utilizes the previously developed tissue culture-based technology for propagation and improvement of polymer production in transgenic switchgrass plants (WO 2010/102220 A1 and US 2010/0229256 A1 to Somleva and Ali).

The stress-inducing conditions were established using non-transformed, wild-type plants. Polyethylene glycol (PEG) and NaCl were chosen for induction of drought and salinity stresses, respectively. Hundreds of plants were regenerated from immature inflorescence-derived callus cultures from Alamo genotype 56. After 3-4 weeks culture on MS medium for plant regeneration, phenotypically uniform plants were transferred to larger tissue culture containers containing the same medium supplemented with different concentrations of PEG and NaCl. Since the first stress-induced changes in plant morphology, such as leaf wilting and yellowing were observed after 3-4 days of treatment in preliminary experiments, this time period was used in the subsequent experiments. The relative water content (RWC), levels of photosynthetic pigments and abundance of the chloroplastic Cu—Zn superoxide dismutase (SOD) protein were used as stress markers. They were measured as follows: RWC according to Smart & Bingham, 1974, *Plant Physiol.* 53: 258-260, pigments as described by Lichtenhaler, 1987, *Methods Enzymol.*, 148: 350-382 and SOD using a Plant SOD ELISA kit (MyBioSource).

Three different concentrations of the stress inducing agents were tested in 3 replicates each (10 plants/replicate). Based on the results from these treatments, 200 mM NaCl and 15% PEG were used in the experiments with the TF plants.

Plants regenerated from immature inflorescence-derived callus cultures initiated from well characterized TF lines along with wild type plants (regenerated from non-transformed cultures) were subjected to stress-inducing treatments under the conditions described above. Non-treated transgenic and wild type plants served as controls. All treatments were conducted in 3-4 replicates (10 plants per replicate).

Figure 10:
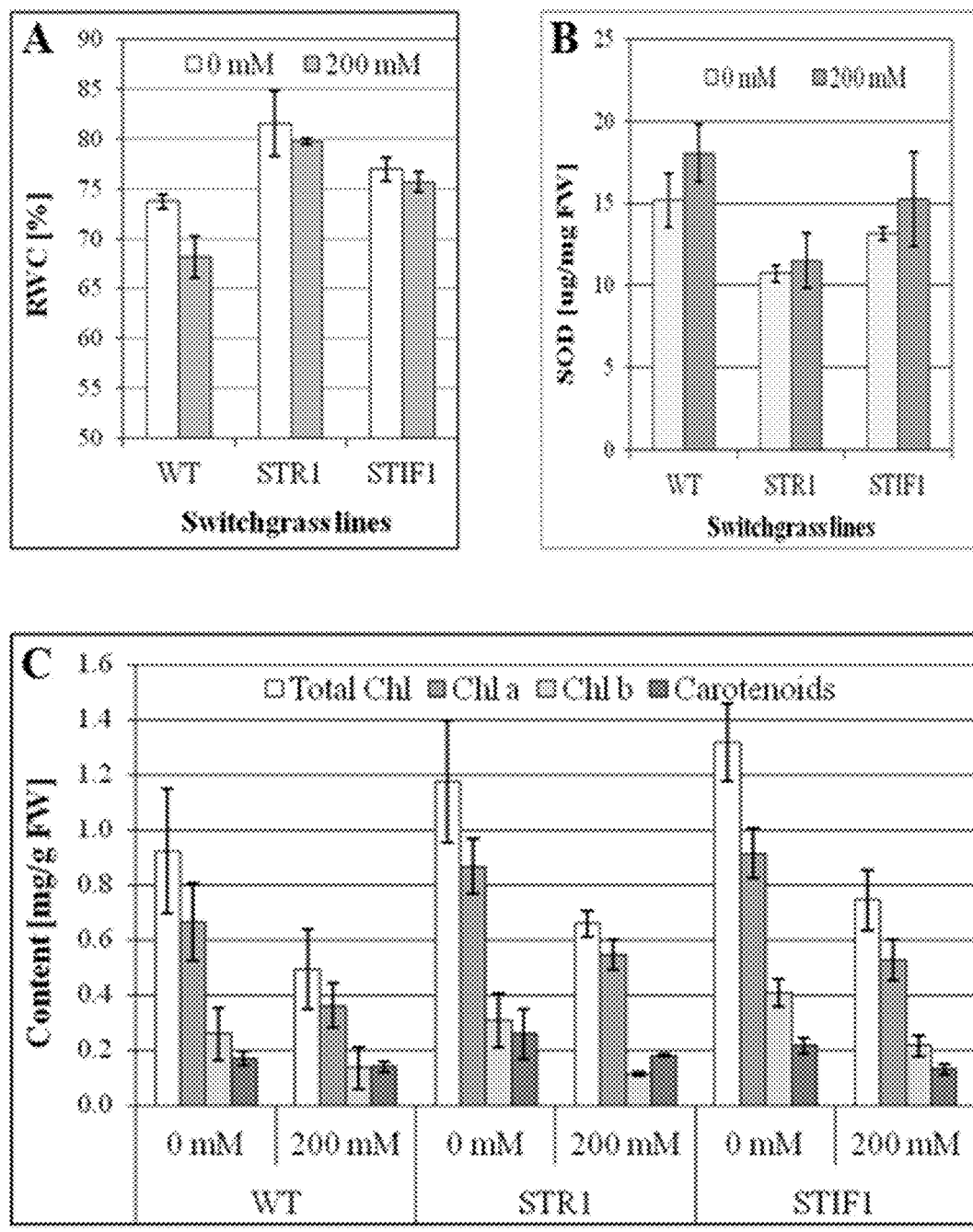
FIG. 10 illustrates the effect of high salinity stress on relative water content (A), the abundance of the chloroplastic Cu—Zn superoxide dismutase (SOD) protein (B) and levels of photosynthetic pigments (C) in switchgrass plants overexpressing the PvSTR1 and PvSTIF1 genes. Bars represent mean±SD values (n=3).

As shown in the example in FIG. 10, treatment with 200 mM NaCl resulted in a slight decrease in RWC in the transgenic plants—2.2% and 1.6% in PvSTR1 and PvSTIF1 plants, respectively, while RWC in the wild-type plants was reduced with 7.6% compared to the non-treated control (FIG. 10A). Interestingly, RWC in the non-stressed TF plants was 4-8% higher than the relative water content in the wild type plants. Non-treated transgenic plants contained significantly lower amounts of the chloroplastic Cu—Zn superoxide dismutase (SOD) protein (as determined by ELISA) compared to non-stressed wild-type plants (FIG. 10B). High salinity stress conditions induced a similar increase in SOD levels in the PvSTIF1 and wild-type plants (16% and 19%, respectively) while the SOD protein content detected in the PvSTR1 plants was with about 7% higher than in the non-treated control (FIG. 10B). The non-treated TF plants also contained higher levels of photosynthetic pigments—27% and 43% higher total chlorophyll content in PvSTR1 and PvSTIF1 plants, respectively, compared to the unstressed wild type plants (FIG. 10C). The salinity stress caused a significant decrease (37-63%) in the chlorophyll content in both transgenic and wild type plants. The content of carotenoids in the stressed wild type plants was reduced with 18.2% compared to the non-treated plants, while in the TF plants it was 30-39% lower than in the corresponding control plants (FIG. 10C). Similar changes in the stress markers were observed when the plants were subjected to PEG-induced drought stress.

This is the first report demonstrating the effect of the overexpression of the transcription factors of the invention on plant stress response and the possibility to test the role of any transcription factors in this process under in vitro conditions.

Example 7

Global Gene Expression Analysis of Switchgrass Transgenic Lines Overexpressing PvSTR1, PvSTIF1 and PvBMY1

To identify the genes whose regulation by the transcription factors of the invention resulted in the observed improved biomass yield and stress tolerance (Examples 5 and 6), gene expression profiling was performed using an Affymetrix switchgrass cDNA GeneChip.

Gene expression microarrays, data processing and normalization: Three of the best performing switchgrass lines overexpressing one of the TF genes (TABLES 6-8) were selected for the microarray gene expression analysis. Total RNA was isolated from the second leaf of vegetative tillers (3-4 tillers per plant) as described in Example 3. RNA extracts from three plants from each line were pooled and their quality was evaluated using RNA Nano Chip (Agilent Technologies) according to the manufacturer's instructions. The microarray analysis was conducted using an Affymetrix switchgrass GeneChip containing probes to query approximately 43,344 transcripts following the manufacturer's protocol website: affymetrix.com). Raw numeric values representing the signal of each feature were imported into AffylmGUI and the data were background corrected, normalized, and summarized using Robust Multiarray Averaging (RMA). A linear model was used to average data between the replicates and to detect differential expression. Data quality was assessed using box and scatter plots to compare the intensity distributions of all samples and to assess the gene expression variation between the replicates, respectively. Genes with significant probe sets (FDR<0.1) with ≥2.0-fold changes compared to the corresponding wild-type controls were considered differentially expressed.

Identification and functional annotations of differentially expressed genes regulated by PvSTR1, PvSTIF1 and PvBMY1: Since the genome sequence of switchgrass is not well annotated, a reciprocal BLAST analysis (a common computational method for predicting putative orthologs consisting of two subsequent sets of BLAST analysis) was performed for functional annotation of the differentially expressed genes and their corresponding orthologs. The first BLAST was conducted using the well annotated whole genome sequences of maize, sorghum, rice and *Arabidopsis*. BLASTN or TBLASTX are generally used for analyses of a polynucleotide sequence, while BLASTP or TBLASTN— for a polypeptide sequence. The first set of BLAST results may optionally be filtered. The full-length sequences of either the filtered results or non-filtered results are then BLASTed back (second BLAST) against sequences from the organism from which the query sequence is derived. The results of the first and second BLASTs are then compared. If this returns the switchgrass gene originally used as the highest scorer, then the two genes are considered putative orthologs.

Figure 11:
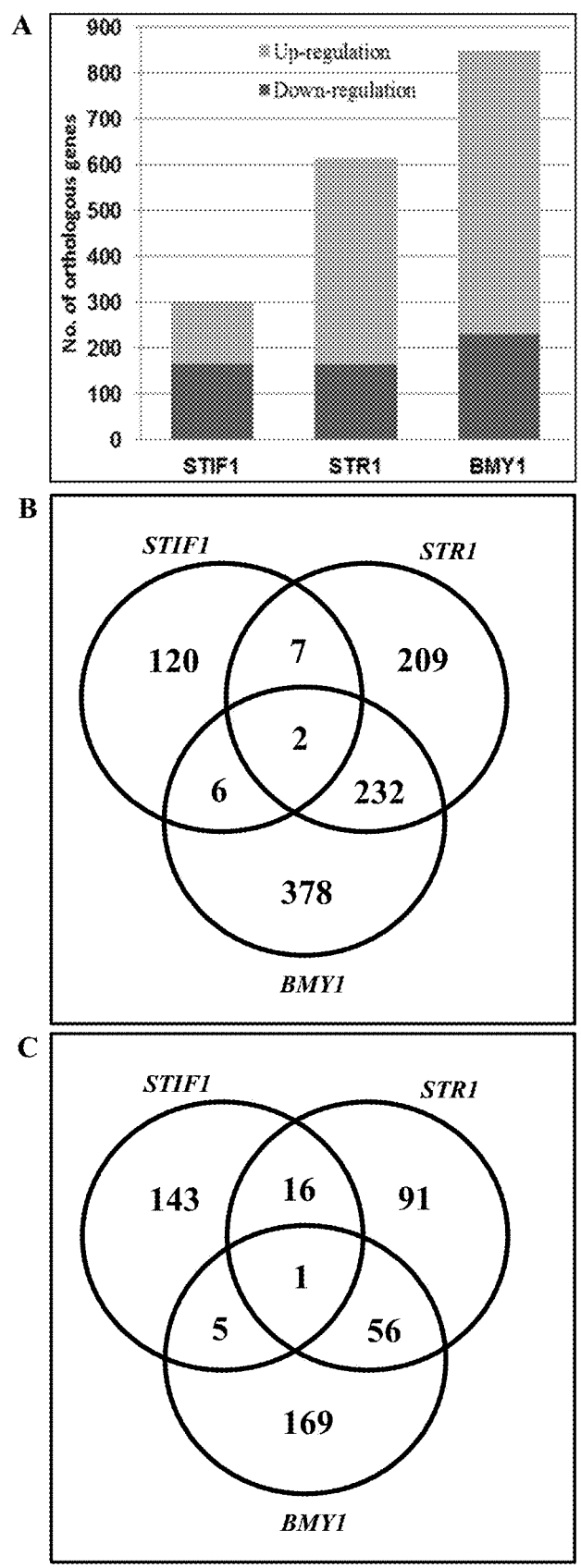
FIG. 11 illustrates the large number of switchgrass genes, including transcription factors whose expression is impacted by over-expression of PvSTR1, PvSTIF1 and PvBMY1. The data is presented as the total number of regulated orthologs (A) as well as the numbers of up-regulated (B) and down-regulated (C) genes common for the three TFs.

The numbers of the annotated genes up- or down-regulated by PvSTR1, PvSTIF1 and PvBMY1 in transgenic switchgrass plants are shown in FIG. 11A. A further analysis of the gene expression data revealed that 450, 135, and 619 genes were up-regulated (FIG. 11B) and 165, 164, and 231 genes were down-regulated (FIG. 11C) by PvSTR1, PvS-TIF1 and PvBMY1, respectively. Only 1-2 genes were commonly regulated by all three TFs. A relatively small portion of the differentially expressed genes regulated by PvSTIF1 was also regulated by the other two TFs, while more than 280 genes were regulated by both PvSTR1 and PvBMY1 (FIG. 11B-C).

These findings indicate that the transcription factors of the invention regulate the expression of genes involved in key processes and pathways by different mechanisms.

Downstream transcription factors regulated by PvSTR1, PvSTIF1 and PvBMY1: Among the up-regulated genes identified by microarray analysis of transgenic switchgrass lines, 80 were predicted to be transcription factors based on the presence of a DNA-binding domain (Plants TF database v. 3.0). Several of these homologous TF genes have functionally been validated in model and crop plants as regulators of genes involved in economically important agronomic traits, such as biomass production, grain yield and abiotic stress tolerance.

These results confirm that the transcription factors of the current invention appear to function as global transcriptional regulators. The number and variety of the transcription factor genes identified by the microarray analysis indicate that PvSTR1, PvSTIF1 and PvBMY1 regulate key genes in several major pathways and their branches either directly or through downstream transcription factors.

Figure 12A:
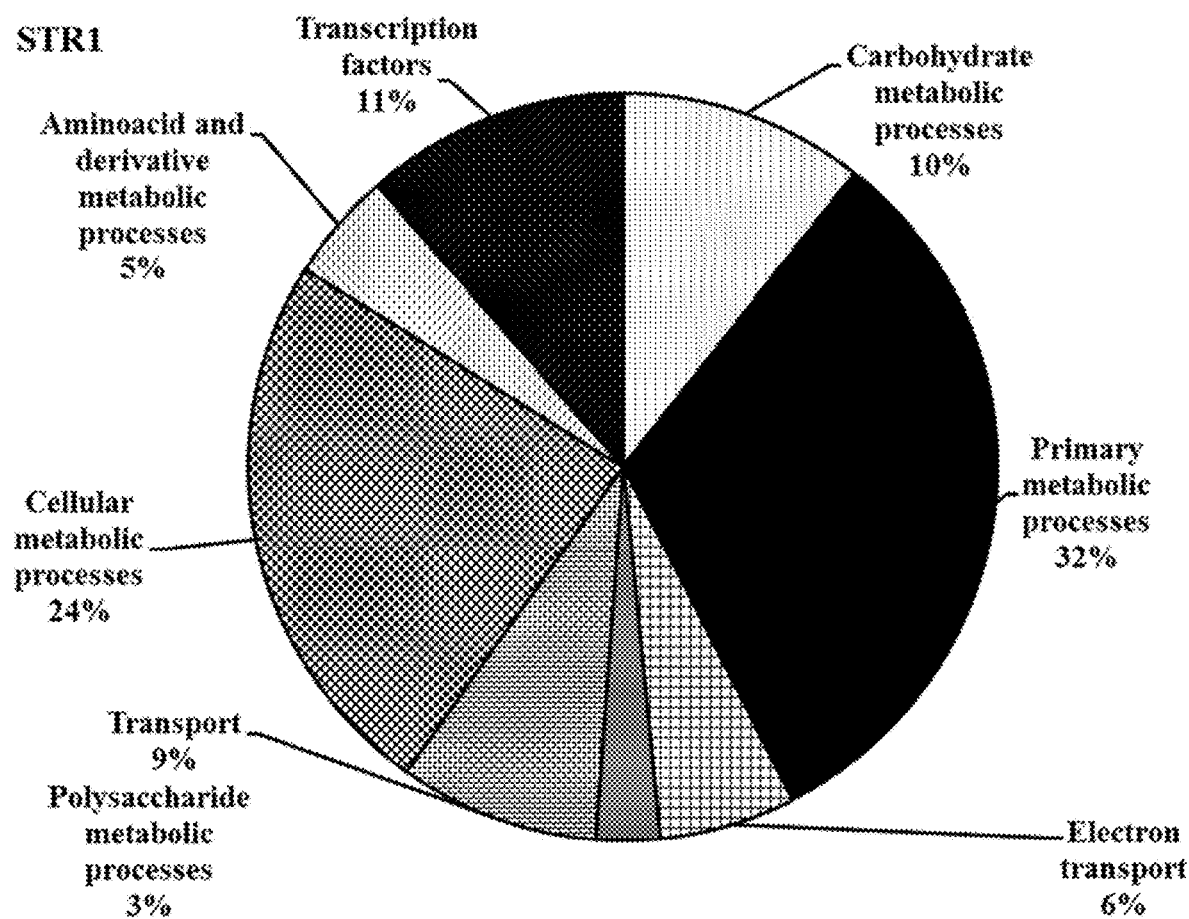
FIG. 12 presents the gene ontology analysis of differentially expressed genes regulated by PvSTR1 (A), PvSTIF1 (B) and PvBMY1 (C) transcription factors. Descriptions of biological functions were assigned on the basis of information retrieved from the world wide web at: bioinfo.cau.edu.cn/agriGO/index.php (P-value calculated by Fisher exact test). Genes that showed more than 2-fold up-regulation and the top enriched pathways are considered for the graphs.
Figure 12B:
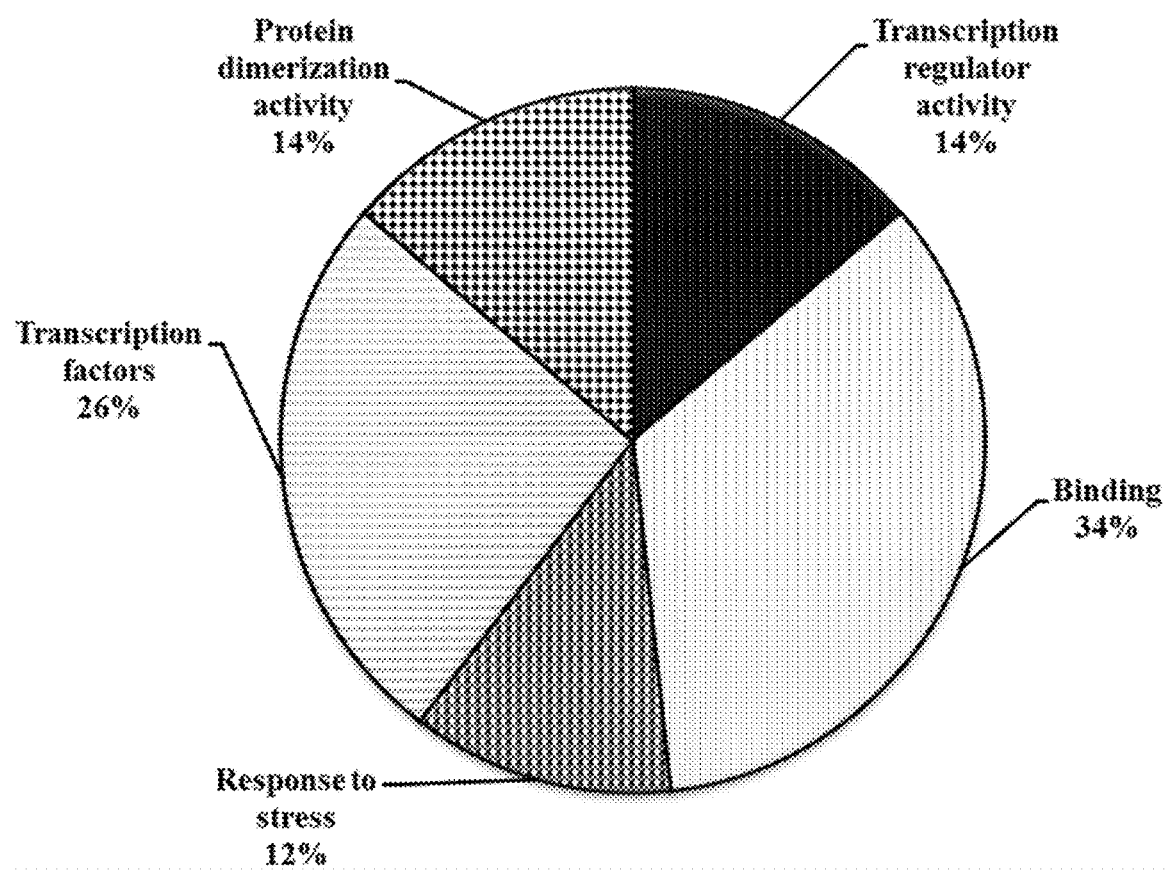
Figure 12C:
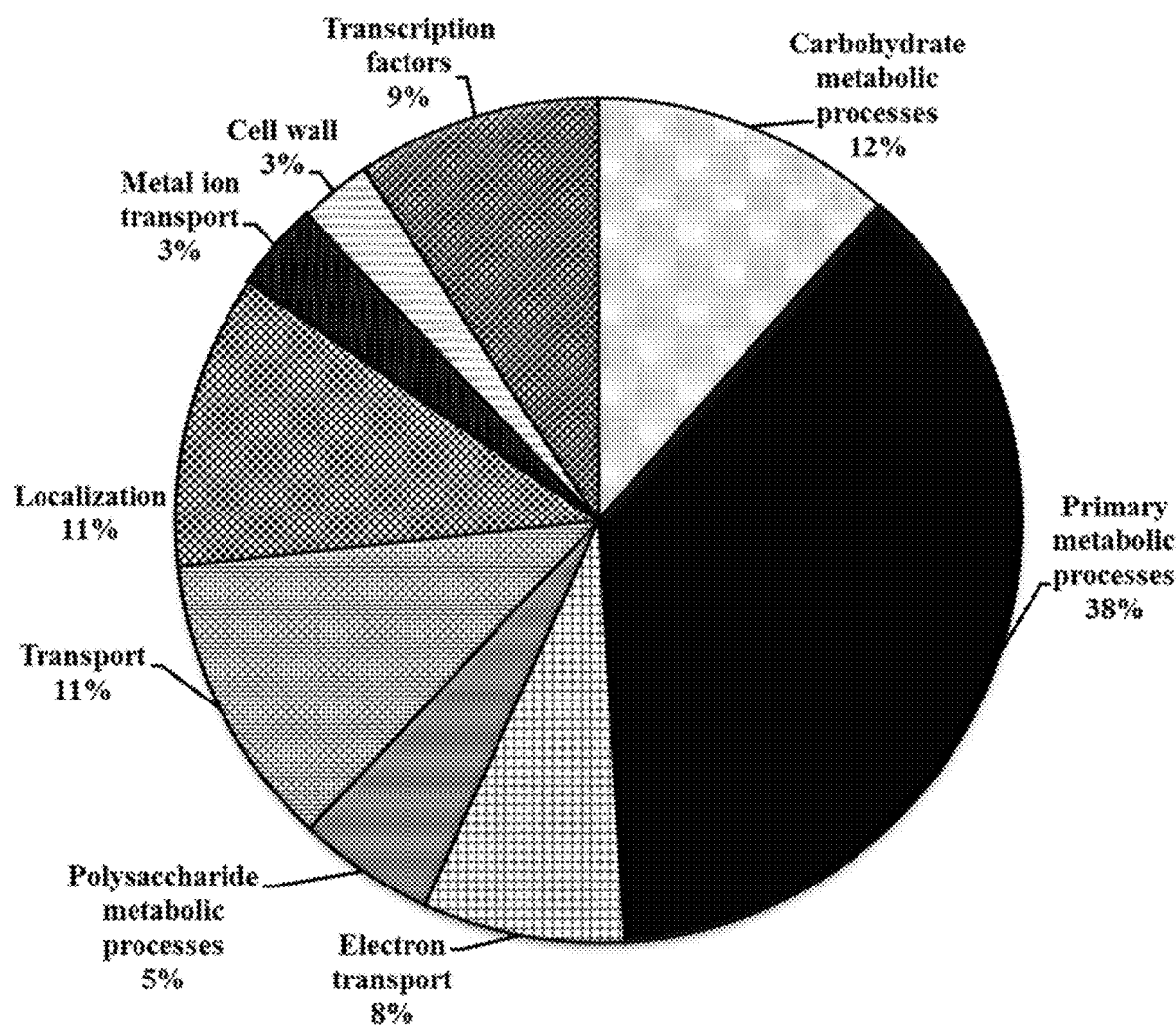

Pathway analysis of differentially expressed genes: For more detailed analysis of the regulatory pattern of the transcription factors of the invention, the differential expression data was used for identification of metabolic and/or signaling pathways or portions of a pathway up-regulated in transgenic switchgrass plants. To investigate the biological functions of differentially expressed genes, gene ontology (GO) analysis was performed to identify the "biological processes category" using a publicly available database website: bioinfo.cau.edu.cn/agriGO/index.php). The results revealed that PvSTR1 and BMY1 significantly increased the expression of several genes involved in primary metabolic processes, such as photosynthesis and carbohydrate metabolism, and in amino acid and cell wall biosynthesis related pathways, while most of the genes up-regulated by PvSTIF1 were categorized as transcription factors (FIG. 12).

Taken together, the results presented here and in Example 5 indicate that central carbon metabolism in the transgenic plants in which the transcription factors have been over expressed results in major global impact on central carbon metabolism.

Transcriptional regulatory network of the central carbon metabolism in switchgrass: Central carbon metabolism (CCM) is crucial for plant growth and development because of its key role in the generation of accessible energy and primary building blocks for other metabolic pathways. The gene expression analysis of switchgrass lines overexpressing PvSTR1, PvSTIF1 and PvBMY1 revealed a distinctive up-regulation of several genes involved in photosynthesis and carbohydrate metabolism as well as in the primary metabolic processes, which are not only necessary for plant growth and development but often confer highly desirable traits.

Example 8

Transcription Factor-Mediated Modifications of Economically Valuable Traits

The switchgrass transcription factors characterized in this invention (SEQ ID NOs: 1-6) and their homologs (SEQ ID NOs: 7-18) can be introduced into the genome of other plants, including but not limited to the varieties of grain and forage cereals and grasses, oilseeds, biomass crops, legumes, trees, and vegetables. The orthologous genes identified in this invention (see Example 1) can also be used for genetic engineering of economically important crops and model plant systems. It is well known, that transcription factor gene sequences are conserved across different species lines, including plants (Goodrich et al., 1993, *Cell* 75:519-530; Lin et al., 1991, *Nature* 353: 569-571). Since the sequences of the switchgrass TFs STR1, STIF1, and BMY1 are related to sequences in other plant species, one skilled in the art can expect that, when expressed in other plants, the switchgrass TF genes and/or their orthologs can have similar effects on plant metabolism and phenotype to those demonstrated herein. For optimal results, both sequential and phylogenetical analyses of the TF genes need to be performed. Since sorghum (*Sorghum bicolor* L.) and maize (*Zea mays* L.) are closely related to switchgrass (FIG. 5), both the switchgrass genes and their corresponding orthologs (FIG. 4) can be expressed to increase the photosynthetic activity, to up-regulate the carbon and nitrogen metabolism as well as to improve the stress tolerance of these crops resulting in higher biomass and/or grain production. In sorghum, for example, PvSTR1, PvSTIF1 and PvBMY1 and their respective orthologs with accession numbers XP002463183, XP002452171 and XP002463163 (identified using the methods described in Example 1) would be expected to have similar effects, while in soybean (*Glycine max* L.), the orthologous genes (accession numbers NP001238200, XP003522453 and XP003546199) would be preferred due to the distant phylogenetic relation between this crop and switchgrass (FIG. 5). In crops with unknown whole genome sequence, orthologous genes from phylogenetically close species can be used. For example, Arabidopsis orthologs of the transcription factors of the invention can be expressed in camelina to achieve the desired trait modification.

The coding sequences can be cloned in expression cassettes and assembled in single- or multi-gene vectors using the methods provided in the invention. Any of the methods for plant transformation described herein can be used to introduce the TF genes into the target plant. For example, particle bombardment with whole plasmids or minimum cassettes can be used for gene delivery to callus cultures initiated from immature zygotic embryos in wheat (Okubara et al., 2002, *Theor. Appl. Genet.* 106: 74-83) and barley (Wan & Lemaux, 1994, *Plant Physiol.* 104: 37-48) and to callus induced from immature leaf rolls from sugarcane (Snyman et al., 2006, *Plant Cell Rep.* 25: 1016-1023) and energy cane (Fouad et al., 2009, *In Vitro Cell. Dev. Biol.* 45: S74). The expression of switchgrass transcription factors and their orthologs can be engineered by *Agrobacterium*-mediated transformation in different crops, such as rice (Sahoo et al., 2011, *Plant Methods* 7:49-60), other small grain crops (reviewed in Shrawat and Lörz, 2006, *Plant Biotech. J.* 4: 575-603), industrial crops (cotton, Leelavathi et al., 2004, *Plant Cell Rep.* 22: 465-470; tobacco, Horsch et al., 1985, *Science* 227: 1229-1231) as well as crops with $C_4$ photosynthesis, such as maize, sugarcane, sorghum, sweet sorghum, and pearl millet (reviewed in Somleva et al., 2013, *Plant Biotech. J.* 11: 233-252). The floral dip method can be used for transformation of oilseed crops, such as canola (Li et al., 2010, *Int. J. Biol.* 2: 127-131) and camelina (Liu et al., 2012, *In Vitro Cell. Dev. Biol.* 48: 462-468). Both physical and biological transformation methods have been developed for some crops (e.g., soybean, reviewed in Yamada et al., 2012, *Breed. Sci.* 61: 480-494) and the more efficient method can be used for the purposes of this invention.

Different promoters can be useful for controlling the expression of the TFs of the invention depending on the crop and phenotype of interest. Both constitutive and inducible promoters (responding to environmental, chemical and hormonal signals) can be used. For example, the maize light-inducible cab-m5 promoter is suitable for engineering bioenergy crops, such as switchgrass (Somleva et al., 2008, *Plant Biotech. J.* 6: 663-678) and sugarcane (Petrasovitch et al., 2012, *Plant Biotech J.* 10: 569-578) because of its high activity in leaf tissue.

Promoters capable of driving the expression of a TF gene in an organ-specific and developmentally-regulated manner are of a particular interest for modifications of economically valuable traits. The engineered spatiotemporal activity of the transcription factors of the invention can be useful, for example, for increased grain yield in maize, rice, wheat, barley and grain varieties of sorghum, for increased oil content in canola and camelina, and for modifications of the biomass composition in bioenergy crops, such as switchgrass, sugarcane, *Miscanthus*, sweet sorghum and energy cane. The transcription factor genes of the invention, their homologs and orthologs can be overexpressed in photosynthetic tissues during different stages of embryo and seed development for improvement of grain yield without increasing the production of vegetative biomass. This approach requires the use of promoters with high activity and tightly controlled specificity. Promising candidates are the promoters of the maize genes cyclin delta 2 (Locus #GRMZM2G476685; SEQ ID NO: 22), phospholipase 2A (Locus #GRMZM2G154523; SEQ ID NO: 23), sucrose transporter (Locus #GRMZM2G081589; SEQ ID NO: 24), and cell wall invertase (Locus #GRMZM2G139300; SEQ ID NO: 25) which have been shown to be expressed in leaves but not in the fertilized ovaries at the onset of seed development (Kakumanu et al., 2012, *Plant Physiol.* 160: 846-847).

Since the genes characterized in the presented invention are global transcriptional regulators, trait modifications can also be achieved through modulating the expression of downstream transcription factors. For example, 10 bZIP transcription factors regulated by the TFs of the invention were identified in transgenic switchgrass by gene expression microarray analysis (see Example 7). Members of the bZIP TF family have been characterized in different plant species and linked to various developmental and physiological processes, such as panicle and seed development, endosperm-specific expression of storage protein genes, vegetative growth and abiotic stress tolerance (reviewed in Nijhawan et al., 2008, *Plant Physiol.* 146: 333-350). In total, 18 MYB transcription factors regulated by PvSTR1, PvSTIF1 and PvBMY1 were also identified in this study (TABLE 8). Some of these genes are well known for their role in major biological processes—development and cell differentiation, photosynthesis and secondary metabolism, stress tolerance and defense response (reviewed in Ambawat et al., 2013, *Physiol. Mol. Biol. Plants* 19: 307-321) and can be useful in different approaches to crop improvement.

Example 9

Transformation of Other Crop Species

*Agrobacterium*-Mediated Transformation of *Miscanthus* Species

*Miscanthus* has been extensively evaluated as a bioenergy crop in Europe since the early 1980s (Lewandowski et al., 2003, *Biomass and Bioenergy*, 25: 335-361) and, more recently, in North America (Heaton et al., 2008, *Global Change Biology*, 14: 2000-2014). The research on biomass productivity and environmental impact has mainly been focused on *M. sacchariflorus* and *Miscanthus x giganteus,* a pollen sterile hybrid between *M. sacchariflorus* and *M. sinensis* (Jorgensen & Muhs, 2001, *In* M. B. Jones and M. Walsh (eds.), *Miscanthus* for energy and fibre. James & James (Science Publishers) Ltd., London, pp. 68-852).

For the development of tissue culture and transformation systems, *Miscanthus x giganteus* plants established in soil from rhizomes and grown under greenhouse conditions at 27° C. with a 16-hour photoperiod using supplemental sodium halide lamps (200 mol/m²/s) were used as an explant source. Immature inflorescences, axillary meristems, and basal portions of leaves were harvested and used for culture initiation after surface sterilization. The initial explants and resultant cultures were incubated at 27° C., in the dark. Their response to various concentrations and combinations of plant growth regulators and different nitrate-to-ammonium ratios in the tissue culture medium was tested. After 3-4 weeks of culture, the number of explants forming callus was scored and the callus type was determined according to visual appearance and morphogenetic ability. Callus formation was observed from all types of explants with significant differences in the callus induction frequency and the ratio of the callus types formed. The results revealed that immature inflorescences were the best explants for callus initiation and that MS basal medium supplemented with the synthetic auxin 2,4-D as a sole plant growth regulator was optimal for callus initiation, induction of somatic embryo formation and suppression of precocious plant regeneration in these cultures.

Two approaches to improving the medium for callus initiation and growth were used. The experiments were performed with callus cultures propagated by monthly transfers on to MS medium containing 5 mg/L of 2,4-D and 30 g/L sucrose for 6-9 months. To determine the optimal auxin concentration for callus growth, pre-weighed pieces of embryogenic callus (30 pieces per replication, 2 replications per variant) were plated on MS medium supplemented with 1, 2, 3, 4, and 5 mg/L of 2,4-D. Cultures grown on MS medium without any plant growth regulators served as a control. After 4 weeks, all calluses were weighed and their growth rate was calculated as %=[(callus final fresh weight−callus initial fresh weight)/callus initial fresh weight]×100. Since the highest growth rate was detected in the presence of 2 mg/L of 2,4-D, this concentration was used for callus initiation, propagation and selection in the transformation experiments.

For further optimization of the tissue culture procedure, the effects of several anti-necrotic compounds on callus growth and embryogenic response were evaluated. Briefly, pre-weighed embryogenic callus (27-77 mg fresh weight per replication, 2 replications per variant) was plated on MS medium containing 2 mg/L 2,4-D and supplemented with ascorbic acid (15 mg/L), cysteine (40 mg/L), and silver nitrate (5 mg/L) alone or in different combinations. Culture growth and development were monitored on a weekly basis and callus growth rate was calculated as described above after 4 weeks. The results showed that callus growth was promoted by ascorbic acid and cysteine and not affected by silver nitrate. Although the highest growth rate was detected in calluses grown in the presence of all three anti-necrotic compounds, some undesired changes in the development of these cultures were also observed. Taken together, the results demonstrated that MS medium supplemented with 2 mg/L of 2,4-D, 15 mg/L of ascorbic acid and 40 mg/L of cysteine was optimal for the growth and development of embryogenic callus cultures.

Since young, developing panicles proved to be an excellent source of explants for callus initiation in *Miscanthus x giganteus,* these studies were further extended in order to develop a novel protocol for in vitro production of immature inflorescences and callus initiation from them. The possibility for vegetative propagation by node cultures was also explored. The top culm node and the nodes below the top one of tillers prior to flowering from plants grown under greenhouse conditions were used as explant sources. After surface sterilization, the nodal segments were incubated in a 10% aqueous solution of polyvinylpyrrolidone (PVP40, Sigma), split longitudinally and plated on to MS medium containing 10 mg/L BAP and 30 g/L sucrose. Individual spikelets from panicles formed from the top node were plated on the optimized medium for callus initiation described above. Resultant calluses were propagated by transfers every 3-4 weeks on to a fresh medium and used in transformation experiments. For plant regeneration, calluses initiated from in vitro developed panicles were plated on hormone-free MS medium and incubated at 27° C. with a 16 h photoperiod (cool white fluorescent bulbs, 80 µmol/m$^2$/s) and subcultured every 3-4 weeks. Plantlets with 3-4 leaves were transferred to larger tissue culture containers with the same medium and grown for another 2-3 weeks prior to transfer to soil.

Shoots produced from nodal segments below the top node were also cultured on hormone-free MS medium for 3-4 weeks prior to transfer to soil.

*Agrobacterium*-mediated transformation of established embryogenic callus cultures initiated from in vitro developed panicles was performed following the previously described procedure for switchgrass transformation (Somleva, 2006, *Agrobacterium Protocols* Wang K., ed., pp 65-74: Humana Press; Somleva et al., 2002, *Crop Sci.* 42: 2080-2087) with the following modifications: infected cultures were co-cultivated with *Agrobacterium tumefaciens* for 5-10 days prior to transfer to a medium supplemented with 3 mg/L bialaphos for callus selection. Using the developed methods, *Miscanthus* species can be engineered with the transcription factor genes of the invention for increased production of biomass and/or modifications of its composition for bioenergy applications.

*Miscanthus sinensis* callus cultures were initiated from mature caryopses and their embryogenic potential was evaluated as described previously for switchgrass (U.S. Pat. No. 8,487,159 to Somleva et al.). They were transformed following the procedure for *Agrobacterium*-mediated transformation of switchgrass (Somleva, 2006, *Agrobacterium Protocols* Wang K., ed., pp 65-74: Humana Press; Somleva et al., 2002, *Crop Sci.* 42: 2080-2087).

*Agrobacterium*-Mediated Transformation of Maize

The binary vectors provided in the invention can be used for *Agrobacterium*-mediated transformation of maize following a previously described procedure (Frame et al., 2006, Agrobacterium Protocols Wang K., ed., Vol. 1, pp 185-199, Humana Press).

Plant material: Plants grown in a greenhouse are used as an explant source. Ears are harvested 9-13 d after pollination and surface sterilized with 80% ethanol.

Explant isolation, infection and co-cultivation: Immature zygotic embryos (1.2-2.0 mm) are aseptically dissected from individual kernels and incubated in *A. tumefaciens* strain EHA101 culture (grown in 5 ml N6 medium supplemented with 100 µM acetosyringone for stimulation of the bacterial vir genes for 2-5 h prior to transformation) at room temperature for 5 min. The infected embryos are transferred scutellum side up on to a co-cultivation medium (N6 agar-solidified medium containing 300 mg/l cysteine, 5 µM silver nitrate and 100 µM acetosyringone) and incubated at 20° C., in the dark for 3 d. Embryos are transferred to N6 resting medium containing 100 mg/l cefotaxime, 100 mg/l vancomycin and 5 µM silver nitrate and incubated at 28° C., in the dark for 7 d.

Callus selection: All embryos are transferred on to the first selection medium (the resting medium described above supplemented with 1.5 mg/l bialaphos) and incubated at 28° C., in the dark for 2 weeks followed by subculture on a selection medium containing 3 mg/l bialaphos. Proliferating pieces of callus are propagated and maintained by subculture on the same medium every 2 weeks.

Plant regeneration and selection: Bialaphos-resistant embryogenic callus lines are transferred on to regeneration medium I (MS basal medium supplemented with 60 g/l sucrose, 1.5 mg/l bialaphos and 100 mg/l cefotaxime and solidified with 3 g/l Gelrite) and incubated at 25° C., in the dark for 2 to 3 weeks. Mature embryos formed during this period are transferred on to regeneration medium II (the same as regeneration medium I with 3 mg/l bialaphos) for germination in the light (25° C., 80-100 µE/m²/s light intensity, 16/8-h photoperiod). Regenerated plants are ready for transfer to soil within 10-14 days.

Agrobacterium-Mediated Transformation of Sorghum

The vectors provided in the invention can be used for sorghum transformation following a previously described procedure (Zhao, 2006, Agrobacterium Protocols Wang K., ed., Vol. 1, pp 233-244, Humana Press).

Plant material: Plants grown under greenhouse, growth chamber or field conditions are used as an explant source. Immature panicles are harvested 9-12 d post pollination and individual kernels are surface sterilized with 50% bleach for 30 min followed by three washes with sterile distilled water.

Explant isolation, infection and co-cultivation: Immature zygotic embryos (1-1.5 mm) are aseptically dissected from individual kernels and incubated in A. tumefaciens strain LBA4404 suspension in PHI-I liquid medium (MS basal medium supplemented with 1 g/l casamino acids, 1.5 mg/l 2,4-D, 68.5 g/l sucrose, 36 g/l glucose and 100 µM acetosyringone) at room temperature for 5 min. The infected embryos are transferred with embryonic axis down on to a co-cultivation PHI-T medium (agar-solidified modified PHI-I medium containing 2.0 mg/l 2,4-D, 20 g/l sucrose, 10 g/l glucose, 0.5 g/l MES, 0.7 g/l proline, 10 mg/l ascorbic acid and 100 µM acetosyringone) and incubated at 25° C., in the dark for 3 d. For resting, embryos are transferred to the same medium (without acetosyringone) supplemented with 100 mg/l carbenicillin and incubated at 28° C., in the dark for 4 d.

Callus selection: Embryos are transferred on to the first selection medium PHI-U (PHI-T medium described above supplemented with 1.5 mg/l 2,4-D, 100 mg/l carbenicillin and 5 mg/l PPT without glucose and acetosyringone) and incubated at 28° C., in the dark for 2 weeks followed by subculture on a selection medium containing 10 mg/l PPT. Proliferating pieces of callus are propagated and maintained by subculture on the same medium every 2 weeks for the remainder of the callus selection process of 10 weeks.

Plant regeneration and selection: Herbicide-resistant callus is transferred on to regeneration medium I (PHI-U medium supplemented with 0.5 mg/l kinetin) and incubated at 28° C., in the dark for 2 to 3 weeks for callus growth and embryo development. Cultures are transferred on to regeneration medium II (MS basal medium with 0.5 mg/l zeatin, 700 mg/l proline, 60 g/l sucrose and 100 mg/l carbenicillin) for shoot formation (28° C., in the dark). After 2-3 weeks, shoots are transferred on to a rooting medium (regeneration II medium supplemented with 20 g/l sucrose, 0.5 mg/l NAA and 0.5 mg/l IBA) and grown at 25° C., 270 µE/m²/s light intensity with a 16/8-h photoperiod. When the regenerated plants are 8-10 cm tall, they can be transferred to soil and grown under greenhouse conditions.

Agrobacterium-Mediated Transformation of Barley

The vectors provided in the invention can be used for transformation of barley as described by Tingay et al., 1997, Plant J. 11: 1369-1376.

Plant material: Plants of the spring cultivar Golden Promise are grown under greenhouse or growth chamber conditions at 18° C. with a 16/8 hours photoperiod. Spikes are harvested when the zygotic embryos are 1.5-2.5 mm in length. Developing caryopses are sterilized with sodium hypochlorite (15 w/v chlorine) for 10 min and rinsed four times with sterile water.

Explant Isolation, Infection and Co-Cultivation:

Immature zygotic embryos are aseptically dissected from individual kernels and after removal of the embryonic axes are placed scutellum side up on a callus induction medium (Gelrite-solidified MS basal medium containing 30 g/l maltose, 1.0 g/l casein hydrolysate, 0.69 g/l proline and 2.5 mg/L dicamba. Embryos are incubated at 24° C. in the dark during subsequent culture. One day after isolation, the embryos are incubated in A. tumefaciens strain AGL1 culture (grown from a single colony in MG/L medium) followed by a transfer on to the medium described above.

Callus Selection:

After co-cultivation for 2-3 d, embryos are transferred on to the callus induction medium supplemented with 3 mg/l bialaphos and 150 mg/l Timentin. Cultures are selected for about 2 months with transfers to a fresh selection medium every 2 weeks.

Plant Regeneration and Selection:

Bialaphos-resistant embryogenic callus lines are transferred to a Phytagel-solidified regeneration medium containing 1 mg/l BA and 3 mg/l bialaphos for selection of transgenic plants and grown at 24° C. under fluorescent lights with a 16/8 h photoperiod. For root development, regenerated plants are transferred to a hormone-free callus induction medium supplemented with 1 mg/l bialaphos. After development of a root system, plants are transferred to soil and grown in a greenhouse or a growth chamber under the conditions described above.

Agrobacterium-Mediated Transformation of Rice

The binary vectors provided in the invention can be used for Agrobacterium-mediated transformation of rice following a previously described procedure (Herve and Kayano, 2006, Agrobacterium Protocols Wang K., ed., Vol. 1, pp 213-222, Humana Press).

Plant material: Mature seeds from japonica rice varieties grown in a greenhouse are used as an explant source.

Culture transformation and selection: Dehusked seeds are surface sterilized with 70% ethanol for 1 min and 3% sodium hypochlorite for 30 min followed by six washes with sterile distilled water. Seeds are plated embryo side up on an induction medium (Gelrite-solidified N6 basal medium supplemented with 300 mg/l casamino acids, 2.88 g/l proline, 30 g/l sucrose and 2 mg/l 2,4-D) and incubated at 32° C., under continuous light for 5 d. Germinated seeds with swelling of the scutellum are infected with A. tumefaciens strain LBA4404 (culture from 3-day-old plates resuspended in N6 medium supplemented with 100 µM acetosyringone, 68.5 g/l sucrose and 36 g/l glucose) at room temperature for 2 min followed by transfer on to a co-cultivation medium (N6 Gelrite-solidified medium containing 300 mg/l casamino acids, 30 g/l sucrose, 10 g/l glucose, 2 mg/l 2,4-D and 100 µM acetosyringone) and incubation at 25° C., in the dark for 3 d.

For selection of transformed embryogenic tissues, whole seedlings washed with 250 mg/l cephotaxine are transferred on to N6 agar-solidified medium containing 300 mg/l casamino acids, 2.88 g/l proline, 30 g/l sucrose, 2 mg/l 2,4-D, 100 mg/l cefotaxime, 100 mg/l vancomycin and 35 mg/l G418 disulfate). Cultures are incubated at 32° C., under continuous light for 2-3 weeks.

Plant regeneration and selection: Resistant proliferating calluses are transferred on to agar-solidified N6 medium containing 300 mg/l casamino acids, 500 mg/l proline, 30 g/l sucrose, 1 mg/l NAA, 5 mg/l ABA, 2 mg/l kinetin, 100 mg/l cefotaxime, 100 mg/l vancomycin and 20 mg/l G418 disulfate. After one week of growth at 32° C., under continuous light, the surviving calluses are transferred on to MS medium (solidified with 10 g/l agarose) supplemented with 2 g/l casamino acids, 30 g/l sucrose, 30 g/l sorbitol, 0.02 mg/l NAA, 2 mg/l kinetin, 100 mg/l cefotaxime, 100 mg/l vancomycin and 20 mg/l G418 disulfate and incubated under the same conditions for another week followed by a transfer on to the same medium with 7 g/l agarose. After 2 weeks, the emerging shoots are transferred on to Gelrite-solidified MS hormone-free medium containing 30 g/l sucrose and grown under continuous light for 1-2 weeks to promote shoot and root development. When the regenerated plants are 8-10 cm tall, they can be transferred to soil and grown under greenhouse conditions. After about 10-16 weeks, transgenic seeds are harvested.

Indica rice varieties are transformed with *Agrobacterium* following a similar procedure (Datta and Datta, 2006, *Agrobacterium Protocols* Wang K., ed., Vol. 1, pp 201-212, Humana Press).

Microprojectile Bombardment-Mediated Transformation of Sugarcane

An expression cassette containing a transcription factor gene can be co-introduced with a cassette of a marker gene (e.g., npt) into sugarcane via biolistics following a previously described protocol (Taparia et al., 2012, *In Vitro Cell. Dev. Biol.* 48: 15-22))

Plant material: Greenhouse-grown plants with 6-8 visible nodes are used as an explant source. Tops are collected and surface sterilized with 70% ethanol. The outermost leaves are removed under aseptic conditions and immature leaf whorl cross sections (about 2 mm) are cut from the region 1-10 cm above the apical node.

Culture initiation, transformation and selection: The isolated leaf sections are cultured on MS basal media supplemented with 20 g/l sucrose, 1.86 mg/l p-chlorophenoxy-acetic acid (CPA), 1.86 mg/l NAA and 0.09 mg/l BA at 28° C., under 30 µmol/m$^2$/s light intensity and a 16/8-h photoperiod for 7 d. Embryogenic cultures are subcultured to fresh medium and used for transformation.

For microprojectile bombardment, leaf disks are plated on the culture initiation medium supplemented with 0.4 M sorbitol 4 hours before gene transfer. Plasmid DNA (200 ng) containing the expression cassettes of a TF and a marker gene is precipitated onto 1.8 mg gold particles (0.6 µm) following a previously described procedure (Altpeter and Sandhu, 2010, *Genetic transformation—biolistics,* Davey & Anthony eds., pp 217-237, Wiley, Hoboken). The DNA (10 ng per shot) is delivered to the explants by a PDS-1000 Biolistc particle delivery system (Biorad) using 1100-psi rupture disk, 26.5 mmHg chamber vacuum and a shelf distance of 6 cm. pressure). The bombarded explants are transferred to the culture initiation medium described above and incubated for 4 days.

For selection, cultures are transferred on to the initiation medium supplemented with 30 mg/l geneticin and incubated for 10 d followed by another selection cycle under the same conditions.

Plant regeneration and selection: Cultures are transferred on to the selection medium described above without CPA and grown at 28° C., under 100 µmol/m$^2$/s light intensity with a 16/8-h photoperiod. Leaf disks with small shoots (about 0.5 cm) are plated on a hormone-free medium with 30 mg/l geneticin for shoot growth and root development. Prior to transfer to soil, roots of regenerated plants can be dipped into a commercially available root promoting powder.

Transformation of Wheat by Microprojectile Bombardment

The gene constructs provided in the invention can be used for wheat transformation by microprojectile bombardment following a previously described protocol (Weeks et al., 1993, *Plant Physiol.* 102: 1077-1084).

Plant material: Plants from the spring wheat cultivar Bobwhite are grown at 18-20° C. day and 14-16° C. night temperatures under a 16 h photoperiod. Spikes are collected 10-12 weeks after sowing (12-16 days post anthesis). Individual caryopses at the early-medium milk stage are sterilized with 70% ethanol for 5 min and 20% sodium hypochlorite for 15 min followed by three washes with sterile water.

Culture initiation, transformation and selection: Immature zygotic embryos (0.5-1.5 mm) are dissected under aseptic conditions, placed scutellum side up on a culture induction medium (Phytagel-solidified MS medium containing 20 g/l sucrose and 1.5 mg/l 2,4-D) and incubated at 27° C., in the light (43 µmol/m$^2$/s) for 3-5 d.

For microprojectile bombardment, embryo-derived calluses are plated on the culture initiation medium supplemented with 0.4 M sorbitol 4 hours before gene transfer. Plasmid DNA containing the expression cassettes of a TF and the marker gene bar is precipitated onto 0.6-µm gold particles and delivered to the explants as described for sugarcane.

The bombarded explants are transferred to callus selection medium (the culture initiation medium described above containing 1-2 mg/l bialaphos) and subcultured every 2 weeks.

Plant regeneration and selection: After one-two selection cycles, cultures are transferred on to MS regeneration medium supplemented with 0.5 mg/l dicamba and 2 mg/l bialaphos. For root formation, the resulting bialaphos-resistant shoots are transferred to hormone-free half-strength MS medium. Plants with well-developed roots are transferred to soil and acclimated to lower humidity at 21° C. with a 16-h photoperiod (300 µmol/m$^2$/s) for about 2 weeks prior to transfer to a greenhouse.

*Agrobacterium*-Mediated Transformation of Camelina

The gene constructs provided in the invention can be used for camelina transformation by floral dip following a previously described protocol (International Patent Application WO 2011034946).

Plant material: Plants grown from seeds under greenhouse conditions (24° C./18° C. day/night temperatures) with unopened flower buds are used for floral dip transformation.

*Agrobacterium* culture preparation and plant inoculation: The constructs of interest are introduced into *Agrobacterium* strain GV3101 by electroporation. A single colony of GV3101 is obtained from a freshly streaked plate and is inoculated into 5 mL LB medium. After overnight growth at 28° C., 2 ml of culture is transferred to a 500-mL flask containing 300 ml of LB and incubated overnight at 28° C. Cells are pelleted by centrifugation (6000 rpm, 20 min) and diluted to an OD$_{600}$ 0.8 with the infiltration medium containing 5% sucrose and 0.05% (v/v) Silwet-L77 (Lehle Seeds, Round Rock, Tex., USA). Camelina plants are transformed as follows. Pots containing plants at the flowering stage are placed in a vacuum desiccator (Bel-Art, Pequannock, N.J., USA) and their inflorescences are immersed into the *Agrobacterium* culture. A vacuum (85 kPa) is applied for 5 min. Plants are removed from the desiccators, covered with plastic bags and kept at room temperature, in the dark for 24 h. Plants are grown in a greenhouse for seed formation.

Identification of transgenic seeds: To identify bialaphos-resistant seeds, seeds from inoculated plants are harvested, sterilized with 70% ethanol and 10% bleach followed by washes with sterile water. Sterilized seeds are placed on germination and selection medium (half-strength MS basal medium) containing 10 mg/L bialaphos and incubated in a growth chamber at 23/20° C. (day/night) with a 16-h photoperiod (3000 lux). Seedlings with green cotyledons are transferred to soil about six days after initiation of germination.

*Agrobacterium*-Mediated Transformation of *Brassica napus*

Plant material: Mature seeds are surface sterilized in 10% commercial bleach for 30 min with gentle shaking and washed three times with sterile distilled water.

Culture initiation and transformation: Seeds are plated on germination medium (MS basal medium supplemented with 30 g/l sucrose) and incubated at 24° C. with a 16-h photoperiod at a light intensity of 60-80 µE/m²/s for 4-5 d. For transformation, cotyledons with ~2 mm of the petiole at the base are excised from the resulting seedlings, immersed in *Agrobacterium tumefaciens* strain EHA101 suspension (grown from a single colony in 5 ml of minimal medium supplemented with appropriate antibiotics at 28° C. for 48 h) for 1 s and immediately embedded to a depth of ~2 mm in a co-cultivation medium (MS basal medium with 30 g/l sucrose and 20 µM benzyladenine). The inoculated cotyledons are incubated under the same growth conditions for 48 h.

Plant regeneration and selection: After co-cultivation, cotyledons are transferred on to a regeneration medium comprising MS medium supplemented with 30 g/l sucrose and 20 µM benzyladenine, 300 mg/l timentin and 20 mg/l kanamycin sulfate. After 2-3 weeks, regenerated shoots are cut and maintained on MS medium for shoot elongation containing 30 g/l sucrose, 300 mg/l timentin, and 20 mg/l kanamycin sulfate. The elongated shoots are transferred to a rooting medium comprising MS basal medium supplemented with 30 g/l sucrose, 2 mg/l indole butyric acid (IBA) and 500 mg/L carbenicillin. After root formation, plants are transferred to soil and grown to seed maturity under growth chamber or greenhouse conditions.

*Agrobacterium*-Mediated Transformation of Soybean

The soybean orthologs of the switchgrass transcription factor genes identified in the invention (FIG. 4) are assembled in binary vectors (TABLE 9) and used for *Agrobacterium*-mediated transformation of soybean following a previously described procedure (Ko et al., 2006, *Agrobacterium Protocols* Wang K., ed., Vol. 1, pp 397-405, Humana Press).

Plant material: Immature seeds from soybean plants grown under greenhouse or field conditions are used as an explant source. Young pods are harvested and surface sterilized with 70% 2-propanol for 30 sec and 25% Clorox for 20 min followed by three washes with sterile distilled water.

Culture transformation and selection: Under aseptic conditions, immature seeds are removed from the pods and the cotyledons are separated from the seed coat followed by incubation in *A. tumefaciens* culture (grown from a single colony at 28° C., overnight) in co-cultivation medium (MS salts and B5 vitamins) supplemented with 30 g/l sucrose, 40 mg/l 2,4-D and 40 mg/l acetosyringone for 60 min. Infected explants are plated abaxial side up on agar-solidified co-cultivation medium and incubated at 25° C., in the dark for 4 d.

For selection of transformed tissues, cotyledons washed with 500 mg/l cephotaxine are placed abaxial side up on a medium for induction of somatic embryo formation (Gelrite-solidified MS medium containing 30 g/l sucrose, 40 mg/l 2,4-D, 500 mg/l cefotaxime, and 10 mg/l hygromycin) and incubated at 25° C., under a 23-h photoperiod (10-20 µE/m²/s) for 2 weeks. After another two weeks of growth under the same conditions in the presence of 25 mg/l hygromycin, the antibiotic-resistant somatic embryos are transferred on MS medium for embryo maturation supplemented with 60 g/l maltose, 500 mg/l cefotaxime, and 10 mg/l hygromycin and grown under the same conditions for 8 weeks with 2-week subculture intervals.

Plant regeneration and selection: The resulting cotyledonary stage embryos are desiccated at 25° C., under a 23-h photoperiod (60-80 µE/m²/s) for 5-7 d followed by culture on MS regeneration medium containing 30 g/l sucrose and 500 mg/l cefotaxime for 4-6 weeks for shoot and root development. When the plants are 5-10 cm tall, they are transferred to soil and grown in a greenhouse after acclimatization for 7 d.

TABLE 9

Plant transformation vectors for overexpression of the orthologous transcription factor genes GmSTR1, GmSTIF1 and GmBMY1 in soybean.

| Vector ID* | TF gene/marker | Annotation | SEQ ID | Coordinates (bp) |
|---|---|---|---|---|
| pMBXS884 | GmSTR1/hpt | *Agrobacterium* T-DNA right border | 26 | 12780-12805 |
| | | CaMV35S promoter to drive GmSTR1gene | | 9566-11260 |
| | | GmSTR1coding region | | 11269-12124 |
| | | nos terminator | | 12258-12532 |
| | | CaMV35S promoter to drive hptII gene | | 7707-9292 |
| | | hptII coding region | | 6456-7692 |
| | | CaMV35S polyA terminator | | 6248-6450 |
| | | *Agrobacterium* T-DNA left border | | 6173-6198 |
| pMBXS885 | GmSTIF1/hpt | *Agrobacterium* T-DNA right border | 27 | 12384-12409 |
| | | CaMV35S promoter to drive GmSTIF1gene | | 9566-11260 |
| | | GmSTIF1 coding region | | 11269-12055 |
| | | nos terminator | | 11862-12136 |
| | | CaMV35S promoter to drive hptII gene | | 7707-9292 |
| | | hptII coding region | | 6456-7692 |
| | | CaMV35S polyA terminator | | 6248-6450 |
| | | *Agrobacterium* T-DNA left border | | 6173-6198 |
| pMBXS886 | GmBMY1/hpt | *Agrobacterium* T-DNA right border | 28 | 12459-12484 |
| | | CaMV35S promoter to drive GmBMY1gene | | 9566-11260 |
| | | GmBMY1coding region | | 11269-11782 |

TABLE 9-continued

Plant transformation vectors for overexpression of the orthologous transcription factor genes GmSTR1, GmSTIF1 and GmBMY1 in soybean.

| Vector ID* | TF gene/marker | Annotation | SEQ ID | Coordinates (bp) |
|---|---|---|---|---|
| | | nos terminator | | 11937-12211 |
| | | CaMV35S promoter to drive hptII gene | | 7707-9292 |
| | | hptII coding region | | 6456-7692 |
| | | CaMV35S polyA terminator | | 6248-6450 |
| | | *Agrobacterium* T-DNA left border | | 6173-6198 |

*All vectors are based on the transformation vector pCambia3300 found on the world wide web at cambia.org; the hpt gene (conferring resistance to hygromycin) is used as a marker for selection of transformed explants and plants.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method for producing a genetically modified plant or plant cell having an increased carbon flow, the method comprising: a) transforming one or more host plants or plant cells with a vector comprising a nucleic acid encoding a polypeptide having at least 95% identity to SEQ ID NO: 4 operably linked to a promoter; and (b) selecting one or more transformed plants or plant cells for increased carbon flow by selecting for one or more of increased biomass yield, increased starch yield, increased glucose content, or increased sucrose content as compared to a control plant lacking the vector, wherein the promoter is light inducible.

2. The method according to claim 1, the method further comprising collecting seeds comprising the vector from the selected plant.

3. The method according to claim 1, the method further comprising regenerating a plant from the selected plant cell and collecting seeds comprising the vector from the regenerated plant.

4. The method of claim 1, wherein the selected plant further exhibits increased tolerance to one or more abiotic stress factors of excess or deficiency of water and/or light, high or low temperature, or high salinity, as compared to a control plant lacking the vector.

5. The method of claim 1, wherein the promoter comprises positions 8951 to 10645 of SEQ ID NO: 21.

6. The method of claim 1, wherein the host plant is a monocotyledonous plant or a dicotyledonous plant.

7. The method of claim 6, wherein the host plant is switchgrass.

8. The method of claim 6, wherein the host plant is maize.

9. The method of claim 6, wherein the host plant is sugar cane.

10. The method according to claim 1, wherein the host plant is *Miscanthus, Medicago*, sweet sorghum, grain sorghum, sugar cane, energy cane, elephant grass, maize, wheat, barley, oat, rice, soybean, oil palm, safflower, sesame, flax, cotton, sunflower, Camelina, *Brassica napus, Brassica carinata, Brassica juncea*, pearl millet, or foxtail millet.

11. The method of claim 1, wherein the polypeptide has at least 99% sequence identity to SEQ ID NO: 4.

12. The method of claim 11, wherein the host plant is *Miscanthus, Medicago*, sweet sorghum, grain sorghum, sugar cane, energy cane, elephant grass, maize, wheat, barley, oat, rice, soybean, oil palm, safflower, sesame, flax, cotton, sunflower, Camelina, *Brassica napus, Brassica carinata, Brassica juncea*, pearl millet, or foxtail millet.

13. The method of claim 1, wherein the polypeptide comprises SEQ ID NO: 4.

14. The method of claim 13, wherein the host plant is *Miscanthus, Medicago*, sweet sorghum, grain sorghum, sugar cane, energy cane, elephant grass, maize, wheat, barley, oat, rice, soybean, oil palm, safflower, sesame, flax, cotton, sunflower, Camelina, *Brassica napus, Brassica carinata, Brassica juncea*, pearl millet, or foxtail millet.

15. The method according to claim 1, wherein the nucleic acid comprises SEQ ID NO: 1.

\* \* \* \* \*

SEQUENCE LISTING

<160> NUMBER OF SEQ ID NOS: 77

<210> SEQ ID NO 1
<211> LENGTH: 975
<212> TYPE: DNA
<213> ORGANISM: Panicum virgatum

<400> SEQUENCE: 1

```
atgtgcggcg gggccattct cagtgatctc tactcaccag tgaggcggac ggtcactgcc      60
ggtgacctat ggggagagag tggcagcagc aagaatgtga agaactggaa aaggagttct     120
tggaagtttg atgaaggcga tgaagacttt gaagctgatt tcaaggattt tgaggattgc     180
agtagcgagg aggaggtaga ttttggacat gaggaaaaag aattccaatt gaacagttcg     240
aatttcgtgg aattcaatgg ccatactgcc aaagtcacca gcaggaagcg aaagatccag     300
taccgaggga tccggcggcg gccttgcggc aaatgggcag cagaaatcag agacccacag     360
aagggcgtcc gagtttggct tggcacgttc agcactgccg aggaagctgc aagggcatat     420
gacgtggaag ctctacgcat acgtggcaag aaagccaaga tgaatttccc taccaccatc     480
acagctgctg ggaaacacca ccggcagcgt gtggctcgac cggcaaagaa gacgtcacaa     540
gagagcctga agtcaagcaa tgcctctggt catgtcatct cagcaggcag cagtactgat     600
ggcaccgttg tcaagatcga gttgtcacag tcaccagctt ctccactacc agtgtccagc     660
gcatggcttg atgcttttga gctgaagcag cttggtggag aaaccctga agctgatggg     720
agagaaaccc ctgaagaaac tgatcatgaa acgggagtga cagcggatat gttttttggc     780
aatggcgaag tgcggctttc agatgatttt gcgtcttacg agccttaccc aaattttatg     840
cagttacctt atctagaagg tgactcgtat gaaaacattg acactctttt caacggtgaa     900
gctgctcagg atgagtgaa catcggaggt ctttggaatt tcgatgatgt gccaatggac     960
cgtggtgttt actga                                                     975
```

<210> SEQ ID NO 2
<211> LENGTH: 579
<212> TYPE: DNA
<213> ORGANISM: Panicum virgatum

<400> SEQUENCE: 2

```
atgcatatgt atcctttcta catacatgca ggttacggga cgagaatgca ctaccgtggc    60
gtgcggcggc ggccgtgggg caagtgggcg gcggagatcc gtgaccccgc caaggcggcg   120
cgtgtgtggc tcggcacctt cgacaccgcg gaggccgccg ccgcagcgta cgacgacgcc   180
gcgctccggt tcaagggcgc caaggccaag ctcaactttc cgagcgcgt ccgcggccgt    240 accggccagg gcgcgttcct cgtcagccct ggcgtccccc agcagccgcc gccgtcttcc   300
ctgccaactg cagccgccgc gccgacgccg ttccccggct tgatgcggta cgcgcaactc   360
cagggttgga gcagcgggaa catcgcggcc agcaacaccg tggtgatct cgcgccgccg    420 gcacaggcgt cgtcgtcggt gcagattctg gacttctcga cgcagcaact actccggggc   480
tcaccgacaa cgttcggccc accgccgacg acgtcggcat cgatgtccag gactagcaga   540
gtagatgagg cgcacgagag ttgcgatgct cctgactga                          579
```

<210> SEQ ID NO 3
<211> LENGTH: 654
<212> TYPE: DNA
<213> ORGANISM: Panicum virgatum

<400> SEQUENCE: 3

```
atgccggact ccgacaacga gtccggcggg ccgagcaacg cggagttctc gtcgccgcgg    60
gagcaggacc ggttcctgcc gatcgcgaac gtgagccgga tcatgaagaa ggcgctcccg   120
gcgaacgcca agatctccaa ggacgccaag gagacggtgc aggagtgcgt ctccgagttc   180
atctccttca tcaccggcga ggcctccgac aagtgccagc gcgagaagcg caagaccatc   240
aacggcgacg acctcctctg gccatgacc acgctcggct tcgaggacta catcgagcca   300
ctcaagctct acctccacaa gttccgcgag ctcgagggcg agaaggtggc ctccggcgcc   360
gcgggctcct ccggctccgc ctcgcagccc cagagagaga caacgccgtc cgcgcacaat   420
ggcgccgccg ggccgtcgg ctacggcatg tacggcgccg cgccggggc cggcggaggc    480 agcggcatga tcatgatgat ggggcagccg atgtacggct cccaccggg cgcgtcgggg   540 tacccgcagc ccccgcacca ccacatggtg atgggcgcta aggtggcgc ctacggccac    600 ggcggcggct cgtcgccatc gctgtcgggg ctcggcaggc aggacaggct atga         654
```

<210> SEQ ID NO 4
<211> LENGTH: 324
<212> TYPE: PRT
<213> ORGANISM: Panicum virgatum

<400> SEQUENCE: 4

Met Cys Gly Gly Ala Ile Leu Ser Asp Leu Tyr Ser Pro Val Arg Arg
1               5                   10                  15

Thr Val Thr Ala Gly Asp Leu Trp Gly Glu Ser Gly Ser Ser Lys Asn
            20                  25                  30

Val Lys Asn Trp Lys Arg Ser Ser Trp Lys Phe Asp Glu Gly Asp Glu
        35                  40                  45

Asp Phe Glu Ala Asp Phe Lys Asp Phe Glu Asp Cys Ser Ser Glu Glu
    50                  55                  60

Glu Val Asp Phe Gly His Glu Glu Lys Glu Phe Gln Leu Asn Ser Ser
65                  70                  75                  80

Asn Phe Val Glu Phe Asn Gly His Thr Ala Lys Val Thr Ser Arg Lys
                85                  90                  95

Arg Lys Ile Gln Tyr Arg Gly Ile Arg Arg Arg Pro Trp Gly Lys Trp
            100                 105                 110

```
Ala Ala Glu Ile Arg Asp Pro Gln Lys Gly Val Arg Val Trp Leu Gly
            115                 120                 125

Thr Phe Ser Thr Ala Glu Ala Ala Arg Ala Tyr Asp Val Glu Ala
    130                 135                 140

Leu Arg Ile Arg Gly Lys Lys Ala Lys Met Asn Phe Pro Thr Thr Ile
145                 150                 155                 160

Thr Ala Ala Gly Lys His His Arg Gln Arg Val Ala Arg Pro Ala Lys
                165                 170                 175

Lys Thr Ser Gln Glu Ser Leu Lys Ser Ser Asn Ala Ser Gly His Val
            180                 185                 190

Ile Ser Ala Gly Ser Ser Thr Asp Gly Thr Val Val Lys Ile Glu Leu
            195                 200                 205

Ser Gln Ser Pro Ala Ser Pro Leu Pro Val Ser Ser Ala Trp Leu Asp
    210                 215                 220

Ala Phe Glu Leu Lys Gln Leu Gly Gly Glu Thr Pro Glu Ala Asp Gly
225                 230                 235                 240

Arg Glu Thr Pro Glu Glu Thr Asp His Glu Thr Gly Val Thr Ala Asp
                245                 250                 255

Met Phe Phe Gly Asn Gly Glu Val Arg Leu Ser Asp Asp Phe Ala Ser
                260                 265                 270

Tyr Glu Pro Tyr Pro Asn Phe Met Gln Leu Pro Tyr Leu Glu Gly Asp
            275                 280                 285

Ser Tyr Glu Asn Ile Asp Thr Leu Phe Asn Gly Glu Ala Ala Gln Asp
            290                 295                 300

Gly Val Asn Ile Gly Gly Leu Trp Asn Phe Asp Asp Val Pro Met Asp
305                 310                 315                 320

Arg Gly Val Tyr

<210> SEQ ID NO 5
<211> LENGTH: 192
<212> TYPE: PRT
<213> ORGANISM: Panicum virgatum

<400> SEQUENCE: 5

Met His Met Tyr Pro Phe Tyr Ile His Ala Gly Tyr Gly Thr Arg Met
1               5                   10                  15

His Tyr Arg Gly Val Arg Arg Pro Trp Gly Lys Trp Ala Ala Glu
            20                  25                  30

Ile Arg Asp Pro Ala Lys Ala Ala Arg Val Trp Leu Gly Thr Phe Asp
            35                  40                  45

Thr Ala Glu Ala Ala Ala Ala Tyr Asp Asp Ala Ala Leu Arg Phe
    50                  55                  60

Lys Gly Ala Lys Ala Lys Leu Asn Phe Pro Glu Arg Val Arg Gly Arg
65                  70                  75                  80

Thr Gly Gln Gly Ala Phe Leu Val Ser Pro Gly Val Pro Gln Gln Pro
                85                  90                  95

Pro Pro Ser Ser Leu Pro Thr Ala Ala Ala Pro Thr Pro Phe Pro
            100                 105                 110

Gly Leu Met Arg Tyr Ala Gln Leu Gln Gly Trp Ser Ser Gly Asn Ile
            115                 120                 125

Ala Ala Ser Asn Thr Gly Gly Asp Leu Ala Pro Pro Ala Gln Ala Ser
    130                 135                 140

Ser Ser Val Gln Ile Leu Asp Phe Ser Thr Gln Leu Leu Arg Gly
145                 150                 155                 160
```

Ser Pro Thr Thr Phe Gly Pro Pro Thr Thr Ser Ala Ser Met Ser
            165                 170                 175

Arg Thr Ser Arg Val Asp Glu Ala His Glu Ser Cys Asp Ala Pro Asp
        180                 185                 190

<210> SEQ ID NO 6
<211> LENGTH: 217
<212> TYPE: PRT
<213> ORGANISM: Panicum virgatum

<400> SEQUENCE: 6

Met Pro Asp Ser Asp Asn Glu Ser Gly Gly Pro Ser Asn Ala Glu Phe
1               5                   10                  15

Ser Ser Pro Arg Glu Gln Asp Arg Phe Leu Pro Ile Ala Asn Val Ser
            20                  25                  30

Arg Ile Met Lys Lys Ala Leu Pro Ala Asn Ala Lys Ile Ser Lys Asp
        35                  40                  45

Ala Lys Glu Thr Val Gln Glu Cys Val Ser Glu Phe Ile Ser Phe Ile
    50                  55                  60

Thr Gly Glu Ala Ser Asp Lys Cys Gln Arg Glu Lys Arg Lys Thr Ile
65                  70                  75                  80

Asn Gly Asp Asp Leu Leu Trp Ala Met Thr Thr Leu Gly Phe Glu Asp
                85                  90                  95

Tyr Ile Glu Pro Leu Lys Leu Tyr Leu His Lys Phe Arg Glu Leu Glu
            100                 105                 110

Gly Glu Lys Val Ala Ser Gly Ala Ala Gly Ser Ser Gly Ser Ala Ser
        115                 120                 125

Gln Pro Gln Arg Glu Thr Thr Pro Ser Ala His Asn Gly Ala Ala Gly
    130                 135                 140

Ala Val Gly Tyr Gly Met Tyr Gly Ala Gly Ala Gly Ala Gly Gly Gly
145                 150                 155                 160

Ser Gly Met Ile Met Met Met Gly Gln Pro Met Tyr Gly Ser Pro Pro
                165                 170                 175

Gly Ala Ser Gly Tyr Pro Gln Pro Pro His His His Met Val Met Gly
            180                 185                 190

Ala Lys Gly Gly Ala Tyr Gly His Gly Gly Gly Ser Ser Pro Ser Leu
        195                 200                 205

Ser Gly Leu Gly Arg Gln Asp Arg Leu
    210                 215

<210> SEQ ID NO 7
<211> LENGTH: 981
<212> TYPE: DNA
<213> ORGANISM: Panicum virgatum

<400> SEQUENCE: 7
atgtgcggtg ggctattct cagtgatctc tactcaccag tgaggcggac ggtcactgcc      60
ggtgacctat ggggagagag cggcagcacc aagaatgtga agaactggaa aaggaggagt    120
tcttggaagt ttgatgaaga cgatgatgac tttgaagctg atttcgagga tttcaacgat    180
tgcagtagcg aggaggaggt ggattttgta cgtgaggaaa aagaattcca attgaacagt    240
tcgaattttg tggaactcaa cggccatacc accaaagtcg ccagcaggaa gcgaaagacc    300
cagtaccgag ggatccgacg gcgcccgtgg ggcaaatggg cagctgaaat cagagaccca    360
cagaagggcg tccgagtttg gcttggcacg ttcagcactg ccgaggaagc tgcaaaggca    420

```
tatgacgtgg aagctctacg catacgtggc aagaaagcca aggtgaattt ccctaacacc    480
atcacagctg ctgggaaaca ccaccggcag catgtggctc gaccagcaaa gaggatgtca    540
caagagagcc tgaagtcaag cgatgcctct ggtcatgtcg tctcagcagg cagcagtact    600
gatggcaccg ttgtcaagat tgagttgata gagtcaccag cttctccact accagtgtcc    660
agcgcatggc ttgatgcttt tgagctgaac caacttggtg gattaaggca ccttgaagct    720
gatgggagag aaaccactga agaaactgat catgaaacgg gagtgacagc agatatggtt    780
tttggcgatg gcaaagtgcg gctttcagat gattttgcgt cttacgagcc ttacccaaat    840
tttatgcagt taccttacct ggaaggtaac tcgtatgaaa acattgacac tcttttcaac    900
ggtgaagccg ctcaggatgg cgtgaacatc ggaggtctct ggaatttcga cgatgtgcca    960
atggaccgtg gtgtttacta a                                              981
```

<210> SEQ ID NO 8
<211> LENGTH: 1110
<212> TYPE: DNA
<213> ORGANISM: Panicum virgatum

<400> SEQUENCE: 8

```
atgtgcggcg gtgcgatcct cgccaacctc accaagcagc cgggcccgcg ccggctcacg     60
gagcgggacc tctggcagga gaagaagaag cccaagaggg gcgccggcgg ggggaggcgc    120
tggttcctgg ctgaggagga tgaggacttc gaggccgact tcgaggactt ccagggcgac    180
tccgatgagt cggatttgga actcggggag ggggaggacg acgacgtcgt cgagatcaag    240
cccttcgccg ccaagaggac ttcctccaaa gatggcttaa gcaccatgac tactgctggt    300
tatgatggcc ctgcagcaag gtcagccaaa aggaagagaa agaatcaata caggggcatc    360
cgccagcgcc cttggggtaa gtgggctgct gagatcagag atcctcagaa gggtgttcgt    420
gtttggcttg gtactttcaa cagtcctgag gaagctgcaa gagcttatga tgctgaagca    480
cgcaggatcc gtggtaagaa ggccaaggtt aacttccctg atgcaccaac agttgctcag    540
aagcgccgta gtgggccagc tgctgctaaa gcacccaaat caagtgtgga acagaagcct    600
accgtcaaac cagcagtgaa caaccttgcc aacgcaaatg catcctaccc acctgctgac    660
tacacctcaa gcaagccatc tgttcagcat gccaatatgg catttcatct agcaatgaac    720
tctgctagtc ctattgagga tccagttatg aatctgcact ctgaccaggg aagtaactct    780
tttgattgct cagacttgag ctgggagaat gataccaaga cttcagacat aacatccatt    840
gctcccattt ccaccatagc tgaaggtgac gagtctgcat ttgtcaacag caatttgaac    900
aactcactgg tgccttctgt tatggagaac aatgcagttg atctcactga tgggctgaca    960
gatttagaac cgtacatgag gtttcttctg gatgatggtg caagtgagtc aattgataac   1020
cttctgaacc ttgatggatc tgaggatgtt atgagcaaca tggatctctg gagctttgat   1080
gacatgcctg ctgctggcga tttctattga                                   1110
```

<210> SEQ ID NO 9
<211> LENGTH: 1113
<212> TYPE: DNA
<213> ORGANISM: Panicum virgatum

<400> SEQUENCE: 9

```
atgtgcggcg gtgcgatcct cgccaacctc accaagcagc cgggcccgcg ccggctcacg     60
gagcgggacc tctggcagga gaagaagaag cccaagagga gcgccggcgg gggtaggcgc    120
tggttcctgg ctgaggagga tgaggacttc gaggccgact tcgaggactt ccagggcgac    180
```

```
tccgacgagt cagatttgga gctcggggag ggggaggacg acgacgtcgt cgagatcaag    240
cccttcgccg ccaagaggac ttcctccaaa gatggcttaa gcaccatgat tactgctggt    300
tatgatggcc ctgcagcaag gtcagccaaa aggaagagaa agaatcaata cagggcatc    360 cgccagcgcc cttggggtaa gtgggctgct gagatcagag atcctcagaa gggtgttcgt    420
gtctggcttg gtactttcaa cagtcctgag gaagctgcaa gagcttatga tgctgaagca    480
cgcaggatcc gtggtaagaa ggccaaggtt aacttccctg atgcaccaac agttctcag    540 aagcgtcgta gtggcccagc tgccgctaaa gcacccaagt taagtgtgga acagaagcct    600
actgtcaaac cagcagtgaa caaccttgcc aacgcaaatg catctttcta cccacctgct    660
gactacacct caaaccagca atttgttcag catgccaata tgccatttca tccagcaatg    720
aactctgcta gtcctactga ggatccagtt atgaatctgc actctgacca gggaagtaac    780
tcttttgatt gctcagactt gagctgggag aatgatacca agacttcaga cataacatcc    840
attgctccca tttccaccat agctgaaggt gatgagtctg catttgtcaa cagcaatttg    900
aacaactcac tggtgccttc tgttatgggg aacaatgcag ttgatctcac tgatgggctg    960
acagatttag aaccctacat gaggtttctt ctggatgatg gtgcaagtga gtcaattgat   1020
aaccttctga accttgatgg atctgaggat gttatgagca acatggatct ctggagcttt   1080
gatgacatgc ctgccactgg cgatttctat tga                                1113

<210> SEQ ID NO 10
<211> LENGTH: 960
<212> TYPE: DNA
<213> ORGANISM: Panicum virgatum

<400> SEQUENCE: 10
atgtgcgggg gcgccattct cgcggaactc atcccgtcgc cgcgccgggc ggcgtcgaag     60
ccggtgaccg cgggccacct ctggccggcg ggctccgaca ccaagaaggc cggcagcggg    120
aggagcaaga ggcaccagct cgccgacgtc gacgactttg aggccgcctt cgaggacttc    180
gccgacgatt ttgacaagga ggaggtcgag gaccaccatt tcgtgttctc gtccaaatcc    240
gcattctccc cagcccacgg cgtgcgcgcg gcgacccaga gaggcgcgg ccgccgccac    300 ttccgcggca tccggcagcg cccctggggc aagtgggcgg cggagatccg cgacccgcac    360
aagggcaccc gcgtctggct cggcaccttc aacaccgccg aggacgccgc ccgggcctac    420
gacgtcgagg cacgccgcct ccgcggcagc aaggccaagg tcaacttccc cgcggccggc    480
gcgcgcccac gccgcggcaa cgcgccgaga ccgcagcgcc accatgccgc agcgcagccc    540
gcgttgcttg caggagagaa gcggaaggag gaggagatcg tcgtgaagcc tgaaattggg    600
gcgtcgttcg acttcgacgt gggcagcttc ttcgacacgg ccttccccgc ggcgccgccg    660
gccatggaga actccttcgc cggcagcacc gggtcggagt ccggtagccc cgcaaagaag    720
atgagatacg acaacgactc gtcgtccgat gggatgagct ccggcggcgg ctccgcgctg    780
gagctcgctg acgagctcgc gttcgatccg ttcatgctgc tccagatgcc ctactcgggc    840
gggtacgagt ccctcgacgg cctgttcgcc gtcgacgccg cccaggacgt gaacaacgac    900
atgaacggcg tcagcctgtg gagcttcgac gagttccccg acgacagcgc tgttttctaa    960

<210> SEQ ID NO 11
<211> LENGTH: 570
<212> TYPE: DNA
<213> ORGANISM: Panicum virgatum
```

<400> SEQUENCE: 11

```
aacgtgacga gaagcaggca ctaccgtggc gtgcggcggc ggccgtgggg caagtgggcg        60
gcggagatcc gtgaccccgc caaggcggcg cgcgtgtggc tcggcaccttc cgacaccgcg      120
gaggccgccg ctgcagcgta cgacgacgcc gcgctccggt tcaagggcgc caaggccaag      180
ctcaacttcc ccgagcgcgt ccgaggccgc accggccagg gcgcgttcct cgtcagccct      240
tgcgtccccc agcagcagcc gccgtcgccg tcttccatgc caactgcagc cgcgccgttc      300
cccggcctga tccggtatgc acagctgctc cagggttgga acagcgggag catcgcggcc      360
agcaacaccg tgacctcgcc gccgccgcg gccttgccaa tgccgccggc acaggcgtcg       420
tcgtcggtgc agattctgga cttctcgacg cagcagctcc tccggggctc gccgacaacg      480
ttcggcggcc caccgccgcc gacgtcggca tcgatgtcca ggactagcag agtagatgag      540
gcgcacgaga gttgcaatgc tcctgactga                                         570
```

<210> SEQ ID NO 12
<211> LENGTH: 558
<212> TYPE: DNA
<213> ORGANISM: Panicum virgatum

<400> SEQUENCE: 12

```
ggtcggaggc ggcactaccg aggggtgcgg cagcggccgt gggggaagtg ggcggcagag        60
atccgggacc ccaagaaggc ggcgcgggtg tggctgggca ccttcgacac ggcggaggac      120
gccgccatcg cctacgacga ggcggcgctc cggttcaagg gcaccaaggc caagctcaac      180
ttcccggagc gcgtccaggg ccgcaccgac ctgggcttcc tcgtcacccg cggcgtcccg      240
gaccggcacc accaccaagg cgcggcggcg gcgcaggcgc agctcatgat gctggcccgc      300
ggcggcggcg gcggcgtcaa cctgccgttc ggagccgcgt cgccgttctc gccctcgccc      360
tcgccctcgt cggcgccgca gatcctggac ttctccacgc agcagctcat ccggcccgac      420
ccgccgtcgc cggccgccgc gatgtcgtcg tcgggcgctg ctccgtccac gccgtcgtcc      480
acgaccacgg cgtcgtcgcc cggtggcggt gcatggccgt acggtgggga gcaccacagg      540
aataaaaaag acgcgtga                                                      558
```

<210> SEQ ID NO 13
<211> LENGTH: 1089
<212> TYPE: DNA
<213> ORGANISM: Panicum virgatum

<400> SEQUENCE: 13

```
atgtgccacg ccgcggtggc ggactcgggg gagcagcacg ggcggcggct tctcgccgcc        60
ggcgacggcg gcgaggagga ccgccgccag cagcagcagc agcccagcc gctggagccc       120
gtggtgatgg aagccaacac ggcggcgtcg ccggcgctgt cgcggggcag gcaggcccgg      180
gagatgtcgg ccatggtggc cgcgctggcc agggtggtcg ccggctcggc ccgccggcc        240
aaggcgcccc ccaggccgt gcaggatgcc tccgcggagg aggcgtggtg gccgtacgac       300
gagctcgccg ccgagccgtc ccctgctttc gtgctcgacg gctacagcga gacgcagccg       360
ctgccggagc actactggcc ttcggctgcg gggcgacag aggcggcgac ttcctcgcag        420
acgcattacc gtgccgcctc tgctgccgcg gccgaggagg aggtaccttc gccgtcgtcc      480
gcctccgccg ccgccgggc gagcagcagc ggcagcgcgg cgacgcggaa gcgttaccgc       540
ggcgtgcggc agcgtccgtg gggggaagtgg gcggcggaga tccgtgaccc gcacaaggcg      600
gcgcgcgtgt ggctgggcac cttcgacacc gccgaggccg ccgcccgggc ctacgatggc      660
```

```
gccgcgctta ggttccgcgg cagccgcgcc aggctcaact tccccgagtc cgccacgctc      720
ccgtccccgc cgccgccgga tccggcctcg cgcgcattgc cgccgccgcc gcccaggccg      780
gacgcgcttc tggagtcgca ggctcaggcg ccctccaccg gcggcggcat ggagcaatac      840
gcggagtacg ccaggctctt gcagagcgcc ggcggcgacc ccggcggctc atccgggacg      900
ccaagtggca cgttgcctcc ccctcctcct cctgcagcgt acagcttcgc cgcccagggc      960
gtgacaccgt tcagctacct gtcgccgccg cagagccgcg gcgagccagc aggcaacccc     1020
gcggcggcgt gggcggcgag ccactaccac ggctcgtacc cgccgtggcg gtgggaccac     1080
tcaggttga                                                             1089

<210> SEQ ID NO 14
<211> LENGTH: 654
<212> TYPE: DNA
<213> ORGANISM: Panicum virgatum

<400> SEQUENCE: 14
atgccggact ccgacaaaga gtccggctgg ccgagcaacg cggagttctc gtcgccgcgg       60
gagcaggacc ggttcctgcc gatcgcgaac gtcagccgga tcatgaagat ggcgctcccg      120
gcgaacgcca agatctccaa ggacgccaag gagacggtgc aggagtgcgt ctccgagttc      180
atctccttca tcaccggcga ggcctccgac aagtgccagc gcgagaagcg caagaccatc      240
aacggcgacg acctcctctg ggccatgacc acgctcggct tcgaggacta catcgagccg      300
ctcaagctct acctccacaa gttccgcgag ctcgagggcg agaaggtggc ctccggcgcc      360
gcgggctcct ccggctccgg ctcgcagccg cagagggaga cgacgccgtc cgcgcacaat      420
ggcgccggcg gggccgtcgg ctacggcatt tacggcgccg cgccggggc aggcggaggc      480 agcggcatga tcatgatgat ggggcagccg atgtacaact ccccaccggg cgcgtcaggg      540
tacccgcagc ccccgcacca ccagatggtg atggccgcga aggtggcgc ctacggccac      600 ggcggcggct cgtcgccgtc gccgccgggg ctcggcaggc aggacaggct ttga            654

<210> SEQ ID NO 15
<211> LENGTH: 609
<212> TYPE: DNA
<213> ORGANISM: Panicum virgatum

<400> SEQUENCE: 15
atgccggact cggacaacga ctccggcggc ccgagcaacg ccggcggcga gctgtcgtcg       60
ccgcgggagc aggacaggtt cctccccatc gcgaacgtga gccggatcat gaagaaggcg      120
ctcccggcga acgccaagat cagcaaggac gccaaggaga cggtgcagga gtgcgtctcc      180
gagttcatct ccttcatcac cggcgaggcc tccgacaagt gccagcgcga gaagcgcaag      240
accatcaacg gcgacgacct gctctgggcc atgaccacgc tcggcttcga ggactacgtc      300
gagccgctca gcactacct ccacaagttc cgcgagatcg agggcgagag gcggccgcc      360 tcctcgggcg cctcgggctc cgccgccgcg cagcagcagg cgacgtggc gaggggcgcc      420 accaatgccg gcgggtacgc cgggtacagc gccggcggca tgatgatgat ggggcagccg      480
atgtacggct cgccgcagca gcagcaccaa cagcatcaca tggcaatggg aggcagaggc      540
ggttacggcc atcaaggagg cggcggctcg tcgtcgtcgt cggggcttgg ccggcaagac      600
agggcgtga                                                             609

<210> SEQ ID NO 16
```

<211> LENGTH: 543
<212> TYPE: DNA
<213> ORGANISM: Panicum virgatum

<400> SEQUENCE: 16

```
atggcggacg cgccagcgag ccccgggggc ggcggcggga ccacgagag cgggagcccc    60
aggggcggcg ccggggcggg ggcggcggc gtcagggagc aggacaggtt cctgcccatc   120
gccaacatca gccgcatcat gaagaaggcc atcccggcca cgggaagat cgccaaggac   180
gccaaggaga ccgtgcagga gtgcgtctcc gagttcatat ccttcatcac cagcgaggcg   240
agtgacaagt gccagaggga gaagaggaag accatcaacg ggacgaccct actgtgggcc   300
atggccacgt tggggttcga ggactacata gaacccctca aggtgtacct gcagaagtac   360
agagagatgg agggtgatag caagttaact gcaaaaactg gcgatggctc tattaaaaag   420
gatgcccttg gccatggggg agcaagtagc tcagccacac aagggatggg ccaacaagga   480
gcgtacaacc aaggaatggg ttatatgcaa cctcagtacc ataacggaga catctcaaac   540
taa                                                                 543
```

<210> SEQ ID NO 17
<211> LENGTH: 486
<212> TYPE: DNA
<213> ORGANISM: Panicum virgatum

<400> SEQUENCE: 17

```
atggcggacg acggcgggag ccacgagggc ggcggcggcg tccgggagca ggaccggttc    60
ctgcccatcg ccaacatcag ccgcatcatg aagaaggccg tcccggctaa cggcaagatc   120
gccaaggatg ccaaggagac cctgcaggag tgcgtctccg agttcatctc cttcgtcacc   180
agcgaggcca gcgacaagtg ccagaaggag aagcgcaaga ccatcaacgg cgatgatctg   240
ctctgggcga tggctacgct cggattcgag gagtacgtcg agcccctcaa gatgtaccta   300
cacaagtaca gagagatgga gggtgatagt aagttgtcta caaaggctgg tgagggctct   360
gtaaagaagg atgcaattag tccccatggt ggcaccagta gctcaagtaa ccagttggtt   420
caacatggag tttacaacca agggatgggc tatatgcaac cacagtacca taatggggat   480
acctaa                                                              486
```

<210> SEQ ID NO 18
<211> LENGTH: 384
<212> TYPE: DNA
<213> ORGANISM: Panicum virgatum

<400> SEQUENCE: 18

```
atggcggacg cgccagcgag ccccgggggc ggcggcggga ccacgagag tgggagcccc    60
aagggcggcg gcggggcgg aggcggcggc gtcagggagc aggacaggtt cctgcccatc   120
gccaacatca gccgcatcat gaagaaggcc atcccggcca cgggaagat cgccaaggac   180
gccaaggaga ccgtgcagga gtgcgtctcc gaattcatct ccttcatcac cagcgaggcg   240
agtgacaagt gccagaggga gaagaggaag accatcaacg ggacgaccct actgtgggcc   300
atggccacgc tggggttcga ggactacata gaacccctca aggtgtacct gcagaagtac   360
agagaggtca caaaacactt atag                                          384
```

<210> SEQ ID NO 19
<211> LENGTH: 12168
<212> TYPE: DNA
<213> ORGANISM: Artificial Sequence
<220> FEATURE:
<223> OTHER INFORMATION: Synthetic construct pMBXS809

<400> SEQUENCE: 19

```
gtaaacctaa gagaaaagag cgtttattag aataacggat atttaaaagg gcgtgaaaag    60
gtttatccgt tcgtccattt gtatgtgcat gccaaccaca gggttcccct cgggatcaaa   120
gtactttgat ccaaccoctc cgctgctata gtgcagtcgg cttctgacgt tcagtgcagc   180
cgtcttctga aaacgacatg tcgcacaagt cctaagttac gcgacaggct gccgccctgc   240
ccttttcctg gcgttttctt gtcgcgtgtt ttagtcgcat aaagtagaat acttgcgact   300
agaaccggag acattacgcc atgaacaaga gcgccgccgc tggcctgctg gctatgccc    360
gcgtcagcac cgacgaccag gacttgacca accaacgggc cgaactgcac gcggccggct   420
gcaccaagct gttttccgag aagatcaccg caccaggcg cgaccgcccg gagctggcca    480
ggatgcttga ccacctacgc cctggcgacg ttgtgacagt gaccaggcta gaccgcctgg   540
cccgcagcac ccgcgaccta ctggacattg ccgagcgcat ccaggaggcc ggcgcgggcc   600
tgcgtagcct ggcagagccg tgggccgaca ccaccacgcc ggccggccgc atggtgttga   660
ccgtgttcgc cggcattgcc gagttcgagc gttccctaat catcgaccgc acccggagcg   720
ggcgcgaggc cgccaaggcc cgaggcgtga agtttggccc cgccctaccc ctcacccogg   780
cacagatcgc gcacgcccgc gagctgatcg accaggaagg ccgcaccgtg aaagaggcgg   840
ctgcactgct tggcgtgcat cgctcgaccc tgtaccgcgc acttgagcgc agcgaggaag   900
tgacgcccac cgaggccagg cggcgcgtg ccttccgtga ggacgcattg accgaggccg     960
acgccctggc ggccgccgag aatgaacgcc aagaggaaca agcatgaaac cgcaccagga  1020
cggccaggac gaaccgtttt tcattaccga agagatcgag gcggagatga tcgcggccgg  1080
gtacgtgttc gagccgcccg cgcacgtctc aaccgtgcgg ctgcatgaaa tcctggccgg  1140
tttgtctgat gccaagctgg cggcctggcc ggccagcttg gccgctgaag aaaccgagcg  1200
ccgccgtcta aaaggtgat gtgtatttga gtaaaacagc ttgcgtcatg cggtcgctgc    1260
gtatatgatg cgatgagtaa ataaacaaat acgcaagggg aacgcatgaa ggttatcgct   1320
gtacttaacc agaaaggcgg gtcaggcaag acgaccatcg caacccatct agcccgcgcc   1380
ctgcaactcg ccggggccga tgttctgtta gtcgattccg atcccagggg cagtgcccgc   1440
gattgggcgg ccgtgcggga agatcaaccg ctaaccgttg tcggcatcga ccgcccgacg   1500
attgaccgcg acgtgaaggc catcggccgg cgcgacttcg tagtgatcga cggagcgccc  1560
caggcggcgg acttggctgt gtccgcgatc aaggcagccg acttcgtgct gattccggtg  1620
cagccaagcc cttacgacat atgggccacc gccgacctgg tggagctggt taagcagcgc   1680
attgaggtca cggatggaag gctacaagcg gcctttgtcg tgtcgcgggc gatcaaaggc   1740
acgcgcatcg gcgtgaggt tgccgaggcg ctggccgggt acgagctgcc cattcttgag   1800
tcccgtatca cgcagcgcgt gagctaccca ggcactgccg ccgccggcac aaccgttctt   1860
gaatcagaac ccgagggcga cgctgcccgc gaggtccagg cgctggccgc tgaaattaaa   1920
tcaaaactca tttgagttaa tgaggtaaag agaaaatgag caaaagcaca aacacgctaa    1980
gtgccggccg tccgagcgca cgcagcagca aggctgcaac gttggccagc ctggcagaca   2040
cgccagccat gaagcgggtc aactttcagt tgccggcgga ggatcacacc aagctgaaga  2100
tgtacgcggt acgccaaggc aagaccatta ccgagctgct atctgaatac atcgcgcagc  2160
taccagagta aatgagcaaa tgaataaatg agtagatgaa tttagcggc taaaggaggc    2220
```

```
ggcatggaaa atcaagaaca accaggcacc gacgccgtgg aatgccccat gtgtggagga      2280
acgggcggtt ggccaggcgt aagcggctgg gttgtctgcc ggccctgcaa tggcactgga      2340 accccaagc ccgaggaatc ggcgtgacgg tcgcaaacca tccggcccgg tacaaatcgg       2400
cgcggcgctg ggtgatgacc tggtggagaa gttgaaggcc gcgcaggccg cccagcggca      2460
acgcatcgag gcagaagcac gccccggtga atcgtggcaa gcggccgctg atcgaatccg      2520
caaagaatcc cggcaaccgc cggcagccgg tgccgccgtcg attaggaagc cgcccaaggg    2580
cgacgagcaa ccagattttt tcgttccgat gctctatgac gtgggcaccc gcgatagtcg      2640
cagcatcatg gacgtggccg ttttccgtct gtcgaagcgt gaccgacgag ctggcgaggt      2700
gatccgctac gagcttccag acgggcacgt agaggtttcc gcagggccgg ccggcatggc      2760
cagtgtgtgg gattacgacc tggtactgat ggcggtttcc catctaaccg aatccatgaa      2820
ccgataccgg gaagggaagg gagacaagcc cggccgcgtg ttccgtccac acgttgcgga     2880
cgtactcaag ttctgccggc gagccgatgg cggaaagcag aaagacgacc tggtagaaac      2940
ctgcattcgg ttaaacacca cgcacgttgc catgcagcgt acgaagaagg ccaagaacgg      3000
ccgcctggtg acggtatccg agggtgaagc cttgattagc cgctacaaga tcgtaaagag      3060
cgaaaccggg cggccggagt acatcgagat cgagctagct gattggatgt accgcgagat      3120
cacagaaggc aagaacccgg acgtgctgac ggttcacccc gattacttt tgatcgatcc       3180 cggcatcggc cgttttctct accgcctggc acgccgcgcc gcaggcaagg cagaagccag      3240
atggttgttc aagacgatct acgaacgcag tggcagcgcc ggagagttca agaagttctg      3300
tttcaccgtg cgcaagctga tcgggtcaaa tgacctgccg gagtacgatt tgaaggagga     3360
ggcggggcag gctggcccga tcctagtcat gcgctaccgc aacctgatcg agggcgaagc     3420
atccgccggt tcctaatgta cggagcagat gctagggcaa attgccctag caggggaaaa   3480
aggtcgaaaa ggtctctttc ctgtggatag cacgtacatt gggaacccaa agccgtacat     3540
tgggaaccgg aacccgtaca ttgggaaccc aaagccgtac attgggaacc ggtcacacat    3600
gtaagtgact gatataaaag agaaaaaagg cgattttttcc gcctaaaact ctttaaaact    3660
tattaaaact cttaaaaccc gcctggcctg tgcataactg tctggccagc gcacagccga     3720
agagctgcaa aaagcgccta cccttcggtc gctgcgctcc ctacgccccg ccgcttcgcg     3780
tcggcctatc gcgccgctg gccgctcaaa aatggctggc ctacggccag gcaatctacc     3840
agggcgcgga caagccgcgc cgtcgccact cgaccgccgg cgcccacatc aaggcaccct    3900
gcctcgcgcg tttcggtgat gacggtgaaa acctctgaca catgcagctc ccggagacgg     3960
tcacagcttg tctgtaagcg gatgccggga gcagacaagc ccgtcagggc gcgtcagcgg    4020
gtgttggcgg gtgtcgggc gcagccatga cccagtcacg tagcgatagc ggagtgtata     4080
ctggcttaac tatgcggcat cagagcagat tgtactgaga gtgcaccata tgcggtgtga    4140
aataccgcac agatgcgtaa ggagaaaata ccgcatcagg cgctcttccg cttcctcgct    4200
cactgactcg ctgcgctcgg tcgttcggct gcggcgagcg gtatcagctc actcaaaggc     4260
ggtaatacgg ttatccacag aatcagggga taacgcagga agaacatgt gagcaaaagg    4320 ccagcaaaag gccaggaacc gtaaaaaggc cgcgttgctg cgttttttcc ataggctccg     4380
cccccctgac gagcatcaca aaaatcgacg ctcaagtcag aggtggcgaa acccgacagg    4440
actataaaga taccaggcgt ttccccctgg aagctccctc gtgcgctctc ctgttccgac    4500
cctgccgctt accggatacc tgtccgcctt tctcccttcg ggaagcgtgg cgctttctca     4560
tagctcacgc tgtaggtatc tcagttcggt gtaggtcgtt cgctccaagc tgggctgtgt   4620
```

```
gcacgaaccc cccgttcagc ccgaccgctg cgccttatcc ggtaactatc gtcttgagtc   4680
caacccggta agacacgact tatcgccact ggcagcagcc actggtaaca ggattagcag   4740
agcgaggtat gtaggcggtg ctacagagtt cttgaagtgg tggcctaact acggctacac   4800
tagaaggaca gtatttggta tctgcgctct gctgaagcca gttaccttcg gaaaaagagt   4860
tggtagctct tgatccggca aacaaaccac cgctggtagc ggtggttttt ttgtttgcaa   4920
gcagcagatt acgcgcagaa aaaaaggatc tcaagaagat cctttgatct tttctacggg   4980
gtctgacgct cagtggaacg aaaactcacg ttaagggatt ttggtcatgc attctaggta   5040
ctaaaacaat tcatccagta aaatataata ttttattttc tcccaatcag gcttgatccc   5100
cagtaagtca aaaatagctc gacatactg ttcttcccg atatcctccc tgatcgaccg   5160
gacgcagaag gcaatgtcat accacttgtc cgccctgccg cttctcccaa gatcaataaa   5220
gccacttact ttgccatctt tcacaaagat gttgctgtct cccaggtcgc cgtgggaaaa   5280
gacaagttcc tcttcgggct tttccgtctt taaaaaatca tacagctcgc gcggatcttt   5340
aaatggagtg tcttcttccc agttttcgca atccacatcg ccagatcgt tattcagtaa   5400 gtaatccaat tcggctaagc ggctgtctaa gctattcgta tagggacaat ccgatatgtc   5460
gatggagtga aagagcctga tgcactccgc atacagctcg ataatctttt cagggctttg   5520
ttcatcttca tactcttccg agcaaaggac gccatcggcc tcactcatga gcagattgct   5580
ccagccatca tgccgttcaa agtgcaggac ctttggaaca ggcagctttc cttccagcca   5640
tagcatcatg tccttttccc gttccacatc ataggtggtc cctttatacc ggctgtccgt   5700 cattttaaa tataggtttt cattttctcc caccagctta tataccttag caggagacat   5760
tccttccgta tcttttacgc agcggtattt ttcgatcagt tttttcaatt ccggtgatat   5820
tctcatttta gccatttatt atttccttcc tcttttctac agtatttaaa gatacccaa    5880 gaagctaatt ataacaagac gaactccaat tcactgttcc ttgcattcta aaaccttaaa   5940
taccagaaaa cagcttttc aaagttgttt tcaaagttgg cgtataacat agtatcgacg   6000
gagccgattt tgaaaccgcg gtgatcacag gcagcaacgc tctgtcatcg ttacaatcaa   6060
catgctaccc tccgcgagat catccgtgtt tcaaacccgg cagcttagtt gccgttcttc   6120
cgaatagcat cggtaacatg agcaaagtct gccgccttac aacggctctc ccgctgacgc   6180
cgtcccggac tgatgggctg cctgtatcga gtggtgattt tgtgccgagc tgccggtcgg   6240
ggagctgttg gctggctggt ggcaggatat attgtggtgt aaacaaattg acgcttagac   6300
aacttaataa cacattgcgg acgttttaa tgtactgaat taacgccgaa ttaattcggg   6360
ggatctggat tttagtactg gattttggtt ttaggaatta gaaattttat tgatagaagt   6420
attttacaaa tacaaataca tactaagggt ttcttatatg ctcaacacat gagcgaaacc   6480
ctataggaac cctaattccc ttatctggga actactcaca cattattatg gagaaactcg   6540
agtcaaatct cggtgacggg caggaccgga cggggcggta ccggcaggct gaagtccagc   6600
tgccagaaac ccacgtcatg ccagttcccg tgcttgaagc cggccgcccg cagcatgccg   6660 cgggggcat atccgagcgc ctcgtgcatg cgcacgctcg ggtcgttggg cagcccgatg   6720
acagcgacca cgctcttgaa gccctgtgcc tccaggact tcagcaggtg ggtgtagagc   6780
gtggagccca gtcccgtccg ctggtggcgg ggggagacgt acacggtcga ctcggccgtc   6840
cagtcgtagg cgttgcgtgc cttcaggggg cccgcgtagg cgatgccggc gacctcgccg   6900
tccacctcgg cgacgagcca gggatagcgc tcccgcagac ggacgaggtc gtccgtccac   6960
```

```
tcctgcggtt cctgcggctc ggtacggaag ttgaccgtgc ttgtctcgat gtagtggttg    7020
acgatggtgc agaccgccgg catgtccgcc tcggtggcac ggcggatgtc ggccgggcgt    7080
cgttctgggc tcatggtaga ccgcttggta tctgcattac aatgaaatga gcaaagacta    7140
tgtgagtaac actggtcaac actagggaga aggcatcgag caagatacgt atgtaaagag    7200
aagcaatata gtgtcagttg gtagatacta gataccatca ggaggtaagg agagcaacaa    7260
aaaggaaact ctttatttt aaattttgtt acaacaaaca agcagatcaa tgcatcaaaa    7320
tactgtcagt acttatttct tcagacaaca atatttaaaa caagtgcatc tgatcttgac    7380
ttatggtcac aataaaggag cagagataaa catcaaaatt tcgtcattta tatttattcc    7440
ttcaggcgtt aacaatttaa cagcacacaa acaaaaacag aataggaata tctaattttg    7500
gcaaataata agctctgcag acgaacaaat tattatagta tcgcctataa tatgaatccc    7560
tatactattg acccatgtag tatgaagcct gtgcctaaat taacagcaaa cttctgaatc    7620
caagtgccct ataacaccaa catgtgctta aataaatacc gctaagcacc aaattacaca    7680
tttctcgtat tgctgtgtag gttctatctt cgtttcgtac taccatgtcc ctatattttg    7740
ctgctacaaa ggacggcaag taatcagcac aggcagaaca cgatttcaga gtgtaattct    7800
agatccagct aaaccactct cagcaatcac cacacaagag agcattcaga gaaacgtggc    7860
agtaacaaag gcagagggcg gagtgagcgc gtaccgaaga cggtctcgag agagatagat    7920
ttgtagagag agactggtga tttcagcgtg tcctctccaa atgaaatgaa cttccttata    7980
tagaggaagg tcttgcgaag gatagtggga ttgtgcgtca tcccttacgt cagtggagat    8040
atcacatcaa tccacttgct ttgaagacgt ggttggaacg tcttcttttt ccacgatgct    8100
cctcgtgggt gggggtccat ctttgggacc actgtcggca gaggcatctt gaacgatagc    8160 cttttccttta tcgcaatgat ggcatttgta ggtgccacct tccttttcta ctgtcctttt    8220
gatgaagtga cagatagctg ggcaatggaa tccgaggagg tttcccgata ttacccttg    8280 ttgaaaagtc tcaatagccc tttggtcttc tgagactgta tctttgatat tcttggagta    8340
gacgagagtg tcgtgctcca ccatgttatc acatcaatcc acttgctttg aagacgtggt    8400
tggaacgtct tcttttttcca cgatgctcct cgtgggtggg ggtccatctt tgggaccact    8460
gtcggcagag gcatcttgaa cgatagcctt cctttatcg caatgatggc atttgtaggt    8520
gccaccttcc ttttctactg tccttttgat gaagtgacag atagctgggc aatggaatcc    8580
gaggaggttt cccgatatta cccttttgttg aaaagtctca atagcccttt ggtcttctga    8640
gactgtatct ttgatattct tggagtagac gagagtgtcg tgctccacca tgttggcaag    8700
ctgctctagc caatacgcaa accgcctctc cccgcgcgtt ggccgattca ttaatgcagc    8760
tggcacgaca ggtttcccga ctggaaagcg ggcagtgagc gcaacgcaat taatgtgagt    8820
tagctcactc attaggcacc ccaggcttta cactttatgc ttccggctcg tatgttgtgt    8880
ggaattgtga gcggataaca atttcacaca ggaaacagct atgaccatga ttacgaattg    8940
gggtttaaac cacggaagat ccaggtctcg agactaggag acgatggga ggcgcaacgc    9000 gcgatgggga gggggcggc gctgaccttt ctggcgaggt cgaggtagcg atcgagcagc    9060
tgcagcgcgg acacgatgag gaagacgaag atagccgcca tggacatgtt cgccagcggc    9120
ggcggagcga ggctgagccg gtctctccgg cctccggtcg gcgttaagtt ggggatcgta    9180
acgtgacgtg tctcgtctcc acggatcgac acaaccggcc tactcgggtg cacgacgccg    9240
cgataagggc gagatgtccg tgcacgcagc ccgtttggag tcctcgttgc ccacgaaccg    9300
accccttaca gaacaaggcc tagcccaaaa ctattctgag ttgagctttt gagcctagcc    9360
```

```
cacctaagcc gagcgtcatg aactgatgaa cccactacca ctagtcaagg caaaccacaa    9420
ccacaaatgg atcaattgat ctagaacaat ccgaaggagg ggaggccacg tcacactcac    9480
accaaccgaa atatctgcca gaatcagatc aaccggccaa taggacgcca gcgagcccaa    9540
cacctggcga cgccgcaaaa ttcaccgcga ggggcaccgg gcacggcaaa acaaaagcc     9600 cggcgcggtg agaatatctg gcgactggcg gagacctggt ggccagcgcg cggccacatc    9660
agccacccca tccgcccacc tcacctccgg cgagccaatg gcaactcgtc ttaagattcc    9720
acgagataag gacccgatcg ccggcgacgc tatttagcca ggtgcgcccc ccacggtaca    9780
ctccaccagc ggcatctata gcaaccggtc cagcactttc acgctcagct tcagcaagat    9840
ctaccgtctt cggtacgcgc tcactccgcc ctctgccttt gttactgcca cgtttctctg    9900
aatgctctct tgtgtggtga ttgctgagag tggtttagct ggatctagaa ttacactctg    9960
aaatcgtgtt ctgcctgtgc tgattacttg ccgtcctttg tagcagcaaa atatagggac   10020
atggtagtac gaaacgaaga tagaacctac acagcaatac gagaaatgtg taatttggtg   10080
cttagcggta tttatttaag cacatgttgg tgttataggg cacttggatt cagaagtttg   10140
ctgttaattt aggcacaggc ttcatactac atgggtcaat agtataggga ttcatattat   10200
aggcgatact ataataattt gttcgtctgc agagcttatt atttgccaaa attagatatt   10260
cctattctgt ttttgtttgt gtgctgttaa attgttaacg cctgaaggaa taaatataaa   10320
tgacgaaatt ttgatgttta tctctgctcc tttattgtga ccataagtca agatcagatg   10380
cacttgtttt aaatattgtt gtctgaagaa ataagtactg acagtatttt gatgcattga   10440
tctgcttgtt tgttgtaaca aaatttaaaa ataaagagtt tcctttttgt tgctctcctt   10500
acctcctgat ggtatctagt atctaccaac tgatactata ttgcttctct ttacatacgt   10560
atcttgctcg atgccttctc ctagtgttga ccagtgttac tcacatagtc tttgctcatt   10620
tcattgtaat gcagatacca agcggttaat taaatgtgcg gcggggccat tctcagtgat   10680
ctctactcac cagtgaggcg gacggtcact gccggtgacc tatggggaga gagtggcagc   10740
agcaagaatg tgaagaactg gaaaaggagt tcttggaagt ttgatgaagg cgatgaagac   10800
tttgaagctg atttcaagga ttttgaggat tgcagtagcg aggaggaggt agattttgga   10860
catgaggaaa aagaattcca attgaacagt tcgaatttcg tggaattcaa tggccatact   10920
gccaaagtca ccagcaggaa gcgaaagatc cagtaccgag ggatccggcg gcggccttgg   10980
ggcaaatggg cagcagaaat cagagaccca cagaagggcg tccgagtttg gcttggcacg   11040
ttcagcactg ccgaggaagc tgcaagggca tatgacgtgg aagctctacg catacgtggc   11100
aagaaagcca agatgaattt ccctaccacc atcacagctg ctgggaaaca ccaccggcag   11160
cgtgtggctc gaccggcaaa gaagacgtca caagagagcc tgaagtcaag caatgcctct   11220
ggtcatgtca tctcagcagg cagcagtact gatggcaccg ttgtcaagat cgagttgtca   11280
cagtcaccag cttctccact accagtgtcc agcgcatggc ttgatgcttt tgagctgaag   11340
cagcttggtg gagaaacccc tgaagctgat gggagagaaa cccctgaaga aactgatcat   11400
gaaacgggag tgcagcgga tatgttttt ggcaatggcg aagtgcggct ttcagatgat   11460
tttgcgtctt acgagcctta cccaaatttt atgcagttac cttatctaga aggtgactcg   11520
tatgaaaaca ttgacactct tttcaacggt gaagctgctc aggatggagt gaacatcgga   11580
ggtctttgga atttcgatga tgtgccaatg accgtggtg tttactgagg cgcgccatcg   11640
ttcaaacatt tggcaataaa gtttcttaag attgaatcct gttgccggtc ttgcgatgat   11700
```

-continued

```
tatcatataa tttctgttga attacgttaa gcatgtaata attaacatgt aatgcatgac    11760
gttatttatg agatgggttt ttatgattag agtcccgcaa ttatacattt aatacgcgat    11820
agaaaacaaa atatagcgcg caaactagga taaattatcg cgcgcggtgt catctatgtt    11880
actagatccg atgataagct gtcaaacatg acctcaggat gaagcttggc actggccgtc    11940
gttttacaac gtcgtgactg ggaaaaccct ggcgttaccc aacttaatcg ccttgcagca    12000
catccccctt tcgccagctg gcgtaatagc gaagaggccc gcaccgatcg cccttcccaa    12060
cagttgcgca gcctgaatgg cgaatgctag agcagcttga gcttggatca gattgtcgtt    12120
tcccgccttc agtttaaact atcagtgttt gacaggatat attggcgg                 12168

<210> SEQ ID NO 20
<211> LENGTH: 11772
<212> TYPE: DNA
<213> ORGANISM: Artificial Sequence
<220> FEATURE:
<223> OTHER INFORMATION: Synthetic construct pMBXS810

<400> SEQUENCE: 20
gtaaacctaa gagaaaagag cgtttattag aataacggat atttaaaagg gcgtgaaaag      60
gtttatccgt tcgtccattt gtatgtgcat gccaaccaca gggttcccct cgggatcaaa     120
gtactttgat ccaacccctc cgctgctata gtgcagtcgg cttctgacgt tcagtgcagc     180
cgtcttctga aaacgacatg tcgcacaagt cctaagttac gcgacaggct gccgccctgc     240
ccttttcctg gcgttttctt gtcgcgtgtt ttagtcgcat aaagtagaat acttgcgact     300
agaaccggag acattacgcc atgaacaaga gcgccgccgc tggcctgctg gctatgccc      360 gcgtcagcac cgacgaccag gacttgacca accaacgggc cgaactgcac gcggccggct     420
gcaccaagct gttttccgag aagatcaccg gcaccaggcg cgaccgcccg gagctggcca     480
ggatgcttga ccacctacgc cctggcgacg ttgtgacagt gaccaggcta gaccgcctgg     540
cccgcagcac ccgcgaccta ctggacattg ccgagcgcat ccaggaggcc ggcgcgggcc     600
tgcgtagcct ggcagagccg tgggccgaca ccaccacgcc ggccggccgc atggtgttga     660
ccgtgttcgc cggcattgcc gagttcgagc gttccctaat catcgaccgc acccggagcg     720
ggcgcgaggc cgccaaggcc cgaggcgtga agtttggccc ccgccctacc ctcaccccgg     780
cacagatcgc gcacgcccgc gagctgatcg accaggaagg ccgcaccgtg aaagaggcgg     840
ctgcactgct tggcgtgcat cgctcgaccc tgtaccgcgc acttgagcgc agcgaggaag     900
tgacgcccac cgaggccagg cggcgcggtg ccttccgtga ggacgcattg accgaggccg     960
acgccctggc ggccgccgag aatgaacgcc aagaggaaca agcatgaaac cgcaccagga    1020
cggccaggac gaaccgtttt tcattaccga agagatcgag gcggagatga tcgcggccgg    1080
gtacgtgttc gagccgcccg cgcacgtctc aaccgtgcgg ctgcatgaaa tcctggccgg    1140
tttgtctgat gccaagctgg cggcctggcc ggccagcttg gccgctgaag aaaccgagcg    1200
ccgccgtcta aaaggtgatg tgtatttga gtaaaacagc ttgcgtcatg cggtcgctgc    1260
gtatatgatg cgatgagtaa ataaacaaat acgcaagggg aacgcatgaa ggttatcgct    1320
gtacttaacc agaaaggcgg gtcaggcaag acgaccatcg caacccatct agcccgcgcc    1380
ctgcaactcg ccggggccga tgttctgtta gtcgattccg atccccaggg cagtgcccgc    1440
gattgggcgg ccgtgcggga agatcaaccg ctaaccgttg tcggcatcga ccgcccgacg    1500
attgaccgcg acgtgaaggc catcggccgg cgcgacttcg tagtgatcga cggagcgccc    1560
caggcggcgg acttggctgt gtccgcgatc aaggcagccg acttcgtgct gattccggtg    1620
```

```
cagccaagcc cttacgacat atgggccacc gccgacctgg tggagctggt taagcagcgc   1680
attgaggtca cggatggaag gctacaagcg gcctttgtcg tgtcgcgggc gatcaaaggc   1740
acgcgcatcg gcggtgaggt tgccgaggcg ctggccgggt acgagctgcc cattcttgag   1800
tcccgtatca cgcagcgcgt gagctaccca ggcactgccg ccgccggcac aaccgttctt   1860
gaatcagaac ccgagggcga cgctgcccgc gaggtccagg cgctggccgc tgaaattaaa   1920
tcaaaactca tttgagttaa tgaggtaaag agaaaatgag caaaagcaca aacacgctaa   1980
gtgccggccg tccgagcgca cgcagcagca aggctgcaac gttggccagc ctggcagaca   2040
cgccagccat gaagcgggtc aactttcagt tgccggcgga ggatcacacc aagctgaaga   2100
tgtacgcggt acgccaaggc aagaccatta ccgagctgct atctgaatac atcgcgcagc   2160
taccagagta aatgagcaaa tgaataaatg agtagatgaa ttttagcggc taaaggaggc   2220
ggcatggaaa atcaagaaca accaggcacc gacgccgtgg aatgccccat gtgtggagga   2280
acgggcggtt ggccaggcgt aagcggctgg gttgtctgcc ggccctgcaa tggcactgga   2340
acccccaagc ccgaggaatc ggcgtgacgg tcgcaaacca tccggcccgg tacaaatcgg   2400
cgcggcgctg ggtgatgacc tggtggagaa gttgaaggcc gcgcaggccg cccagcggca   2460
acgcatcgag gcagaagcac gccccggtga atcgtggcaa gcggccgctg atcgaatccg   2520
caaagaatcc cggcaaccgc cggcagccgg tgcgccgtcg attaggaagc cgcccaaggg   2580
cgacgagcaa ccagattttt tcgttccgat gctctatgac gtgggcaccc gcgatagtcg   2640
cagcatcatg gacgtggccg ttttccgtct gtcgaagcgt gaccgacgag ctggcgaggt   2700
gatccgctac gagcttccag acgggcacgt agaggtttcc gcagggccgg ccggcatggc   2760
cagtgtgtgg gattacgacc tggtactgat ggcggtttcc catctaaccg aatccatgaa   2820
ccgataccgg gaagggaagg gagacaagcc cggccgcgtg ttccgtccac acgttgcgga   2880
cgtactcaag ttctgccggc gagccgatgg cggaaagcag aaagacgacc tggtagaaac   2940
ctgcattcgg ttaaacacca cgcacgttgc catgcagcgt acgaagaagg ccaagaacgg   3000
ccgcctggtg acggtatccg agggtgaagc cttgattagc cgctacaaga tcgtaaagag   3060
cgaaaccggg cggccggagt acatcgagat cgagctagct gattggatgt accgcgagat   3120
cacagaaggc aagaacccgg acgtgctgac ggttcacccc gattacttt tgatcgatcc   3180
cggcatcggc cgttttctct accgcctggc acgccgcgcc gcaggcaagg cagaagccag   3240
atggttgttc aagacgatct acgaacgcag tggcagcgcc ggagagttca agaagttctg   3300
tttcaccgtg cgcaagctga tcgggtcaaa tgacctgccg gagtacgatt tgaaggagga   3360
ggcggggcag gctggcccga tcctagtcat gcgctaccgc aacctgatcg agggcgaagc   3420
atccgccggt tcctaatgta cggagcagat gctagggcaa attgccctag cagggggaaaa   3480
aggtcgaaaa ggtctctttc ctgtggatag cacgtacatt gggaacccaa agccgtacat   3540
tgggaaccga aacccgtaca ttgggaaccc aaagccgtac attgggaacc ggtcacacat   3600
gtaagtgact gatataaaag agaaaaaagg cgatttttcc gcctaaaact ctttaaaact   3660
tattaaaact cttaaaaccc gcctggcctg tgcataactg tctggccagc gcacagccga   3720
agagctgcaa aaagcgccta cccttcggtc gctgcgctcc ctacgccccg ccgcttcgcg   3780
tcggcctatc gcggccgctg gccgctcaaa aatggctggc ctacggccag gcaatctacc   3840
agggcgcgga caagccgcgc cgtcgccact gaccgccgg cgcccacatc aaggcaccct   3900
gcctcgcgcg tttcggtgat gacggtgaaa acctctgaca catgcagctc ccggagacgg   3960
```

```
tcacagcttg tctgtaagcg gatgccggga gcagacaagc ccgtcagggc gcgtcagcgg   4020
gtgttggcgg gtgtcgggc gcagccatga cccagtcacg tagcgatagc ggagtgtata    4080
ctggcttaac tatgcggcat cagagcagat tgtactgaga gtgcaccata tgcggtgtga   4140
aataccgcac agatgcgtaa ggagaaaata ccgcatcagg cgctcttccg cttcctcgct   4200
cactgactcg ctgcgctcgg tcgttcggct gcggcgagcg gtatcagctc actcaaaggc   4260
ggtaatacgg ttatccacag aatcagggga taacgcagga agaacatgt gagcaaaagg    4320
ccagcaaaag gccaggaacc gtaaaaaggc cgcgttgctg gcgtttttcc ataggctccg   4380
cccccctgac gagcatcaca aaaatcgacg ctcaagtcag aggtggcgaa acccgacagg   4440
actataaaga taccaggcgt ttccccctgg aagctccctc gtgcgctctc ctgttccgac   4500
cctgccgctt accggatacc tgtccgcctt tctcccttcg ggaagcgtgg cgctttctca   4560
tagctcacgc tgtaggtatc tcagttcggt gtaggtcgtt cgctccaagc tgggctgtgt   4620
gcacgaaccc cccgttcagc ccgaccgctg cgccttatcc ggtaactatc gtcttgagtc   4680
caacccggta agacacgact tatcgccact ggcagcagcc actggtaaca ggattagcag   4740
agcgaggtat gtaggcggtg ctacagagtt cttgaagtgg tggcctaact acggctacac   4800
tagaaggaca gtatttggta tctgcgctct gctgaagcca gttaccttcg gaaaaagagt   4860
tggtagctct tgatccggca aacaaaccac cgctggtagc ggtggttttt ttgtttgcaa   4920
gcagcagatt acgcgcagaa aaaaaggatc tcaagaagat cctttgatct tttctacggg   4980
gtctgacgct cagtggaacg aaaactcacg ttaagggatt ttggtcatgc attctaggta   5040
ctaaaacaat tcatccagta aaatataata ttttattttc tcccaatcag gcttgatccc   5100
cagtaagtca aaaaatagct cgacatactg ttcttccccg atatcctccc tgatcgaccg   5160
gacgcagaag gcaatgtcat accacttgtc cgccctgccg cttctcccaa gatcaataaa   5220
gccacttact ttgccatctt tcacaaagat gttgctgtct cccaggtcgc cgtgggaaaa   5280
gacaagttcc tcttcgggct tttccgtctt taaaaaatca tacagctcgc gcggatcttt   5340
aaatggagtg tcttcttccc agttttcgca atccacatcg gccagatcgt tattcagtaa   5400
gtaatccaat tcggctaagc ggctgtctaa gctattcgta tagggacaat ccgatatgtc   5460
gatggagtga agagcctga tgcactccgc atacagctcg ataatctttt cagggctttg    5520
ttcatcttca tactcttccg agcaaaggac gccatcggcc tcactcatga gcagattgct   5580
ccagccatca tgccgttcaa agtgcaggac ctttggaaca ggcagctttc cttccagcca   5640
tagcatcatg tccttttccc gttccacatc ataggtggtc cctttatacc ggctgtccgt   5700
catttttaaa ataggttttt catttttctcc caccagctta tataccttag caggagacat   5760
tccttccgta tcttttacgc agcggtattt ttcgatcagt ttttttcaatt ccggtgatat   5820
tctcatttta gccatttatt atttccttcc tcttttctac agtatttaaa gatacccaa    5880
gaagctaatt ataacaagac gaactccaat tcactgttcc ttgcattcta aaaccttaaa   5940
taccagaaaa cagcttttc aaagttgttt tcaaagttgg cgtataacat agtatcgacg    6000
gagccgattt tgaaaccgcg gtgatcacag gcagcaacgc tctgtcatcg ttacaatcaa   6060
catgctaccc tccgcgagat catccgtgtt tcaaacccgg cagcttagtt gccgttcttc   6120
cgaatagcat cggtaacatg agcaaagtct gccgccttac aacggctctc ccgctgacgc   6180
cgtcccggac tgatgggctg cctgtatcga gtggtgattt tgtgccgagc tgccggtcgg   6240
ggagctgttg gctggctggt ggcaggatat attgtggtgt aaacaaattg acgcttagac   6300
aacttaataa cacattgcgg acgtttttaa tgtactgaat taacgccgaa ttaattcggg   6360
```

-continued

```
ggatctggat tttagtactg gattttggtt ttaggaatta gaaattttat tgatagaagt    6420
attttacaaa tacaaataca tactaagggt ttcttatatg ctcaacacat gagcgaaacc    6480
ctataggaac cctaattccc ttatctggga actactcaca cattattatg gagaaactcg    6540
agtcaaatct cggtgacggg caggaccgga cggggcggta ccggcaggct gaagtccagc    6600
tgccagaaac ccacgtcatg ccagttcccg tgcttgaagc cggccgcccg cagcatgccg    6660 cgggggggcat atccgagcgc ctcgtgcatg cgcacgctcg ggtcgttggg cagcccgatg    6720
acagcgacca cgctcttgaa gccctgtgcc tccagggact tcagcaggtg ggtgtagagc    6780
gtggagccca gtcccgtccg ctggtggcgg ggggagacgt acacggtcga ctcggccgtc    6840
cagtcgtagg cgttgcgtgc cttccagggg cccgcgtagg cgatgccggc gacctcgccg    6900
tccacctcgg cgacgagcca gggatagcgc tcccgcagac ggacgaggtc gtccgtccac    6960
tcctgcggtt cctgcggctc ggtacggaag ttgaccgtgc ttgtctcgat gtagtggttg    7020
acgatggtgc agaccgccgg catgtccgcc tcggtggcac ggcggatgtc ggccgggcgt    7080
cgttctgggc tcatggtaga ccgcttggta tctgcattac aatgaaatga gcaaagacta    7140
tgtgagtaac actggtcaac actagggaga aggcatcgag caagatacgt atgtaaagag    7200
aagcaatata gtgtcagttg gtagatacta gataccatca ggaggtaagg agagcaacaa    7260
aaaggaaact ctttattttt aaattttgtt acaacaaaca agcagatcaa tgcatcaaaa    7320
tactgtcagt acttatttct tcagacaaca atatttaaaa caagtgcatc tgatcttgac    7380
ttatggtcac aataaaggag cagagataaa catcaaaatt tcgtcattta tatttattcc    7440
ttcaggcgtt aacaatttaa cagcacacaa acaaaaacag aataggaata tctaattttg    7500
gcaaataata agctctgcag acgaacaaat tattatagta tcgcctataa tatgaatccc    7560
tatactattg acccatgtag tatgaagcct gtgcctaaat taacagcaaa cttctgaatc    7620
caagtgccct ataacaccaa catgtgctta aataaatacc gctaagcacc aaattacaca    7680
tttctcgtat tgctgtgtag gttctatctt cgtttcgtac taccatgtcc ctatattttg    7740
ctgctacaaa ggacggcaag taatcagcac aggcagaaca cgatttcaga gtgtaattct    7800
agatccagct aaaccactct cagcaatcac cacacaagag agcattcaga gaaacgtggc    7860
agtaacaaag gcagagggcg gagtgagcgc gtaccgaaga cggtctcgag agagatagat    7920
ttgtagagag agactggtga tttcagcgtg tcctctccaa atgaaatgaa cttccttata    7980
tagaggaagg tcttgcgaag gatagtggga ttgtgcgtca tcccttacgt cagtggagat    8040
atcacatcaa tccacttgct ttgaagacgt ggttggaacg tcttcttttt ccacgatgct    8100
cctcgtgggt gggggtccat ctttgggacc actgtcggca gaggcatctt gaacgatagc    8160 cttttccttta tcgcaatgat ggcatttgta ggtgccacct tcctttttcta ctgtcctttt    8220 gatgaagtga cagatagctg ggcaatggaa tccgaggagg tttcccgata ttacccttttg    8280 ttgaaaagtc tcaatagccc tttggtcttc tgagactgta tctttgatat tcttggagta    8340
gacgagagtg tcgtgctcca ccatgttatc acatcaatcc acttgctttg aagacgtggt    8400
tggaacgtct tctttttcca cgatgctcct cgtgggtggg ggtccatctt tgggaccact    8460
gtcggcagag gcatcttgaa cgatagcctt tcctttatcg caatgatggc atttgtaggt    8520
gccaccttcc ttttctactg tccttttgat gaagtgacag atagctgggc aatggaatcc    8580
gaggaggttt cccgatatta ccctttgttg aaaagtctca atagccctttt ggtcttctga    8640 gactgtatct ttgatattct tggagtagac gagagtgtcg tgctccacca tgttggcaag    8700
```

```
ctgctctagc caatacgcaa accgcctctc cccgcgcgtt ggccgattca ttaatgcagc    8760
tggcacgaca ggtttcccga ctggaaagcg ggcagtgagc gcaacgcaat taatgtgagt    8820
tagctcactc attaggcacc ccaggcttta cactttatgc ttccggctcg tatgttgtgt    8880
ggaattgtga gcggataaca atttcacaca ggaaacagct atgaccatga ttacgaattg    8940
gggtttaaac cacggaagat ccaggtctcg agactaggag acggatggga ggcgcaacgc    9000
gcgatgggga gggggcggc gctgaccttt ctggcgaggt cgaggtagcg atcgagcagc    9060
tgcagcgcgg acacgatgag gaagacgaag atagccgcca tggacatgtt cgccagcggc    9120
ggcggagcga ggctgagccg gtctctccgg cctccggtcg gcgttaagtt ggggatcgta    9180
acgtgacgtg tctcgtctcc acggatcgac acaaccggcc tactcgggtg cacgacgccg    9240
cgataagggc gagatgtccg tgcacgcagc ccgtttggag tcctcgttgc ccacgaaccg    9300
accccttaca gaacaaggcc tagcccaaaa ctattctgag ttgagctttt gagcctagcc    9360
cacctaagcc gagcgtcatg aactgatgaa cccactacca ctagtcaagg caaaccacaa    9420
ccacaaatgg atcaattgat ctagaacaat ccgaaggagg ggaggccacg tcacactcac    9480
accaaccgaa atatctgcca gaatcagatc aaccggccaa taggacgcca gcgagcccaa    9540
cacctggcga cgccgcaaaa ttcaccgcga ggggcaccgg gcacggcaaa aacaaaagcc    9600
cggcgcggtg agaatatctg gcgactggcg gagacctggt ggccagcgcg cggccacatc    9660
agccacccca tccgcccacc tcacctccgg cgagccaatg gcaactcgtc ttaagattcc    9720
acgagataag gacccgatcg ccggcgacgc tatttagcca ggtgcgcccc ccacggtaca    9780
ctccaccagc ggcatctata gcaaccggtc cagcactttc acgctcagct tcagcaagat    9840
ctaccgtctt cggtacgcgc tcactccgcc ctctgccttt gttactgcca cgtttctctg    9900
aatgctctct tgtgtggtga ttgctgagag tggtttagct ggatctagaa ttacactctg    9960
aaatcgtgtt ctgcctgtgc tgattacttg ccgtcctttg tagcagcaaa atatagggac   10020
atggtagtac gaaacgaaga tagaacctac acagcaatac gagaaatgtg taatttggtg   10080
cttagcggta tttatttaag cacatgttgg tgttataggg cacttggatt cagaagtttg   10140
ctgttaattt aggcacaggc ttcatactac atgggtcaat agtataggga ttcatattat   10200
aggcgatact ataataattt gttcgtctgc agagcttatt atttgccaaa attagatatt   10260
cctattctgt ttttgtttgt gtgctgttaa attgttaacg cctgaaggaa taaatataaa   10320
tgacgaaatt ttgatgttta tctctgctcc tttattgtga ccataagtca agatcagatg   10380
cacttgtttt aaatattgtt gtctgaagaa ataagtactg acagtatttt gatgcattga   10440
tctgcttgtt tgttgtaaca aaatttaaaa ataaagagtt tccttttgt tgctctcctt   10500
acctcctgat ggtatctagt atctaccaac tgatactata ttgcttctct ttacatacgt   10560
atcttgctcg atgccttctc ctagtgttga ccagtgttac tcacatagtc tttgctcatt   10620
tcattgtaat gcagatacca agcggttaat taaatgcata tgtatccttt ctacatacat   10680
gcaggttacg ggacgagaat gcactaccgt ggcgtgcggc ggcggccgtg gggcaagtgg   10740
gcggcggaga tccgtgaccc cgccaaggcg gcgcgtgtgt ggctcggcac cttcgacacc   10800
gcggaggccg ccgccgcagc gtacgacgac gccgcgctcc ggttcaaggg cgccaaggcc   10860
aagctcaact ttcccgagcg cgtccgcggc cgtaccggcc agggcgcgtt cctcgtcagc   10920
cctggcgtcc cccagcagcc gccgccgtct tccctgccaa ctgcagccgc cgcgccgacg   10980
ccgttccccg gcttgatgcg gtacgcgcaa ctccagggtt ggagcagcgg gaacatcgcg   11040
gccagcaaca ccggtggtga tctcgcgccg ccggcacagg cgtcgtcgtc ggtgcagatt   11100
```

```
ctggacttct cgacgcagca actactccgg ggctcaccga caacgttcgg cccaccgccg    11160
acgacgtcgg catcgatgtc caggactagc agagtagatg aggcgcacga gagttgcgat    11220
gctcctgact gaggcgcgcc atcgttcaaa catttggcaa taaagtttct taagattgaa    11280
tcctgttgcc ggtcttgcga tgattatcat ataatttctg ttgaattacg ttaagcatgt    11340
aataattaac atgtaatgca tgacgttatt tatgagatgg ttttttatga ttagagtccc    11400
gcaattatac atttaatacg cgatagaaaa caaaatatag cgcgcaaact aggataaatt    11460
atcgcgcgcg gtgtcatcta tgttactaga tccgatgata agctgtcaaa catgacctca    11520
ggatgaagct tggcactggc cgtcgtttta caacgtcgtg actgggaaaa ccctggcgtt    11580
acccaactta atcgccttgc agcacatccc cctttcgcca gctggcgtaa tagcgaagag    11640
gcccgcaccg atcgcccttc ccaacagttg cgcagcctga atggcgaatg ctagagcagc    11700
ttgagcttgg atcagattgt cgtttcccgc cttcagttta actatcagt gtttgacagg    11760 atatattggc gg                                                        11772

<210> SEQ ID NO 21
<211> LENGTH: 12509
<212> TYPE: DNA
<213> ORGANISM: Artificial Sequence
<220> FEATURE:
<223> OTHER INFORMATION: Synthetic construct pMBXS855

<400> SEQUENCE: 21
gtaaacctaa gagaaaagag cgtttattag aataacggat atttaaaagg gcgtgaaaag      60
gtttatccgt tcgtccattt gtatgtgcat gccaaccaca gggttcccct cgggatcaaa     120
gtactttgat ccaaccccte cgctgctata gtgcagtcgg cttctgacgt tcagtgcagc     180
cgtcttctga aaacgacatg tcgcacaagt cctaagttac gcgacaggct gccgccctgc     240
ccttttcctg gcgttttctt gtcgcgtgtt ttagtcgcat aaagtagaat acttgcgact     300
agaaccggag acattacgcc atgaacaaga gcgccgccgc tggcctgctg ggctatgccc     360
gcgtcagcac cgacgaccag gacttgacca accaacgggc cgaactgcac gcggccggct     420
gcaccaagct gttttccgag aagatcaccg gcaccaggcg cgaccgcccg gagctggcca     480
ggatgcttga ccacctacgc cctggcgacg ttgtgacagt gaccaggcta gaccgcctgg     540
cccgcagcac ccgcgaccta ctggacattg ccgagcgcat ccaggaggcc ggcgcgggcc     600
tgcgtagcct ggcagagccg tgggccgaca ccaccacgcc ggccggccgc atggtgttga     660
ccgtgttcgc cggcattgcc gagttcgagc gttccctaat catcgaccgc acccggagcg     720
ggcgcgaggc cgccaaggcc cgaggcgtga agtttggccc ccgccctacc ctcaccccgg     780
cacagatcgc gcacgcccgc gagctgatcg accaggaagg ccgcaccgtg aaagaggcgg     840
ctgcactgct tggcgtgcat cgctcgaccc tgtaccgcgc acttgagcgc agcgaggaag     900
tgacgcccac cgaggccagg cggcgcggtg ccttccgtga ggacgcattg accgaggccg     960
acgccctggc ggccgccgag aatgaacgcc aagaggaaca agcatgaaac cgcaccagga    1020
cggccaggac gaaccgtttt tcattaccga agagatcgag gcggagatga tcgcggccgg    1080
gtacgtgttc gagccgcccg cgcacgtctc aaccgtgcgg ctgcatgaaa tcctggccgg    1140
tttgtctgat gccaagctgg cggcctggcc ggccagcttg gccgctgaag aaaccgagcg    1200
ccgccgtcta aaaaggtgat gtgtatttga gtaaaacagc ttgcgtcatg cggtcgctgc    1260
gtatatgatg cgatgagtaa ataaacaaat acgcaagggg aacgcatgaa ggttatcgct    1320
```

```
gtacttaacc agaaaggcgg gtcaggcaag acgaccatcg caacccatct agcccgcgcc      1380
ctgcaactcg ccggggccga tgttctgtta gtcgattccg atccccaggg cagtgcccgc      1440
gattgggcgg ccgtgcggga agatcaaccg ctaaccgttg tcggcatcga ccgcccgacg      1500
attgaccgcg acgtgaaggc catcggccgg cgcgacttcg tagtgatcga cggagcgccc      1560
caggcggcgg acttggctgt gtccgcgatc aaggcagccg acttcgtgct gattccggtg      1620
cagccaagcc cttacgacat atgggccacc gccgacctgg tggagctggt taagcagcgc      1680
attgaggtca cggatggaag gctacaagcg gcctttgtcg tgtcgcgggc gatcaaaggc      1740
acgcgcatcg gcggtgaggt tgccgaggcg ctggccgggt acgagctgcc cattcttgag      1800
tcccgtatca cgcagcgcgt gagctaccca ggcactgccg ccgccggcac aaccgttctt      1860
gaatcagaac ccgagggcga cgctgcccgc gaggtccagg cgctggccgc tgaaattaaa      1920
tcaaaactca tttgagttaa tgaggtaaag agaaaatgag caaaagcaca aacacgctaa      1980
gtgccggccg tccgagcgca cgcagcagca aggctgcaac gttggccagc ctggcagaca      2040
cgccagccat gaagcgggtc aactttcagt tgccggcgga ggatcacacc aagctgaaga      2100
tgtacgcggt acgccaaggc aagaccatta ccgagctgct atctgaatac atcgcgcagc      2160
taccagagta aatgagcaaa tgaataaatg agtagatgaa ttttagcggc taaaggaggc      2220
ggcatggaaa atcaagaaca accaggcacc gacgccgtgg aatgccccat gtgtggagga      2280
acgggcggtt ggccaggcgt aagcggctgg gttgtctgcc ggccctgcaa tggcactgga      2340 accccaagc ccgaggaatc ggcgtgacgg tcgcaaacca tccggcccgg tacaaatcgg      2400
cgcggcgctg ggtgatgacc tggtggagaa gttgaaggcc gcgcaggccg cccagcggca      2460
acgcatcgag gcagaagcac gccccggtga atcgtggcaa gcggccgctg atcgaatccg      2520
caaagaatcc cggcaaccgc cggcagccgg tgcgccgtcg attaggaagc cgcccaaggg      2580
cgacgagcaa ccagattttt tcgttccgat gctctatgac gtgggcaccc gcgatagtcg      2640
cagcatcatg gacgtggccg ttttccgtct gtcgaagcgt gaccgacgag ctggcgaggt      2700
gatccgctac gagcttccag acgggcacgt agaggtttcc gcagggccgg ccggcatggc      2760
cagtgtgtgg gattacgacc tggtactgat ggcggttccc catctaaccg aatccatgaa      2820
ccgataccgg gaagggaagg gagacaagcc cggccgcgtg ttccgtccac acgttgcgga      2880
cgtactcaag ttctgccggc gagccgatgg cggaaagcag aaagacgacc tggtagaaac      2940
ctgcattcgg ttaaacacca cgcacgttgc catgcagcgt acgaagaagg ccaagaacgg      3000
ccgcctggtg acggtatccg agggtgaagc cttgattagc cgctacaaga tcgtaaagag      3060
cgaaaccggg cggccggagt acatcgagat cgagctagct gattggatgt accgcgagat      3120
cacagaaggc aagaacccgg acgtgctgac ggttcacccc gattacttt tgatcgatcc      3180 cggcatcggc cgttttctct accgcctggc acgccgcgcc gcaggcaagg cagaagccag      3240
atggttgttc aagacgatct acgaacgcag tggcagcgcc ggagagttca agaagttctg      3300
tttcaccgtg cgcaagctga tcgggtcaaa tgacctgccg gagtacgatt tgaaggagga      3360 ggcgggcag gctggcccga tcctagtcat gcgctaccgc aacctgatcg agggcgaagc      3420
atccgccggt tcctaatgta cggagcagat gctagggcaa attgccctag caggggaaaa      3480
aggtcgaaaa ggtctctttc ctgtggatag cacgtacatt gggaacccaa agccgtacat      3540
tgggaaccgg aacccgtaca ttgggaaccc aaagccgtac attgggaacc ggtcacacat      3600
gtaagtgact gatataaaag agaaaaaagg cgatttttcc gcctaaaact ctttaaaact      3660
tattaaaact cttaaaaccc gcctggcctg tgcataactg tctggccagc gcacagccga      3720
```

```
agagctgcaa aaagcgccta cccttcggtc gctgcgctcc ctacgcccg ccgcttcgcg    3780 tcggcctatc gcggccgctg gccgctcaaa aatggctggc ctacgccag gcaatctacc    3840 agggcgcgga caagccgcgc cgtcgccact cgaccgccgg cgcccacatc aaggcaccct    3900
gcctcgcgcg tttcggtgat gacggtgaaa acctctgaca catgcagctc ccggagacgg    3960
tcacagcttg tctgtaagcg gatgccggga gcagacaagc ccgtcagggc gcgtcagcgg    4020
gtgttggcgg gtgtcgggc gcagccatga cccagtcacg tagcgatagc ggagtgtata    4080
ctggcttaac tatgcggcat cagagcagat tgtactgaga gtgcaccata tgcggtgtga    4140
aataccgcac agatgcgtaa ggagaaaata ccgcatcagg cgctcttccg cttcctcgct    4200
cactgactcg ctgcgctcgg tcgttcggct gcggcgagcg tatcagctc actcaaaggc    4260 ggtaatacgg ttatccacag aatcagggga taacgcagga agaacatgt gagcaaaagg    4320 ccagcaaaag gccaggaacc gtaaaaaggc cgcgttgctg gcgttttttcc ataggctccg    4380 cccccctgac gagcatcaca aaaatcgacg ctcaagtcag aggtggcgaa acccgacagg    4440
actataaaga taccaggcgt ttccccctgg aagctccctc gtgcgctctc ctgttccgac    4500
cctgccgctt accggatacc tgtccgcctt tctcccttcg ggaagcgtgg cgctttctca    4560
tagctcacgc tgtaggtatc tcagttcggt gtaggtcgtt cgctccaagc tgggctgtgt    4620
gcacgaaccc cccgttcagc ccgaccgctg cgccttatcc ggtaactatc gtcttgagtc    4680
caacccggta agacacgact tatcgccact ggcagcagcc actggtaaca ggattagcag    4740
agcgaggtat gtaggcggtg ctacagagtt cttgaagtgg tggcctaact acggctacac    4800
tagaaggaca gtatttggta tctgcgctct gctgaagcca gttaccttcg gaaaaagagt    4860
tggtagctct tgatccggca acaaaccac cgctggtagc ggtggttttt tgtttgcaa    4920 gcagcagatt acgcgcagaa aaaaggatc tcaagaagat cctttgatct tttctacggg    4980
gtctgacgct cagtggaacg aaaactcacg ttaagggatt ttggtcatgc attctaggta    5040
ctaaaacaat tcatccagta aaatataata ttttattttc tcccaatcag gcttgatccc    5100
cagtaagtca aaaatagct cgacatactg ttcttccccg atatcctccc tgatcgaccg    5160
gacgcagaag gcaatgtcat accacttgtc cgccctgccg cttctcccaa gatcaataaa    5220
gccacttact tgccatctt tcacaaagat gttgctgtct cccaggtcgc cgtgggaaaa    5280
gacaagttcc tcttcgggct tttccgtctt taaaaaatca tacagctcgc gcggatcttt    5340
aaatggagtg tcttcttccc agttttcgca atccacatcg ccagatcgt tattcagtaa    5400 gtaatccaat tcggctaagc ggctgtctaa gctattcgta tagggacaat ccgatatgtc    5460
gatggagtga aagagcctga tgcactccgc atacagctcg ataatctttt cagggctttg    5520
ttcatcttca tactcttccg agcaaaggac gccatcggcc tcactcatga gcagattgct    5580
ccagccatca tgccgttcaa agtgcaggac ctttggaaca ggcagctttc cttccagcca    5640
tagcatcatg tcctttttcc gttccacatc ataggtggtc cctttatacc ggctgtccgt    5700
cattttaaaa tataggtttt cattttctcc caccagctta tataccttag caggagacat    5760
tccttccgta tcttttacgc agcggtattt ttcgatcagt ttttttcaatt ccggtgatat    5820 tctcatttta gccatttatt atttccttcc tcttttctac agtatttaaa gatacccaa    5880 gaagctaatt ataacaagac gaactccaat tcactgttcc ttgcattcta aaaccttaaa    5940
taccagaaaa cagcttttc aaagttgttt tcaaagttgg cgtataacat agtatcgacg    6000
gagccgattt tgaaaccgcg gtgatcacag gcagcaacgc tctgtcatcg ttacaatcaa    6060
```

```
catgctaccc tccgcgagat catccgtgtt tcaaacccgg cagcttagtt gccgttcttc    6120
cgaatagcat cggtaacatg agcaaagtct gccgccttac aacggctctc ccgctgacgc    6180
cgtcccggac tgatgggctg cctgtatcga gtggtgattt tgtgccgagc tgccggtcgg    6240
ggagctgttg gctggctggt ggcaggatat attgtggtgt aaacaaattg acgcttagac    6300
aacttaataa cacattgcgg acgttttttaa tgtactgaat taacgccgaa ttaattcggg    6360
ggatctggat tttagtactg gattttggtt ttaggaatta gaaattttat tgatagaagt    6420 atttttacaaa tacaaataca tactaagggt ttcttatatg ctcaacacat gagcgaaacc    6480
ctataggaac cctaattccc ttatctggga actactcaca cattattatg gagaaactcg    6540
agtcaaatct cggtgacggg caggaccgga cggggcggta ccggcaggct gaagtccagc    6600
tgccagaaac ccacgtcatg ccagttcccg tgcttgaagc cggccgcccg cagcatgccg    6660 cgggggggcat atccgagcgc ctcgtgcatg cgcacgctcg ggtcgttggg cagcccgatg    6720
acagcgacca cgctcttgaa gccctgtgcc tccaggact tcagcaggtg ggtgtagagc     6780
gtggagccca gtcccgtccg ctggtggcgg ggggagacgt acacggtcga ctcggccgtc    6840
cagtcgtagg cgttgcgtgc cttccagggg cccgcgtagg cgatgccggc gacctcgccg    6900
tccacctcgg cgacgagcca gggatagcgc tcccgcagac ggacgaggtc gtccgtccac    6960
tcctgcggtt cctgcggctc ggtacggaag ttgaccgtgc ttgtctcgat gtagtggttg    7020
acgatggtgc agaccgccgg catgtccgcc tcggtgcac ggcggatgtc ggccgggcgt     7080
cgttctgggc tcatggtaga ccgcttggta tctgcattac aatgaaatga gcaaagacta    7140
tgtgagtaac actggtcaac actagggaga aggcatcgag caagatacgt atgtaaagag    7200
aagcaatata gtgtcagttg gtagatacta gataccatca ggaggtaagg agagcaacaa    7260
aaaggaaact ctttattttt aaattttgtt acaacaaaca agcagatcaa tgcatcaaaa    7320
tactgtcagt acttatttct tcagacaaca atatttaaaa caagtgcatc tgatcttgac    7380
ttatggtcac aataaaggag cagagataaa catcaaaatt tcgtcatta tatttattcc     7440 ttcaggcgtt aacaatttaa cagcacacaa acaaaaacag aataggaata tctaatttg     7500 gcaaataata agctctgcag acgaacaaat tattatagta tcgcctataa tatgaatccc    7560
tatactattg acccatgtag tatgaagcct gtgcctaaat taacagcaaa cttctgaatc    7620
caagtgccct ataacaccaa catgtgctta aataaatacc gctaagcacc aaattacaca    7680
tttctcgtat tgctgtgtag gttctatctt cgtttcgtac taccatgtcc ctatattttg    7740
ctgctacaaa ggacggcaag taatcagcac aggcagaaca cgatttcaga gtgtaattct    7800
agatccagct aaaccactct cagcaatcac cacacaagag agcattcaga gaaacgtggc    7860
agtaacaaag gcagagggcg gagtgagcgc gtaccgaaga cggtctcgag agagatagat    7920
ttgtagagag agactggtga tttcagcgtg tcctctccaa atgaaatgaa cttccttata    7980
tagaggaagg tcttgcgaag gatagtggga ttgtgcgtca tcccttacgt cagtggagat    8040
atcacatcaa tccacttgct ttgaagacgt ggttggaacg tcttcttttt ccacgatgct    8100
cctcgtgggt gggggtccat ctttgggacc actgtcggca gaggcatctt gaacgatagc    8160 cttttcctttta tcgcaatgat ggcatttgta ggtgccacct tcctttttcta ctgtcctttt   8220 gatgaagtga cagatagctg ggcaatggaa tccgaggagg tttcccgata ttacccttg     8280 ttgaaaagtc tcaatagccc tttggtcttc tgagactgta tctttgatat tcttggagta    8340
gacgagagtg tcgtgctcca ccatgttatc acatcaatcc acttgctttg aagacgtggt    8400
tggaacgtct tcttttttcca cgatgctcct cgtgggtggg ggtccatctt tgggaccact    8460
```

```
gtcggcagag gcatcttgaa cgatagcctt tcctttatcg caatgatggc atttgtaggt    8520
gccaccttcc ttttctactg tccttttgat gaagtgacag atagctgggc aatggaatcc    8580
gaggaggttt cccgatatta ccctttgttg aaaagtctca atagcccttt ggtcttctga    8640
gactgtatct ttgatattct tggagtagac gagagtgtcg tgctccacca tgttggcaag    8700
ctgctctagc caatacgcaa accgcctctc ccgcgcgtt ggccgattca ttaatgcagc     8760
tggcacgaca ggtttcccga ctggaaagcg ggcagtgagc gcaacgcaat taatgtgagt    8820
tagctcactc attaggcacc ccaggcttta cactttatgc ttccggctcg tatgttgtgt    8880
ggaattgtga gcggataaca atttcacaca ggaaacagct atgaccatga ttacgaattg    8940
gggtttaaac cacggaagat ccaggtctcg agactaggag acggatggga ggcgcaacgc    9000
gcgatgggga gggggcggc gctgaccttt ctggcgaggt cgaggtagcg atcgagcagc     9060
tgcagcgcgg acacgatgag gaagacgaag atagccgcca tggacatgtt cgccagcggc    9120
ggcggagcga ggctgagccg gtctctccgg cctccggtcg gcgttaagtt ggggatcgta    9180
acgtgacgtg tctcgtctcc acggatcgac acaaccggcc tactcgggtg cacgacgccg    9240
cgataagggc gagatgtccg tgcacgcagc ccgtttggag tcctcgttgc ccacgaaccg    9300
accccttaca gaacaaggcc tagcccaaaa ctattctgag ttgagctttt gagcctagcc    9360
cacctaagcc gagcgtcatg aactgatgaa cccactacca ctagtcaagg caaaccacaa    9420
ccacaaatgg atcaattgat ctagaacaat ccgaaggagg ggaggccacg tcacactcac    9480
accaaccgaa atatctgcca gaatcagatc aaccggccaa taggacgcca gcgagcccaa    9540
cacctggcga cgccgcaaaa ttcaccgcga ggggcaccgg gcacggcaaa aacaaaagcc    9600
cggcgcggtg agaatatctg gcgactggcg gagacctggt ggccagcgcg cggccacatc    9660
agccacccca tccgcccacc tcacctccgg cgagccaatg gcaactcgtc ttaagattcc    9720
acgagataag gacccgatcg ccggcgacgc tatttagcca ggtgcgcccc ccacggtaca    9780
ctccaccagc ggcatctata gcaaccggtc cagcactttc acgctcagct tcagcaagat    9840
ctaccgtctt cggtacgcgc tcactccgcc ctctgccttt gttactgcca cgtttctctg    9900
aatgctctct tgtgtggtga ttgctgagag tggtttagct ggatctagaa ttacactctg    9960
aaatcgtgtt ctgcctgtgc tgattacttg ccgtcctttg tagcagcaaa atatagggac   10020
atggtagtac gaaacgaaga tagaacctac acagcaatac gagaaatgtg taatttggtg   10080
cttagcggta tttatttaag cacatgttgg tgttataggg cacttggatt cagaagtttg   10140
ctgttaattt aggcacaggc ttcatactac atgggtcaat agtatagga ttcatattat    10200 aggcgatact ataataattt gttcgtctgc agagcttatt atttgccaaa attagatatt   10260
cctattctgt ttttgtttgt gtgctgttaa attgttaacg cctgaaggaa taaatataaa   10320
tgacgaaatt ttgatgttta tctctgctcc tttattgtga ccataagtca agatcagatg   10380
cacttgtttt aaatattgtt gtctgaagaa ataagtactg acagtatttt gatgcattga   10440
tctgcttgtt tgttgtaaca aaatttaaaa ataaagagtt tccttttgt tgctctcctt    10500 acctcctgat ggtatctagt atctaccaac tgatactata ttgcttctct ttacatacgt   10560
atcttgctcg atgccttctc ctagtgttga ccagtgttac tcacatagtc tttgctcatt   10620
tcattgtaat gcagatacca agcggttaat taaatgccgg actccgacaa cgagtccggc   10680
gggccgagca acgcggagtt ctcgtcgccg cgggagcagg accggttcct gccgatcgcg   10740
aacgtgagcc ggatcatgaa gaaggcgctc ccggcgaacg ccaagatctc caaggacgcc   10800
```

-continued

```
aaggagacgg tgcaggagtg cgtctccgag ttcatctcct tcatcaccgg cgaggcctcc    10860
gacaagtgcc agcgcgagaa gcgcaagacc atcaacggcg acgacctcct ctgggccatg    10920
accacgctcg gcttcgagga ctacatcgag ccactcaagc tctacctcca caagttccgc    10980
gagctcgagg gcgagaaggt ggcctccggc gccgcgggct cctccggctc cgcctcgcag    11040
ccccagagag agacaacgcc gtccgcgcac aatggcgccg ccggggccgt cggctacggc    11100
atgtacggcg ccggcgccgg ggccggcgga ggcagcggca tgatcatgat gatggggcag    11160
ccgatgtacg gctccccacc gggcgcgtcg gggtacccgc agccccgca ccaccacatg    11220 gtgatgggcg ctaaaggtgg cgcctacggc cacggcggcg gctcgtcgcc atcgctgtcg    11280
gggctcggca ggcaggacag gctatgaatg ccggactccg acaacgagtc cggcgggccg    11340
agcaacgcgg agttctcgtc gccgcgggag caggaccggt tcctgccgat cgcgaacgtg    11400
agccggatca tgaagaaggc gctcccggcg aacgccaaga tctccaagga cgccaaggag    11460
acggtgcagg agtgcgtctc cgagttcatc tccttcatca ccggcgaggc ctccgacaag    11520
tgccagcgcg agaagcgcaa gaccatcaac ggcgacgacc tcctctgggc catgaccacg    11580
ctcggcttcg aggactacat cgagccactc aagctctacc tccacaagtt ccgcgagctc    11640
gagggcgaga aggtggcctc cggcgccgcg ggctcctccg gctccgcctc gcagccccag    11700
agagagacaa cgccgtccgc gcacaatggc gccgccgggg ccgtcggcta cggcatgtac    11760
ggcgccggcg ccggggccgg cggaggcagc ggcatgatca tgatgatggg gcagccgatg    11820
tacggctccc caccgggcgc gtcggggtac ccgcagcccc gcaccacca catggtgatg    11880 ggcgctaaag gtggcgccta cggccacggc ggcggctcgt cgccatcgct gtcggggctc    11940
ggcaggcagg acaggctatg aaactgcagg gcgcgccatc gttcaaacat ttggcaataa    12000
agtttcttaa gattgaatcc tgttgccggt cttgcgatga ttatcatata atttctgttg    12060
aattacgtta agcatgtaat aattaacatg taatgcatga cgttatttat gagatgggtt    12120
tttatgatta gagtcccgca attatacatt taatacgcga tagaaaacaa aatatagcgc    12180
gcaaactagg ataaattatc gcgcgcggtg tcatctatgt tactagatcc gatgataagc    12240
tgtcaaacat gacctcagga tgaagcttgg cactggccgt cgttttacaa cgtcgtgact    12300
gggaaaaccc tggcgttacc caacttaatc gccttgcagc acatcccct ttcgccagct     12360 ggcgtaatag cgaagaggcc cgcaccgatc gcccttccca acagttgcgc agcctgaatg    12420
gcgaatgcta gagcagcttg agcttggatc agattgtcgt ttcccgcctt cagtttaaac    12480
tatcagtgtt tgacaggata tattggcgg                                      12509
```

<210> SEQ ID NO 22
<211> LENGTH: 1120
<212> TYPE: DNA
<213> ORGANISM: Zea mays

<400> SEQUENCE: 22

```
ccttttttacc attttctata tcctttgcat cggcgccgta gataattgtt ggctgaaatt      60
catgccagct atatgctatg tttcgaccta ggattggctg cgcagagatg gtggtagggc     120
acgccaattt atttgagata caggttctcc atacgttcct tcacttcatt gcaatgcagc     180
agagtcatat atatacctga atcccaatcc caacaaaggt acggacctct gtgtcgtgtc     240
gtcctcctcc tccggataca ttgcgtttaa tttcgaccgt atggatggat ggatggatgt     300
ggatgtggtg gccgtaatca tgtactagct tgctttgggg ggtcatacga ttgattgatt     360
gattgattgc acgggcatac caggcttcag tgtatttgct gctctgtaga tactttactc     420
```

| | | | | |
|---|---|---|---|---|
| atgtgaaacc cataagggtc ggagtgagct agggcctgtg cggccggcac atagggatcg | | | | 480 |
| gacggatgga tcggtggtgg tatgctagta tatatgcatg gtactacagc tactacccct | | | | 540 |
| cctcctcctc ctcctcccat agtgtatgtg tatgtgtatg agcagcagca ggccgtatcg | | | | 600 |
| acaggcccaa cagacagacg atggatcaga tcggatctcc acaccttgcc tggctcgagt | | | | 660 |
| agatcttgac catccgtgct ccaatcatgg ccatggccgc cggactgcag agcaccaggc | | | | 720 |
| atgccatccg gaccctacta ctactaccag tcgcttacac acctctgccc caaccgtgtc | | | | 780 |
| tcattcttgg cagtttgggg aggaaggaag cccaatcttg tccctaaaaa acgctgttcc | | | | 840 |
| atgtaagtga ccagacgacg actatactag atcactagcc cctcgaatcc tcgatgaaaa | | | | 900 |
| gaaaaaataa aagtcgcgag cagtcacgct cgccgaactc aacgtccggc cgggaaggaa | | | | 960 |
| attaacggcg acagagggtc ggtccccttt cgttcggaag tcggaactgt cattggtcgc | | | | 1020 |
| cgtcgtcgtc gcgtcactgg catgtggggg cctcggtcgg caaaccatcg agagccgaga | | | | 1080 |
| gccgggagag agagagagag gatggcaggt gcacatgcat | | | | 1120 |

<210> SEQ ID NO 23
<211> LENGTH: 1020
<212> TYPE: DNA
<213> ORGANISM: Zea mays

<400> SEQUENCE: 23

| | | | | |
|---|---|---|---|---|
| cacatcgtgc caagttcgag gcccattgat gcactttgct tacatatata ctcgtttaaa | | | | 60 |
| gcatgagttt cgtgtattgt gtgtcataca cgaagcacat atatctaatt ttctctccca | | | | 120 |
| agtttcgtct aacaactaga taagataagc cttacctctt gcatgagcaa ccaaccatac | | | | 180 |
| aaccaccacg agtgctttct cctcccccctt gttgatgatg tcgtatatta acctcaacaa | | | | 240 |
| cctaccatct cttcctcgt ctgcttcttc ctcacccaaa ttcttctgta ccaccataga | | | | 300 |
| tgacatcgag taggccatcc tgctggtctc cgactcgcta accgcagcgc cccaccgcga | | | | 360 |
| caccgtctttt accttccccc gtcgacaagc gcttcggaga gacaataagg caagaacaac | | | | 420 |
| cgagtgagag gaggagacgc tccggatctc gagtttagtt ttatgttagt tgttgacaaa | | | | 480 |
| gaaattgtga tatattatgg tcgataataa tatatatata ttgctgggta tcgaatgttt | | | | 540 |
| atgtgtcgtc gtaacatgcg gatatgtact agtatatata ttatttgtca tctcaagtga | | | | 600 |
| gggacctaac catccatcac ccgtagccaa tgacgcagtc ggatcaacga dacacaggtg | | | | 660 |
| gttgactcgg tcggatgcgt tcgatcatgt cttagcgata gattactggt ttatcagcct | | | | 720 |
| tcgataaatg tgttgttttg agtattattc tgagtgcagg cttttgtagg cttgtaacaa | | | | 780 |
| gtgggcagtg acaagattat taatggttgt taacaagtta gtttcatggt gggagagtgc | | | | 840 |
| gttagcagtg tcctagatat aagcaatatc aacttctact agttgtacag tattttattt | | | | 900 |
| ttatagatta cagtgcaaca gtcgaccatg catctagctt tactagcggt gatcatcgtc | | | | 960 |
| gtccacgaca caagcaatca tattctgtga cactctttcc tcgtccttat caacccaatt | | | | 1020 |

<210> SEQ ID NO 24
<211> LENGTH: 920
<212> TYPE: DNA
<213> ORGANISM: Zea mays

<400> SEQUENCE: 24

| | | | | |
|---|---|---|---|---|
| acaaaagaag attagactaa tccaacagaa ttagtaaatt cagaattctg tatggcgagt | | | | 60 |
| gaggtagact atcaaaaaag agaatgaata tgtagatgaa gatctactaa ttttaagagc | | | | 120 |

```
tatttacaaa gtctattaga gacattttct tataataata accaaattta cctttacaaa      180
ataatatgac tagtcttttg gagttgctcc aataaaacat ataaaatggt actagtatgt      240
gtgtaaacct ttaacttctc gaaaagggac atattttttt agtgagacag aatatcatta      300
gtgaaaaatt gacttttgga ttggatctga taagctaaat gggaaacgta catgcgtcgg      360
tcggtgtcca ttagttactt gacagcgtcc agctctggtc acggtttgag attctattct      420
accagagtag tgtttgaaga taagataaa tttaatcact atatatatat acaatcaaac       480
taaacacaag tagaagtgta atataagaag aagaaaaaaa aatctagaca atgtttggta      540
tgactttaga acaaaattct aagaagagc tggcaagagc aataaacacc ctaactaaca       600
agttgtatac tctcgcatgt aaaattgcaa ctccattaaa aacaatccaa ttaatccaat      660
ttgttgatgt tgcccctata tctttttttt tctaccaact atactacgta tcttgatgaa      720
tctccatcaa tgcttggcaa acccccccta ccaagaaaca gattaaggac gggaatacgg      780
gatggatagc cttcccaaac ggataaaacc ttcggcccgc cgtctcgctg ccggtggggc      840
acacgccata aaccacacgc gccggccgcc cccgcccgtg gcctttaaaa aaccccccgct     900 cccggcgctc gcttttcgct                                                 920

<210> SEQ ID NO 25
<211> LENGTH: 992
<212> TYPE: DNA
<213> ORGANISM: Zea mays

<400> SEQUENCE: 25
agtatgccaa ctgaaacgga tgacacatac acttcgtgaa ccaatcgata ttttacttgc       60
ttctatgtta aataatgtta taatacaata ttttattcaa atgctaaaac ttattactag      120
ataaaaataa aatttaatta tcttcaaaaa ctaaccaata gatattccat cataactaca      180
tttaccaaac taatatacta aaaatatag gataattact aaattaatcg tgcaataatc      240
agtatttatg agattgataa ttttaaatttt tgtgggctac aaacaaaaat taaaacttac     300
ttttcaagtt ggagataaga acaatggtag acgtagctcg ggatggtatg gcgtcggtgc      360
agacggttac cctttgtgcg aagtggcgcg ggcacgaggg tggggacttg gtacatgcat      420
gagagagagg aagaacgaaa caacttctca aattaaagca tatgaaaatc acctaatttt      480
tgtctgtcgg tggaaactaa taactagttt ttattatctt ttttaataag gatccacgaa      540
aattattttt gaccgatgaa aatcctggat cttcgtatta tgtttcgcct tttcccgact      600
ctttgcatgc tagatttcca tgcttggact aaaacgaaga taataaaacc aatctatcat      660
tttcacacga tgtattcata cttgcaatag ataaaccact actccgacgg gatttgcttt      720
ctgacctctg aaatcttgga aggattatgt gtctacactt ctcgatcgag gggaaaaagt      780
cgtagtacca agttgtagtt aaatttgttt cttcgatgac aaaacaaagg agagggccc      840 gcgcggcgca gcgcagcgca gttggctggt tccggaacac gaaaaccaag cacactccac      900
cagctgccat ccaccggggtt ggatggagat tacaatactc gaatagtcag ccagccagcc      960
ggcttgaacg tgcagttttc ccctataaaa cg                                   992

<210> SEQ ID NO 26
<211> LENGTH: 13601
<212> TYPE: DNA
<213> ORGANISM: Artificial Sequence
<220> FEATURE:
<223> OTHER INFORMATION: Synthetic construct pMBXS884
<220> FEATURE:
<221> NAME/KEY: modified_base
```

<222> LOCATION: (11171)..(11176)
<223> OTHER INFORMATION: A, T, C or G
<220> FEATURE:
<221> NAME/KEY: misc_feature
<222> LOCATION: (11171)..(11176)
<223> OTHER INFORMATION: n is a, c, g, or t

<400> SEQUENCE: 26

| | | | | | |
|---|---|---|---|---|---|
| catgccaacc | acagggttcc | cctcgggatc | aaagtacttt | gatccaaccc | ctccgctgct | 60 |
| atagtgcagt | cggcttctga | cgttcagtgc | agccgtcttc | tgaaaacgac | atgtcgcaca | 120 |
| agtcctaagt | tacgcgacag | gctgccgccc | tgccctttc | ctggcgtttt | cttgtcgcgt | 180 |
| gttttagtcg | cataaagtag | aatacttgcg | actagaaccg | gagacattac | gccatgaaca | 240 |
| agagcgccgc | cgctggcctg | ctgggctatg | cccgcgtcag | caccgacgac | caggacttga | 300 |
| ccaaccaacg | ggccgaactg | cacgcggccg | gctgcaccaa | gctgttttcc | gagaagatca | 360 |
| ccggcaccag | gcgcgaccgc | ccggagctgg | ccaggatgct | tgaccaccta | cgccctggcg | 420 |
| acgttgtgac | agtgaccagg | ctagaccgcc | tggcccgcag | caccccgcgac | ctactggaca | 480 |
| ttgccgagcg | catccaggag | gccggcgcgg | gcctgcgtag | cctggcagag | ccgtgggccg | 540 |
| acaccaccac | gccggccggc | cgcatggtgt | tgaccgtgtt | cgccggcatt | gccgagttcg | 600 |
| agcgttccct | aatcatcgac | cgcacccgga | gcgggcgcga | ggccgccaag | gcccgaggcg | 660 |
| tgaagtttgg | cccccgccct | accctcaccc | cggcacagat | cgcgcacgcc | cgcgagctga | 720 |
| tcgaccagga | aggccgcacc | gtgaaagagg | cggctgcact | gcttggcgtg | catcgctcga | 780 |
| ccctgtaccg | cgcacttgag | cgcagcgagg | aagtgacgcc | caccgaggcc | aggcggcgcg | 840 |
| gtgccttccg | tgaggacgca | ttgaccgagg | ccgacgccct | ggcggccgcc | gagaatgaac | 900 |
| gccaagagga | acaagcatga | aaccgcacca | ggacggccag | gacgaaccgt | ttttcattac | 960 |
| cgaagagatc | gaggcggaga | tgatcgcggc | cgggtacgtg | ttcgagccgc | ccgcgcacgt | 1020 |
| ctcaaccgtg | cggctgcatg | aaatcctggc | cggtttgtct | gatgccaagc | tggcggcctg | 1080 |
| gccggccagc | ttggccgctg | aagaaaccga | gcgccgccgt | ctaaaaaggt | gatgtgtatt | 1140 |
| tgagtaaaac | agcttgcgtc | atgcggtcgc | tgcgtatatg | atgcgatgag | taaataaaca | 1200 |
| aatacgcaag | gggaacgcat | gaaggttatc | gctgtactta | accagaaagg | cgggtcaggc | 1260 |
| aagacgacca | tcgcaaccca | tctagcccgc | gccctgcaac | tcgccggggc | cgatgttctg | 1320 |
| ttagtcgatt | ccgatcccca | gggcagtgcc | cgcgattggg | cggccgtgcg | gaagatcaa | 1380 |
| ccgctaaccg | ttgtcggcat | cgaccgcccg | acgattgacc | gcgacgtgaa | ggccatcggc | 1440 |
| cggcgcgact | tcgtagtgat | cgacggagcg | ccccaggcgg | cggacttggc | tgtgtccgcg | 1500 |
| atcaaggcag | ccgacttcgt | gctgattccg | gtgcagccaa | gcccttacga | catatgggcc | 1560 |
| accgccgacc | tggtggagct | ggttaagcag | cgcattgagg | tcacggatgg | aaggctacaa | 1620 |
| gcggcctttg | tcgtgtcgcg | ggcgatcaaa | ggcacgcgca | tcggcggtga | ggttgccgag | 1680 |
| gcgctggccg | ggtacgagct | gcccattctt | gagtcccgta | tcacgcagcg | cgtgagctac | 1740 |
| ccaggcactg | ccgccgccgg | cacaaccgtt | cttgaatcag | aacccgaggg | cgacgctgcc | 1800 |
| cgcgaggtcc | aggcgctggc | cgctgaaatt | aaatcaaaac | tcatttgagt | taatgaggta | 1860 |
| aagagaaaat | gagcaaaagc | acaaacacgc | taagtgccgg | ccgtccgagc | gcacgcagca | 1920 |
| gcaaggctgc | aacgttggcc | agcctggcag | acacgccagc | catgaagcgg | gtcaactttc | 1980 |
| agttgccggc | ggaggatcac | accaagctga | agatgtacgc | ggtacgccaa | ggcaagacca | 2040 |
| ttaccgagct | gctatctgaa | tacatcgcgc | agctaccaga | gtaaatgagc | aaatgaataa | 2100 |

```
atgagtagat gaattttagc ggctaaagga ggcggcatgg aaaatcaaga acaaccaggc    2160
accgacgccg tggaatgccc catgtgtgga ggaacgggcg gttggccagg cgtaagcggc    2220
tgggttgtct gccggccctg caatggcact ggaaccccca agcccgagga atcggcgtga    2280
cggtcgcaaa ccatccggcc cggtacaaat cggcgcggcg ctgggtgatg acctggtgga    2340
gaagttgaag gccgcgcagg ccgcccagcg gcaacgcatc gaggcagaag cacgccccgg    2400
tgaatcgtgg caagcggccg ctgatcgaat ccgcaaagaa tcccggcaac cgccggcagc    2460
cggtgcgccg tcgattagga agccgcccaa gggcgacgag caaccagatt ttttcgttcc    2520
gatgctctat gacgtgggca cccgcgatag tcgcagcatc atggacgtgg ccgttttccg    2580
tctgtcgaag cgtgaccgac gagctggcga ggtgatccgc tacgagcttc cagacgggca    2640
cgtagaggtt tccgcagggc cggccggcat ggccagtgtg tgggattacg acctggtact    2700
gatggcggtt tcccatctaa ccgaatccat gaaccgatac cgggaaggga agggagacaa    2760
gcccggccgc gtgttccgtc cacacgttgc ggacgtactc aagttctgcc ggcgagccga    2820
tggcggaaag cagaaagacg acctggtaga aacctgcatt cggttaaaca ccacgcacgt    2880
tgccatgcag cgtacgaaga aggccaagaa cggccgcctg gtgacggtat ccgagggtga    2940
agccttgatt agccgctaca agatcgtaaa gagcgaaacc gggcggccgg agtacatcga    3000
gatcgagcta gctgattgga tgtaccgcga gatcacagaa ggcaagaacc cggacgtgct    3060
gacggttcac cccgattact ttttgatcga tcccggcatc ggccgttttc tctaccgcct    3120
ggcacgccgc gccgcaggca aggcagaagc cagatggttg ttcaagacga tctacgaacg    3180
cagtggcagc gccggagagt tcaagaagtt ctgtttcacc gtgcgcaagc tgatcgggtc    3240
aaatgacctg ccggagtacg atttgaagga ggaggcgggg caggctggcc cgatcctagt    3300
catgcgctac cgcaacctga tcgagggcga agcatccgcc ggttcctaat gtacggagca    3360
gatgctaggg caaattgccc tagcagggga aaaaggtcga aaaggtctct ttcctgtgga    3420
tagcacgtac attgggaacc caaagccgta cattgggaac cggaacccgt acattgggaa    3480
cccaaagccg tacattggga accggtcaca catgtaagtg actgatataa aagagaaaaa    3540
aggcgatttt tccgcctaaa actctttaaa acttattaaa actcttaaaa cccgcctggc    3600
ctgtgcataa ctgtctggcc agcgcacagc cgaagagctg caaaaagcgc ctacccttcg    3660
gtcgctgcgc tccctacgcc ccgccgcttc gcgtcggcct atcgcggccg ctggccgctc    3720
aaaaatggct ggcctacggc caggcaatct accagggcgc ggacaagccg cgccgtcgcc    3780
actcgaccgc cggcgcccac atcaaggcac cctgcctcgc gcgtttcggt gatgacggtg    3840
aaaacctctg acacatgcag ctcccggaga cggtcacagc ttgtctgtaa gcggatgccg    3900
ggagcagaca gcccgtcag ggcgcgtcag cgggtgttgg cgggtgtcgg ggcgcagcca    3960
tgacccagtc acgtagcgat agcggagtgt atactggctt aactatgcgg catcagagca    4020
gattgtactg agagtgcacc atatgcggtg tgaaataccg cacagatgcg taaggagaaa    4080
ataccgcatc aggcgctctt ccgcttcctc gctcactgac tcgctgcgct cggtcgttcg    4140
gctgcggcga gcggtatcag ctcactcaaa ggcggtaata cggttatcca cagaatcagg    4200
ggataacgca ggaaagaaca tgtgagcaaa aggccagcaa aaggccagga accgtaaaaa    4260
ggccgcgttg ctggcgtttt tccataggct ccgcccccct gacgagcatc acaaaaatcg    4320
acgctcaagt cagaggtggc gaaacccgac aggactataa agataccagg cgtttccccc    4380
tggaagctcc ctcgtgcgct ctcctgttcc gaccctgccg cttaccggat acctgtccgc    4440 cttctccct tcgggaagcg tggcgctttc tcatagctca cgctgtaggt atctcagttc    4500
```

```
ggtgtaggtc gttcgctcca agctgggctg tgtgcacgaa ccccccgttc agcccgaccg    4560
ctgcgcctta tccggtaact atcgtcttga gtccaacccg gtaagacacg acttatcgcc    4620
actggcagca gccactggta acaggattag cagagcgagg tatgtaggcg gtgctacaga    4680
gttcttgaag tggtggccta actacggcta cactagaagg acagtatttg gtatctgcgc    4740
tctgctgaag ccagttacct tcggaaaaag agttggtagc tcttgatccg gcaaacaaac    4800
caccgctggt agcggtggtt ttttttgtttg caagcagcag attacgcgca gaaaaaaagg    4860
atctcaagaa gatcctttga tcttttctac ggggtctgac gctcagtgga acgaaaactc    4920
acgttaaggg attttggtca tgcattctag gtactaaaac aattcatcca gtaaaatata    4980 atatttatt ttctcccaat caggcttgat ccccagtaag tcaaaaaata gctcgacata    5040
ctgttcttcc ccgatatcct ccctgatcga ccggacgcag aaggcaatgt cataccactt    5100
gtccgccctg ccgcttctcc caagatcaat aaagccactt actttgccat ctttcacaaa    5160
gatgttgctg tctcccaggt cgccgtggga aaagacaagt tcctcttcgg cttttccgt    5220 ctttaaaaaa tcatacagct cgcgcggatc tttaaatgga gtgtcttctt cccagttttc    5280
gcaatccaca tcggccagat cgttattcag taagtaatcc aattcggcta agcggctgtc    5340
taagctattc gtatagggac aatccgatat gtcgatggag tgaaagagcc tgatgcactc    5400
cgcatacagc tcgataatct tttcagggct ttgttcatct tcatactctt ccgagcaaag    5460
gacgccatcg gcctcactca tgagcagatt gctccagcca tcatgccgtt caaagtgcag    5520
gacctttgga acaggcagct ttccttccag ccatagcatc atgtcctttt cccgttccac    5580
atcataggtg gtccctttat accggctgtc cgtcattttt aaatataggt tttcattttc    5640
tcccaccagc ttatatacct tagcaggaga cattccttcc gtatctttta cgcagcggta    5700 ttttcgatc agtttttca attccggtga tattctcatt ttagccattt attatttcct    5760
tcctcttttc tacagtattt aaagatacc caagaagcta attataacaa gacgaactcc    5820
aattcactgt tccttgcatt ctaaaacctt aaataccaga aaacagcttt tcaaagttg    5880 ttttcaaagt tggcgtataa catagtatcg acggagccga ttttgaaacc gcggtgatca    5940
caggcagcaa cgctctgtca tcgttacaat caacatgcta ccctccgcga gatcatccgt    6000
gtttcaaacc cggcagctta gttgccgttc ttccgaatag catcggtaac atgagcaaag    6060
tctgccgcct tacaacggct ctcccgctga cgccgtcccg gactgatggg ctgcctgtat    6120
cgagtggtga ttttgtgccg agctgccggt cggggagctg ttggctggct ggtggcagga    6180
tatattgtgg tgtaaacaaa ttgacgctta gacaacttaa taacacattg cggacgtttt    6240
taatgtactg aattaacgcc gaattaattc ggggatctg gatttagta ctggatttg    6300 gttttaggaa ttagaaattt tattgataga agtatttac aaatacaaat acatactaag    6360
ggtttcttat atgctcaaca catgagcgaa accctatagg aaccctaatt cccttatctg    6420
ggaactactc acacattat atggagaaac tcgagggatc ccggtcggca tctactctat    6480
tcctttgccc tcggacgagt gctggggcgt cggtttccac tatcggcgag tacttctaca    6540
cagccatcgg tccagacggc cgcgcttctg cgggcgattt tgtacgcccc gacagtcccg    6600
gctccggatc ggacgattgc gtcgcatcga ccctgcgccc aagctgcatc atcgaaattg    6660
ccgtcaacca agctctgata gagttggtca agaccaatgc ggagcatata cgccccggagc    6720 cgcggcgatc ctgcaagctc cggatgcctc cgctcgaagt agcgcgtctg ctgctccata    6780
caagccaacc acggcctcca gaagaagatg ttggcgacct cgtattggga atccccgaac    6840
```

```
atcgcctcgc tccagtcaat gaccgctgtt atgcggccat tgtccgtcag gacattgttg    6900
gagccgaaat ccgcgtgcac gaggtgccgg acttcgggc  agtcctcggc ccaaagcatc    6960
agctcatcga gagcctgcgc gacggacgca ctgacggtgt cgtccatcac agtttgccag    7020
tgatacacat ggggatcagc aatcgcgcat atgaaatcac gccatgtagt gtattgaccg    7080
attccttgcg gtccgaatgg gccgaacccg ctcgtctggc taagatcggc cgcagcgatc    7140
gcatccatgg cctccgcgac cggctgcagt tatcatcatc atcatagaca cacgaaataa    7200
agtaatcaga ttatcagtta aagctatgta atatttacac cataaccaat caattaaaaa    7260
atagatcagt ttaaagaaag atcaaagctc aaaaaaataa aaagagaaaa gggtcctaac    7320
caagaaaatg aaggagaaaa actagaaatt tacctgcaga acagcgggca gttcggtttc    7380
aggcaggtct tgcaacgtga caccctgtgc acggcgggag atgcaatagg tcaggctctc    7440
gctgaattcc ccaatgtcaa gcacttccgg aatcgggagc gcggccgatg caaagtgccg    7500
ataaacataa cgatctttgt agaaaccatc ggcgcagcta tttacccgca ggacatatcc    7560
acgccctcct acatcgaagc tgaaagcacg agattcttcg ccctccgaga gctgcatcag    7620
gtcggagacg ctgtcgaact tttcgatcag aaacttctcg acagacgtcg cggtgagttc    7680
aggcttttc  atggtagagg agctcgccgc ttggtatctg cattacaatg aaatgagcaa    7740
agactatgtg agtaacactg gtcaacacta gggagaaggc atcgagcaag atacgtatgt    7800
aaagagaagc aatatagtgt cagttggtag atactagata ccatcaggag gtaaggagag    7860
caacaaaaag gaaactcttt attttaaat  tttgttacaa caaacaagca gatcaatgca    7920
tcaaaatact gtcagtactt atttcttcag acaacaatat ttaaaacaag tgcatctgat    7980
cttgacttat ggtcacaata aaggagcaga gataaacatc aaaatttcgt catttatatt    8040
tattccttca ggcgttaaca atttaacagc acacaaacaa aaacagaata ggaatatcta    8100
attttggcaa ataataagct ctgcagacga acaaattatt atagtatcgc ctataatatg    8160
aatccctata ctattgaccc atgtagtatg aagcctgtgc ctaaattaac agcaaacttc    8220
tgaatccaag tgccctataa caccaacatg tgcttaaata aataccgcta agcaccaaat    8280
tacacatttc tcgtattgct gtgtaggttc tatcttcgtt tcgtactacc atgtccctat    8340
attttgctgc tacaaaggac ggcaagtaat cagcacaggc agaacacgat ttcagagtgt    8400
aattctagat ccagctaaac cactctcagc aatcaccaca caagagagca ttcagagaaa    8460
cgtggcagta acaaaggcag agggcggagt gagcgcgtac cgaagacggt agatctctcg    8520
agagagatag atttgtagag agagactggt gatttcagcg tgtcctctcc aaatgaaatg    8580
aacttcctta tatagaggaa ggtcttgcga aggatagtgg gattgtgcgt catcccttac    8640
gtcagtggag atatcacatc aatccacttg ctttgaagac gtggttggaa cgtcttcttt    8700
ttccacgatg ctcctcgtgg gtggggtcc  atctttggga ccactgtcgg cagaggcatc    8760
ttgaacgata gcctttcctt tatcgcaatg atggcatttg taggtgccac cttccttttc    8820
tactgtcctt ttgatgaagt gacagatagc tgggcaatgg aatccgagga ggtttcccga    8880
tattaccctt tgttgaaaag tctcaatagc cctttggtct tctgagactg tatctttgat    8940
attcttggag tagacgagag tgtcgtgctc caccatgtta tcacatcaat ccacttgctt    9000
tgaagacgtg gttggaacgt cttctttttc cacgatgctc ctcgtgggtg gggtccatc    9060
tttgggacca ctgtcggcag aggcatcttg aacgatagcc tttcctttat cgcaatgatg    9120
gcatttgtag gtgccacctt ccttttctac tgtccttttg atgaagtgac agatagctgg    9180
gcaatggaat ccgaggaggt ttcccgatat taccctttgt tgaaaagtct caatagccct    9240
```

```
ttggtcttct gagactgtat ctttgatatt cttggagtag acgagagtgt cgtgctccac    9300
catgttggca agctgctcta gccaatacgc aaaccgcctc tccccgcgcg ttggccgatt    9360
cattaatgca gctggcacga caggtttccc gactggaaag cgggcagtga gcgcaacgca    9420
attaatgtga gttagctcac tcattaggca ccccaggctt tacactttat gcttccggct    9480
cgtatgttgt gtggaattgt gagcggataa caatttcaca caggaaacag ctatgaccat    9540
gattacgaat tcgagctcgg taccccacgg aagatccagg tctcgagact aggagacgga    9600
tgggaggcgc aacgcgcgat ggggaggggg gcggcgctga cctttctggc gaggtcgagg    9660
tagcgatcga gcagctgcag cgcggacacg atgaggaaga cgaagatagc cgccatggac    9720
atgttcgcca gcggcggcgg agcgaggctg agccggtctc tccggcctcc ggtcggcgtt    9780
aagttgggga tcgtaacgtg acgtgtctcg tctccacgga tcgacacaac cggcctactc    9840
gggtgcacga cgccgcgata agggcgagat gtccgtgcac gcagcccgtt tggagtcctc    9900
gttgcccacg aaccgacccc ttacagaaca aggcctagcc caaaactatt ctgagttgag    9960
cttttgagcc tagcccacct aagccgagcg tcatgaactg atgaacccac taccactagt   10020
caaggcaaac cacaaccaca aatggatcaa ttgatctaga acaatccgaa ggaggggagg   10080
ccacgtcaca ctcacaccaa ccgaaatatc tgccagaatc agatcaaccg gccaatagga   10140
cgccagcgag cccaacacct ggcgacgccg caaaattcac cgcgaggggc accgggcacg   10200
gcaaaaacaa agcccggcg cggtgagaat atctggcgac tggcggagac ctggtggcca    10260
gcgcgcggcc acatcagcca ccccatccgc ccacctcacc tccggcgagc caatggcaac   10320
tcgtcttaag attccacgag ataaggaccc gatcgccggc gacgctattt agccaggtgc   10380
gcccccacg gtacactcca ccagcggcat ctatagcaac cggtccagca ctttcacgct    10440
cagcttcagc aagatctacc gtcttcggta cgcgctcact ccgccctctg cctttgttac   10500
tgccacgttt ctctgaatgc tctcttgtgt ggtgattgct gagagtggtt tagctggatc   10560
tagaattaca ctctgaaatc gtgttctgcc tgtgctgatt acttgccgtc ctttgtagca   10620
gcaaaatata gggacatggt agtacgaaac gaagatagaa cctacacagc aatacgagaa   10680
atgtgtaatt tggtgcttag cggtatttat ttaagcacat gttggtgtta tagggcactt   10740
ggattcagaa gtttgctgtt aatttaggca caggcttcat actacatggg tcaatagtat   10800
agggattcat attataggcg atactataat aatttgttcg tctgcagagc ttattatttg   10860
ccaaaattag atattcctat tctgttttg tttgtgtgct gttaaattgt taacgcctga    10920
aggaataaat ataaatgacg aaattttgat gtttatctct gctcctttat tgtgaccata   10980
agtcaagatc agatgcactt gttttaaata ttgttgtctg aagaaataag tactgacagt   11040
attttgatgc attgatctgc ttgttgttg taacaaaatt taaaaataaa gagtttcctt    11100
tttgttgctc tccttacctc ctgatggtat ctagtatcta ccaactgata ctatattgct   11160
tctctttaca nnnnnntctt gctcgatgcc ttctcctagt gttgaccagt gttactcaca   11220
tagtctttgc tcatttcatt gtaatgcaga taccaagcgg ttaattaact atgagtcttt   11280
tccttttacg attcctccac ttctccaact acatcaaagg gagtacaacc gcaaagtccg   11340
tagccttcca ggtgcgcgct gagaaattcg cgaaccgcaa gcgtaagaat cagtatagag   11400
gcatacgcca gagaccgtgg ggtaagtggg ccgccgaaat ccgtgatcca cgtaagggag   11460
tgcgagtctg gcttggcacg ttcaatactg cagaagaagc ggcgagggcg tatgatgcag   11520
aggcaaggcg tataagggt aagaaagcga aagttaattt tcctgaggag gctcccggga    11580
```

-continued

```
cctctgtcaa acgttccaaa gtgaatcccc aggaaaacct ttcgcacaaa ttcggcgccg    11640
gcaacaatca catggatttg gtggagcaga agccgctggt taatcagtac gcaaacatgg    11700
cgtcatttcc ggggagcggg aatggattaa cctctctacc aagtagcgat gacgtgacac    11760
tatacttcag tagcgaccag ggctccaact catttgggtg gtccgagcag gggccgaaaa    11820
ctcctgaaat aagcagcatg ttaagcgccc cactcgattg tgaatctcat ttcgtacaaa    11880
atgctaacca acagccgaat tcacagaatg tcgtgtccat ggaggatgac tcagctaaaa    11940
ggctgagcga agaacgcgtt gatattgagt cggagctaaa attcttccaa atggcgtact    12000
tggaaggatc atggggcgac acaagtctcg agtcgctcct gtcggagat acgacgcaag     12060 acggcgggaa tctaatgaat ctatggagct tcgatgatat tccatcaatg tcttctggcg    12120
tgtttatgag tcttttcctt ttacgattcc tccacttctc caactacatc aaagggagta    12180
caaccgcaaa gtccgtagcc ttccaggtgc gcgctgagaa attcgcgaac cgcaagcgta    12240
agaatcagta tagaggcata cgccagagac cgtggggtaa gtgggccgcc gaaatccgtg    12300
atccacgtaa gggagtgcga gtctggcttg gcacgttcaa tactgcagaa gaagcggcga    12360
gggcgtatga tgcagaggca aggcgtataa ggggtaagaa agcgaaagtt aatttttcctg   12420 aggaggctcc cgggacctct gtcaaacgtt ccaaagtgaa tccccaggaa aacctttcgc    12480
acaaattcgg cgccggcaac aatcacatgg atttggtgga gcagaagccg ctggttaatc    12540
agtacgcaaa catggcgtca tttccgggga gcgggaatgg attaacctct ctaccaagta    12600
gcgatgacgt gacactatac ttcagtagcg accagggctc caactcattt gggtggtccg    12660 agcagggcc gaaaactcct gaaataagca gcatgttaag cgccccactc gattgtgaat     12720
ctcatttcgt acaaaatgct aaccaacagc cgaattcaca gaatgtcgtg tccatggagg    12780
atgactcagc taaaaggctg agcgaagaac gcgttgatat tgagtcggag ctaaaattct    12840
tccaaatggc gtacttggaa ggatcatggg gcgacacaag tctcgagtcg ctcctgtcgg    12900
gagatacgac gcaagacggc gggaatctaa tgaatctatg gagcttcgat gatattccat    12960
caatgtcttc tggcgtgttt gcagggcgcg ccatcgttca aacatttggc aataaagttt    13020
cttaagattg aatcctgttg ccggtcttgc gatgattatc atataatttc tgttgaatta    13080
cgttaagcat gtaataatta acatgtaatg catgacgtta tttatgagat gggtttttat    13140
gattagagtc ccgcaattat acatttaata cgcgatagaa aacaaaatat agcgcgcaaa    13200
ctaggataaa ttatcgcgcg cggtgtcatc tatgttacta gatccgatga taagctgtca    13260
aacatgaaag cttggcactg gccgtcgttt tacaacgtcg tgactgggaa acccctggcg    13320
ttacccaact taatcgcctt gcagcacatc ccccttcgc cagctggcgt aatagcgaag      13380
aggcccgcac cgatcgccct tcccaacagt tgcgcagcct gaatggcgaa tgctagcaga    13440
gcttgagctt ggatcagatt gtcgtttccc gccttcagtt taaactatca gtgtttgaca    13500
ggatatattg gcgggtaaac ctaagagaaa agagcgttta ttagaataac ggatatttaa    13560
aagggcgtga aaaggtttat ccgttcgtcc atttgtatgt g                        13601
```

<210> SEQ ID NO 27
<211> LENGTH: 12866
<212> TYPE: DNA
<213> ORGANISM: Artificial Sequence
<220> FEATURE:
<223> OTHER INFORMATION: Synthetic construct pMBXS885
<220> FEATURE:
<221> NAME/KEY: modified_base
<222> LOCATION: (11171)..(11176)
<223> OTHER INFORMATION: A, T, C or G
<220> FEATURE:
<221> NAME/KEY: misc_feature
<222> LOCATION: (11171)..(11176)
<223> OTHER INFORMATION: n is a, c, g, or t

<400> SEQUENCE: 27

| | | | | | |
|---|---|---|---|---|---|
| catgccaacc | acagggttcc | cctcgggatc | aaagtacttt | gatccaaccc | ctccgctgct | 60 |
| atagtgcagt | cggcttctga | cgttcagtgc | agccgtcttc | tgaaaacgac | atgtcgcaca | 120 |
| agtcctaagt | tacgcgacag | gctgccgccc | tgcccttttc | ctggcgtttt | cttgtcgcgt | 180 |
| gttttagtcg | cataaagtag | aatacttgcg | actagaaccg | agacattac | gccatgaaca | 240 |
| agagcgccgc | cgctggcctg | ctgggctatg | cccgcgtcag | caccgacgac | caggacttga | 300 |
| ccaaccaacg | ggccgaactg | cacgcggccg | gctgcaccaa | gctgttttcc | gagaagatca | 360 |
| ccggcaccag | gcgcgaccgc | ccggagctgg | ccaggatgct | tgaccaccta | cgccctggcg | 420 |
| acgttgtgac | agtgaccagg | ctagaccgcc | tggcccgcag | cacccgcgac | ctactggaca | 480 |
| ttgccgagcg | catccaggag | gccggcgcgg | gcctgcgtag | cctggcagag | ccgtgggccg | 540 |
| acaccaccac | gccggccggc | cgcatggtgt | tgaccgtgtt | cgccggcatt | gccgagttcg | 600 |
| agcgttccct | aatcatcgac | cgcacccgga | gcgggcgcga | ggccgccaag | gcccgaggcg | 660 |
| tgaagtttgg | cccccgccct | accctcaccc | cggcacagat | cgcgcacgcc | cgcgagctga | 720 |
| tcgaccagga | aggccgcacc | gtgaaagagg | cggctgcact | gcttggcgtg | catcgctcga | 780 |
| ccctgtaccg | cgcacttgag | cgcagcgagg | aagtgacgcc | caccgaggcc | aggcggcgcg | 840 |
| gtgccttccg | tgaggacgca | ttgaccgagg | ccgacgccct | ggcggccgcc | gagaatgaac | 900 |
| gccaagagga | acaagcatga | aaccgcacca | ggacggccag | gacgaaccgt | ttttcattac | 960 |
| cgaagagatc | gaggcggaga | tgatcgcggc | cgggtacgtg | ttcgagccgc | ccgcgcacgt | 1020 |
| ctcaaccgtg | cggctgcatg | aaatcctggc | cggtttgtct | gatgccaagc | tggcggcctg | 1080 |
| gccggccagc | ttggccgctg | aagaaaccga | gcgccgccgt | ctaaaaaggt | gatgtgtatt | 1140 |
| tgagtaaaac | agcttgcgtc | atgcggtcgc | tgcgtatatg | atgcgatgag | taaataaaca | 1200 |
| aatacgcaag | gggaacgcat | gaaggttatc | gctgtactta | accagaaagg | cgggtcaggc | 1260 |
| aagacgacca | tcgcaaccca | tctagcccgc | gccctgcaac | tcgccggggc | cgatgttctg | 1320 |
| ttagtcgatt | ccgatcccca | gggcagtgcc | cgcgattggg | cggccgtgcg | gaagatcaa | 1380 |
| ccgctaaccg | ttgtcggcat | cgaccgcccg | acgattgacc | gcgacgtgaa | ggccatcggc | 1440 |
| cggcgcgact | tcgtagtgat | cgacggagcg | ccccaggcgg | cggacttggc | tgtgtccgcg | 1500 |
| atcaaggcag | ccgacttcgt | gctgattccg | gtgcagccaa | gcccttacga | catatgggcc | 1560 |
| accgccgacc | tggtggagct | ggttaagcag | cgcattgagg | tcacggatgg | aaggctacaa | 1620 |
| gcggcctttg | tcgtgtcgcg | ggcgatcaaa | ggcacgcgca | tcggcggtga | ggttgccgag | 1680 |
| gcgctggccg | ggtacgagct | gcccattctt | gagtcccgta | tcacgcagcg | cgtgagctac | 1740 |
| ccaggcactg | ccgccgccgg | cacaaccgtt | cttgaatcag | aacccgaggg | cgacgctgcc | 1800 |
| cgcgaggtcc | aggcgctggc | cgctgaaatt | aaatcaaaac | tcatttgagt | taatgaggta | 1860 |
| aagagaaaat | gagcaaaagc | acaaacacgc | taagtgccgg | ccgtccgagc | gcacgcagca | 1920 |
| gcaaggctgc | aacgttggcc | agcctggcag | acacgccagc | catgaagcgg | gtcaactttc | 1980 |
| agttgccggc | ggaggatcac | accaagctga | agatgtacgc | ggtacgccaa | ggcaagacca | 2040 |
| ttaccgagct | gctatctgaa | tacatcgcgc | agctaccaga | gtaaatgagc | aaatgaataa | 2100 |
| atgagtagat | gaattttagc | ggctaaagga | ggcggcatgg | aaaatcaaga | acaaccaggc | 2160 |

```
accgacgccg tggaatgccc catgtgtgga ggaacgggcg gttggccagg cgtaagcggc   2220
tgggttgtct gccggccctg caatggcact ggaaccccca agcccgagga atcggcgtga   2280
cggtcgcaaa ccatccggcc cggtacaaat cggcgcggcg ctgggtgatg acctggtgga   2340
gaagttgaag gccgcgcagg ccgcccagcg gcaacgcatc gaggcagaag cacgccccgg   2400
tgaatcgtgg caagcggccg ctgatcgaat ccgcaaagaa tcccggcaac cgccggcagc   2460
cggtgcgccg tcgattagga agccgcccaa gggcgacgag caaccagatt ttttcgttcc   2520
gatgctctat gacgtgggca cccgcgatag tcgcagcatc atggacgtgg ccgttttccg   2580
tctgtcgaag cgtgaccgac gagctggcga ggtgatccgc tacgagcttc cagacgggca   2640
cgtagaggtt tccgcagggc cggccggcat ggccagtgtg tgggattacg acctggtact   2700
gatggcggtt tccatctaa ccgaatccat gaaccgatac cgggaaggga agggagacaa   2760
gcccggccgc gtgttccgtc cacacgttgc ggacgtactc aagttctgcc ggcgagccga   2820
tggcggaaag cagaaagacg acctggtaga aacctgcatt cggttaaaca ccacgcacgt   2880
tgccatgcag cgtacgaaga aggccaagaa cggccgcctg gtgacggtat ccagggtga   2940 agccttgatt agccgctaca agatcgtaaa gagcgaaacc gggcggccgg agtacatcga   3000
gatcgagcta gctgattgga tgtaccgcga gatcacagaa ggcaagaacc cggacgtgct   3060
gacggttcac cccgattact ttttgatcga tcccggcatc ggccgttttc tctaccgcct   3120
ggcacgccgc gccgcaggca aggcagaagc cagatggttg ttcaagacga tctacgaacg   3180
cagtggcagc gccggagagt tcaagaagtt ctgtttcacc gtgcgcaagc tgatcgggtc   3240
aaatgacctg ccggagtacg atttgaagga ggaggcgggg caggctggcc cgatcctagt   3300
catgcgctac cgcaacctga tcgagggcga agcatccgcc ggttcctaat gtacggagca   3360
gatgctaggg caaattgccc tagcagggga aaaaggtcga aaaggtctct ttcctgtgga   3420
tagcacgtac attgggaacc caaagccgta cattgggaac cggaacccgt acattgggaa   3480
cccaaagccg tacattggga accggtcaca catgtaagtg actgatataa aagagaaaaa   3540
aggcgatttt tccgcctaaa actctttaaa acttattaaa actcttaaaa cccgcctggc   3600
ctgtgcataa ctgtctggcc agcgcacagc cgaagagctg caaaaagcgc ctacccttcg   3660
gtcgctgcgc tccctacgcc ccgccgcttc gcgtcggcct atcgcggccg ctggccgctc   3720
aaaaatggct ggcctacggc caggcaatct accaggcgc ggacaagccg cgccgtcgcc   3780
actcgaccgc cggcgcccac atcaaggcac cctgcctcgc gcgtttcggt gatgacggtg   3840
aaaacctctg acacatgcag ctcccggaga cggtcacagc ttgtctgtaa gcggatgccg   3900
ggagcagaca agcccgtcag ggcgcgtcag cgggtgttgg cgggtgtcgg ggcgcagcca   3960
tgacccagtc acgtagcgat agcggagtgt atactggctt aactatgcgg catcagagca   4020
gattgtactg agagtgcacc atatgcggtg tgaaataccg cacagatgcg taaggagaaa   4080
ataccgcatc aggcgctctt ccgcttcctc gctcactgac tcgctgcgct cggtcgttcg   4140
gctgcggcga gcggtatcag ctcactcaaa ggcggtaata cggttatcca cagaatcagg   4200
ggataacgca ggaaagaaca tgtgagcaaa aggccagcaa aaggccagga accgtaaaaa   4260
ggccgcgttg ctggcgtttt tccataggct ccgcccccct gacgagcatc acaaaaatcg   4320
acgctcaagt cagaggtggc gaaacccgac aggactataa agataccagg cgtttccccc   4380
tggaagctcc ctcgtgcgct ctcctgttcc gaccctgccg cttaccggat acctgtccgc   4440
ctttctccct tcgggaagcg tggcgctttc tcatagctca cgctgtaggt atctcagttc   4500
ggtgtaggtc gttcgctcca agctgggctg tgtgcacgaa ccccccgttc agcccgaccg   4560
```

```
ctgcgcctta tccggtaact atcgtcttga gtccaacccg gtaagacacg acttatcgcc   4620
actggcagca gccactggta acaggattag cagagcgagg tatgtaggcg gtgctacaga   4680
gttcttgaag tggtggccta actacggcta cactagaagg acagtatttg gtatctgcgc   4740
tctgctgaag ccagttacct tcggaaaaag agttggtagc tcttgatccg gcaaacaaac   4800
caccgctggt agcggtggtt ttttgtttg caagcagcag attacgcgca gaaaaaagg   4860 atctcaagaa gatcctttga tcttttctac ggggtctgac gctcagtgga acgaaaactc   4920
acgttaaggg attttggtca tgcattctag gtactaaaac aattcatcca gtaaatata   4980 atattttatt ttctcccaat caggcttgat ccccagtaag tcaaaaaata gctcgacata   5040
ctgttcttcc ccgatatcct ccctgatcga ccggacgcag aaggcaatgt cataccactt   5100
gtccgccctg ccgcttctcc caagatcaat aaagccactt actttgccat cttttcacaaa   5160 gatgttgctg tctcccaggt cgccgtggga aaagacaagt tcctcttcgg gcttttccgt   5220
ctttaaaaaa tcatacagct cgcgcggatc tttaaatgga gtgtcttctt cccagttttc   5280
gcaatccaca tcggccagat cgttattcag taagtaatcc aattcggcta agcggctgtc   5340
taagctattc gtatagggac aatccgatat gtcgatggag tgaaagagcc tgatgcactc   5400
cgcatacagc tcgataatct tttcagggct tgttcatct tcatactctt ccgagcaaag   5460
gacgccatcg gcctcactca tgagcagatt gctccagcca tcatgccgtt caaagtgcag   5520
gacctttgga acaggcagct ttccttccag ccatagcatc atgtcctttt cccgttccac   5580
atcataggtg gtcccttat accggctgtc cgtcattttt aaatataggt tttcattttc   5640
tcccaccagc ttatatacct tagcaggaga cattccttcc gtatctttta cgcagcggta   5700
tttttcgatc agttttttca attccggtga tattctcatt ttagccattt attatttcct   5760
tcctcttttc tacagtattt aaagataccc caagaagcta attataacaa gacgaactcc   5820
aattcactgt tccttgcatt ctaaaacctt aaataccaga aaacagcttt ttcaaagttg   5880
ttttcaaagt tggcgtataa catagtatcg acggagccga ttttgaaacc gcggtgatca   5940
caggcagcaa cgctctgtca tcgttacaat caacatgcta ccctccgcga gatcatccgt   6000
gtttcaaacc cggcagctta gttgccgttc ttccgaatag catcggtaac atgagcaaag   6060
tctgccgcct tacaacggct ctcccgctga cgccgtcccg gactgatggg ctgcctgtat   6120
cgagtggtga ttttgtgccg agctgccggt cggggagctg ttggctggct ggtggcagga   6180
tatattgtgg tgtaaacaaa ttgacgctta gacaacttaa taacacattg cggacgtttt   6240
taatgtactg aattaacgcc gaattaattc gggggatctg gattttagta ctggattttg   6300
gttttaggaa ttagaaattt tattgataga agtatttac aaatacaaat acatactaag   6360
ggtttcttat atgctcaaca catgagcgaa accctatagg aacccaatt cccttatctg   6420 ggaactactc acacattatt atggagaaac tcgagggatc ccggtcggca tctactctat   6480
tcctttgccc tcggacgagt gctggggcgt cggtttccac tatcggcgag tacttctaca   6540
cagccatcgg tccagacggc cgcgcttctg cgggcgattt gtgtacgccc gacagtcccg   6600
gctccggatc ggacgattgc gtcgcatcga ccctgcgccc aagctgcatc atcgaaattg   6660
ccgtcaacca agctctgata gagttggtca agaccaatgc ggagcatata cgcccggagc   6720
cgcggcgatc ctgcaagctc cggatgcctc cgctcgaagt agcgcgtctg ctgctccata   6780
caagccaacc acgcctcca gaagaagatg ttggcgacct cgtattggga atccccgaac   6840
atcgcctcgc tccagtcaat gaccgctgtt atgcggccat tgtccgtcag gacattgttg   6900
```

```
gagccgaaat ccgcgtgcac gaggtgccgg acttcggggc agtcctcggc ccaaagcatc    6960
agctcatcga gagcctgcgc gacggacgca ctgacggtgt cgtccatcac agtttgccag    7020
tgatacacat ggggatcagc aatcgcgcat atgaaatcac gccatgtagt gtattgaccg    7080
attccttgcg gtccgaatgg gccgaacccg ctcgtctggc taagatcggc cgcagcgatc    7140
gcatccatgg cctccgcgac cggctgcagt tatcatcatc atcatagaca cacgaaataa    7200
agtaatcaga ttatcagtta aagctatgta atatttacac cataaccaat caattaaaaa    7260
atagatcagt ttaaagaaag atcaaagctc aaaaaaataa aaagagaaaa gggtcctaac    7320
caagaaaatg aaggagaaaa actagaaatt tacctgcaga acagcgggca gttcggtttc    7380
aggcaggtct tgcaacgtga caccctgtgc acggcgggag atgcaatagg tcaggctctc    7440
gctgaattcc ccaatgtcaa gcacttccgg aatcgggagc gcggccgatg caaagtgccg    7500
ataaacataa cgatctttgt agaaaccatc ggcgcagcta tttacccgca ggacatatcc    7560
acgccctcct acatcgaagc tgaaagcacg agattcttcg ccctccgaga gctgcatcag    7620
gtcggagacg ctgtcgaact tttcgatcag aaacttctcg acagacgtcg cggtgagttc    7680 aggcttttc atggtagagg agctcgccgc ttggtatctg cattacaatg aaatgagcaa     7740
agactatgtg agtaacactg gtcaacacta gggagaaggc atcgagcaag atacgtatgt    7800
aaagagaagc aatatagtgt cagttggtag atactagata ccatcaggag gtaaggagag    7860
caacaaaaag gaaactcttt attttaaat tttgttacaa caaacaagca gatcaatgca     7920
tcaaaatact gtcagtactt atttcttcag acaacaatat ttaaaacaag tgcatctgat    7980
cttgacttat ggtcacaata aaggagcaga gataaacatc aaaatttcgt catttatatt    8040
tattccttca ggcgttaaca atttaacagc acacaaacaa aaacagaata ggaatatcta    8100
attttggcaa ataataagct ctgcagacga acaaattatt atagtatcgc ctataatatg    8160
aatccctata ctattgaccc atgtagtatg aagcctgtgc ctaaattaac agcaaacttc    8220
tgaatccaag tgccctataa caccaacatg tgcttaaata ataccgcta agcaccaaat     8280 tacacatttc tcgtattgct gtgtaggttc tatcttcgtt tcgtactacc atgtccctat    8340
attttgctgc tacaaaggac ggcaagtaat cagcacaggc agaacacgat ttcagagtgt    8400
aattctagat ccagctaaac cactctcagc aatcaccaca caagagagca ttcagagaaa    8460
cgtggcagta acaaaggcag agggcggagt gagcgcgtac cgaagacggt agatctctcg    8520
agagagatag atttgtagag agagactggt gatttcagcg tgtcctctcc aaatgaaatg    8580
aacttcctta tatagaggaa ggtcttgcga aggatagtgg gattgtgcgt catcccttac    8640
gtcagtggag atatcacatc aatccacttg cttgaagac gtggttggaa cgtcttcttt      8700
ttccacgatg ctcctcgtgg gtggggtcc atctttggga ccactgtcgg cagaggcatc      8760
ttgaacgata gcctttcctt tatcgcaatg atggcatttg taggtgccac cttcctttc      8820 tactgtcctt ttgatgaagt gacagatagc tgggcaatgg aatccgagga ggtttcccga    8880
tattacccct tgttgaaaag tctcaatagc cctttggtct tctgagactg tatctttgat    8940
attcttggag tagacgagag tgtcgtgctc caccatgtta tcacatcaat ccacttgctt    9000
tgaagacgtg gttggaacgt cttcttttc cacgatgctc ctcgtgggtg ggggtccatc     9060
tttgggacca ctgtcggcag aggcatcttg aacgatagcc tttcctttat cgcaatgatg    9120
gcatttgtag gtgccacctt cctttctac tgtccttttg atgaagtgac agatagctgg     9180
gcaatggaat ccgaggaggt ttcccgatat taccctttgt tgaaaagtct caatagccct    9240
ttggtcttct gagactgtat ctttgatatt cttggagtag acgagagtgt cgtgctccac    9300
```

```
catgttggca agctgctcta gccaatacgc aaaccgcctc tccccgcgcg ttggccgatt   9360
cattaatgca gctggcacga caggtttccc gactggaaag cgggcagtga gcgcaacgca   9420
attaatgtga gttagctcac tcattaggca ccccaggctt tacactttat gcttccggct   9480
cgtatgttgt gtggaattgt gagcggataa caatttcaca caggaaacag ctatgaccat   9540
gattacgaat tcgagctcgg taccccacgg aagatccagg tctcgagact aggagacgga   9600
tgggaggcgc aacgcgcgat ggggaggggg gcggcgctga cctttctggc gaggtcgagg   9660
tagcgatcga gcagctgcag cgcggacacg atgaggaaga cgaagatagc cgccatggac   9720
atgttcgcca gcggcggcgg agcgaggctg agccggtctc tccggcctcc ggtcggcgtt   9780
aagttgggga tcgtaacgtg acgtgtctcg tctccacgga tcgacacaac cggcctactc   9840
gggtgcacga cgccgcgata agggcgagat gtccgtgcac gcagcccgtt tggagtcctc   9900
gttgcccacg aaccgacccc ttacagaaca aggcctagcc caaaactatt ctgagttgag   9960
cttttgagcc tagcccacct aagccgagcg tcatgaactg atgaacccac taccactagt  10020
caaggcaaac cacaaccaca aatggatcaa ttgatctaga caatccgaa ggaggggagg   10080
ccacgtcaca ctcacaccaa ccgaaatatc tgccagaatc agatcaaccg gccaatagga  10140
cgccagcgag cccaacacct ggcgacgccg caaaattcac cgcgaggggc accgggcacg  10200
gcaaaaacaa aagcccggcg cggtgagaat atctggcgac tggcggagac ctggtggcca  10260
gcgcgcggcc acatcagcca ccccatccgc ccacctcacc tccggcgagc caatggcaac  10320
tcgtcttaag attccacgag ataaggaccc gatcgccggc gacgctattt agccaggtgc  10380
gccccccacg gtacactcca ccagcggcat ctatagcaac cggtccagca ctttcacgct  10440
cagcttcagc aagatctacc gtcttcggta cgcgctcact ccgccctctg cctttgttac  10500
tgccacgttt ctctgaatgc tctcttgtgt ggtgattgct gagagtggtt tagctggatc  10560
tagaattaca ctctgaaatc gtgttctgcc tgtgctgatt acttgccgtc ctttgtagca  10620
gcaaaatata gggacatggt agtacgaaac gaagatagaa cctacacagc aatacgagaa  10680
atgtgtaatt tggtgcttag cggtatttat ttaagcacat gttggtgtta tagggcactt  10740
ggattcagaa gtttgctgtt aatttaggca caggcttcat actacatggg tcaatagtat  10800
agggattcat attataggcg atactataat aatttgttcg tctgcagagc ttattatttg  10860
ccaaaattag atattcctat tctgtttttg tttgtgtgct gttaaattgt taacgcctga  10920
aggaataaat ataaatgacg aaattttgat gtttatctct gctcctttat tgtgaccata  10980
agtcaagatc agatgcactt gttttaaata ttgttgtctg aagaaataag tactgacagt  11040
attttgatgc attgatctgc ttgtttgttg taacaaaatt taaaaataaa gagtttcctt  11100
tttgttgctc tccttacctc ctgatggtat ctagtatcta ccaactgata ctatattgct  11160
tctctttaca nnnnnntctt gctcgatgcc ttctcctagt gttgaccagt gttactcaca  11220
tagtctttgc tcatttcatt gtaatgcaga taccaagcgg ttaattaact atgtgcggcg  11280
gggccattct cagtgatctc tactcaccag tgaggcggac ggtcactgcc ggtgacctat  11340
ggggagagag tggcagcagc aagaatgtga agaactggaa aaggagttct tggaagtttg  11400
atgaaggcga tgaagacttt gaagctgatt tcaaggattt tgaggattgc agtagcgagg  11460
aggaggtaga ttttggacat gaggaaaaag aattccaatt gaacagttcg aatttcgtgg  11520
aattcaatgg ccatactgcc aaagtcacca gcaggaagcg aaagatccag taccgaggga  11580
tccggcggcg gccttggggc aaatgggcag cagaaatcag agacccacag aagggcgtcc  11640
```

```
gagtttggct tggcacgttc agcactgccg aggaagctgc aagggcatat gacgtggaag    11700
ctctacgcat acgtggcaag aaagccaaga tgaatttccc taccaccatc acagctgctg    11760
ggaaacacca ccggcagcgt gtggctcgac cggcaaagaa gacgtcacaa gagagcctga    11820
agtcaagcaa tgcctctggt catgtcatct cagcaggcag cagtactgat ggcaccgttg    11880
tcaagatcga gttgtcacag tcaccagctt ctccactacc agtgtccagc gcatggcttg    11940
atgcttttga gctgaagcag cttggtggag aaacccctga agctgatggg agagaaaccc    12000
ctgaagaaac tgatcatgaa acgggagtga cagcggatat gttttttggc aatggcgaag    12060
tgcggctttc agatgatttt gcgtcttacg agccttaccc aaattttatg cagttacctt    12120
atctagaagg tgactcgtat gaaaacattg acactctttt caacggtgaa gctgctcagg    12180
atggagtgaa catcggaggt ctttggaatt tcgatgatgt gccaatggac cgtggtgttt    12240
actgagcagg gcgcgccatc gttcaaacat ttggcaataa agtttcttaa gattgaatcc    12300
tgttgccggt cttgcgatga ttatcatata atttctgttg aattacgtta agcatgtaat    12360
aattaacatg taatgcatga cgttatttat gagatgggtt tttatgatta gagtcccgca    12420
attatacatt taatacgcga tagaaaacaa aatatagcgc gcaaactagg ataaattatc    12480
gcgcgcggtg tcatctatgt tactagatcc gatgataagc tgtcaaacat gaaagcttgg    12540
cactggccgt cgttttacaa cgtcgtgact gggaaaaccc tggcgttacc caacttaatc    12600
gccttgcagc acatccccct ttcgccagct ggcgtaatag cgaagaggcc cgcaccgatc    12660
gcccttccca acagttgcgc agcctgaatg gcgaatgcta gagcagcttg agcttggatc    12720
agattgtcgt ttcccgcctt cagtttaaac tatcagtgtt tgacaggata tattggcggg    12780
taaacctaag agaaagagc gtttattaga ataacggata tttaaagggg cgtgaaaagg    12840
tttatccgtt cgtccatttg tatgtg                                          12866

<210> SEQ ID NO 28
<211> LENGTH: 13841
<212> TYPE: DNA
<213> ORGANISM: Artificial Sequence
<220> FEATURE:
<223> OTHER INFORMATION: Synthetic construct pMBXS886
<220> FEATURE:
<221> NAME/KEY: modified_base
<222> LOCATION: (11171)..(11176)
<223> OTHER INFORMATION: A, T, C or G
<220> FEATURE:
<221> NAME/KEY: misc_feature
<222> LOCATION: (11171)..(11176)
<223> OTHER INFORMATION: n is a, c, g, or t

<400> SEQUENCE: 28
catgccaacc acagggttcc cctcgggatc aaagtacttt gatccaaccc ctccgctgct      60
atagtgcagt cggcttctga cgttcagtgc agccgtcttc tgaaaacgac atgtcgcaca     120
agtcctaagt tacgcgacag gctgccgccc tgcccttttc ctggcgtttt cttgtcgcgt     180
gttttagtcg cataaagtag aatacttgcg actagaaccg gagacattac gccatgaaca     240
agagcgccgc cgctggcctg ctgggctatg cccgcgtcag caccgacgac caggacttga     300
ccaaccaacg ggccgaactg cacgcggccg gctgcaccaa gctgttttcc gagaagatca     360
ccggcaccag gcgcgaccgc ccggagctgg ccaggatgct tgaccaccta cgccctggcg     420
acgttgtgac agtgaccagg ctagaccgcc tggcccgcag cacccgcgac ctactggaca     480
ttgccgagcg catccaggag gccggcgcgg gcctgcgtag cctggcagag ccgtgggccg     540
acaccaccac gccggccggc cgcatggtgt tgaccgtgtt cgccggcatt gccgagttcg     600
```

```
agcgttccct aatcatcgac cgcacccgga gcgggcgcga ggccgccaag gcccgaggcg    660
tgaagtttgg cccccgccct accctcaccc cggcacagat cgcgcacgcc cgcgagctga    720
tcgaccagga aggccgcacc gtgaaagagg cggctgcact gcttggcgtg catcgctcga    780
ccctgtaccg cgcacttgag cgcagcgagg aagtgacgcc caccgaggcc aggcggcgcg    840
gtgccttccg tgaggacgca ttgaccgagg ccgacgccct ggcggccgcc gagaatgaac    900
gccaagagga acaagcatga aaccgcacca ggacggccag gacgaaccgt ttttcattac    960
cgaagagatc gaggcggaga tgatcgcggc cgggtacgtg ttcgagccgc ccgcgcacgt   1020
ctcaaccgtg cggctgcatg aaatcctggc cggtttgtct gatgccaagc tggcggcctg   1080
gccggccagc ttggccgctg aagaaaccga gcgccgccgt ctaaaaaggt gatgtgtatt   1140
tgagtaaaac agcttgcgtc atgcggtcgc tgcgtatatg atgcgatgag taaataaaca   1200
aatacgcaag gggaacgcat gaaggttatc gctgtactta accagaaagg cgggtcaggc   1260
aagacgacca tcgcaaccca tctagcccgc gccctgcaac tcgccgggc cgatgttctg    1320 ttagtcgatt ccgatcccca gggcagtgcc cgcgattggg cggccgtgcg gaagatcaa    1380 ccgctaaccg ttgtcggcat cgaccgcccg acgattgacc gcgacgtgaa ggccatcggc   1440
cggcgcgact tcgtagtgat cgacggagcg ccccaggcgg cggacttggc tgtgtccgcg   1500
atcaaggcag ccgacttcgt gctgattccg gtgcagccaa gcccttacga catatgggcc   1560
accgccgacc tggtggagct ggttaagcag cgcattgagg tcacggatgg aaggctacaa   1620
gcggcctttg tcgtgtcgcg ggcgatcaaa ggcacgcgca tcggcggtga ggttgccgag   1680
gcgctggccg ggtacgagct gcccattctt gagtcccgta tcacgcagcg cgtgagctac   1740
ccaggcactg ccgccgccgg cacaaccgtt cttgaatcag aacccgaggg cgacgctgcc   1800
cgcgaggtcc aggcgctggc cgctgaaatt aaatcaaaac tcatttgagt taatgaggta   1860
aagagaaaat gagcaaaagc acaaacacgc taagtgccgg ccgtccgagc gcacgcagca   1920
gcaaggctgc aacgttggcc agcctggcag acacgccagc catgaagcgg gtcaactttc   1980
agttgccggc ggaggatcac accaagctga agatgtacgc ggtacgccaa ggcaagacca   2040
ttaccgagct gctatctgaa tacatcgcgc agctaccaga gtaaatgagc aaatgaataa   2100
atgagtagat gaattttagc ggctaaagga ggcggcatgg aaaatcaaga acaaccaggc   2160
accgacgccg tggaatgccc catgtgtgga ggaacgggcg gttggccagg cgtaagcggc   2220
tgggttgtct gccggccctg caatggcact ggaaccccca gcccgaggaa tcggcgtga    2280 cggtcgcaaa ccatccggcc cggtacaaat cggcgcggcg ctgggtgatg acctggtgga   2340
gaagttgaag gccgcgcagg ccgcccagcg gcaacgcatc gaggcagaag cacgccccgg   2400
tgaatcgtgg caagcggccg ctgatcgaat ccgcaaagaa tcccggcaac cgccggcagc   2460
cggtgcgccg tcgattagga agccgcccaa gggcgacgag caaccagatt ttttcgttcc   2520
gatgctctat gacgtgggca cccgcgatag tcgcagcatc atggacgtgg ccgttttccg   2580
tctgtcgaag cgtgaccgac gagctggcga ggtgatccgc tacgagcttc agacgggca    2640 cgtagaggtt tccgcagggc cggcggcat ggccagtgtg tgggattacg acctggtact    2700
gatggcggtt tccatctaa ccgaatccat gaaccgatac cggaaggga agggagacaa     2760 gcccggccgc gtgttccgtc cacacgttgc ggacgtactc aagttctgcc ggcgagccga   2820
tggcggaaag cagaaagacg acctggtaga aacctgcatt cggttaaaca ccacgcacgt   2880
tgccatgcag cgtacgaaga aggccaagaa cggccgcctg gtgacggtat ccgagggtga   2940
```

```
agccttgatt agccgctaca agatcgtaaa gagcgaaacc gggcggccgg agtacatcga   3000
gatcgagcta gctgattgga tgtaccgcga gatcacagaa ggcaagaacc cggacgtgct   3060
gacggttcac cccgattact ttttgatcga tcccggcatc ggccgttttc tctaccgcct   3120
ggcacgccgc gccgcaggca aggcagaagc cagatggttg ttcaagacga tctacgaacg   3180
cagtggcagc gccggagagt tcaagaagtt ctgtttcacc gtgcgcaagc tgatcgggtc   3240
aaatgacctg ccggagtacg atttgaagga ggaggcgggg caggctggcc cgatcctagt   3300
catgcgctac cgcaacctga tcgagggcga agcatccgcc ggttcctaat gtacggagca   3360
gatgctaggg caaattgccc tagcagggga aaaaggtcga aaaggtctct ttcctgtgga   3420
tagcacgtac attgggaacc caaagccgta cattgggaac cggaacccgt acattgggaa   3480
cccaaagccg tacattggga accggtcaca catgtaagtg actgatataa aagagaaaaa   3540
aggcgatttt tccgcctaaa actctttaaa acttattaaa actcttaaaa cccgcctggc   3600
ctgtgcataa ctgtctggcc agcgcacagc cgaagagctg caaaaagcgc ctacccttcg   3660
gtcgctgcgc tccctacgcc ccgccgcttc gcgtcggcct atcgcggccg ctggccgctc   3720
aaaaatggct ggcctacggc caggcaatct accagggcgc ggacaagccg cgccgtcgcc   3780
actcgaccgc cggcgcccac atcaaggcac cctgcctcgc gcgtttcggt gatgacggtg   3840
aaaacctctg acacatgcag ctcccggaga cggtcacagc ttgtctgtaa gcggatgccg   3900
ggagcagaca agcccgtcag ggcgcgtcag cgggtgttgg cgggtgtcgg ggcgcagcca   3960
tgacccagtc acgtagcgat agcggagtgt atactggctt aactatgcgg catcagagca   4020
gattgtactg agagtgcacc atatgcggtg tgaaataccg cacagatgcg taaggagaaa   4080
ataccgcatc aggcgctctt ccgcttcctc gctcactgac tcgctgcgct cggtcgttcg   4140
gctgcggcga gcggtatcag ctcactcaaa ggcggtaata cggttatcca cagaatcagg   4200
ggataacgca ggaaagaaca tgtgagcaaa aggccagcaa aaggccagga accgtaaaaa   4260
ggccgcgttg ctggcgtttt tccataggct ccgcccccct gacgagcatc acaaaaatcg   4320
acgctcaagt cagaggtggc gaaacccgac aggactataa agataccagg cgtttccccc   4380
tggaagctcc ctcgtgcgct ctcctgttcc gaccctgccg cttaccggat acctgtccgc   4440
ctttctccct tcgggaagcg tggcgctttc tcatagctca cgctgtaggt atctcagttc   4500
ggtgtaggtc gttcgctcca agctgggctg tgtgcacgaa ccccccgttc agcccgaccg   4560
ctgcgcctta tccggtaact atcgtcttga gtccaacccg gtaagacacg acttatcgcc   4620
actggcagca gccactggta acaggattag cagagcgagg tatgtaggcg gtgctacaga   4680
gttcttgaag tggtggccta actacggcta cactagaagg acagtatttg gtatctgcgc   4740
tctgctgaag ccagttacct tcggaaaaag agttggtagc tcttgatccg gcaaacaaac   4800
caccgctggt agcggtggtt tttttgtttg caagcagcag attacgcgca gaaaaaaagg   4860
atctcaagaa gatcctttga tcttttctac ggggtctgac gctcagtgga acgaaaactc   4920
acgttaaggg attttggtca tgcattctag gtactaaaac aattcatcca gtaaatata    4980 atatttatt ttctcccaat caggcttgat ccccagtaag tcaaaaaata gctcgacata    5040
ctgttcttcc ccgatatcct ccctgatcga ccggacgcag aaggcaatgt cataccactt   5100
gtccgccctg ccgcttctcc caagatcaat aaagccactt actttgccat ctttcacaaa   5160
gatgttgctg tctcccaggt cgccgtggga aaagacaagt tcctcttcgg gcttttccgt   5220
cttttaaaaa tcatacagct cgcgcggatc tttaaatgga gtgtcttctt ccagttttc    5280 gcaatccaca tcggccagat cgttattcag taagtaatcc aattcggcta gcggctgtc    5340
```

```
taagctattc gtatagggac aatccgatat gtcgatggag tgaaagagcc tgatgcactc    5400
cgcatacagc tcgataatct tttcagggct ttgttcatct tcatactctt ccgagcaaag    5460
gacgccatcg gcctcactca tgagcagatt gctccagcca tcatgccgtt caaagtgcag    5520
gacctttgga acaggcagct ttccttccag ccatagcatc atgtccttt cccgttccac     5580
atcataggtg gtccctttat accggctgtc cgtcattttt aaatataggt tttcattttc    5640
tcccaccagc ttatatacct tagcaggaga cattccttcc gtatctttta cgcagcggta    5700
tttttcgatc agttttttca attccggtga tattctcatt ttagccattt attatttcct    5760
tcctcttttc tacagtattt aaagataccc caagaagcta attataacaa gacgaactcc    5820
aattcactgt tccttgcatt ctaaaacctt aaataccaga aaacagcttt ttcaaagttg    5880
ttttcaaagt tggcgtataa catagtatcg acggagccga ttttgaaacc gcggtgatca    5940
caggcagcaa cgctctgtca tcgttacaat caacatgcta ccctccgcga gatcatccgt    6000
gtttcaaacc cggcagctta gttgccgttc ttccgaatag catcggtaac atgagcaaag    6060
tctgccgcct tacaacggct ctcccgctga cgccgtcccg gactgatggg ctgcctgtat    6120
cgagtggtga ttttgtgccg agctgccggt cggggagctg ttggctggct ggtggcagga    6180
tatattgtgg tgtaaacaaa ttgacgctta gacaacttaa taacacattg cggacgtttt    6240
taatgtactg aattaacgcc gaattaattc ggggatctg gatttagta ctggattttg      6300
gttttaggaa ttagaaattt tattgataga agtattttac aaatacaaat acatactaag    6360
ggtttcttat atgctcaaca catgagcgaa accctatagg aaccctaatt cccttatctg    6420
ggaactactc acacattatt atggagaaac tcgagggatc ccgtcggca tctactctat     6480
tcctttgccc tcggacgagt gctggggcgt cggtttccac tatcggcgag tacttctaca    6540
cagccatcgg tccagacggc cgcgcttctg cgggcgattt gtgtacgccc gacagtcccg    6600
gctccggatc ggacgattgc gtcgcatcga ccctgcgccc aagctgcatc atcgaaattg    6660
ccgtcaacca agctctgata gagttggtca agaccaatgc ggagcatata cgcccggagc    6720
cgcggcgatc ctgcaagctc cggatgcctc cgctcgaagt agcgcgtctg ctgctccata    6780
caagccaacc acggcctcca gaagaagatg ttggcgacct cgtattggga atccccgaac    6840
atcgcctcgc tccagtcaat gaccgctgtt atgcggccat tgtccgtcag gacattgttg    6900
gagccgaaat ccgcgtgcac gaggtgccgg acttcggggc agtcctcggc ccaaagcatc    6960
agctcatcga gagcctgcgc gacggacgca ctgacggtgt cgtccatcac agtttgccag    7020
tgatacacat ggggatcagc aatcgcgcat atgaaatcac gccatgtagt gtattgaccg    7080
attccttgcg gtccgaatgg gccgaacccg ctcgtctggc taagatcggc cgcagcgatc    7140
gcatccatgc cctccgcgac cggctgcagt tatcatcatc atcatagaca cacgaaataa    7200
agtaatcaga ttatcagtta aagctatgta atatttacac cataaccaat caattaaaaa    7260
atagatcagt ttaaagaaag atcaaagctc aaaaaaataa aaagagaaaa gggtcctaac    7320
caagaaaatg aaggagaaaa actagaaatt tacctgcaga acagcgggca gttcggtttc    7380
aggcaggtct tgcaacgtga caccctgtgc acggcgggag atgcaatagg tcaggctctc    7440
gctgaattcc ccaatgtcaa gcacttccgg aatcgggagc gcggccgatg caaagtgccg    7500
ataaacataa cgatctttgt agaaaccatc ggcgcagcta tttacccgca ggacatatcc    7560
acgccctcct acatcgaagc tgaaagcacg agattcttcg ccctccgaga gctgcatcag    7620
gtcggagacg ctgtcgaact tttcgatcag aaacttctcg acagacgtcg cggtgagttc    7680
```

```
aggcttttc  atggtagagg  agctcgccgc  ttggtatctg  cattacaatg  aaatgagcaa   7740
agactatgtg  agtaacactg  gtcaacacta  gggagaaggc  atcgagcaag  atacgtatgt   7800
aaagagaagc  aatatagtgt  cagttggtag  atactagata  ccatcaggag  gtaaggagag   7860
caacaaaaag  gaaactcttt  attttaaat   tttgttacaa  caaacaagca  gatcaatgca   7920
tcaaaatact  gtcagtactt  atttcttcag  acaacaatat  ttaaaacaag  tgcatctgat   7980
cttgacttat  ggtcacaata  aaggagcaga  gataaacatc  aaaatttcgt  catttatatt   8040
tattccttca  ggcgttaaca  atttaacagc  acacaaacaa  aaacagaata  ggaatatcta   8100
attttggcaa  ataataagct  ctgcagacga  acaaattatt  atagtatcgc  ctataatatg   8160
aatccctata  ctattgaccc  atgtagtatg  aagcctgtgc  ctaaattaac  agcaaacttc   8220
tgaatccaag  tgccctataa  caccaacatg  tgcttaaata  ataccgcta   agcaccaaat   8280 tacacatttc  tcgtattgct  gtgtaggttc  tatcttcgtt  tcgtactacc  atgtccctat   8340
attttgctgc  tacaaaggac  ggcaagtaat  cagcacaggc  agaacacgat  ttcagagtgt   8400
aattctagat  ccagctaaac  cactctcagc  aatcaccaca  aagagagca   ttcagagaaa   8460 cgtggcagta  acaaaggcag  agggcggagt  gagcgcgtac  cgaagacggt  agatctctcg   8520
agagagatag  atttgtagag  agagactggt  gatttcagcg  tgtcctctcc  aaatgaaatg   8580
aacttcctta  tatagaggaa  ggtcttgcga  aggatagtgg  gattgtgcgt  catcccttac   8640
gtcagtggag  atatcacatc  aatccacttg  ctttgaagac  gtggttggaa  cgtcttcttt   8700
ttccacgatg  ctcctcgtgg  gtggggtcc   atctttggga  ccactgtcgg  cagaggcatc   8760
ttgaacgata  gcctttcctt  tatcgcaatg  atggcatttg  taggtgccac  cttccttttc   8820
tactgtcctt  ttgatgaagt  gacagatagc  tgggcaatgg  aatccgagga  ggtttcccga   8880
tattcccctt  tgttgaaaag  tctcaatagc  cctttggtct  tctgagactg  tatctttgat   8940
attcttggag  tagacgagag  tgtcgtgctc  caccatgtta  tcacatcaat  ccacttgctt   9000
tgaagacgtg  gttggaacgt  cttcttttc   cacgatgctc  ctcgtgggtg  ggtgtccatc   9060
tttgggacca  ctgtcggcag  aggcatcttg  aacgatagcc  tttcctttat  cgcaatgatg   9120
gcatttgtag  gtgccacctt  ccttttctac  tgtccttttg  atgaagtgac  agatagctgg   9180
gcaatggaat  ccgaggaggt  ttcccgatat  acccttttgt  tgaaaagtct  caatagccct   9240
ttggtcttct  gagactgtat  cttgatatt   cttggagtag  acgagagtgt  cgtgctccac   9300
catgttggca  agctgctcta  gccaatacgc  aaaccgcctc  tccccgcgcg  ttggccgatt   9360
cattaatgca  gctggcacga  caggtttccc  gactggaaag  cgggcagtga  gcgcaacgca   9420
attaatgtga  gttagctcac  tcattaggca  ccccaggctt  tacactttat  gcttccggct   9480
cgtatgttgt  gtggaattgt  gagcggataa  caatttcaca  caggaaacag  ctatgaccat   9540
gattacgaat  tcgagctcgg  taccccacgg  aagatccagg  tctcgagact  aggagacgga   9600
tgggaggcgc  aacgcgcgat  ggggaggggg  gcggcgctga  cctttctggc  gaggtcgagg   9660
tagcgatcga  gcagctgcag  cgcggacacg  atgaggaaga  cgaagatagc  cgccatggac   9720
atgttcgcca  gcggcggcgg  agcgaggctg  agccggtctc  tccggcctcc  ggtcggcgtt   9780
aagtggggga  tcgtaacgtg  acgtgtctcg  tctccacgga  tcgacacaac  cggcctactc   9840
gggtgcacga  cgccgcgata  agggcgagat  gtccgtgcac  gcagcccgtt  tggagtcctc   9900
gttgcccacg  aaccgacccc  ttacagaaca  aggcctagcc  caaaactatt  ctgagttgag   9960
cttttgagcc  tagcccacct  aagccgagcg  tcatgaactg  atgaacccac  taccactagt  10020
caaggcaaac  cacaaccaca  aatggatcaa  ttgatctaga  acaatccgaa  ggagggagg   10080
```

```
ccacgtcaca ctcacaccaa ccgaaatatc tgccagaatc agatcaaccg gccaatagga    10140
cgccagcgag cccaacacct ggcgacgccg caaaattcac cgcgaggggc accgggcacg    10200
gcaaaaacaa aagcccggcg cggtgagaat atctggcgac tggcggagac ctggtggcca    10260
gcgcgcggcc acatcagcca ccccatccgc ccacctcacc tccggcgagc caatggcaac    10320
tcgtcttaag attccacgag ataaggaccc gatcgccggc gacgctattt agccaggtgc    10380
gccccccacg gtacactcca ccagcggcat ctatagcaac cggtccagca ctttcacgct    10440
cagcttcagc aagatctacc gtcttcggta cgcgctcact ccgccctctg cctttgttac    10500
tgccacgttt ctctgaatgc tctcttgtgt ggtgattgct gagagtggtt tagctggatc    10560
tagaattaca ctctgaaatc gtgttctgcc tgtgctgatt acttgccgtc ctttgtagca    10620
gcaaaatata gggacatggt agtacgaaac gaagatagaa cctacacagc aatacgagaa    10680
atgtgtaatt tggtgcttag cggtatttat ttaagcacat gttggtgtta tagggcactt    10740
ggattcagaa gtttgctgtt aatttaggca caggcttcat actacatggg tcaatagtat    10800
agggattcat attataggcg atactataat aatttgttcg tctgcagagc ttattatttg    10860
ccaaaattag atattcctat tctgtttttg tttgtgtgct gttaaattgt taacgcctga    10920
aggaataaat ataaatgacg aaattttgat gtttatctct gctcctttat tgtgaccata    10980
agtcaagatc agatgcactt gttttaaata ttgttgtctg aagaaataag tactgacagt    11040
attttgatgc attgatctgc ttgtttgttg taacaaaatt taaaaataaa gagtttcctt    11100
tttgttgctc tccttacctc ctgatggtat ctagtatcta ccaactgata ctatattgct    11160
tctctttaca nnnnnntctt gctcgatgcc ttctcctagt gttgaccagt gttactcaca    11220
tagtctttgc tcatttcatt gtaatgcaga taccaagcgg ttaattaact atgtgcggcg    11280
gggccattct cagtgatctc tactcaccag tgaggcggac ggtcactgcc ggtgacctat    11340
ggggagagag tggcagcagc aagaatgtga agaactggaa aaggagttct tggaagtttg    11400
atgaaggcga tgaagacttt gaagctgatt tcaaggattt tgaggattgc agtagcgagg    11460
aggaggtaga ttttggacat gaggaaaaag aattccaatt gaacagttcg aatttcgtgg    11520
aattcaatgg ccatactgcc aaagtcacca gcaggaagcg aaagatccag taccgaggga    11580
tccggcggcg gccttggggc aaatgggcag cagaaatcag agacccacag aagggcgtcc    11640
gagtttggct tggcacgttc agcactgccg aggaagctgc aagggcatat gacgtggaag    11700
ctctacgcat acgtggcaag aaagccaaga tgaatttccc taccaccatc acagctgctg    11760
ggaaacacca ccggcagcgt gtggctcgac cggcaaagaa gacgtcacaa gagagcctga    11820
agtcaagcaa tgcctctggt catgtcatct cagcaggcag cagtactgat ggcaccgttg    11880
tcaagatcga gttgtcacag tcaccagctt ctccactacc agtgtccagc gcatggcttg    11940
atgcttttga gctgaagcag cttggtggag aaacccctga agctgatggg agagaaaccc    12000
ctgaagaaac tgatcatgaa acgggagtga cagcggatat gttttttggc aatggcgaag    12060
tgcggctttc agatgatttt gcgtcttacg agccttaccc aaattttatg cagttacctt    12120
atctagaagg tgactcgtat gaaaacattg acactctttt caacggtgaa gctgctcagg    12180
atggagtgaa catcggaggt ctttggaatt tcgatgatgt gccaatggac cgtggtgttt    12240
actgaatgtg cggcggggcc attctcagtg atctctactc accagtgagg cggacggtca    12300
ctgccggtga cctatgggga gagtggca gcagcaagaa tgtgaagaac tggaaaagga    12360
gttcttggaa gtttgatgaa ggcgatgaag actttgaagc tgatttcaag gattttgagg    12420
```

```
attgcagtag cgaggaggag gtagattttg gacatgagga aaaagaattc caattgaaca    12480
gttcgaattt cgtggaattc aatggccata ctgccaaagt caccagcagg aagcgaaaga    12540
tccagtaccg agggatccgg cggcggcctt ggggcaaatg ggcagcagaa atcagagacc    12600
cacagaaggg cgtccgagtt tggcttggca cgttcagcac tgccgaggaa gctgcaaggg    12660
catatgacgt ggaagctcta cgcatacgtg gcaagaaagc caagatgaat ttccctacca    12720
ccatcacagc tgctgggaaa caccaccggc agcgtgtggc tcgaccggca agaagacgt     12780 cacaagagag cctgaagtca agcaatgcct ctggtcatgt catctcagca ggcagcagta    12840
ctgatggcac cgttgtcaag atcgagttgt cacagtcacc agcttctcca ctaccagtgt    12900
ccagcgcatg gcttgatgct tttgagctga agcagcttgg tggagaaacc cctgaagctg    12960
atgggagaga accccctgaa gaaactgatc atgaaacggg agtgcacgcg gatatgtttt    13020
ttggcaatgg cgaagtgcgg cttttcagatg attttgcgtc ttacgagcct tacccaaatt    13080
ttatgcagtt accttatcta gaaggtgact cgtatgaaaa cattgacact cttttcaacg    13140
gtgaagctgc tcaggatgga gtgaacatcg gaggtctttg gaatttcgat gatgtgccaa    13200
tggaccgtgg tgtttactga gcagggcgcg ccatcgttca acatttggc aataaagttt     13260 cttaagattg aatcctgttg ccggtcttgc gatgattatc atataatttc tgttgaatta    13320
cgttaagcat gtaataatta acatgtaatg catgacgtta tttatgagat gggttttat     13380 gattagagtc ccgcaattat acatttaata cgcgatagaa acaaaatat agcgcgcaaa     13440 ctaggataaa ttatcgcgcg cggtgtcatc tatgttacta gatccgatga taagctgtca    13500
aacatgaaag cttggcactg gccgtcgttt tacaacgtcg tgactgggaa accctggcg     13560 ttacccaact taatcgcctt gcagcacatc cccctttcgc cagctggcgt aatagcgaag    13620
aggcccgcac cgatcgccct tcccaacagt tgcgcagcct gaatggcgaa tgctagcaca    13680
gcttgagctt ggatcagatt gtcgtttccc gccttcagtt taaactatca gtgtttgaca    13740
ggatatattg gcgggtaaac ctaagagaaa agagcgttta ttagaataac ggatatttaa    13800
aagggcgtga aaaggtttat ccgttcgtcc atttgtatgt g                        13841
```

<210> SEQ ID NO 29
<211> LENGTH: 87
<212> TYPE: PRT
<213> ORGANISM: Panicum virgatum

<400> SEQUENCE: 29

Val Thr Ser Arg Lys Arg Lys Ile Gln Tyr Arg Gly Ile Arg Arg
1               5                   10                  15

Pro Trp Gly Lys Trp Ala Ala Glu Ile Arg Asp Pro Gln Lys Gly Val
                20                  25                  30

Arg Val Trp Leu Gly Thr Phe Ser Thr Ala Glu Glu Ala Arg Ala
            35                  40                  45

Tyr Asp Val Glu Ala Leu Arg Ile Arg Gly Lys Lys Ala Lys Met Asn
        50                  55                  60

Phe Pro Thr Thr Ile Thr Ala Ala Gly Lys His His Arg Gln Arg Val
65                  70                  75                  80

Ala Arg Pro Ala Lys Lys Thr
                85

<210> SEQ ID NO 30
<211> LENGTH: 87
<212> TYPE: PRT
<213> ORGANISM: Setaria italica

<400> SEQUENCE: 30

Val Ala Arg Arg Lys Arg Lys Thr Gln Tyr Arg Gly Ile Arg Arg Arg
1               5                   10                  15

Pro Trp Gly Lys Trp Ala Ala Glu Ile Arg Asp Pro Cys Lys Gly Val
            20                  25                  30

Arg Val Trp Leu Gly Thr Tyr Asn Thr Ala Glu Glu Ala Ala Arg Ala
        35                  40                  45

Tyr Asp Val Ala Ala Arg Ile Arg Gly Lys Lys Ala Lys Val Asn
50                  55                  60

Phe Pro Asp Thr Ile Thr Ala Ser Ala Lys Arg Leu Pro Gly Arg Val
65                  70                  75                  80

Pro Arg Pro Ala Lys Lys Val
                85

<210> SEQ ID NO 31
<211> LENGTH: 87
<212> TYPE: PRT
<213> ORGANISM: Sorghum bicolor

<400> SEQUENCE: 31

Val Ala Ser Arg Lys Arg Arg Thr Gln Tyr Arg Gly Ile Arg Arg Arg
1               5                   10                  15

Pro Trp Gly Lys Trp Ala Ala Glu Ile Arg Asp Pro Arg Lys Gly Val
            20                  25                  30

Arg Val Trp Leu Gly Thr Tyr Ser Thr Ala Glu Glu Ala Ala Arg Ala
        35                  40                  45

Tyr Asp Thr Ala Ala Trp Arg Ile Arg Gly Lys Lys Ala Lys Val Asn
50                  55                  60

Phe Pro Ser Ala Ile Thr Asn Pro Glu Lys Arg Arg Arg Gly Arg Val
65                  70                  75                  80

Ala Arg Pro Arg Lys Lys Ile
                85

<210> SEQ ID NO 32
<211> LENGTH: 94
<212> TYPE: PRT
<213> ORGANISM: Oryza sativa

<400> SEQUENCE: 32

Gly Gly Ser Arg Lys Arg Lys Thr Arg Tyr Arg Gly Ile Arg Gln Arg
1               5                   10                  15

Pro Trp Gly Lys Trp Ala Ala Glu Ile Arg Asp Pro Arg Lys Gly Val
            20                  25                  30

Arg Val Trp Leu Gly Thr Phe Gly Thr Ala Glu Glu Ala Ala Met Ala
        35                  40                  45

Tyr Asp Val Glu Ala Arg Arg Ile Arg Gly Lys Lys Ala Lys Val Asn
50                  55                  60

Phe Pro Asp Ala Ala Ala Ala Pro Lys Arg Pro Arg Arg Ser Ser
65                  70                  75                  80

Ala Lys His Ser Pro Gln Gln Gln Lys Ala Arg Ser Ser Ser
                85                  90

<210> SEQ ID NO 33
<211> LENGTH: 110
<212> TYPE: PRT
<213> ORGANISM: Jatropha curcas

<400> SEQUENCE: 33

Phe Asn Gly Gln Ala Glu Lys Ser Ala Lys Arg Lys Arg Lys Asn Gln
1               5                   10                  15

Tyr Arg Gly Ile Arg Gln Arg Pro Trp Gly Lys Trp Ala Ala Glu Ile
            20                  25                  30

Arg Asp Pro Arg Lys Gly Val Arg Val Trp Leu Gly Thr Phe Asn Thr
        35                  40                  45

Ala Glu Glu Ala Ala Arg Ala Tyr Asp Ala Glu Ala Arg Arg Ile Arg
    50                  55                  60

Gly Lys Lys Ala Lys Val Asn Phe Pro Glu Glu Ala Pro His Ala Ser
65                  70                  75                  80

Pro Lys Arg Pro Ser Lys Ala Asn Ser Gln Lys Ser Leu Gly Lys Thr
                85                  90                  95

Asn Leu Ala Glu Asn Leu Asn Tyr Leu Asp Asn Pro Glu Gln
            100                 105                 110

<210> SEQ ID NO 34
<211> LENGTH: 110
<212> TYPE: PRT
<213> ORGANISM: Populus trichocarpa

<400> SEQUENCE: 34

Phe Ser Gly Pro Ala Glu Lys Ser Ala Lys Arg Lys Arg Lys Asn Gln
1               5                   10                  15

Phe Arg Gly Ile Arg Gln Arg Pro Trp Gly Lys Trp Ala Ala Glu Ile
            20                  25                  30

Arg Asp Pro Arg Lys Gly Val Arg Val Trp Leu Gly Thr Phe Asn Thr
        35                  40                  45

Ala Glu Glu Ala Ala Arg Ala Tyr Asp Ser Glu Ala Arg Arg Ile Arg
    50                  55                  60

Gly Lys Lys Ala Lys Val Asn Phe Pro Asp Glu Ala Pro Cys Ala Ser
65                  70                  75                  80

Ala Arg His Pro Ile Lys Glu Asn Ser Gln Lys Arg Leu Thr Lys Ala
                85                  90                  95

Asn Leu Ser Gln Asp Phe Ser Tyr Leu Ser Asn Pro Glu Thr
            100                 105                 110

<210> SEQ ID NO 35
<211> LENGTH: 117
<212> TYPE: PRT
<213> ORGANISM: Gossypium hirsutum

<400> SEQUENCE: 35

Phe Asn Gly Gln Ala Glu Lys Cys Ala Lys Arg Lys Arg Lys Asn Gln
1               5                   10                  15

Tyr Arg Gly Ile Arg Gln Arg Pro Trp Gly Lys Trp Ala Ala Glu Ile
            20                  25                  30

Arg Asp Pro Arg Lys Gly Val Arg Val Trp Leu Gly Thr Phe Asn Thr
        35                  40                  45

Ala Glu Glu Ala Ala Arg Ala Tyr Asp Ala Glu Ala Arg Arg Ile Arg
    50                  55                  60

Gly Lys Lys Ala Lys Val Asn Phe Pro Asn Glu Thr Pro Arg Thr Ser
65                  70                  75                  80

Pro Lys His Ala Val Lys Thr Asn Ser Gln Lys Pro Leu Ser Lys Ser
                85                  90                  95

Asn Ser Ser Pro Val Gln Pro Asn Leu Asn Gln Asn Tyr Asn Tyr Leu

-continued

```
                100                 105                 110

Asn Gln Pro Glu Gln
        115

<210> SEQ ID NO 36
<211> LENGTH: 117
<212> TYPE: PRT
<213> ORGANISM: Theobroma cacao

<400> SEQUENCE: 36

Phe Asn Gly Gln Ala Glu Lys Ser Ala Lys Arg Lys Arg Lys Asn Gln
1               5                   10                  15

Tyr Arg Gly Ile Arg Gln Arg Pro Trp Gly Lys Trp Ala Ala Glu Ile
            20                  25                  30

Arg Asp Pro Arg Lys Gly Val Arg Val Trp Leu Gly Thr Phe Asn Thr
        35                  40                  45

Ala Glu Glu Ala Ala Arg Ala Tyr Asp Ala Glu Ala Arg Arg Ile Arg
    50                  55                  60

Gly Lys Lys Ala Lys Val Asn Phe Pro Asp Glu Ala Pro Arg Thr Ser
65                  70                  75                  80

Pro Lys Arg Ala Val Lys Ala Asn Ser Gln Lys Ser Leu Ser Arg Ser
                85                  90                  95

Asn Leu Ser Pro Val Gln Pro Asn Leu Asp Gln Asn Phe Asn Tyr Leu
                100                 105                 110

Ser Lys Pro Glu Gln
        115

<210> SEQ ID NO 37
<211> LENGTH: 117
<212> TYPE: PRT
<213> ORGANISM: Malus domestica

<400> SEQUENCE: 37

Phe Asp Gly Gln Ala Glu Lys Ser Ala Lys Arg Lys Arg Lys Asn Gln
1               5                   10                  15

Tyr Arg Gly Ile Arg Gln Arg Pro Trp Gly Lys Trp Ala Ala Glu Ile
            20                  25                  30

Arg Asp Pro Arg Lys Gly Val Arg Val Trp Leu Gly Thr Phe Asn Thr
        35                  40                  45

Ala Glu Glu Ala Ala Arg Ala Tyr Asp Ala Glu Ala Arg Arg Ile Arg
    50                  55                  60

Gly Lys Lys Ala Lys Val Asn Phe Pro Glu Glu Thr Pro Cys Ala Ser
65                  70                  75                  80

Ala Lys Arg Ser Ile Lys Glu Asn Pro Gln Lys Leu Ile Ala Lys Thr
                85                  90                  95

Asn Leu Asn Gly Thr Gln Ser Asn Pro Asn Gln Asn Phe Asn Phe Val
                100                 105                 110

Asn Asp Ser Ser Glu
        115

<210> SEQ ID NO 38
<211> LENGTH: 118
<212> TYPE: PRT
<213> ORGANISM: Morus alba

<400> SEQUENCE: 38

Ser Asp Gly Gln Ala Glu Lys Ser Ala Lys Arg Lys Arg Lys Asn Gln
1               5                   10                  15
```

```
Tyr Arg Gly Ile Arg Gln Arg Pro Trp Gly Lys Trp Ala Ala Glu Ile
             20                  25                  30

Arg Asp Pro Arg Lys Gly Val Arg Val Trp Leu Gly Thr Phe Asn Thr
         35                  40                  45

Ala Glu Glu Ala Ala Arg Ala Tyr Asp Ala Glu Ala Arg Arg Ile Arg
     50                  55                  60

Gly Lys Lys Ala Lys Val Asn Phe Pro Asp Glu Thr Pro Arg Ala Leu
 65                  70                  75                  80

Pro Lys His Pro Val Lys Glu Ser Pro Lys Arg Ser Leu Pro Lys Glu
                 85                  90                  95

Asn Ser Asn Ser Thr Glu Ser Asn Leu Asn Asn Gln Ser Phe Asn Ser
            100                 105                 110

Val Asn Asn Ser Asp Leu
        115
```

<210> SEQ ID NO 39
<211> LENGTH: 105
<212> TYPE: PRT
<213> ORGANISM: Cucumis sativus

<400> SEQUENCE: 39

```
Phe Asn Glu Gln Ala Glu Lys Ser Ala Asn Thr Lys Arg Lys Asn Gln
 1               5                  10                  15

Tyr Arg Gly Ile Arg Gln Arg Pro Trp Gly Lys Trp Ala Ala Glu Ile
             20                  25                  30

Arg Asp Pro Arg Lys Gly Ala Arg Val Trp Leu Gly Thr Phe Asn Thr
         35                  40                  45

Ala Glu Glu Ala Ala Arg Ala Tyr Asp Ala Glu Ala Arg Arg Ile Arg
     50                  55                  60

Gly Asn Lys Ala Arg Val Asn Phe Pro Asp Glu Pro Leu Pro Asn Thr
 65                  70                  75                  80

Gln Lys Arg Lys Asn Ser Gln Lys Ser Lys Gln His Ile Lys Glu Asn
                 85                  90                  95

Val Lys Ala Asn Gln His Pro Asn Gln
            100                 105
```

<210> SEQ ID NO 40
<211> LENGTH: 113
<212> TYPE: PRT
<213> ORGANISM: Solanum lycopersicum

<400> SEQUENCE: 40

```
Ser Asn Cys Glu Ala Asp Arg Ser Ser Lys Arg Lys Arg Lys Asn Gln
 1               5                  10                  15

Tyr Arg Gly Ile Arg Gln Arg Pro Trp Gly Lys Trp Ala Ala Glu Ile
             20                  25                  30

Arg Asp Pro Arg Lys Gly Ile Arg Val Trp Leu Gly Thr Phe Asn Ser
         35                  40                  45

Ala Glu Glu Ala Ala Arg Ala Tyr Asp Ala Glu Ala Arg Arg Ile Arg
     50                  55                  60

Gly Lys Lys Ala Lys Val Asn Phe Pro Asp Glu Ala Pro Val Ser Val
 65                  70                  75                  80

Ser Arg Arg Ala Ile Lys Gln Asn Pro Gln Lys Ala Leu Arg Glu Glu
                 85                  90                  95

Thr Leu Asn Thr Val Gln Pro Asn Met Thr Tyr Ile Ser Asn Leu Asp
            100                 105                 110
```

Gly

<210> SEQ ID NO 41
<211> LENGTH: 113
<212> TYPE: PRT
<213> ORGANISM: Capsicum annuum

<400> SEQUENCE: 41

Ser Ser Cys Asp Thr Glu Lys Ser Lys Arg Lys Arg Lys Asn Gln
1               5                   10                  15

Tyr Arg Gly Ile Arg Gln Arg Pro Trp Gly Lys Trp Ala Ala Glu Ile
                20                  25                  30

Arg Asp Pro Arg Lys Gly Ile Arg Val Trp Leu Gly Thr Phe Asn Ser
            35                  40                  45

Ala Glu Glu Ala Ala Arg Ala Tyr Asp Val Ala Ala Arg Ile Arg
    50                  55                  60

Gly Lys Lys Ala Lys Val Asn Phe Pro Asp Gly Ser Pro Ala Ser Ala
65                  70                  75                  80

Ser Arg Arg Ala Val Lys Pro Asn Pro Gln Glu Ala Leu Arg Glu Glu
                85                  90                  95

Ile Leu Asn Thr Val Gln Pro Asn Thr Thr Tyr Ile Asn Asn Leu Asp
                100                 105                 110

Gly

<210> SEQ ID NO 42
<211> LENGTH: 113
<212> TYPE: PRT
<213> ORGANISM: Nicotiana tabacum

<400> SEQUENCE: 42

Ser Asp Lys Asp Ala Asp Arg Ser Ser Lys Arg Lys Arg Lys Asn Gln
1               5                   10                  15

Tyr Arg Gly Ile Arg Gln Arg Pro Trp Gly Lys Trp Ala Ala Glu Ile
                20                  25                  30

Arg Asp Pro Arg Lys Gly Val Arg Val Trp Leu Gly Thr Phe Asn Thr
            35                  40                  45

Ala Glu Glu Ala Ala Arg Ala Tyr Asp Val Glu Ala Arg Arg Ile Arg
    50                  55                  60

Gly Asn Lys Ala Lys Val Asn Phe Pro Asp Glu Ala Pro Val Pro Ala
65                  70                  75                  80

Ser Arg Arg Thr Val Lys Val Asn Pro Gln Lys Val Leu Pro Lys Glu
                85                  90                  95

Ile Leu Asp Ser Val Gln Pro Asp Ser Thr Ile Ile Asn Asn Met Glu
                100                 105                 110

Asp

<210> SEQ ID NO 43
<211> LENGTH: 108
<212> TYPE: PRT
<213> ORGANISM: Glycine max

<400> SEQUENCE: 43

Phe Gln Gly Arg Ala Glu Ile Ser Ala Asn Arg Lys Arg Lys Asn Gln
1               5                   10                  15

Tyr Arg Gly Ile Arg Gln Arg Pro Trp Gly Lys Trp Ala Ala Glu Ile
                20                  25                  30

Arg Asp Pro Arg Lys Gly Val Arg Val Trp Leu Gly Thr Phe Asn Thr
            35                  40                  45

Ala Glu Glu Ala Ala Arg Ala Tyr Asp Ala Glu Ala Arg Arg Ile Arg
 50                  55                  60

Gly Lys Lys Ala Lys Val Asn Phe Pro Glu Ala Pro Gly Thr Ser Ser
 65                  70                  75                  80

Val Lys Arg Ser Lys Val Asn Pro Gln Glu Asn Leu Lys Thr Val Gln
                 85                  90                  95

Pro Asn Leu Gly His Lys Phe Ser Ala Gly Asn Asn
            100                 105

<210> SEQ ID NO 44
<211> LENGTH: 105
<212> TYPE: PRT
<213> ORGANISM: Arachis hypogaea

<400> SEQUENCE: 44

Val Lys Ala Gln Ser Glu Lys Ser Ala Lys Arg Lys Arg Lys Asn Gln
 1               5                  10                  15

Tyr Arg Gly Ile Arg Gln Arg Pro Trp Gly Lys Trp Ala Ala Glu Ile
             20                  25                  30

Arg Asp Pro Arg Lys Gly Val Arg Val Trp Leu Gly Thr Phe Ser Thr
            35                  40                  45

Ala Glu Glu Ala Ala Arg Ala Tyr Asp Ala Glu Ala Arg Arg Ile Arg
 50                  55                  60

Gly Lys Lys Ala Lys Val Asn Phe Pro Glu Glu Ala Pro Arg Thr Pro
 65                  70                  75                  80

Pro Lys Arg Ala Arg Pro Asn Leu Asn Ala Val Gln Pro Asn Leu Ser
                 85                  90                  95

His Lys Phe Ser Val Gly Asn Asn Met
            100                 105

<210> SEQ ID NO 45
<211> LENGTH: 108
<212> TYPE: PRT
<213> ORGANISM: Medicago truncatula

<400> SEQUENCE: 45

Ser Lys Ser Asn Glu Gln Gly Glu Lys Glu Leu Lys Arg Lys Arg Lys
 1               5                  10                  15

Asn Gln Tyr Arg Gly Ile Arg Gln Arg Pro Trp Gly Lys Trp Ala Ala
             20                  25                  30

Glu Ile Arg Asp Pro Arg Lys Gly Val Arg Val Trp Leu Gly Thr Phe
            35                  40                  45

Asn Thr Ala Glu Glu Ala Ala Arg Ala Tyr Asp Ala Glu Ala Arg Arg
 50                  55                  60

Ile Arg Gly Lys Lys Ala Lys Val Asn Phe Pro Glu Glu Ala Pro Asn
 65                  70                  75                  80

Ala Ser Ser Lys Arg Leu Lys Thr Asn Ser Glu Thr Gln Leu Leu Asp
                 85                  90                  95

Lys Asn Leu Asn Ser Phe Lys Cys Glu Asn Ile Glu
            100                 105

<210> SEQ ID NO 46
<211> LENGTH: 114
<212> TYPE: PRT
<213> ORGANISM: Zea mays

-continued

```
<400> SEQUENCE: 46

Tyr Asp Ala Pro Ala Ala Arg Leu Ala Lys Arg Lys Arg Lys Asn Gln
1               5                   10                  15

Tyr Arg Gly Ile Arg Gln Arg Pro Trp Gly Lys Trp Ala Ala Glu Ile
            20                  25                  30

Arg Asp Pro Gln Lys Gly Val Arg Val Trp Leu Gly Thr Phe Asn Ser
        35                  40                  45

Pro Glu Glu Ala Arg Ala Tyr Asp Ala Glu Ala Arg Arg Ile Arg
    50                  55                  60

Gly Lys Lys Ala Lys Val Asn Phe Pro Asp Ala Pro Ala Val Gly Gln
65                  70                  75                  80

Lys Cys Arg Ser Ser Ala Ser Ala Lys Ala Leu Lys Ser Cys Val
                85                  90                  95

Glu Gln Lys Pro Ile Val Lys Thr Asp Met Asn Ile Leu Ala Asn Thr
            100                 105                 110

Asn Ala

<210> SEQ ID NO 47
<211> LENGTH: 114
<212> TYPE: PRT
<213> ORGANISM: Brachypodium distachyon

<400> SEQUENCE: 47

Phe Asp Gly Pro Ala Glu Arg Ser Ala Lys Arg Lys Arg Lys Asn Gln
1               5                   10                  15

Phe Arg Gly Ile Arg Gln Arg Pro Trp Gly Lys Trp Ala Ala Glu Ile
            20                  25                  30

Arg Asp Pro Asn Lys Gly Val Arg Val Trp Leu Gly Thr Phe Asn Ser
        35                  40                  45

Ala Glu Glu Ala Ala Arg Ala Tyr Asp Ala Glu Ala Arg Arg Ile Arg
    50                  55                  60

Gly Asn Lys Ala Lys Val Asn Phe Pro Glu Glu Pro Arg Ala Ala Gln
65                  70                  75                  80

Lys Arg Arg Ala Gly Pro Ala Ala Ala Lys Val Pro Lys Ser Arg Val
                85                  90                  95

Glu Gln Lys Pro Asn Val Lys Pro Ala Val Asn Asn Leu Ala Asn Thr
            100                 105                 110

Asn Ala

<210> SEQ ID NO 48
<211> LENGTH: 108
<212> TYPE: PRT
<213> ORGANISM: Triticum aestivum

<400> SEQUENCE: 48

Asp Asp Asp Cys Ala Ser Gly Ser Ala Arg Lys Arg Lys Asn Gln Phe
1               5                   10                  15

Arg Gly Ile Arg Arg Arg Pro Trp Gly Lys Trp Ala Ala Glu Ile Arg
            20                  25                  30

Asp Pro Arg Lys Gly Val Arg Val Trp Leu Gly Thr Tyr Asn Ser Ala
        35                  40                  45

Glu Glu Ala Ala Arg Ala Tyr Asp Val Glu Ala Arg Arg Ile Arg Gly
    50                  55                  60

Lys Lys Ala Glu Val Asn Phe Pro Glu Glu Ala Pro Met Ala Pro Gln
65                  70                  75                  80
```

```
Gln Arg Cys Ala Thr Ala Val Lys Val Pro Glu Phe Asn Thr Glu Gln
                85                  90                  95

Lys Pro Val Leu Asn Thr Met Gly Asn Ala Asp Val
            100                 105
```

<210> SEQ ID NO 49
<211> LENGTH: 102
<212> TYPE: PRT
<213> ORGANISM: Hordeum vulgare

<400> SEQUENCE: 49

```
Tyr Asp Gly Gly Arg Ala Ala His Ala Ala Ser Arg Lys Lys Arg Thr
1               5                   10                  15

Gly His Leu His Gly Ile Arg Gln Arg Pro Trp Gly Lys Trp Ala Ala
            20                  25                  30

Glu Ile Arg Asp Pro His Lys Gly Thr Arg Val Trp Leu Gly Thr Phe
        35                  40                  45

Asp Thr Ala Asp Ala Ala Arg Ala Tyr Asp Val Ala Ala Arg Arg
    50                  55                  60

Leu Arg Gly Ser Lys Ala Lys Val Asn Phe Pro Asp Ala Ala Arg Thr
65                  70                  75                  80

Gly Ala Arg Pro Arg Arg Ala Ser Arg Thr Ala Gln Lys Pro Gln
                85                  90                  95

Cys Pro Pro Ala Arg Thr
            100
```

<210> SEQ ID NO 50
<211> LENGTH: 92
<212> TYPE: PRT
<213> ORGANISM: Zea mays

<400> SEQUENCE: 50

```
Thr Leu Thr Thr Thr Met Arg His Tyr Arg Gly Val Arg Arg Arg Pro
1               5                   10                  15

Trp Gly Lys Trp Ala Ala Glu Ile Arg Asp Pro Ala Lys Ala Ala Arg
            20                  25                  30

Val Trp Leu Gly Thr Phe Asp Thr Ala Glu Ala Ala Ala Ala Ala Tyr
        35                  40                  45

Asp Arg Ala Ala Leu Gln Phe Lys Gly Ala Lys Ala Lys Leu Asn Phe
    50                  55                  60

Pro Glu Arg Val Arg Gly Arg Thr Gly Gln Gly Ala Phe Leu Val Ser
65                  70                  75                  80

Pro Gly Ile Pro Gln Pro Pro Val Ser Ala Pro
                85                  90
```

<210> SEQ ID NO 51
<211> LENGTH: 96
<212> TYPE: PRT
<213> ORGANISM: Sorghum bicolor

<400> SEQUENCE: 51

```
Thr Ser Thr Thr Thr Met Arg His Tyr Arg Gly Val Arg Arg Arg Pro
1               5                   10                  15

Trp Gly Lys Trp Ala Ala Glu Ile Arg Asp Pro Ala Lys Ala Ala Arg
            20                  25                  30

Val Trp Leu Gly Thr Phe Asp Thr Ala Glu Ala Ala Ala Ala Ala Tyr
        35                  40                  45

Asp Asp Ala Ala Leu Arg Phe Lys Gly Ala Lys Ala Lys Leu Asn Phe
```

```
            50                  55                  60
Pro Glu Arg Val Arg Gly Arg Thr Gly Gln Gly Ala Phe Leu Val Ser
 65                  70                  75                  80

Pro Gly Ile Pro Gln Pro Pro Pro Val Ser Ala Pro Pro Leu
                 85                  90                  95

<210> SEQ ID NO 52
<211> LENGTH: 91
<212> TYPE: PRT
<213> ORGANISM: Panicum virgatum

<400> SEQUENCE: 52

Tyr Gly Thr Arg Met His Tyr Arg Gly Val Arg Arg Pro Trp Gly
  1               5                  10                  15

Lys Trp Ala Ala Glu Ile Arg Asp Pro Ala Lys Ala Ala Arg Val Trp
                 20                  25                  30

Leu Gly Thr Phe Asp Thr Ala Glu Ala Ala Ala Ala Tyr Asp Asp
             35                  40                  45

Ala Ala Leu Arg Phe Lys Gly Ala Lys Ala Lys Leu Asn Phe Pro Glu
         50                  55                  60

Arg Val Arg Gly Arg Thr Gly Gln Gly Ala Phe Leu Val Ser Pro Gly
 65                  70                  75                  80

Val Pro Gln Gln Pro Pro Ser Ser Leu Pro
                 85                  90

<210> SEQ ID NO 53
<211> LENGTH: 100
<212> TYPE: PRT
<213> ORGANISM: Hordeum vulgare

<400> SEQUENCE: 53

Gly Arg Lys Arg His Tyr Arg Gly Val Arg Gln Arg Pro Trp Gly Lys
  1               5                  10                  15

Trp Ala Ala Glu Ile Arg Asp Pro Lys Lys Ala Ala Arg Val Trp Leu
                 20                  25                  30

Gly Thr Phe Asp Thr Ala Glu Asp Ala Ala Ile Ala Tyr Asp Glu Ala
             35                  40                  45

Ala Leu Arg Phe Lys Gly Thr Lys Ala Lys Leu Asn Phe Pro Glu Arg
         50                  55                  60

Val Gln Gly Arg Thr Asp Leu Gly Phe Val Val Thr Arg Gly Ile Pro
 65                  70                  75                  80

Asp Arg Leu Gln Gln Gln His Tyr Pro Ala Ala Val Gly Ala Pro
                 85                  90                  95

Ala Met Arg Pro
            100

<210> SEQ ID NO 54
<211> LENGTH: 99
<212> TYPE: PRT
<213> ORGANISM: Brachypodium distachyon

<400> SEQUENCE: 54

Gly Arg Lys Arg His Tyr Arg Gly Val Arg Gln Arg Pro Trp Gly Lys
  1               5                  10                  15

Trp Ala Ala Glu Ile Arg Asp Pro Lys Lys Ala Ala Arg Val Trp Leu
                 20                  25                  30

Gly Thr Phe Asp Thr Ala Glu Asp Ala Ala Ile Ala Tyr Asp Glu Ala
             35                  40                  45
```

-continued

Ala Leu Arg Phe Lys Gly Thr Lys Ala Lys Leu Asn Phe Pro Glu Arg
        50                  55                  60

Val Gln Gly Arg Thr Asp Leu Gly Phe Val Val Thr Arg Gly Ile Pro
 65                  70                  75                  80

Asp Arg Ser Ser Leu His His Gln Gln His Tyr Pro Gly Ser Thr Ala
                85                  90                  95

Met Arg Pro

<210> SEQ ID NO 55
<211> LENGTH: 101
<212> TYPE: PRT
<213> ORGANISM: Oryza sativa

<400> SEQUENCE: 55

Gly Arg Arg Arg His Tyr Arg Gly Val Arg Gln Arg Pro Trp Gly Lys
 1               5                  10                  15

Trp Ala Ala Glu Ile Arg Asp Pro Lys Lys Ala Ala Arg Val Trp Leu
                20                  25                  30

Gly Thr Phe Asp Thr Ala Glu Asp Ala Ala Ile Ala Tyr Asp Glu Ala
            35                  40                  45

Ala Leu Arg Phe Lys Gly Thr Lys Ala Lys Leu Asn Phe Pro Glu Arg
        50                  55                  60

Val Gln Gly Arg Thr Asp Leu Gly Phe Leu Val Thr Arg Gly Ile Pro
 65                  70                  75                  80

Pro Ala Ala Thr His Gly Gly Tyr Tyr Pro Ser Ser Ser Pro Ala
                85                  90                  95

Ala Gly Ala Cys Pro
            100

<210> SEQ ID NO 56
<211> LENGTH: 105
<212> TYPE: PRT
<213> ORGANISM: Jatropha curcas

<400> SEQUENCE: 56

Asn Thr Arg Arg Arg His Tyr Arg Gly Val Arg Gln Arg Pro Trp Gly
 1               5                  10                  15

Lys Trp Ala Ala Glu Ile Arg Asp Pro Lys Lys Ala Ala Arg Val Trp
                20                  25                  30

Leu Gly Thr Phe Asp Thr Ala Glu Asp Ala Ala Leu Ala Tyr Asp Lys
            35                  40                  45

Ala Ala Leu Lys Phe Lys Gly Thr Lys Ala Lys Leu Asn Phe Pro Glu
        50                  55                  60

Arg Val Gln Gly Lys Pro Glu Phe Ser Tyr Phe Met Thr Ser Ser Gly
 65                  70                  75                  80

Asp Ser Ser Ser Ala Leu Ala Pro Glu Gln Asn Pro Met Ala Ala Ala
                85                  90                  95

Ala Ser Ala Pro Ser Arg His Tyr Leu
            100                 105

<210> SEQ ID NO 57
<211> LENGTH: 101
<212> TYPE: PRT
<213> ORGANISM: Populus trichocarpa

<400> SEQUENCE: 57

Asn Thr Arg Arg Arg His Tyr Arg Gly Val Arg Gln Arg Pro Trp Gly

-continued

```
               1               5                  10                 15
        Lys Trp Ala Ala Glu Ile Arg Asp Pro Lys Lys Ala Ala Arg Val Trp
                        20                  25                 30

Leu Gly Thr Phe Asp Thr Ala Glu Asp Ala Ala Val Ala Tyr Asp Lys
                    35                  40                 45

Ala Ala Leu Lys Phe Lys Gly Thr Lys Ala Lys Leu Asn Phe Pro Glu
             50                  55                 60

Arg Val Gln Gly Arg Thr Glu Phe Gly Tyr Tyr Met Gly Ser Gly Thr
        65                  70                  75                 80

Ser Thr Asn Val Leu Thr Glu Gln Ser Pro Arg Pro Val Ala Pro Pro
                        85                  90                 95

Pro Pro Pro Pro Pro
                    100

<210> SEQ ID NO 58
<211> LENGTH: 97
<212> TYPE: PRT
<213> ORGANISM: Theobroma cacao

<400> SEQUENCE: 58

Glu Glu Asn Thr Arg Arg Arg His Tyr Arg Gly Val Arg Gln Arg Pro
        1               5                  10                 15

Trp Gly Lys Trp Ala Ala Glu Ile Arg Asp Pro Lys Lys Ala Ala Arg
                        20                  25                 30

Val Trp Leu Gly Thr Phe Asp Thr Ala Glu Asp Ala Ala Leu Ala Tyr
                    35                  40                 45

Asp Arg Ala Ala Leu Lys Phe Lys Gly Thr Lys Ala Lys Leu Asn Phe
             50                  55                 60

Pro Glu Arg Val Gln Gly Asn Thr Glu Val Ser Tyr Phe Thr Gly His
        65                  70                  75                 80

Gly Asp Ser Ser Thr Val Arg Pro Asp Gln Asn Pro Thr Pro Ala Ala
                        85                  90                 95

Thr

<210> SEQ ID NO 59
<211> LENGTH: 87
<212> TYPE: PRT
<213> ORGANISM: Medicago truncatula

<400> SEQUENCE: 59

Thr Lys Lys Lys Pro His Tyr Arg Gly Val Arg Gln Arg Pro Trp Gly
        1               5                  10                 15

Lys Trp Ala Ala Glu Ile Arg Asp Pro Lys Lys Ala Ala Arg Val Trp
                        20                  25                 30

Leu Gly Thr Phe Asp Thr Ala Glu Asp Ala Ala Leu Ala Tyr Asp Lys
                    35                  40                 45

Ala Ala Leu Lys Phe Lys Gly Thr Lys Ala Lys Leu Asn Phe Pro Glu
             50                  55                 60

Arg Val Val Gln Cys Asn Ser Tyr Ser Ser Thr Ala Asn Asn Ala Ile
        65                  70                  75                 80

Gln Gln Ser Asp Tyr Val Ser
                    85

<210> SEQ ID NO 60
<211> LENGTH: 110
<212> TYPE: PRT
<213> ORGANISM: Glycine max
```

```
<400> SEQUENCE: 60

Val Thr Lys Lys Pro His Tyr Arg Gly Val Arg Gln Arg Pro Trp Gly
1               5                   10                  15

Lys Trp Ala Ala Glu Ile Arg Asp Pro Lys Lys Ala Ala Arg Val Trp
            20                  25                  30

Leu Gly Thr Phe Glu Thr Ala Glu Asp Ala Ala Leu Ala Tyr Asp Lys
        35                  40                  45

Ala Ala Leu Lys Phe Lys Gly Thr Lys Ala Lys Leu Asn Phe Pro Glu
    50                  55                  60

Arg Leu His Gln Asn Val Pro Tyr Met Gln Gln His Gln Gln Gly Ser
65                  70                  75                  80

Ser Asn Arg Asn Val Phe Pro Phe His Ala Thr Ser Thr Ser Ser
                85                  90                  95

Ser Ala Thr Gly Ser Val Ser Ser Leu Asp Ala Val Ala Pro
            100                 105                 110

<210> SEQ ID NO 61
<211> LENGTH: 108
<212> TYPE: PRT
<213> ORGANISM: Malus domestica

<400> SEQUENCE: 61

Thr Val Arg Arg Arg His Tyr Arg Gly Val Gln Arg Pro Trp Gly
1               5                   10                  15

Lys Trp Ala Ala Glu Ile Arg Asp Pro Lys Lys Ala Ala Arg Val Trp
            20                  25                  30

Leu Gly Thr Phe Glu Thr Ala Glu Asp Ala Ala Ile Ala Tyr Asp Asn
        35                  40                  45

Ala Ala Leu Arg Phe Lys Gly Thr Lys Ala Lys Leu Asn Phe Pro Glu
    50                  55                  60

Arg Val Gln Gly Lys Thr Asp Phe Gly Ile Leu Met Gly Ser Ser Gly
65                  70                  75                  80

Thr Thr Thr Asn Ser Ser Ser Gly Ala Ala Ser Thr Gln Arg Thr Gln
                85                  90                  95

Asn Leu Met Arg Pro Ala Gly Gln Thr Ala Pro Ala
            100                 105

<210> SEQ ID NO 62
<211> LENGTH: 92
<212> TYPE: PRT
<213> ORGANISM: Capsicum annuum

<400> SEQUENCE: 62

Gly Ser Gly Arg Arg His Tyr Arg Gly Val Gln Arg Pro Trp Gly
1               5                   10                  15

Lys Trp Ala Ala Glu Ile Arg Asn Pro Lys Lys Ala Ala Arg Val Trp
            20                  25                  30

Leu Gly Thr Phe Asp Arg Ala Glu Asp Ala Ala Leu Ala Tyr Asp Glu
        35                  40                  45

Ala Ala Val Arg Phe Lys Gly Ser Lys Ala Lys Leu Asn Phe Pro Glu
    50                  55                  60

Arg Leu Val Gln Gly Gln Pro Gln Leu Leu Ser Gln Asp Thr Ser Pro
65                  70                  75                  80

Gln His Asn Ser His Phe Glu Glu Phe Asn Thr
                85                  90
```

<210> SEQ ID NO 63
<211> LENGTH: 107
<212> TYPE: PRT
<213> ORGANISM: Brassica juncea

<400> SEQUENCE: 63

Ser Gly Asp Gly Pro Gln Arg Arg Tyr Arg Gly Val Arg Gln Arg Pro
1               5                   10                  15

Trp Gly Lys Trp Ala Ala Glu Ile Arg Asp Pro Phe Lys Ala Ala Arg
            20                  25                  30

Val Trp Leu Gly Thr Phe Asp Asn Ala Glu Ser Ala Ala Arg Ala Tyr
        35                  40                  45

Asp Glu Ala Ala Leu Arg Phe Arg Gly Asn Lys Ala Lys Leu Asn Phe
    50                  55                  60

Pro Glu Asn Val Lys Leu Val Arg Pro Ala Ser Thr Thr Pro Thr Leu
65                  70                  75                  80

Ser Val Pro Gln Thr Ala Val Gln Arg Pro Thr Gln Leu Arg Asn Ser
                85                  90                  95

Gly Ser Thr Ser Thr Ile Leu Pro Val Arg His
            100                 105

<210> SEQ ID NO 64
<211> LENGTH: 101
<212> TYPE: PRT
<213> ORGANISM: Solanum lycopersicum

<400> SEQUENCE: 64

Asn Asn Glu Lys Arg Arg Arg Gln Tyr Arg Gly Val Arg Gln Arg Pro
1               5                   10                  15

Trp Gly Lys Trp Ala Ala Glu Ile Arg Asp Pro Glu Lys Ala Ala Arg
            20                  25                  30

Val Trp Leu Gly Thr Phe His Thr Ala Glu Asp Ala Ala Ile Ala Tyr
        35                  40                  45

Asp Glu Ala Ala Leu Lys Phe Lys Gly Asn Lys Ala Lys Leu Asn Phe
    50                  55                  60

Pro Glu Arg Val Gln Ser Thr Thr Asp Gln Phe Gly Ile Ser Tyr Leu
65                  70                  75                  80

Ile Thr Asn Thr Asn His Gln Gln His Gln Phe Gln Pro Thr Asn Phe
                85                  90                  95

Leu Pro Asn Ser Asp
            100

<210> SEQ ID NO 65
<211> LENGTH: 107
<212> TYPE: PRT
<213> ORGANISM: Cucumis sativus

<400> SEQUENCE: 65

Arg Val Lys Arg Leu Lys Lys Asn Tyr Arg Gly Val Arg Gln Arg Pro
1               5                   10                  15

Trp Gly Lys Trp Ala Ala Glu Ile Arg Asp Pro Ile Arg Ala Ala Arg
            20                  25                  30

Val Trp Leu Gly Thr Phe Asn Thr Ala Glu Asp Ala Ala Arg Ala Tyr
        35                  40                  45

Asp Glu Ala Ala Ile Lys Phe Arg Gly Pro Arg Ala Lys Leu Asn Phe
    50                  55                  60

Pro Phe Pro Asp Tyr Ser Leu Ser Ser Thr Phe His Ser Ser Pro Pro 65                  70                  75                  80

Pro Ala Ser Thr Thr Thr Ser Ala Ser Ala Ser Phe Ser Pro Ala Ala
                85                  90                  95

Pro Pro Pro Pro Pro Leu Leu Pro Thr Ser Thr
            100                 105

<210> SEQ ID NO 66
<211> LENGTH: 120
<212> TYPE: PRT
<213> ORGANISM: Populus trichocarpa

<400> SEQUENCE: 66

Met Ala Asp Ser Asp Asn Glu Ser Gly Glu Gln Asn Asn Ser Asn Thr
1               5                   10                  15

Asn Tyr Ser Thr Glu Thr Ser Pro Arg Glu Gln Asp Arg Leu Leu Pro
                20                  25                  30

Ile Ala Asn Val Ser Arg Ile Met Lys Lys Ala Leu Pro Ala Asn Ala
                35                  40                  45

Lys Ile Ser Lys Asp Ala Lys Glu Thr Val Gln Glu Cys Val Ser Glu
            50                  55                  60

Phe Ile Ser Phe Ile Thr Gly Glu Ala Ser Asp Lys Cys Gln Arg Glu
65                  70                  75                  80

Lys Arg Lys Thr Ile Asn Gly Asp Asp Leu Leu Trp Ala Met Thr Thr
                85                  90                  95

Leu Gly Phe Glu Asp Tyr Val Glu Pro Leu Lys Ile Tyr Leu Gln Lys
            100                 105                 110

Phe Arg Glu Met Glu Gly Glu Lys
            115                 120

<210> SEQ ID NO 67
<211> LENGTH: 116
<212> TYPE: PRT
<213> ORGANISM: Solanum lycopersicum

<400> SEQUENCE: 67

Met Ala Asp Ser Asp Asn Glu Ser Gly Gly His Asn Asn Ala Asn Ser
1               5                   10                  15

Glu Gly Ser Thr Arg Glu Gln Asp Arg Phe Leu Pro Ile Ala Asn Val
                20                  25                  30

Ser Arg Ile Met Lys Lys Ala Leu Pro Ala Asn Ala Lys Ile Ser Lys
                35                  40                  45

Asp Ala Lys Glu Thr Val Gln Glu Cys Val Ser Glu Phe Ile Ser Phe
            50                  55                  60

Ile Thr Gly Glu Ala Ser Asp Lys Cys Gln Arg Glu Lys Arg Lys Thr
65                  70                  75                  80

Ile Asn Gly Asp Asp Leu Leu Trp Ala Met Thr Thr Leu Gly Phe Glu
                85                  90                  95

Glu Tyr Val Glu Pro Leu Lys Ile Tyr Leu Ala Lys Tyr Arg Glu Met
            100                 105                 110

Glu Gly Glu Lys
        115

<210> SEQ ID NO 68
<211> LENGTH: 118
<212> TYPE: PRT
<213> ORGANISM: Theobroma cacao

<400> SEQUENCE: 68

Met Ala Asp Ser Asp Asn Asp Ser Gly Gly His Asn Ser Asn Ala
1               5                   10                  15

Asn Asn Glu Leu Ser Pro Arg Glu Gln Asp Arg Phe Leu Pro Ile Ala
            20                  25                  30

Asn Val Ser Arg Ile Met Lys Lys Ala Leu Pro Ala Asn Ala Lys Ile
        35                  40                  45

Ser Lys Asp Ala Lys Glu Thr Val Gln Glu Cys Val Ser Glu Phe Ile
50                  55                  60

Ser Phe Ile Thr Gly Glu Ala Ser Asp Lys Cys Gln Arg Glu Lys Arg
65                  70                  75                  80

Lys Thr Ile Asn Gly Asp Asp Leu Leu Trp Ala Met Thr Thr Leu Gly
            85                  90                  95

Phe Glu Asp Tyr Val Glu Pro Leu Lys Val Tyr Leu His Lys Phe Arg
        100                 105                 110

Glu Met Glu Gly Glu Arg
        115

<210> SEQ ID NO 69
<211> LENGTH: 115
<212> TYPE: PRT
<213> ORGANISM: Panicum virgatum

<400> SEQUENCE: 69

Met Pro Asp Ser Asp Asn Glu Ser Gly Gly Pro Ser Asn Ala Glu Phe
1               5                   10                  15

Ser Ser Pro Arg Glu Gln Asp Arg Phe Leu Pro Ile Ala Asn Val Ser
            20                  25                  30

Arg Ile Met Lys Lys Ala Leu Pro Ala Asn Ala Lys Ile Ser Lys Asp
        35                  40                  45

Ala Lys Glu Thr Val Gln Glu Cys Val Ser Glu Phe Ile Ser Phe Ile
50                  55                  60

Thr Gly Glu Ala Ser Asp Lys Cys Gln Arg Glu Lys Arg Lys Thr Ile
65                  70                  75                  80

Asn Gly Asp Asp Leu Leu Trp Ala Met Thr Thr Leu Gly Phe Glu Asp
            85                  90                  95

Tyr Ile Glu Pro Leu Lys Leu Tyr Leu His Lys Phe Arg Glu Leu Glu
        100                 105                 110

Gly Glu Lys
        115

<210> SEQ ID NO 70
<211> LENGTH: 115
<212> TYPE: PRT
<213> ORGANISM: Setaria italica

<400> SEQUENCE: 70

Met Pro Asp Ser Asp Asn Glu Ser Gly Gly Pro Ser Asn Ala Glu Phe
1               5                   10                  15

Ser Ser Pro Arg Glu Gln Asp Arg Phe Leu Pro Ile Ala Asn Val Ser
            20                  25                  30

Arg Ile Met Lys Lys Ala Leu Pro Ala Asn Ala Lys Ile Ser Lys Asp
        35                  40                  45

Ala Lys Glu Thr Val Gln Glu Cys Val Ser Glu Phe Ile Ser Phe Ile
50                  55                  60

Thr Gly Glu Ala Ser Asp Lys Cys Gln Arg Glu Lys Arg Lys Thr Ile
65                  70                  75                  80

Asn Gly Asp Asp Leu Leu Trp Ala Met Thr Thr Leu Gly Phe Glu Asp
                85                  90                  95

Tyr Ile Glu Pro Leu Lys Leu Tyr Leu His Lys Phe Arg Glu Leu Glu
            100                 105                 110

Gly Glu Lys
        115

<210> SEQ ID NO 71
<211> LENGTH: 115
<212> TYPE: PRT
<213> ORGANISM: Sorghum bicolor

<400> SEQUENCE: 71

Met Pro Asp Ser Asp Asn Glu Ser Gly Gly Pro Ser Asn Ala Asp Phe
1               5                   10                  15

Ser Ser Pro Arg Glu Gln Asp Arg Phe Leu Pro Ile Ala Asn Val Ser
            20                  25                  30

Arg Ile Met Lys Lys Ala Leu Pro Ala Asn Ala Lys Ile Ser Lys Asp
        35                  40                  45

Ala Lys Glu Thr Val Gln Glu Cys Val Ser Glu Phe Ile Ser Phe Ile
50                  55                  60

Thr Gly Glu Ala Ser Asp Lys Cys Gln Arg Glu Lys Arg Lys Thr Ile
65                  70                  75                  80

Asn Gly Asp Asp Leu Leu Trp Ala Met Thr Thr Leu Gly Phe Glu Asp
                85                  90                  95

Tyr Ile Glu Pro Leu Lys Leu Tyr Leu His Lys Phe Arg Glu Leu Glu
            100                 105                 110

Gly Glu Lys
        115

<210> SEQ ID NO 72
<211> LENGTH: 115
<212> TYPE: PRT
<213> ORGANISM: Zea mays

<400> SEQUENCE: 72

Met Pro Asp Ser Asp Asn Glu Ser Gly Gly Pro Ser Asn Ala Glu Phe
1               5                   10                  15

Ser Ser Pro Arg Glu Gln Asp Arg Phe Leu Pro Ile Ala Asn Val Ser
            20                  25                  30

Arg Ile Met Lys Lys Ala Leu Pro Ala Asn Ala Lys Ile Ser Lys Asp
        35                  40                  45

Ala Lys Glu Thr Val Gln Glu Cys Val Ser Glu Phe Ile Ser Phe Ile
50                  55                  60

Thr Gly Glu Ala Ser Asp Lys Cys Gln Arg Glu Lys Arg Lys Thr Ile
65                  70                  75                  80

Asn Gly Asp Asp Leu Leu Trp Ala Met Thr Thr Leu Gly Phe Glu Asp
                85                  90                  95

Tyr Val Glu Pro Leu Lys Leu Tyr Leu His Lys Phe Arg Glu Leu Glu
            100                 105                 110

Gly Glu Lys
        115

<210> SEQ ID NO 73
<211> LENGTH: 115
<212> TYPE: PRT
<213> ORGANISM: Hordeum vulgare

<400> SEQUENCE: 73

Met Pro Asp Ser Asp Asn Asp Ser Gly Gly Pro Ser Asn Ala Asp Phe
1               5                   10                  15

Ser Ser Pro Lys Glu Gln Asp Arg Phe Leu Pro Ile Ala Asn Val Ser
            20                  25                  30

Arg Ile Met Lys Lys Ala Leu Pro Ala Asn Ala Lys Ile Ser Lys Asp
        35                  40                  45

Ala Lys Glu Thr Val Gln Glu Cys Val Ser Glu Phe Ile Ser Phe Ile
50                  55                  60

Thr Gly Glu Ala Ser Asp Lys Cys Gln Arg Glu Lys Arg Lys Thr Ile
65                  70                  75                  80

Asn Gly Asp Asp Leu Leu Trp Ala Met Thr Thr Leu Gly Phe Glu Asp
                85                  90                  95

Tyr Met Glu Pro Leu Lys Leu Tyr Leu His Lys Phe Arg Glu Leu Glu
            100                 105                 110

Gly Glu Lys
        115

<210> SEQ ID NO 74
<211> LENGTH: 118
<212> TYPE: PRT
<213> ORGANISM: Oryza sativa

<400> SEQUENCE: 74

Met Pro Asp Ser Asp Asn Asp Ser Gly Gly Pro Ser Asn Tyr Ala Gly
1               5                   10                  15

Gly Glu Leu Ser Ser Pro Arg Glu Gln Asp Arg Phe Leu Pro Ile Ala
            20                  25                  30

Asn Val Ser Arg Ile Met Lys Lys Ala Leu Pro Ala Asn Ala Lys Ile
        35                  40                  45

Ser Lys Asp Ala Lys Glu Thr Val Gln Glu Cys Val Ser Glu Phe Ile
50                  55                  60

Ser Phe Ile Thr Gly Glu Ala Ser Asp Lys Cys Gln Arg Glu Lys Arg
65                  70                  75                  80

Lys Thr Ile Asn Gly Asp Asp Leu Leu Trp Ala Met Thr Thr Leu Gly
                85                  90                  95

Phe Glu Asp Tyr Val Asp Pro Leu Lys His Tyr Leu His Lys Phe Arg
            100                 105                 110

Glu Ile Glu Gly Glu Arg
        115

<210> SEQ ID NO 75
<211> LENGTH: 117
<212> TYPE: PRT
<213> ORGANISM: Brachypodium distachyon

<400> SEQUENCE: 75

Met Pro Asp Ser Asp Asn Asp Ser Gly Gly Pro Ser Asn Thr Gly Gly
1               5                   10                  15

Glu Leu Ser Ser Pro Arg Glu Gln Asp Arg Phe Leu Pro Ile Ala Asn
            20                  25                  30

Val Ser Arg Ile Met Lys Lys Ala Leu Pro Ala Asn Ala Lys Ile Ser
        35                  40                  45

Lys Asp Ala Lys Glu Thr Val Gln Glu Cys Val Ser Glu Phe Ile Ser
50                  55                  60

```
Phe Ile Thr Gly Glu Ala Ser Asp Lys Cys Gln Arg Glu Lys Arg Lys
 65                  70                  75                  80

Thr Ile Asn Gly Asp Asp Leu Leu Trp Ala Met Thr Thr Leu Gly Phe
                 85                  90                  95

Glu Asp Tyr Val Asp Pro Leu Lys His Tyr Leu His Lys Phe Arg Glu
            100                 105                 110

Ile Glu Gly Glu Arg
        115
```

```
<210> SEQ ID NO 76
<211> LENGTH: 115
<212> TYPE: PRT
<213> ORGANISM: Triticum aestivum

<400> SEQUENCE: 76

Met Pro Asp Ser Asp Asn Glu Asp Ser Gly Asn Ala Gly Gly Glu Leu
  1               5                  10                  15

Ser Ser Pro Arg Glu Gln Asp Arg Phe Leu Pro Ile Ala Asn Val Ser
             20                  25                  30

Arg Ile Met Lys Lys Ala Leu Pro Ala Asn Ala Lys Ile Ser Lys Asp
         35                  40                  45

Ala Lys Glu Thr Val Gln Glu Cys Val Ser Glu Phe Ile Ser Phe Ile
 50                  55                  60

Thr Gly Glu Ala Ser Asp Lys Cys Gln Arg Glu Lys Arg Lys Thr Ile
 65                  70                  75                  80

Asn Gly Asp Asp Leu Leu Trp Ala Met Thr Thr Leu Gly Phe Glu Asp
                 85                  90                  95

Tyr Val Asp Pro Leu Lys His Tyr Leu His Lys Phe Arg Glu Ile Glu
            100                 105                 110

Gly Glu Arg
        115
```

```
<210> SEQ ID NO 77
<211> LENGTH: 118
<212> TYPE: PRT
<213> ORGANISM: Glycine max

<400> SEQUENCE: 77

Met Ala Asp Ser Asp Asn Asp Ser Gly Gly Ala His Asn Ala Gly Lys
  1               5                  10                  15

Gly Ser Glu Met Ser Pro Arg Glu Gln Asp Arg Phe Leu Pro Ile Ala
             20                  25                  30

Asn Val Ser Arg Ile Met Lys Lys Ala Leu Pro Ala Asn Ala Lys Ile
             35                  40                  45

Ser Lys Asp Ala Lys Glu Thr Val Gln Glu Cys Val Ser Glu Phe Ile
 50                  55                  60

Ser Phe Ile Thr Gly Glu Ala Ser Asp Lys Cys Gln Arg Glu Lys Arg
 65                  70                  75                  80

Lys Thr Ile Asn Gly Asp Asp Leu Leu Trp Ala Met Thr Thr Leu Gly
                 85                  90                  95

Phe Glu Asp Tyr Val Glu Pro Leu Lys Gly Tyr Leu Gln Arg Phe Arg
            100                 105                 110

Glu Met Glu Gly Glu Lys
        115
```